(12) United States Patent
Lang et al.

(10) Patent No.: US 12,409,217 B2
(45) Date of Patent: Sep. 9, 2025

(54) ADMINISTERING A LYMPHOCYTIC CHORIOMENINGTITIS VIRUS (LCMV) WITH IMPROVED TUMOR REGRESSION PROPERTIES

(71) Applicant: ABALOS THERAPEUTICS GMBH, Duesseldorf (DE)

(72) Inventors: Karl Sebastian Lang, Essen (DE); Halime Kalkavan, Memphis, TN (US)

(73) Assignee: ABALOS THERAPEUTICS GMBH, Duesseldorf (DE)

( * ) Notice: Subject to any disclaimer, the term of this patent is extended or adjusted under 35 U.S.C. 154(b) by 0 days.

(21) Appl. No.: 18/385,250

(22) Filed: Oct. 30, 2023

(65) Prior Publication Data

US 2024/0252611 A1     Aug. 1, 2024

Related U.S. Application Data

(60) Continuation of application No. 16/267,095, filed on Feb. 4, 2019, now Pat. No. 11,801,294, which is a division of application No. 15/567,343, filed as application No. PCT/EP2016/058347 on Apr. 15, 2016, now abandoned.

(30) Foreign Application Priority Data

Apr. 17, 2015  (DE) .......................... 102015207036.0

(51) Int. Cl.
| | | |
|---|---|---|
| *A61K 35/768* | (2015.01) | |
| *A61K 35/76* | (2015.01) | |
| *A61K 39/12* | (2006.01) | |
| *C12N 7/00* | (2006.01) | |
| *A61K 39/00* | (2006.01) | |
| *A61P 35/00* | (2006.01) | |

(52) U.S. Cl.
CPC .............. *A61K 39/12* (2013.01); *A61K 35/76* (2013.01); *A61K 35/768* (2013.01); *C12N 7/00* (2013.01); *A61K 2039/5254* (2013.01); *A61K 2039/585* (2013.01); *A61P 35/00* (2018.01); *C12N 2760/10011* (2013.01); *C12N 2760/10021* (2013.01); *C12N 2760/10032* (2013.01); *C12N 2760/10033* (2013.01)

(58) Field of Classification Search
CPC .................... A61K 35/768; C12N 2760/10032
See application file for complete search history.

(56) References Cited

PUBLICATIONS

Molomut, N., and M. Padnos, Dec. 1965, Inhibition of transplantable and spontaneous murine tumours by the M-P virus, Nature 208:948-950.*
Sevilla, N., and J. C. de la Torre, 2006, Arenavirus Diversity and Evolution: Quasispecies In Vivo, CTMI 299:315-335.*
Koma, T., et al., 2013, Innate Immune Response to Arenaviral Infection: A Focus on the Highly Pathogenic New World Hemorrhagic Arenaviruses, J. Mol. Biol. 425:4893-4903.*
Oldenburg, J., et al., 2007, Differences in tropism and pH dependence for glycoproteins from the Clade B1 arenaviruses: Implications for receptor usage and pathogenicity, Virol. 364:132-139.*
Zapata, J. C., and M. S. Salvato, 2013, Arenavirus Variations Due to Host-Specific Adaptation, Viruses 5:241-278.*

* cited by examiner

*Primary Examiner* — Jeffrey S Parkin
(74) *Attorney, Agent, or Firm* — Michael A. Whittaker

(57) ABSTRACT

The invention relates to arenaviruses for use in the treatment and/or prevention of tumors and also a method for preparing arenaviruses with (improved) tumor-regressive properties.

16 Claims, 9 Drawing Sheets

Specification includes a Sequence Listing.

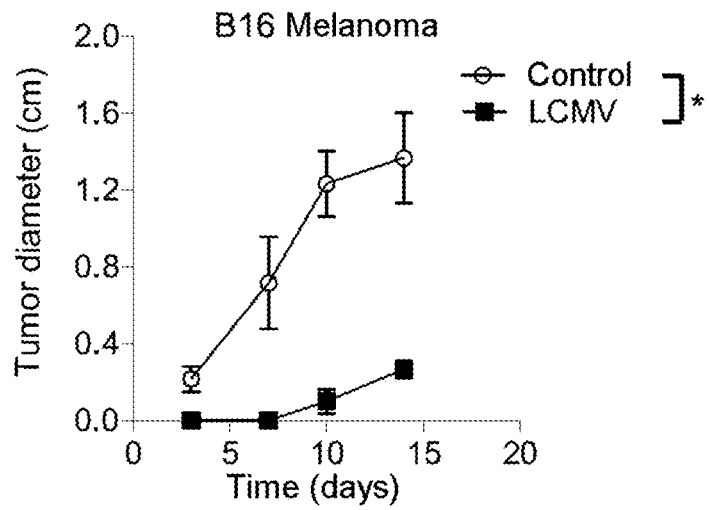
Figure 16
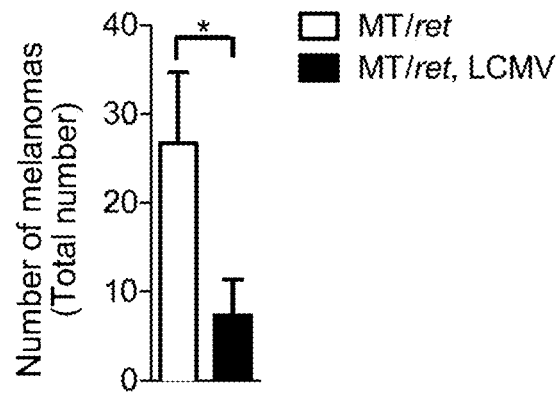
Figure 17
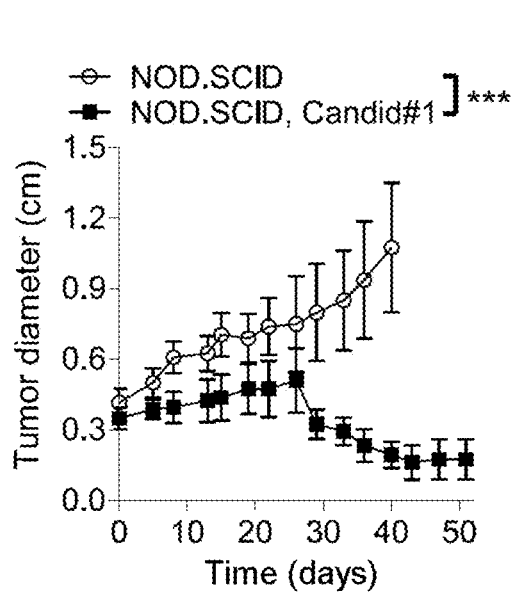 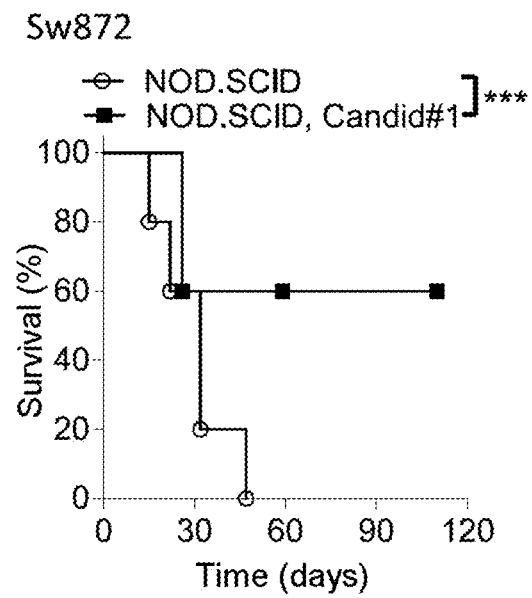
Figure 18A          Figure 18B

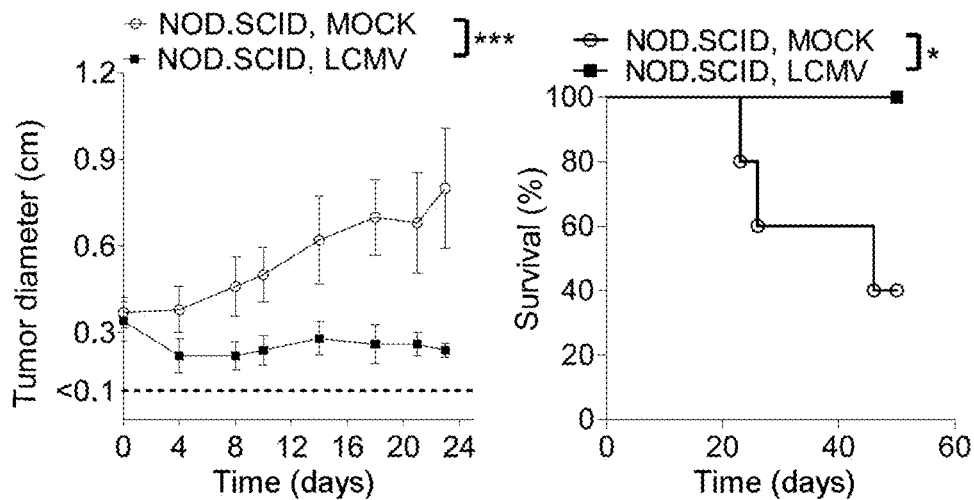
Figure 19A
Figure 19B
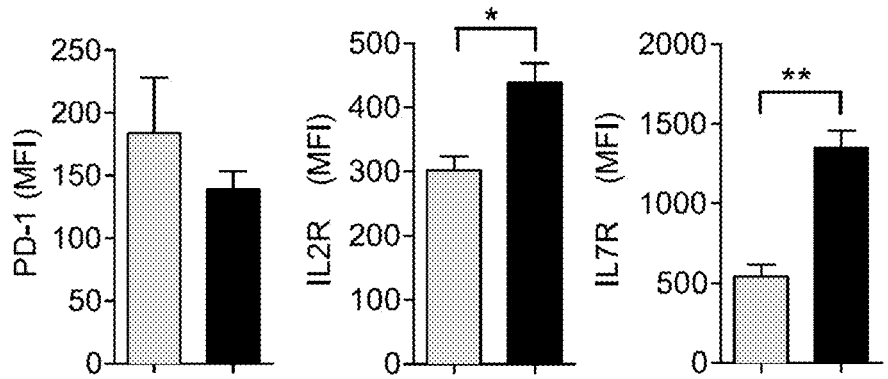
Figure 20
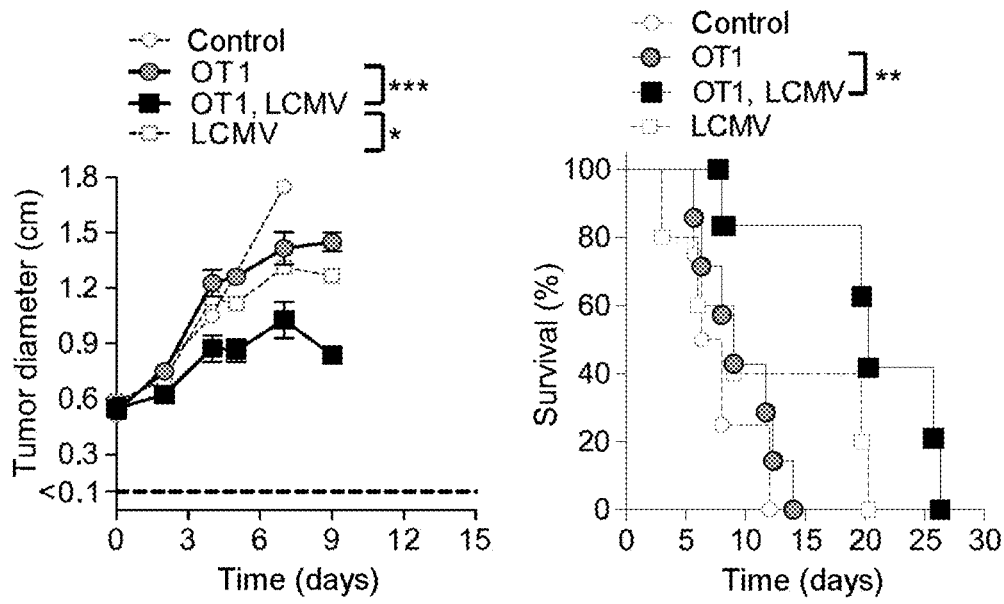
Figure 21A
Figure 21B

SEQUENCE LISTING

```
Sequence total quantity: 6
SEQ ID NO: 1              moltype = RNA  length = 3413
FEATURE                   Location/Qualifiers
modified_base             2
                          mod_base = OTHER
                          note = thymine
modified_base             7
                          mod_base = OTHER
                          note = thymine
modified_base             15
                          mod_base = OTHER
                          note = thymine
modified_base             18
                          mod_base = OTHER
                          note = thymine
modified_base             25..28
                          mod_base = OTHER
                          note = thymine
modified_base             31..32
                          mod_base = OTHER
                          note = thymine
modified_base             37
                          mod_base = OTHER
                          note = thymine
modified_base             39
                          mod_base = OTHER
                          note = thymine
modified_base             42..43
                          mod_base = OTHER
                          note = thymine
modified_base             45
                          mod_base = OTHER
```

-continued

```
                            note = thymine
modified_base               49
                            mod_base = OTHER
                            note = thymine
modified_base               51..54
                            mod_base = OTHER
                            note = thymine
modified_base               56
                            mod_base = OTHER
                            note = thymine
modified_base               58..60
                            mod_base = OTHER
                            note = thymine
modified_base               69
                            mod_base = OTHER
                            note = thymine
modified_base               78
                            mod_base = OTHER
                            note = thymine
modified_base               82..83
                            mod_base = OTHER
                            note = thymine
modified_base               90
                            mod_base = OTHER
                            note = thymine
modified_base               98..99
                            mod_base = OTHER
                            note = thymine
modified_base               102..103
                            mod_base = OTHER
                            note = thymine
modified_base               107..108
                            mod_base = OTHER
                            note = thymine
modified_base               111
                            mod_base = OTHER
                            note = thymine
modified_base               120
                            mod_base = OTHER
                            note = thymine
modified_base               128..132
                            mod_base = OTHER
                            note = thymine
modified_base               142
                            mod_base = OTHER
                            note = thymine
modified_base               144
                            mod_base = OTHER
                            note = thymine
modified_base               150..151
                            mod_base = OTHER
                            note = thymine
modified_base               154
                            mod_base = OTHER
                            note = thymine
modified_base               156..157
                            mod_base = OTHER
                            note = thymine
modified_base               159..160
                            mod_base = OTHER
                            note = thymine
modified_base               165
                            mod_base = OTHER
                            note = thymine
modified_base               169
                            mod_base = OTHER
                            note = thymine
modified_base               171
                            mod_base = OTHER
                            note = thymine
modified_base               174..175
                            mod_base = OTHER
                            note = thymine
modified_base               180
                            mod_base = OTHER
                            note = thymine
modified_base               183..184
                            mod_base = OTHER
                            note = thymine
```

-continued

| | | |
|---|---|---|
| modified_base | 190 | |
| | mod_base = OTHER | |
| | note = thymine | |
| modified_base | 192 | |
| | mod_base = OTHER | |
| | note = thymine | |
| modified_base | 195 | |
| | mod_base = OTHER | |
| | note = thymine | |
| modified_base | 200..201 | |
| | mod_base = OTHER | |
| | note = thymine | |
| modified_base | 203 | |
| | mod_base = OTHER | |
| | note = thymine | |
| modified_base | 211 | |
| | mod_base = OTHER | |
| | note = thymine | |
| modified_base | 214..216 | |
| | mod_base = OTHER | |
| | note = thymine | |
| modified_base | 218..219 | |
| | mod_base = OTHER | |
| | note = thymine | |
| modified_base | 224..225 | |
| | mod_base = OTHER | |
| | note = thymine | |
| modified_base | 227..229 | |
| | mod_base = OTHER | |
| | note = thymine | |
| modified_base | 231 | |
| | mod_base = OTHER | |
| | note = thymine | |
| modified_base | 233..234 | |
| | mod_base = OTHER | |
| | note = thymine | |
| modified_base | 237 | |
| | mod_base = OTHER | |
| | note = thymine | |
| modified_base | 243..244 | |
| | mod_base = OTHER | |
| | note = thymine | |
| modified_base | 254 | |
| | mod_base = OTHER | |
| | note = thymine | |
| modified_base | 257 | |
| | mod_base = OTHER | |
| | note = thymine | |
| modified_base | 271..273 | |
| | mod_base = OTHER | |
| | note = thymine | |
| modified_base | 279 | |
| | mod_base = OTHER | |
| | note = thymine | |
| modified_base | 285 | |
| | mod_base = OTHER | |
| | note = thymine | |
| modified_base | 292 | |
| | mod_base = OTHER | |
| | note = thymine | |
| modified_base | 296..297 | |
| | mod_base = OTHER | |
| | note = thymine | |
| modified_base | 304 | |
| | mod_base = OTHER | |
| | note = thymine | |
| modified_base | 306 | |
| | mod_base = OTHER | |
| | note = thymine | |
| modified_base | 308 | |
| | mod_base = OTHER | |
| | note = thymine | |
| modified_base | 311..312 | |
| | mod_base = OTHER | |
| | note = thymine | |
| modified_base | 314 | |
| | mod_base = OTHER | |
| | note = thymine | |
| modified_base | 318 | |

-continued

```
                              mod_base = OTHER
                              note = thymine
modified_base                 321
                              mod_base = OTHER
                              note = thymine
modified_base                 325
                              mod_base = OTHER
                              note = thymine
modified_base                 327
                              mod_base = OTHER
                              note = thymine
modified_base                 329..332
                              mod_base = OTHER
                              note = thymine
modified_base                 340
                              mod_base = OTHER
                              note = thymine
modified_base                 346
                              mod_base = OTHER
                              note = thymine
modified_base                 351
                              mod_base = OTHER
                              note = thymine
modified_base                 355..357
                              mod_base = OTHER
                              note = thymine
modified_base                 359..360
                              mod_base = OTHER
                              note = thymine
modified_base                 362
                              mod_base = OTHER
                              note = thymine
modified_base                 364
                              mod_base = OTHER
                              note = thymine
modified_base                 368..369
                              mod_base = OTHER
                              note = thymine
modified_base                 382
                              mod_base = OTHER
                              note = thymine
modified_base                 384..386
                              mod_base = OTHER
                              note = thymine
modified_base                 390..391
                              mod_base = OTHER
                              note = thymine
modified_base                 403
                              mod_base = OTHER
                              note = thymine
modified_base                 406..407
                              mod_base = OTHER
                              note = thymine
modified_base                 410..412
                              mod_base = OTHER
                              note = thymine
modified_base                 417
                              mod_base = OTHER
                              note = thymine
modified_base                 422..424
                              mod_base = OTHER
                              note = thymine
modified_base                 427
                              mod_base = OTHER
                              note = thymine
modified_base                 430
                              mod_base = OTHER
                              note = thymine
modified_base                 432..433
                              mod_base = OTHER
                              note = thymine
modified_base                 438
                              mod_base = OTHER
                              note = thymine
modified_base                 440..441
                              mod_base = OTHER
                              note = thymine
modified_base                 443..444
                              mod_base = OTHER
```

|               |                                      |
|---------------|--------------------------------------|
|               | note = thymine                       |
| modified_base | 452                                  |
|               | mod_base = OTHER                     |
|               | note = thymine                       |
| modified_base | 454                                  |
|               | mod_base = OTHER                     |
|               | note = thymine                       |
| modified_base | 457                                  |
|               | mod_base = OTHER                     |
|               | note = thymine                       |
| modified_base | 459..460                             |
|               | mod_base = OTHER                     |
|               | note = thymine                       |
| modified_base | 462                                  |
|               | mod_base = OTHER                     |
|               | note = thymine                       |
| modified_base | 465                                  |
|               | mod_base = OTHER                     |
|               | note = thymine                       |
| modified_base | 472                                  |
|               | mod_base = OTHER                     |
|               | note = thymine                       |
| modified_base | 481                                  |
|               | mod_base = OTHER                     |
|               | note = thymine                       |
| modified_base | 483                                  |
|               | mod_base = OTHER                     |
|               | note = thymine                       |
| modified_base | 488                                  |
|               | mod_base = OTHER                     |
|               | note = thymine                       |
| modified_base | 491                                  |
|               | mod_base = OTHER                     |
|               | note = thymine                       |
| modified_base | 493..494                             |
|               | mod_base = OTHER                     |
|               | note = thymine                       |
| modified_base | 502                                  |
|               | mod_base = OTHER                     |
|               | note = thymine                       |
| modified_base | 505                                  |
|               | mod_base = OTHER                     |
|               | note = thymine                       |
| modified_base | 508                                  |
|               | mod_base = OTHER                     |
|               | note = thymine                       |
| modified_base | 513..515                             |
|               | mod_base = OTHER                     |
|               | note = thymine                       |
| modified_base | 518..519                             |
|               | mod_base = OTHER                     |
|               | note = thymine                       |
| modified_base | 521                                  |
|               | mod_base = OTHER                     |
|               | note = thymine                       |
| modified_base | 523                                  |
|               | mod_base = OTHER                     |
|               | note = thymine                       |
| modified_base | 527                                  |
|               | mod_base = OTHER                     |
|               | note = thymine                       |
| modified_base | 530..531                             |
|               | mod_base = OTHER                     |
|               | note = thymine                       |
| modified_base | 534                                  |
|               | mod_base = OTHER                     |
|               | note = thymine                       |
| modified_base | 538                                  |
|               | mod_base = OTHER                     |
|               | note = thymine                       |
| modified_base | 541                                  |
|               | mod_base = OTHER                     |
|               | note = thymine                       |
| modified_base | 543                                  |
|               | mod_base = OTHER                     |
|               | note = thymine                       |
| modified_base | 550                                  |
|               | mod_base = OTHER                     |
|               | note = thymine                       |

| | |
|---|---|
| modified_base | 553..554<br>mod_base = OTHER<br>note = thymine |
| modified_base | 559<br>mod_base = OTHER<br>note = thymine |
| modified_base | 561<br>mod_base = OTHER<br>note = thymine |
| modified_base | 572..574<br>mod_base = OTHER<br>note = thymine |
| modified_base | 576<br>mod_base = OTHER<br>note = thymine |
| modified_base | 578<br>mod_base = OTHER<br>note = thymine |
| modified_base | 580<br>mod_base = OTHER<br>note = thymine |
| modified_base | 589<br>mod_base = OTHER<br>note = thymine |
| modified_base | 605..606<br>mod_base = OTHER<br>note = thymine |
| modified_base | 609<br>mod_base = OTHER<br>note = thymine |
| modified_base | 611..613<br>mod_base = OTHER<br>note = thymine |
| modified_base | 618<br>mod_base = OTHER<br>note = thymine |
| modified_base | 626<br>mod_base = OTHER<br>note = thymine |
| modified_base | 634<br>mod_base = OTHER<br>note = thymine |
| modified_base | 637<br>mod_base = OTHER<br>note = thymine |
| modified_base | 639<br>mod_base = OTHER<br>note = thymine |
| modified_base | 643<br>mod_base = OTHER<br>note = thymine |
| modified_base | 649..650<br>mod_base = OTHER<br>note = thymine |
| modified_base | 652<br>mod_base = OTHER<br>note = thymine |
| modified_base | 655<br>mod_base = OTHER<br>note = thymine |
| modified_base | 662..664<br>mod_base = OTHER<br>note = thymine |
| modified_base | 670<br>mod_base = OTHER<br>note = thymine |
| modified_base | 675<br>mod_base = OTHER<br>note = thymine |
| modified_base | 679<br>mod_base = OTHER<br>note = thymine |
| modified_base | 682..684<br>mod_base = OTHER<br>note = thymine |
| modified_base | 686<br>mod_base = OTHER<br>note = thymine |
| modified_base | 688 |

|               |          |
|---------------|----------|
|               | mod_base = OTHER |
|               | note = thymine |
| modified_base | 695 |
|               | mod_base = OTHER |
|               | note = thymine |
| modified_base | 697 |
|               | mod_base = OTHER |
|               | note = thymine |
| modified_base | 700 |
|               | mod_base = OTHER |
|               | note = thymine |
| modified_base | 706..707 |
|               | mod_base = OTHER |
|               | note = thymine |
| modified_base | 710..711 |
|               | mod_base = OTHER |
|               | note = thymine |
| modified_base | 715 |
|               | mod_base = OTHER |
|               | note = thymine |
| modified_base | 723 |
|               | mod_base = OTHER |
|               | note = thymine |
| modified_base | 725 |
|               | mod_base = OTHER |
|               | note = thymine |
| modified_base | 728..729 |
|               | mod_base = OTHER |
|               | note = thymine |
| modified_base | 732 |
|               | mod_base = OTHER |
|               | note = thymine |
| modified_base | 745 |
|               | mod_base = OTHER |
|               | note = thymine |
| modified_base | 751..752 |
|               | mod_base = OTHER |
|               | note = thymine |
| modified_base | 757 |
|               | mod_base = OTHER |
|               | note = thymine |
| modified_base | 759 |
|               | mod_base = OTHER |
|               | note = thymine |
| modified_base | 764 |
|               | mod_base = OTHER |
|               | note = thymine |
| modified_base | 766 |
|               | mod_base = OTHER |
|               | note = thymine |
| modified_base | 771 |
|               | mod_base = OTHER |
|               | note = thymine |
| modified_base | 780..781 |
|               | mod_base = OTHER |
|               | note = thymine |
| modified_base | 788..789 |
|               | mod_base = OTHER |
|               | note = thymine |
| modified_base | 794..795 |
|               | mod_base = OTHER |
|               | note = thymine |
| modified_base | 798..799 |
|               | mod_base = OTHER |
|               | note = thymine |
| modified_base | 808 |
|               | mod_base = OTHER |
|               | note = thymine |
| modified_base | 816..817 |
|               | mod_base = OTHER |
|               | note = thymine |
| modified_base | 822..823 |
|               | mod_base = OTHER |
|               | note = thymine |
| modified_base | 833 |
|               | mod_base = OTHER |
|               | note = thymine |
| modified_base | 836..837 |
|               | mod_base = OTHER |

```
                          note = thymine
modified_base             845..846
                          mod_base = OTHER
                          note = thymine
modified_base             848..849
                          mod_base = OTHER
                          note = thymine
modified_base             851
                          mod_base = OTHER
                          note = thymine
modified_base             854
                          mod_base = OTHER
                          note = thymine
modified_base             857
                          mod_base = OTHER
                          note = thymine
modified_base             859..861
                          mod_base = OTHER
                          note = thymine
modified_base             869
                          mod_base = OTHER
                          note = thymine
modified_base             872
                          mod_base = OTHER
                          note = thymine
modified_base             883
                          mod_base = OTHER
                          note = thymine
modified_base             889
                          mod_base = OTHER
                          note = thymine
modified_base             896
                          mod_base = OTHER
                          note = thymine
modified_base             898..899
                          mod_base = OTHER
                          note = thymine
modified_base             901
                          mod_base = OTHER
                          note = thymine
modified_base             903
                          mod_base = OTHER
                          note = thymine
modified_base             911
                          mod_base = OTHER
                          note = thymine
modified_base             915
                          mod_base = OTHER
                          note = thymine
modified_base             918
                          mod_base = OTHER
                          note = thymine
modified_base             921
                          mod_base = OTHER
                          note = thymine
modified_base             933
                          mod_base = OTHER
                          note = thymine
modified_base             938
                          mod_base = OTHER
                          note = thymine
modified_base             940..943
                          mod_base = OTHER
                          note = thymine
modified_base             949
                          mod_base = OTHER
                          note = thymine
modified_base             952
                          mod_base = OTHER
                          note = thymine
modified_base             955
                          mod_base = OTHER
                          note = thymine
modified_base             957
                          mod_base = OTHER
                          note = thymine
modified_base             965
                          mod_base = OTHER
                          note = thymine
```

| | |
|---|---|
| modified_base | 970..972<br>mod_base = OTHER<br>note = thymine |
| modified_base | 976<br>mod_base = OTHER<br>note = thymine |
| modified_base | 979<br>mod_base = OTHER<br>note = thymine |
| modified_base | 983<br>mod_base = OTHER<br>note = thymine |
| modified_base | 985<br>mod_base = OTHER<br>note = thymine |
| modified_base | 989..990<br>mod_base = OTHER<br>note = thymine |
| modified_base | 992<br>mod_base = OTHER<br>note = thymine |
| modified_base | 994<br>mod_base = OTHER<br>note = thymine |
| modified_base | 999<br>mod_base = OTHER<br>note = thymine |
| modified_base | 1001..1002<br>mod_base = OTHER<br>note = thymine |
| modified_base | 1008<br>mod_base = OTHER<br>note = thymine |
| modified_base | 1010..1012<br>mod_base = OTHER<br>note = thymine |
| modified_base | 1015..1016<br>mod_base = OTHER<br>note = thymine |
| modified_base | 1027<br>mod_base = OTHER<br>note = thymine |
| modified_base | 1030<br>mod_base = OTHER<br>note = thymine |
| modified_base | 1032<br>mod_base = OTHER<br>note = thymine |
| modified_base | 1041<br>mod_base = OTHER<br>note = thymine |
| modified_base | 1045<br>mod_base = OTHER<br>note = thymine |
| modified_base | 1048<br>mod_base = OTHER<br>note = thymine |
| modified_base | 1054<br>mod_base = OTHER<br>note = thymine |
| modified_base | 1065<br>mod_base = OTHER<br>note = thymine |
| modified_base | 1069<br>mod_base = OTHER<br>note = thymine |
| modified_base | 1071<br>mod_base = OTHER<br>note = thymine |
| modified_base | 1074<br>mod_base = OTHER<br>note = thymine |
| modified_base | 1086<br>mod_base = OTHER<br>note = thymine |
| modified_base | 1090<br>mod_base = OTHER<br>note = thymine |
| modified_base | 1095 |

-continued

```
                            mod_base = OTHER
                            note = thymine
modified_base    1098
                            mod_base = OTHER
                            note = thymine
modified_base    1100
                            mod_base = OTHER
                            note = thymine
modified_base    1102
                            mod_base = OTHER
                            note = thymine
modified_base    1108..1110
                            mod_base = OTHER
                            note = thymine
modified_base    1112..1113
                            mod_base = OTHER
                            note = thymine
modified_base    1116
                            mod_base = OTHER
                            note = thymine
modified_base    1128..1129
                            mod_base = OTHER
                            note = thymine
modified_base    1137
                            mod_base = OTHER
                            note = thymine
modified_base    1140
                            mod_base = OTHER
                            note = thymine
modified_base    1144
                            mod_base = OTHER
                            note = thymine
modified_base    1146
                            mod_base = OTHER
                            note = thymine
modified_base    1150..1151
                            mod_base = OTHER
                            note = thymine
modified_base    1154
                            mod_base = OTHER
                            note = thymine
modified_base    1159..1160
                            mod_base = OTHER
                            note = thymine
modified_base    1169..1172
                            mod_base = OTHER
                            note = thymine
modified_base    1175
                            mod_base = OTHER
                            note = thymine
modified_base    1177
                            mod_base = OTHER
                            note = thymine
modified_base    1179
                            mod_base = OTHER
                            note = thymine
modified_base    1191..1193
                            mod_base = OTHER
                            note = thymine
modified_base    1205
                            mod_base = OTHER
                            note = thymine
modified_base    1208..1209
                            mod_base = OTHER
                            note = thymine
modified_base    1217
                            mod_base = OTHER
                            note = thymine
modified_base    1220
                            mod_base = OTHER
                            note = thymine
modified_base    1223..1224
                            mod_base = OTHER
                            note = thymine
modified_base    1227
                            mod_base = OTHER
                            note = thymine
modified_base    1241
                            mod_base = OTHER
```

-continued

```
                         note = thymine
modified_base            1243..1245
                         mod_base = OTHER
                         note = thymine
modified_base            1251
                         mod_base = OTHER
                         note = thymine
modified_base            1253
                         mod_base = OTHER
                         note = thymine
modified_base            1255
                         mod_base = OTHER
                         note = thymine
modified_base            1259..1260
                         mod_base = OTHER
                         note = thymine
modified_base            1264
                         mod_base = OTHER
                         note = thymine
modified_base            1267
                         mod_base = OTHER
                         note = thymine
modified_base            1271
                         mod_base = OTHER
                         note = thymine
modified_base            1275
                         mod_base = OTHER
                         note = thymine
modified_base            1277..1278
                         mod_base = OTHER
                         note = thymine
modified_base            1285
                         mod_base = OTHER
                         note = thymine
modified_base            1289..1290
                         mod_base = OTHER
                         note = thymine
modified_base            1292..1293
                         mod_base = OTHER
                         note = thymine
modified_base            1296..1298
                         mod_base = OTHER
                         note = thymine
modified_base            1300
                         mod_base = OTHER
                         note = thymine
modified_base            1305
                         mod_base = OTHER
                         note = thymine
modified_base            1308
                         mod_base = OTHER
                         note = thymine
modified_base            1319
                         mod_base = OTHER
                         note = thymine
modified_base            1321..1322
                         mod_base = OTHER
                         note = thymine
modified_base            1336
                         mod_base = OTHER
                         note = thymine
modified_base            1342
                         mod_base = OTHER
                         note = thymine
modified_base            1345..1347
                         mod_base = OTHER
                         note = thymine
modified_base            1351..1353
                         mod_base = OTHER
                         note = thymine
modified_base            1356..1357
                         mod_base = OTHER
                         note = thymine
modified_base            1362
                         mod_base = OTHER
                         note = thymine
modified_base            1364
                         mod_base = OTHER
                         note = thymine
```

| | | |
|---|---|---|
| modified_base | 1366 mod_base = OTHER note = thymine | |
| modified_base | 1368..1370 mod_base = OTHER note = thymine | |
| modified_base | 1380 mod_base = OTHER note = thymine | |
| modified_base | 1382..1383 mod_base = OTHER note = thymine | |
| modified_base | 1385..1386 mod_base = OTHER note = thymine | |
| modified_base | 1394 mod_base = OTHER note = thymine | |
| modified_base | 1398 mod_base = OTHER note = thymine | |
| modified_base | 1400..1401 mod_base = OTHER note = thymine | |
| modified_base | 1404..1405 mod_base = OTHER note = thymine | |
| modified_base | 1409..1410 mod_base = OTHER note = thymine | |
| modified_base | 1413 mod_base = OTHER note = thymine | |
| modified_base | 1417 mod_base = OTHER note = thymine | |
| modified_base | 1419 mod_base = OTHER note = thymine | |
| modified_base | 1424 mod_base = OTHER note = thymine | |
| modified_base | 1437 mod_base = OTHER note = thymine | |
| modified_base | 1451 mod_base = OTHER note = thymine | |
| modified_base | 1456..1458 mod_base = OTHER note = thymine | |
| modified_base | 1469..1470 mod_base = OTHER note = thymine | |
| modified_base | 1478..1479 mod_base = OTHER note = thymine | |
| modified_base | 1483 mod_base = OTHER note = thymine | |
| modified_base | 1486..1487 mod_base = OTHER note = thymine | |
| modified_base | 1493 mod_base = OTHER note = thymine | |
| modified_base | 1495 mod_base = OTHER note = thymine | |
| modified_base | 1498 mod_base = OTHER note = thymine | |
| modified_base | 1502 mod_base = OTHER note = thymine | |
| modified_base | 1510 mod_base = OTHER note = thymine | |
| modified_base | 1512 | |

```
                               mod_base = OTHER
                               note = thymine
modified_base    1527..1529
                               mod_base = OTHER
                               note = thymine
modified_base    1534
                               mod_base = OTHER
                               note = thymine
modified_base    1544
                               mod_base = OTHER
                               note = thymine
modified_base    1551
                               mod_base = OTHER
                               note = thymine
modified_base    1554
                               mod_base = OTHER
                               note = thymine
modified_base    1560
                               mod_base = OTHER
                               note = thymine
modified_base    1579
                               mod_base = OTHER
                               note = thymine
modified_base    1588
                               mod_base = OTHER
                               note = thymine
modified_base    1591
                               mod_base = OTHER
                               note = thymine
modified_base    1593
                               mod_base = OTHER
                               note = thymine
modified_base    1604
                               mod_base = OTHER
                               note = thymine
modified_base    1613
                               mod_base = OTHER
                               note = thymine
modified_base    1624
                               mod_base = OTHER
                               note = thymine
modified_base    1635
                               mod_base = OTHER
                               note = thymine
modified_base    1638..1639
                               mod_base = OTHER
                               note = thymine
modified_base    1644
                               mod_base = OTHER
                               note = thymine
modified_base    1648
                               mod_base = OTHER
                               note = thymine
modified_base    1653
                               mod_base = OTHER
                               note = thymine
modified_base    1657..1658
                               mod_base = OTHER
                               note = thymine
modified_base    1676
                               mod_base = OTHER
                               note = thymine
modified_base    1680
                               mod_base = OTHER
                               note = thymine
modified_base    1683
                               mod_base = OTHER
                               note = thymine
modified_base    1686
                               mod_base = OTHER
                               note = thymine
modified_base    1692
                               mod_base = OTHER
                               note = thymine
modified_base    1694
                               mod_base = OTHER
                               note = thymine
modified_base    1698..1699
                               mod_base = OTHER
```

|               |                                       |
|---------------|---------------------------------------|
| modified_base | 1702<br>mod_base = OTHER<br>note = thymine |
| modified_base | 1705<br>mod_base = OTHER<br>note = thymine |
| modified_base | 1708<br>mod_base = OTHER<br>note = thymine |
| modified_base | 1714..1715<br>mod_base = OTHER<br>note = thymine |
| modified_base | 1720<br>mod_base = OTHER<br>note = thymine |
| modified_base | 1722<br>mod_base = OTHER<br>note = thymine |
| modified_base | 1728<br>mod_base = OTHER<br>note = thymine |
| modified_base | 1732<br>mod_base = OTHER<br>note = thymine |
| modified_base | 1739..1740<br>mod_base = OTHER<br>note = thymine |
| modified_base | 1742<br>mod_base = OTHER<br>note = thymine |
| modified_base | 1747<br>mod_base = OTHER<br>note = thymine |
| modified_base | 1749<br>mod_base = OTHER<br>note = thymine |
| modified_base | 1762<br>mod_base = OTHER<br>note = thymine |
| modified_base | 1764<br>mod_base = OTHER<br>note = thymine |
| modified_base | 1767..1768<br>mod_base = OTHER<br>note = thymine |
| modified_base | 1772<br>mod_base = OTHER<br>note = thymine |
| modified_base | 1783..1784<br>mod_base = OTHER<br>note = thymine |
| modified_base | 1793<br>mod_base = OTHER<br>note = thymine |
| modified_base | 1795<br>mod_base = OTHER<br>note = thymine |
| modified_base | 1798..1801<br>mod_base = OTHER<br>note = thymine |
| modified_base | 1805<br>mod_base = OTHER<br>note = thymine |
| modified_base | 1807..1811<br>mod_base = OTHER<br>note = thymine |
| modified_base | 1813..1814<br>mod_base = OTHER<br>note = thymine |
| modified_base | 1816..1817<br>mod_base = OTHER<br>note = thymine |
| modified_base | 1827<br>mod_base = OTHER<br>note = thymine |
| modified_base | 1831..1832<br>mod_base = OTHER<br>note = thymine |

| | |
|---|---|
| modified_base | 1834<br>mod_base = OTHER<br>note = thymine |
| modified_base | 1837<br>mod_base = OTHER<br>note = thymine |
| modified_base | 1839..1841<br>mod_base = OTHER<br>note = thymine |
| modified_base | 1845<br>mod_base = OTHER<br>note = thymine |
| modified_base | 1849<br>mod_base = OTHER<br>note = thymine |
| modified_base | 1855<br>mod_base = OTHER<br>note = thymine |
| modified_base | 1857..1859<br>mod_base = OTHER<br>note = thymine |
| modified_base | 1861<br>mod_base = OTHER<br>note = thymine |
| modified_base | 1870<br>mod_base = OTHER<br>note = thymine |
| modified_base | 1872..1873<br>mod_base = OTHER<br>note = thymine |
| modified_base | 1876<br>mod_base = OTHER<br>note = thymine |
| modified_base | 1882<br>mod_base = OTHER<br>note = thymine |
| modified_base | 1886<br>mod_base = OTHER<br>note = thymine |
| modified_base | 1890..1891<br>mod_base = OTHER<br>note = thymine |
| modified_base | 1893..1894<br>mod_base = OTHER<br>note = thymine |
| modified_base | 1899<br>mod_base = OTHER<br>note = thymine |
| modified_base | 1901<br>mod_base = OTHER<br>note = thymine |
| modified_base | 1906..1907<br>mod_base = OTHER<br>note = thymine |
| modified_base | 1912<br>mod_base = OTHER<br>note = thymine |
| modified_base | 1920..1922<br>mod_base = OTHER<br>note = thymine |
| modified_base | 1927<br>mod_base = OTHER<br>note = thymine |
| modified_base | 1929<br>mod_base = OTHER<br>note = thymine |
| modified_base | 1931..1932<br>mod_base = OTHER<br>note = thymine |
| modified_base | 1934..1935<br>mod_base = OTHER<br>note = thymine |
| modified_base | 1939<br>mod_base = OTHER<br>note = thymine |
| modified_base | 1945<br>mod_base = OTHER<br>note = thymine |
| modified_base | 1954..1955 |

|                |               |
|----------------|---------------|
|                | mod_base = OTHER |
|                | note = thymine |
| modified_base  | 1958 |
|                | mod_base = OTHER |
|                | note = thymine |
| modified_base  | 1961 |
|                | mod_base = OTHER |
|                | note = thymine |
| modified_base  | 1963 |
|                | mod_base = OTHER |
|                | note = thymine |
| modified_base  | 1966 |
|                | mod_base = OTHER |
|                | note = thymine |
| modified_base  | 1971 |
|                | mod_base = OTHER |
|                | note = thymine |
| modified_base  | 1974..1975 |
|                | mod_base = OTHER |
|                | note = thymine |
| modified_base  | 1979 |
|                | mod_base = OTHER |
|                | note = thymine |
| modified_base  | 1982 |
|                | mod_base = OTHER |
|                | note = thymine |
| modified_base  | 1991 |
|                | mod_base = OTHER |
|                | note = thymine |
| modified_base  | 1993 |
|                | mod_base = OTHER |
|                | note = thymine |
| modified_base  | 1995 |
|                | mod_base = OTHER |
|                | note = thymine |
| modified_base  | 2012 |
|                | mod_base = OTHER |
|                | note = thymine |
| modified_base  | 2017 |
|                | mod_base = OTHER |
|                | note = thymine |
| modified_base  | 2021 |
|                | mod_base = OTHER |
|                | note = thymine |
| modified_base  | 2028 |
|                | mod_base = OTHER |
|                | note = thymine |
| modified_base  | 2031 |
|                | mod_base = OTHER |
|                | note = thymine |
| modified_base  | 2036..2037 |
|                | mod_base = OTHER |
|                | note = thymine |
| modified_base  | 2041 |
|                | mod_base = OTHER |
|                | note = thymine |
| modified_base  | 2043..2044 |
|                | mod_base = OTHER |
|                | note = thymine |
| modified_base  | 2046 |
|                | mod_base = OTHER |
|                | note = thymine |
| modified_base  | 2048 |
|                | mod_base = OTHER |
|                | note = thymine |
| modified_base  | 2050 |
|                | mod_base = OTHER |
|                | note = thymine |
| modified_base  | 2053..2054 |
|                | mod_base = OTHER |
|                | note = thymine |
| modified_base  | 2057..2058 |
|                | mod_base = OTHER |
|                | note = thymine |
| modified_base  | 2063 |
|                | mod_base = OTHER |
|                | note = thymine |
| modified_base  | 2068 |
|                | mod_base = OTHER |

-continued

| | | |
|---|---|---|
| modified_base | 2074 | |
| | mod_base = OTHER | |
| | note = thymine | |
| modified_base | 2076 | |
| | mod_base = OTHER | |
| | note = thymine | |
| modified_base | 2078 | |
| | mod_base = OTHER | |
| | note = thymine | |
| modified_base | 2081 | |
| | mod_base = OTHER | |
| | note = thymine | |
| modified_base | 2086..2090 | |
| | mod_base = OTHER | |
| | note = thymine | |
| modified_base | 2097..2099 | |
| | mod_base = OTHER | |
| | note = thymine | |
| modified_base | 2101 | |
| | mod_base = OTHER | |
| | note = thymine | |
| modified_base | 2104 | |
| | mod_base = OTHER | |
| | note = thymine | |
| modified_base | 2107 | |
| | mod_base = OTHER | |
| | note = thymine | |
| modified_base | 2109 | |
| | mod_base = OTHER | |
| | note = thymine | |
| modified_base | 2112..2115 | |
| | mod_base = OTHER | |
| | note = thymine | |
| modified_base | 2117 | |
| | mod_base = OTHER | |
| | note = thymine | |
| modified_base | 2125 | |
| | mod_base = OTHER | |
| | note = thymine | |
| modified_base | 2129 | |
| | mod_base = OTHER | |
| | note = thymine | |
| modified_base | 2131 | |
| | mod_base = OTHER | |
| | note = thymine | |
| modified_base | 2134 | |
| | mod_base = OTHER | |
| | note = thymine | |
| modified_base | 2137..2138 | |
| | mod_base = OTHER | |
| | note = thymine | |
| modified_base | 2142 | |
| | mod_base = OTHER | |
| | note = thymine | |
| modified_base | 2148..2149 | |
| | mod_base = OTHER | |
| | note = thymine | |
| modified_base | 2154 | |
| | mod_base = OTHER | |
| | note = thymine | |
| modified_base | 2157 | |
| | mod_base = OTHER | |
| | note = thymine | |
| modified_base | 2162 | |
| | mod_base = OTHER | |
| | note = thymine | |
| modified_base | 2164 | |
| | mod_base = OTHER | |
| | note = thymine | |
| modified_base | 2173 | |
| | mod_base = OTHER | |
| | note = thymine | |
| modified_base | 2177 | |
| | mod_base = OTHER | |
| | note = thymine | |
| modified_base | 2181 | |
| | mod_base = OTHER | |
| | note = thymine | |

-continued

| | |
|---|---|
| modified_base | 2184<br>mod_base = OTHER<br>note = thymine |
| modified_base | 2187..2188<br>mod_base = OTHER<br>note = thymine |
| modified_base | 2192<br>mod_base = OTHER<br>note = thymine |
| modified_base | 2194<br>mod_base = OTHER<br>note = thymine |
| modified_base | 2207<br>mod_base = OTHER<br>note = thymine |
| modified_base | 2209..2210<br>mod_base = OTHER<br>note = thymine |
| modified_base | 2213<br>mod_base = OTHER<br>note = thymine |
| modified_base | 2218<br>mod_base = OTHER<br>note = thymine |
| modified_base | 2223..2225<br>mod_base = OTHER<br>note = thymine |
| modified_base | 2232<br>mod_base = OTHER<br>note = thymine |
| modified_base | 2236<br>mod_base = OTHER<br>note = thymine |
| modified_base | 2238<br>mod_base = OTHER<br>note = thymine |
| modified_base | 2240<br>mod_base = OTHER<br>note = thymine |
| modified_base | 2243<br>mod_base = OTHER<br>note = thymine |
| modified_base | 2250..2251<br>mod_base = OTHER<br>note = thymine |
| modified_base | 2253..2254<br>mod_base = OTHER<br>note = thymine |
| modified_base | 2256<br>mod_base = OTHER<br>note = thymine |
| modified_base | 2258<br>mod_base = OTHER<br>note = thymine |
| modified_base | 2260<br>mod_base = OTHER<br>note = thymine |
| modified_base | 2262<br>mod_base = OTHER<br>note = thymine |
| modified_base | 2264<br>mod_base = OTHER<br>note = thymine |
| modified_base | 2269..2270<br>mod_base = OTHER<br>note = thymine |
| modified_base | 2277<br>mod_base = OTHER<br>note = thymine |
| modified_base | 2279<br>mod_base = OTHER<br>note = thymine |
| modified_base | 2284..2285<br>mod_base = OTHER<br>note = thymine |
| modified_base | 2287<br>mod_base = OTHER<br>note = thymine |
| modified_base | 2293..2299 |

-continued

|                |              |
|----------------|--------------|
|                | mod_base = OTHER |
|                | note = thymine |
| modified_base  | 2305 |
|                | mod_base = OTHER |
|                | note = thymine |
| modified_base  | 2307 |
|                | mod_base = OTHER |
|                | note = thymine |
| modified_base  | 2309 |
|                | mod_base = OTHER |
|                | note = thymine |
| modified_base  | 2322 |
|                | mod_base = OTHER |
|                | note = thymine |
| modified_base  | 2325..2327 |
|                | mod_base = OTHER |
|                | note = thymine |
| modified_base  | 2330..2331 |
|                | mod_base = OTHER |
|                | note = thymine |
| modified_base  | 2333 |
|                | mod_base = OTHER |
|                | note = thymine |
| modified_base  | 2338 |
|                | mod_base = OTHER |
|                | note = thymine |
| modified_base  | 2342 |
|                | mod_base = OTHER |
|                | note = thymine |
| modified_base  | 2345..2346 |
|                | mod_base = OTHER |
|                | note = thymine |
| modified_base  | 2348 |
|                | mod_base = OTHER |
|                | note = thymine |
| modified_base  | 2350..2351 |
|                | mod_base = OTHER |
|                | note = thymine |
| modified_base  | 2353 |
|                | mod_base = OTHER |
|                | note = thymine |
| modified_base  | 2358 |
|                | mod_base = OTHER |
|                | note = thymine |
| modified_base  | 2363 |
|                | mod_base = OTHER |
|                | note = thymine |
| modified_base  | 2367 |
|                | mod_base = OTHER |
|                | note = thymine |
| modified_base  | 2369 |
|                | mod_base = OTHER |
|                | note = thymine |
| modified_base  | 2372..2374 |
|                | mod_base = OTHER |
|                | note = thymine |
| modified_base  | 2376 |
|                | mod_base = OTHER |
|                | note = thymine |
| modified_base  | 2379 |
|                | mod_base = OTHER |
|                | note = thymine |
| modified_base  | 2381 |
|                | mod_base = OTHER |
|                | note = thymine |
| modified_base  | 2390 |
|                | mod_base = OTHER |
|                | note = thymine |
| modified_base  | 2392 |
|                | mod_base = OTHER |
|                | note = thymine |
| modified_base  | 2404 |
|                | mod_base = OTHER |
|                | note = thymine |
| modified_base  | 2421..2423 |
|                | mod_base = OTHER |
|                | note = thymine |
| modified_base  | 2425 |
|                | mod_base = OTHER |

-continued

| | | |
|---|---|---|
| modified_base | 2434..2437<br>mod_base = OTHER<br>note = thymine | |
| modified_base | 2440<br>mod_base = OTHER<br>note = thymine | |
| modified_base | 2446..2448<br>mod_base = OTHER<br>note = thymine | |
| modified_base | 2450<br>mod_base = OTHER<br>note = thymine | |
| modified_base | 2452..2453<br>mod_base = OTHER<br>note = thymine | |
| modified_base | 2457<br>mod_base = OTHER<br>note = thymine | |
| modified_base | 2460..2462<br>mod_base = OTHER<br>note = thymine | |
| modified_base | 2464<br>mod_base = OTHER<br>note = thymine | |
| modified_base | 2467<br>mod_base = OTHER<br>note = thymine | |
| modified_base | 2471<br>mod_base = OTHER<br>note = thymine | |
| modified_base | 2477<br>mod_base = OTHER<br>note = thymine | |
| modified_base | 2481..2482<br>mod_base = OTHER<br>note = thymine | |
| modified_base | 2484<br>mod_base = OTHER<br>note = thymine | |
| modified_base | 2486..2487<br>mod_base = OTHER<br>note = thymine | |
| modified_base | 2490..2492<br>mod_base = OTHER<br>note = thymine | |
| modified_base | 2497<br>mod_base = OTHER<br>note = thymine | |
| modified_base | 2501<br>mod_base = OTHER<br>note = thymine | |
| modified_base | 2504..2505<br>mod_base = OTHER<br>note = thymine | |
| modified_base | 2508..2511<br>mod_base = OTHER<br>note = thymine | |
| modified_base | 2513<br>mod_base = OTHER<br>note = thymine | |
| modified_base | 2527..2530<br>mod_base = OTHER<br>note = thymine | |
| modified_base | 2532<br>mod_base = OTHER<br>note = thymine | |
| modified_base | 2537<br>mod_base = OTHER<br>note = thymine | |
| modified_base | 2541<br>mod_base = OTHER<br>note = thymine | |
| modified_base | 2543<br>mod_base = OTHER<br>note = thymine | |
| modified_base | 2546..2547<br>mod_base = OTHER<br>note = thymine | |

| | | |
|---|---|---|
| modified_base | 2549..2551 | |
| | mod_base = OTHER | |
| | note = thymine | |
| modified_base | 2558 | |
| | mod_base = OTHER | |
| | note = thymine | |
| modified_base | 2560..2562 | |
| | mod_base = OTHER | |
| | note = thymine | |
| modified_base | 2569 | |
| | mod_base = OTHER | |
| | note = thymine | |
| modified_base | 2576 | |
| | mod_base = OTHER | |
| | note = thymine | |
| modified_base | 2580 | |
| | mod_base = OTHER | |
| | note = thymine | |
| modified_base | 2583 | |
| | mod_base = OTHER | |
| | note = thymine | |
| modified_base | 2590..2592 | |
| | mod_base = OTHER | |
| | note = thymine | |
| modified_base | 2595 | |
| | mod_base = OTHER | |
| | note = thymine | |
| modified_base | 2601 | |
| | mod_base = OTHER | |
| | note = thymine | |
| modified_base | 2609 | |
| | mod_base = OTHER | |
| | note = thymine | |
| modified_base | 2614..2615 | |
| | mod_base = OTHER | |
| | note = thymine | |
| modified_base | 2617 | |
| | mod_base = OTHER | |
| | note = thymine | |
| modified_base | 2627 | |
| | mod_base = OTHER | |
| | note = thymine | |
| modified_base | 2629..2630 | |
| | mod_base = OTHER | |
| | note = thymine | |
| modified_base | 2633 | |
| | mod_base = OTHER | |
| | note = thymine | |
| modified_base | 2639..2641 | |
| | mod_base = OTHER | |
| | note = thymine | |
| modified_base | 2644 | |
| | mod_base = OTHER | |
| | note = thymine | |
| modified_base | 2646..2648 | |
| | mod_base = OTHER | |
| | note = thymine | |
| modified_base | 2651 | |
| | mod_base = OTHER | |
| | note = thymine | |
| modified_base | 2657 | |
| | mod_base = OTHER | |
| | note = thymine | |
| modified_base | 2659 | |
| | mod_base = OTHER | |
| | note = thymine | |
| modified_base | 2668 | |
| | mod_base = OTHER | |
| | note = thymine | |
| modified_base | 2671 | |
| | mod_base = OTHER | |
| | note = thymine | |
| modified_base | 2673..2674 | |
| | mod_base = OTHER | |
| | note = thymine | |
| modified_base | 2677 | |
| | mod_base = OTHER | |
| | note = thymine | |
| modified_base | 2681 | |

-continued

|  |  |
|---|---|
|  | mod_base = OTHER |
|  | note = thymine |
| modified_base | 2685 |
|  | mod_base = OTHER |
|  | note = thymine |
| modified_base | 2687 |
|  | mod_base = OTHER |
|  | note = thymine |
| modified_base | 2689 |
|  | mod_base = OTHER |
|  | note = thymine |
| modified_base | 2695 |
|  | mod_base = OTHER |
|  | note = thymine |
| modified_base | 2699..2700 |
|  | mod_base = OTHER |
|  | note = thymine |
| modified_base | 2704..2706 |
|  | mod_base = OTHER |
|  | note = thymine |
| modified_base | 2710 |
|  | mod_base = OTHER |
|  | note = thymine |
| modified_base | 2713..2714 |
|  | mod_base = OTHER |
|  | note = thymine |
| modified_base | 2720 |
|  | mod_base = OTHER |
|  | note = thymine |
| modified_base | 2722 |
|  | mod_base = OTHER |
|  | note = thymine |
| modified_base | 2724 |
|  | mod_base = OTHER |
|  | note = thymine |
| modified_base | 2736 |
|  | mod_base = OTHER |
|  | note = thymine |
| modified_base | 2741..2742 |
|  | mod_base = OTHER |
|  | note = thymine |
| modified_base | 2748..2749 |
|  | mod_base = OTHER |
|  | note = thymine |
| modified_base | 2751 |
|  | mod_base = OTHER |
|  | note = thymine |
| modified_base | 2753 |
|  | mod_base = OTHER |
|  | note = thymine |
| modified_base | 2759 |
|  | mod_base = OTHER |
|  | note = thymine |
| modified_base | 2761..2762 |
|  | mod_base = OTHER |
|  | note = thymine |
| modified_base | 2765..2766 |
|  | mod_base = OTHER |
|  | note = thymine |
| modified_base | 2768 |
|  | mod_base = OTHER |
|  | note = thymine |
| modified_base | 2770 |
|  | mod_base = OTHER |
|  | note = thymine |
| modified_base | 2775 |
|  | mod_base = OTHER |
|  | note = thymine |
| modified_base | 2778..2779 |
|  | mod_base = OTHER |
|  | note = thymine |
| modified_base | 2786 |
|  | mod_base = OTHER |
|  | note = thymine |
| modified_base | 2789 |
|  | mod_base = OTHER |
|  | note = thymine |
| modified_base | 2793 |
|  | mod_base = OTHER |

-continued

| | | |
|---|---|---|
| modified_base | 2798..2799<br>mod_base = OTHER<br>note = thymine | |
| modified_base | 2801<br>mod_base = OTHER<br>note = thymine | |
| modified_base | 2805<br>mod_base = OTHER<br>note = thymine | |
| modified_base | 2824<br>mod_base = OTHER<br>note = thymine | |
| modified_base | 2827..2828<br>mod_base = OTHER<br>note = thymine | |
| modified_base | 2830..2832<br>mod_base = OTHER<br>note = thymine | |
| modified_base | 2836..2838<br>mod_base = OTHER<br>note = thymine | |
| modified_base | 2845<br>mod_base = OTHER<br>note = thymine | |
| modified_base | 2847..2849<br>mod_base = OTHER<br>note = thymine | |
| modified_base | 2854<br>mod_base = OTHER<br>note = thymine | |
| modified_base | 2859<br>mod_base = OTHER<br>note = thymine | |
| modified_base | 2861<br>mod_base = OTHER<br>note = thymine | |
| modified_base | 2864<br>mod_base = OTHER<br>note = thymine | |
| modified_base | 2875..2877<br>mod_base = OTHER<br>note = thymine | |
| modified_base | 2885<br>mod_base = OTHER<br>note = thymine | |
| modified_base | 2889..2890<br>mod_base = OTHER<br>note = thymine | |
| modified_base | 2893<br>mod_base = OTHER<br>note = thymine | |
| modified_base | 2895..2896<br>mod_base = OTHER<br>note = thymine | |
| modified_base | 2901<br>mod_base = OTHER<br>note = thymine | |
| modified_base | 2907<br>mod_base = OTHER<br>note = thymine | |
| modified_base | 2909..2910<br>mod_base = OTHER<br>note = thymine | |
| modified_base | 2912<br>mod_base = OTHER<br>note = thymine | |
| modified_base | 2916<br>mod_base = OTHER<br>note = thymine | |
| modified_base | 2918<br>mod_base = OTHER<br>note = thymine | |
| modified_base | 2920<br>mod_base = OTHER<br>note = thymine | |
| modified_base | 2922<br>mod_base = OTHER<br>note = thymine | |

-continued

| | | |
|---|---|---|
| modified_base | 2925 | |
| | mod_base = OTHER | |
| | note = thymine | |
| modified_base | 2927..2930 | |
| | mod_base = OTHER | |
| | note = thymine | |
| modified_base | 2937..2938 | |
| | mod_base = OTHER | |
| | note = thymine | |
| modified_base | 2940 | |
| | mod_base = OTHER | |
| | note = thymine | |
| modified_base | 2944 | |
| | mod_base = OTHER | |
| | note = thymine | |
| modified_base | 2953..2954 | |
| | mod_base = OTHER | |
| | note = thymine | |
| modified_base | 2960 | |
| | mod_base = OTHER | |
| | note = thymine | |
| modified_base | 2962 | |
| | mod_base = OTHER | |
| | note = thymine | |
| modified_base | 2971 | |
| | mod_base = OTHER | |
| | note = thymine | |
| modified_base | 2979 | |
| | mod_base = OTHER | |
| | note = thymine | |
| modified_base | 2981 | |
| | mod_base = OTHER | |
| | note = thymine | |
| modified_base | 2983 | |
| | mod_base = OTHER | |
| | note = thymine | |
| modified_base | 2985 | |
| | mod_base = OTHER | |
| | note = thymine | |
| modified_base | 2988 | |
| | mod_base = OTHER | |
| | note = thymine | |
| modified_base | 2990..2991 | |
| | mod_base = OTHER | |
| | note = thymine | |
| modified_base | 2993..2994 | |
| | mod_base = OTHER | |
| | note = thymine | |
| modified_base | 2996 | |
| | mod_base = OTHER | |
| | note = thymine | |
| modified_base | 2998..2999 | |
| | mod_base = OTHER | |
| | note = thymine | |
| modified_base | 3001..3006 | |
| | mod_base = OTHER | |
| | note = thymine | |
| modified_base | 3009..3011 | |
| | mod_base = OTHER | |
| | note = thymine | |
| modified_base | 3013 | |
| | mod_base = OTHER | |
| | note = thymine | |
| modified_base | 3019 | |
| | mod_base = OTHER | |
| | note = thymine | |
| modified_base | 3031 | |
| | mod_base = OTHER | |
| | note = thymine | |
| modified_base | 3035 | |
| | mod_base = OTHER | |
| | note = thymine | |
| modified_base | 3039..3040 | |
| | mod_base = OTHER | |
| | note = thymine | |
| modified_base | 3043 | |
| | mod_base = OTHER | |
| | note = thymine | |
| modified_base | 3047 | |

-continued

| | | |
|---|---|---|
| | | mod_base = OTHER |
| | | note = thymine |
| modified_base | 3055 | |
| | | mod_base = OTHER |
| | | note = thymine |
| modified_base | 3057 | |
| | | mod_base = OTHER |
| | | note = thymine |
| modified_base | 3064..3065 | |
| | | mod_base = OTHER |
| | | note = thymine |
| modified_base | 3072 | |
| | | mod_base = OTHER |
| | | note = thymine |
| modified_base | 3074 | |
| | | mod_base = OTHER |
| | | note = thymine |
| modified_base | 3076..3078 | |
| | | mod_base = OTHER |
| | | note = thymine |
| modified_base | 3081..3082 | |
| | | mod_base = OTHER |
| | | note = thymine |
| modified_base | 3089 | |
| | | mod_base = OTHER |
| | | note = thymine |
| modified_base | 3092 | |
| | | mod_base = OTHER |
| | | note = thymine |
| modified_base | 3095 | |
| | | mod_base = OTHER |
| | | note = thymine |
| modified_base | 3101 | |
| | | mod_base = OTHER |
| | | note = thymine |
| modified_base | 3105 | |
| | | mod_base = OTHER |
| | | note = thymine |
| modified_base | 3107 | |
| | | mod_base = OTHER |
| | | note = thymine |
| modified_base | 3109 | |
| | | mod_base = OTHER |
| | | note = thymine |
| modified_base | 3115 | |
| | | mod_base = OTHER |
| | | note = thymine |
| modified_base | 3117..3119 | |
| | | mod_base = OTHER |
| | | note = thymine |
| modified_base | 3121..3122 | |
| | | mod_base = OTHER |
| | | note = thymine |
| modified_base | 3127 | |
| | | mod_base = OTHER |
| | | note = thymine |
| modified_base | 3131 | |
| | | mod_base = OTHER |
| | | note = thymine |
| modified_base | 3136..3137 | |
| | | mod_base = OTHER |
| | | note = thymine |
| modified_base | 3139..3140 | |
| | | mod_base = OTHER |
| | | note = thymine |
| modified_base | 3145 | |
| | | mod_base = OTHER |
| | | note = thymine |
| modified_base | 3147..3148 | |
| | | mod_base = OTHER |
| | | note = thymine |
| modified_base | 3150..3151 | |
| | | mod_base = OTHER |
| | | note = thymine |
| modified_base | 3157..3161 | |
| | | mod_base = OTHER |
| | | note = thymine |
| modified_base | 3164 | |
| | | mod_base = OTHER |

|               |                                        |
|---------------|----------------------------------------|
|               | note = thymine                         |
| modified_base | 3166..3168                             |
|               | mod_base = OTHER                       |
|               | note = thymine                         |
| modified_base | 3170                                   |
|               | mod_base = OTHER                       |
|               | note = thymine                         |
| modified_base | 3174                                   |
|               | mod_base = OTHER                       |
|               | note = thymine                         |
| modified_base | 3181                                   |
|               | mod_base = OTHER                       |
|               | note = thymine                         |
| modified_base | 3187                                   |
|               | mod_base = OTHER                       |
|               | note = thymine                         |
| modified_base | 3189                                   |
|               | mod_base = OTHER                       |
|               | note = thymine                         |
| modified_base | 3195..3196                             |
|               | mod_base = OTHER                       |
|               | note = thymine                         |
| modified_base | 3199..3200                             |
|               | mod_base = OTHER                       |
|               | note = thymine                         |
| modified_base | 3205                                   |
|               | mod_base = OTHER                       |
|               | note = thymine                         |
| modified_base | 3209                                   |
|               | mod_base = OTHER                       |
|               | note = thymine                         |
| modified_base | 3212                                   |
|               | mod_base = OTHER                       |
|               | note = thymine                         |
| modified_base | 3214                                   |
|               | mod_base = OTHER                       |
|               | note = thymine                         |
| modified_base | 3221..3222                             |
|               | mod_base = OTHER                       |
|               | note = thymine                         |
| modified_base | 3226..3227                             |
|               | mod_base = OTHER                       |
|               | note = thymine                         |
| modified_base | 3232                                   |
|               | mod_base = OTHER                       |
|               | note = thymine                         |
| modified_base | 3235..3236                             |
|               | mod_base = OTHER                       |
|               | note = thymine                         |
| modified_base | 3244                                   |
|               | mod_base = OTHER                       |
|               | note = thymine                         |
| modified_base | 3246                                   |
|               | mod_base = OTHER                       |
|               | note = thymine                         |
| modified_base | 3250..3251                             |
|               | mod_base = OTHER                       |
|               | note = thymine                         |
| modified_base | 3257                                   |
|               | mod_base = OTHER                       |
|               | note = thymine                         |
| modified_base | 3259                                   |
|               | mod_base = OTHER                       |
|               | note = thymine                         |
| modified_base | 3263                                   |
|               | mod_base = OTHER                       |
|               | note = thymine                         |
| modified_base | 3267..3268                             |
|               | mod_base = OTHER                       |
|               | note = thymine                         |
| modified_base | 3272                                   |
|               | mod_base = OTHER                       |
|               | note = thymine                         |
| modified_base | 3279                                   |
|               | mod_base = OTHER                       |
|               | note = thymine                         |
| modified_base | 3281                                   |
|               | mod_base = OTHER                       |
|               | note = thymine                         |

-continued

| | | |
|---|---|---|
| modified_base | 3284..3285 mod_base = OTHER note = thymine | |
| modified_base | 3292 mod_base = OTHER note = thymine | |
| modified_base | 3296 mod_base = OTHER note = thymine | |
| modified_base | 3300 mod_base = OTHER note = thymine | |
| modified_base | 3302 mod_base = OTHER note = thymine | |
| modified_base | 3308..3309 mod_base = OTHER note = thymine | |
| modified_base | 3316 mod_base = OTHER note = thymine | |
| modified_base | 3319..3320 mod_base = OTHER note = thymine | |
| modified_base | 3325 mod_base = OTHER note = thymine | |
| modified_base | 3327 mod_base = OTHER note = thymine | |
| modified_base | 3332 mod_base = OTHER note = thymine | |
| modified_base | 3341..3342 mod_base = OTHER note = thymine | |
| modified_base | 3344 mod_base = OTHER note = thymine | |
| modified_base | 3347 mod_base = OTHER note = thymine | |
| modified_base | 3350..3353 mod_base = OTHER note = thymine | |
| modified_base | 3356 mod_base = OTHER note = thymine | |
| modified_base | 3358 mod_base = OTHER note = thymine | |
| modified_base | 3363 mod_base = OTHER note = thymine | |
| modified_base | 3368..3369 mod_base = OTHER note = thymine | |
| modified_base | 3372 mod_base = OTHER note = thymine | |
| modified_base | 3376 mod_base = OTHER note = thymine | |
| modified_base | 3382 mod_base = OTHER note = thymine | |
| modified_base | 3384..3385 mod_base = OTHER note = thymine | |
| modified_base | 3392 mod_base = OTHER note = thymine | |
| modified_base | 3394 mod_base = OTHER note = thymine | |
| modified_base | 3398 mod_base = OTHER note = thymine | |
| modified_base | 3403 | |

|  |  |
| --- | --- |
|  | mod_base = OTHER |
|  | note = thymine |
| modified_base | 3408 |
|  | mod_base = OTHER |
|  | note = thymine |
| modified_base | 3410 |
|  | mod_base = OTHER |
|  | note = thymine |
| misc_feature | 1..3413 |
|  | note = Junin virus strain Candid-1 segment S - AY746353 - virusesM ssrna negative-strand virusesM arenaviridaeM arenavirusM new world arenaviruses |
| source | 1..3413 |
|  | mol_type = other RNA |
|  | organism = unidentified |

SEQUENCE: 1

```
gtgcagtaag gggatcctag gcgatttttgg ttacgctata attgtaactg ttttctgttt    60
ggacaacatc aaaaacatcc attgcacaat ggggcagttc attagcttca tgcaagaaat   120
accaaccttt ttgcaggagg ctctgaacat tgctcttgtt gcagtcagtc tcattgccat   180
cattaagggt atagtgaact tgtacaaaag tggtttattc caattcttg tattcctagc    240
gcttgcagga agatcctgca cagaagaagc tttcaaaatc ggactgcaca ctgagttcca   300
gactgtgtcc ttctcaatgg tgggtctctt tccaacaat ccacatgacc tacctttgtt   360
gtgtaccttta aacaagagcc atctttacat taaggggggc aatgcttcat ttcagatcag   420
ctttgatgat attgcagtat tgttgccaca gtatgatgtt ataatacaac atccagcaga   480
tatgagctgg tgttccaaaa gtgatgatca aatttggttg tctcagtggt tcatgaatgc   540
tgtggggcat gattggcatc tagacccacc atttctgtgt aggaaccgtg caaagacaga   600
aggcttcatc tttcaagtca acacctccaa gactggtgtc aatggaaatt atgctaagaa   660
gtttaagact ggcatgcatc atttatatag agaatatcct gacccttgct tgaatggcaa   720
actgtgctta atgaaggcac aacctaccag ttggcctctc caatgtccac tcgaccacgt   780
taacacatta cacttcctta caagaggtaa aaacattcaa cttccaagga ggtccttgca   840
agcattcttc tcctggtctt tgacagactc atccggcaag gataccctg gaggctattg   900
tctagaagag tggatgctcg tagcagccaa aatgaagtgt tttggcaata ctgctgtagc   960
aaaatgcaat ttgaatcatg actctgaatt ctgtgacatg ttgaggctct ttgattacaa  1020
caaaaatgct atcaaaaccc taaatgatga aactaagaaa caagtaaatc tgatggggca  1080
gacaatcaat gccctgatat ctgacaattt attgatgaaa aacaaaatta gggaactgat  1140
gagtgtccct tactgcaatt acacaaaatt ttggtatgtc aaccacacac tttcaggaca  1200
acactcatta ccaaggtgct ggttaataaa aaacaacagc tatttgaaca tctctgactt  1260
ccgtaatgac tggatattag aaagtgactt cttaatttct gaaatgctaa gcaaagagta  1320
ttcggacagg cagggtaaaa ctcctttgac tttagttgac atctgtattt ggagcacagt  1380
attcttcaca gcgtcactct tccttcactt ggtgggtata ccctcccaca gacacatcag  1440
gggcgaagca tgccctttgc cacacaggtt gaacagcttg ggtggttgca gatgtggtaa  1500
gtaccccaat ctaaagaaac caacagtttg gcgtagagga cactaagacc tcctgagggt  1560
cccaccagc ccgggcacctg cccgggctgg tgtggccccg cagtccgcgg cctggccgcg  1620
gactggggag gcactgctta cagtgcatag gctgccttcg ggaggaacag caagctcggt  1680
ggtaatagag gtgtaggttc ctcctcatag agcttcccat ctagcactga ctgaaacatt  1740
atgcagtcta gcagagcaca gtgtggttca ctggaggcca acttgaaggg agtatccttt  1800
tccctctttt tcttattgac aaccactcca ttgtgatatt tgcataagtg accatatttc  1860
tcccagacct gttgatcaaa ctgcctggct tgttcagatg tgagcttaac atcaaccagt  1920
ttaagatctc ttcttccatg gaggtcaaac aacttcctga tgtcatcgga tccttgagta  1980
gtcacaacca tgtctggagg cagcaagccg atcacgtaac taagaactcc tggcattgca  2040
tcttctatgt ccttcattaa gatgccgtga gagtgtctgc taccatttttt aaaccctttc  2100
tcatcatgtg gttttctgaa gcagtgaatg tactgcttac ctgcaggttg gaataatgcc  2160
atctcaacag ggtcagtggc tggtccttca atgtcgagcc aaagggtgtt ggtgggtcg   2220
agtttcccca ctgcctctct gatgacagct tcttgtatct ctgtcaagtt agccaatctc  2280
aaattctgac cgttttttc cggctgtcta ggaccagcaa ctggtttcct tgtcagatca  2340
atacttgtgt tgtcccatga cctgcctgtg atttgtgatc tagaaccaat ataaggccaa  2400
ccatcgccag aaagacaaag tttgtacaaa aggttttcat aaggatttct attgcctggt  2460
ttctcatcaa taaacatgcc ttctcttcgt ttaacctgaa tggttgattt tatgagggaa  2520
gagaagtttt ctgggtgac tctgattgtt tccaacatgt ttccaccatc aagaatagat   2580
gctccagcct ttactgcagc tgaaagactg aagttgtaac cagaaatatt gatgagcttt  2640
tcatctttag tcacaatctg aaggcagtca tgttcctgag tcagtctgtc aaggtcacttt  2700
aagtttggat acttcacagt gtatagaagc ccaagtgagg ttaaagcttg tatgacactg  2760
ttcattgtct cacctccttg aacagtcatg catgcaattg tcaatgcagg aacagagcca  2820
aactgattgt ttagctttga agggtctttta acatcccata tcctcaccac accatttccc  2880
ccagtccctt gctgttgaaa tcccagtgtt ctcaatatct ctgatctttt agcaagttgt  2940
gactgggaca agttacccat gtaaaccccc tgagagcctg tctctgctct cttatcttg   3000
tttttttaatt tctcaaggtc agacgccaac tccatcagtt catccctccc cagatctccc  3060
accttgaaaa ctgtgtttcg ttgaacactc ctcatggaca tgtcctgtc aacctcttta  3120
ttcaggtccc tcaacttgtt gaggtcttct tccccctttt tagtctttct gagtgcccgc  3180
tgcacctgtg ccacttggtt gaagtcgatg ctgtcagcaa ttagcttggc gtccttcaaa  3240
acatctgact tgacagtctg agtgaattgg ctcaaacctc tccttaagga ctgagtccat  3300
ctaaagcttg gaacctcctt ggagtgtgcc atgccagaag ttctggtgat tttgatctag  3360
aatagagttg ctcagtgaaa gtgttagaca ctatgcctag gatccactgt gcg           3413
```

| SEQ ID NO: 2 | moltype = RNA length = 7114 |
| --- | --- |
| FEATURE | Location/Qualifiers |
| modified_base | 8 |
|  | mod_base = OTHER |
|  | note = thymine |

```
modified_base    12
                 mod_base = OTHER
                 note = thymine
modified_base    15
                 mod_base = OTHER
                 note = thymine
modified_base    21
                 mod_base = OTHER
                 note = thymine
modified_base    25..26
                 mod_base = OTHER
                 note = thymine
modified_base    29
                 mod_base = OTHER
                 note = thymine
modified_base    32..33
                 mod_base = OTHER
                 note = thymine
modified_base    38
                 mod_base = OTHER
                 note = thymine
modified_base    40
                 mod_base = OTHER
                 note = thymine
modified_base    45..46
                 mod_base = OTHER
                 note = thymine
modified_base    48
                 mod_base = OTHER
                 note = thymine
modified_base    51
                 mod_base = OTHER
                 note = thymine
modified_base    53
                 mod_base = OTHER
                 note = thymine
modified_base    57
                 mod_base = OTHER
                 note = thymine
modified_base    59
                 mod_base = OTHER
                 note = thymine
modified_base    63..64
                 mod_base = OTHER
                 note = thymine
modified_base    67
                 mod_base = OTHER
                 note = thymine
modified_base    85
                 mod_base = OTHER
                 note = thymine
modified_base    93
                 mod_base = OTHER
                 note = thymine
modified_base    105
                 mod_base = OTHER
                 note = thymine
modified_base    111
                 mod_base = OTHER
                 note = thymine
modified_base    113
                 mod_base = OTHER
                 note = thymine
modified_base    126
                 mod_base = OTHER
                 note = thymine
modified_base    129
                 mod_base = OTHER
                 note = thymine
modified_base    156..158
                 mod_base = OTHER
                 note = thymine
modified_base    166
                 mod_base = OTHER
                 note = thymine
modified_base    170
                 mod_base = OTHER
                 note = thymine
modified_base    179
```

```
                          mod_base = OTHER
                          note = thymine
modified_base             181
                          mod_base = OTHER
                          note = thymine
modified_base             183
                          mod_base = OTHER
                          note = thymine
modified_base             185
                          mod_base = OTHER
                          note = thymine
modified_base             188
                          mod_base = OTHER
                          note = thymine
modified_base             192
                          mod_base = OTHER
                          note = thymine
modified_base             194
                          mod_base = OTHER
                          note = thymine
modified_base             198
                          mod_base = OTHER
                          note = thymine
modified_base             200
                          mod_base = OTHER
                          note = thymine
modified_base             204
                          mod_base = OTHER
                          note = thymine
modified_base             207
                          mod_base = OTHER
                          note = thymine
modified_base             210
                          mod_base = OTHER
                          note = thymine
modified_base             213..215
                          mod_base = OTHER
                          note = thymine
modified_base             218
                          mod_base = OTHER
                          note = thymine
modified_base             221
                          mod_base = OTHER
                          note = thymine
modified_base             227..229
                          mod_base = OTHER
                          note = thymine
modified_base             232
                          mod_base = OTHER
                          note = thymine
modified_base             237
                          mod_base = OTHER
                          note = thymine
modified_base             239
                          mod_base = OTHER
                          note = thymine
modified_base             242
                          mod_base = OTHER
                          note = thymine
modified_base             245
                          mod_base = OTHER
                          note = thymine
modified_base             249
                          mod_base = OTHER
                          note = thymine
modified_base             253..255
                          mod_base = OTHER
                          note = thymine
modified_base             257..259
                          mod_base = OTHER
                          note = thymine
modified_base             264
                          mod_base = OTHER
                          note = thymine
modified_base             269
                          mod_base = OTHER
                          note = thymine
modified_base             275
                          mod_base = OTHER
```

```
                           note = thymine
modified_base              277
                           mod_base = OTHER
                           note = thymine
modified_base              279..280
                           mod_base = OTHER
                           note = thymine
modified_base              287..288
                           mod_base = OTHER
                           note = thymine
modified_base              293
                           mod_base = OTHER
                           note = thymine
modified_base              295
                           mod_base = OTHER
                           note = thymine
modified_base              297
                           mod_base = OTHER
                           note = thymine
modified_base              302
                           mod_base = OTHER
                           note = thymine
modified_base              304
                           mod_base = OTHER
                           note = thymine
modified_base              306
                           mod_base = OTHER
                           note = thymine
modified_base              309
                           mod_base = OTHER
                           note = thymine
modified_base              319
                           mod_base = OTHER
                           note = thymine
modified_base              331
                           mod_base = OTHER
                           note = thymine
modified_base              337
                           mod_base = OTHER
                           note = thymine
modified_base              343
                           mod_base = OTHER
                           note = thymine
modified_base              366
                           mod_base = OTHER
                           note = thymine
modified_base              375
                           mod_base = OTHER
                           note = thymine
modified_base              384
                           mod_base = OTHER
                           note = thymine
modified_base              412
                           mod_base = OTHER
                           note = thymine
modified_base              425
                           mod_base = OTHER
                           note = thymine
modified_base              442
                           mod_base = OTHER
                           note = thymine
modified_base              445
                           mod_base = OTHER
                           note = thymine
modified_base              452..453
                           mod_base = OTHER
                           note = thymine
modified_base              456
                           mod_base = OTHER
                           note = thymine
modified_base              460
                           mod_base = OTHER
                           note = thymine
modified_base              462
                           mod_base = OTHER
                           note = thymine
modified_base              464..466
                           mod_base = OTHER
                           note = thymine
```

-continued

| | |
|---|---|
| modified_base | 469<br>mod_base = OTHER<br>note = thymine |
| modified_base | 471<br>mod_base = OTHER<br>note = thymine |
| modified_base | 476..478<br>mod_base = OTHER<br>note = thymine |
| modified_base | 480<br>mod_base = OTHER<br>note = thymine |
| modified_base | 483..484<br>mod_base = OTHER<br>note = thymine |
| modified_base | 488<br>mod_base = OTHER<br>note = thymine |
| modified_base | 493<br>mod_base = OTHER<br>note = thymine |
| modified_base | 497<br>mod_base = OTHER<br>note = thymine |
| modified_base | 499<br>mod_base = OTHER<br>note = thymine |
| modified_base | 506..508<br>mod_base = OTHER<br>note = thymine |
| modified_base | 512<br>mod_base = OTHER<br>note = thymine |
| modified_base | 514<br>mod_base = OTHER<br>note = thymine |
| modified_base | 519<br>mod_base = OTHER<br>note = thymine |
| modified_base | 524..525<br>mod_base = OTHER<br>note = thymine |
| modified_base | 531<br>mod_base = OTHER<br>note = thymine |
| modified_base | 533<br>mod_base = OTHER<br>note = thymine |
| modified_base | 536<br>mod_base = OTHER<br>note = thymine |
| modified_base | 538<br>mod_base = OTHER<br>note = thymine |
| modified_base | 546<br>mod_base = OTHER<br>note = thymine |
| modified_base | 549..551<br>mod_base = OTHER<br>note = thymine |
| modified_base | 557<br>mod_base = OTHER<br>note = thymine |
| modified_base | 559<br>mod_base = OTHER<br>note = thymine |
| modified_base | 562<br>mod_base = OTHER<br>note = thymine |
| modified_base | 566<br>mod_base = OTHER<br>note = thymine |
| modified_base | 573..574<br>mod_base = OTHER<br>note = thymine |
| modified_base | 579..581<br>mod_base = OTHER<br>note = thymine |
| modified_base | 587..588 |

```
                        mod_base = OTHER
                        note = thymine
modified_base           597
                        mod_base = OTHER
                        note = thymine
modified_base           605..607
                        mod_base = OTHER
                        note = thymine
modified_base           609
                        mod_base = OTHER
                        note = thymine
modified_base           614
                        mod_base = OTHER
                        note = thymine
modified_base           622
                        mod_base = OTHER
                        note = thymine
modified_base           627
                        mod_base = OTHER
                        note = thymine
modified_base           630
                        mod_base = OTHER
                        note = thymine
modified_base           632..634
                        mod_base = OTHER
                        note = thymine
modified_base           636
                        mod_base = OTHER
                        note = thymine
modified_base           638
                        mod_base = OTHER
                        note = thymine
modified_base           642
                        mod_base = OTHER
                        note = thymine
modified_base           645
                        mod_base = OTHER
                        note = thymine
modified_base           660
                        mod_base = OTHER
                        note = thymine
modified_base           663
                        mod_base = OTHER
                        note = thymine
modified_base           665..666
                        mod_base = OTHER
                        note = thymine
modified_base           669
                        mod_base = OTHER
                        note = thymine
modified_base           674
                        mod_base = OTHER
                        note = thymine
modified_base           677
                        mod_base = OTHER
                        note = thymine
modified_base           679..680
                        mod_base = OTHER
                        note = thymine
modified_base           682..684
                        mod_base = OTHER
                        note = thymine
modified_base           686
                        mod_base = OTHER
                        note = thymine
modified_base           689
                        mod_base = OTHER
                        note = thymine
modified_base           691..692
                        mod_base = OTHER
                        note = thymine
modified_base           694..698
                        mod_base = OTHER
                        note = thymine
modified_base           702
                        mod_base = OTHER
                        note = thymine
modified_base           710
                        mod_base = OTHER
```

```
                            note = thymine
modified_base               713..714
                            mod_base = OTHER
                            note = thymine
modified_base               718..719
                            mod_base = OTHER
                            note = thymine
modified_base               722
                            mod_base = OTHER
                            note = thymine
modified_base               727..729
                            mod_base = OTHER
                            note = thymine
modified_base               736
                            mod_base = OTHER
                            note = thymine
modified_base               738
                            mod_base = OTHER
                            note = thymine
modified_base               742
                            mod_base = OTHER
                            note = thymine
modified_base               744
                            mod_base = OTHER
                            note = thymine
modified_base               747
                            mod_base = OTHER
                            note = thymine
modified_base               749
                            mod_base = OTHER
                            note = thymine
modified_base               752
                            mod_base = OTHER
                            note = thymine
modified_base               755
                            mod_base = OTHER
                            note = thymine
modified_base               760..761
                            mod_base = OTHER
                            note = thymine
modified_base               765..766
                            mod_base = OTHER
                            note = thymine
modified_base               770
                            mod_base = OTHER
                            note = thymine
modified_base               772
                            mod_base = OTHER
                            note = thymine
modified_base               777
                            mod_base = OTHER
                            note = thymine
modified_base               789
                            mod_base = OTHER
                            note = thymine
modified_base               794
                            mod_base = OTHER
                            note = thymine
modified_base               796
                            mod_base = OTHER
                            note = thymine
modified_base               798
                            mod_base = OTHER
                            note = thymine
modified_base               800
                            mod_base = OTHER
                            note = thymine
modified_base               802..803
                            mod_base = OTHER
                            note = thymine
modified_base               811..813
                            mod_base = OTHER
                            note = thymine
modified_base               816..817
                            mod_base = OTHER
                            note = thymine
modified_base               821
                            mod_base = OTHER
                            note = thymine
```

-continued

| | | |
|---|---|---|
| modified_base | 823 | |
| | mod_base = OTHER | |
| | note = thymine | |
| modified_base | 825 | |
| | mod_base = OTHER | |
| | note = thymine | |
| modified_base | 832 | |
| | mod_base = OTHER | |
| | note = thymine | |
| modified_base | 837 | |
| | mod_base = OTHER | |
| | note = thymine | |
| modified_base | 839..841 | |
| | mod_base = OTHER | |
| | note = thymine | |
| modified_base | 854..855 | |
| | mod_base = OTHER | |
| | note = thymine | |
| modified_base | 857 | |
| | mod_base = OTHER | |
| | note = thymine | |
| modified_base | 860 | |
| | mod_base = OTHER | |
| | note = thymine | |
| modified_base | 864..865 | |
| | mod_base = OTHER | |
| | note = thymine | |
| modified_base | 867 | |
| | mod_base = OTHER | |
| | note = thymine | |
| modified_base | 869 | |
| | mod_base = OTHER | |
| | note = thymine | |
| modified_base | 877 | |
| | mod_base = OTHER | |
| | note = thymine | |
| modified_base | 882 | |
| | mod_base = OTHER | |
| | note = thymine | |
| modified_base | 885 | |
| | mod_base = OTHER | |
| | note = thymine | |
| modified_base | 887 | |
| | mod_base = OTHER | |
| | note = thymine | |
| modified_base | 891 | |
| | mod_base = OTHER | |
| | note = thymine | |
| modified_base | 894..895 | |
| | mod_base = OTHER | |
| | note = thymine | |
| modified_base | 897..898 | |
| | mod_base = OTHER | |
| | note = thymine | |
| modified_base | 901..902 | |
| | mod_base = OTHER | |
| | note = thymine | |
| modified_base | 905..906 | |
| | mod_base = OTHER | |
| | note = thymine | |
| modified_base | 912 | |
| | mod_base = OTHER | |
| | note = thymine | |
| modified_base | 918 | |
| | mod_base = OTHER | |
| | note = thymine | |
| modified_base | 927..928 | |
| | mod_base = OTHER | |
| | note = thymine | |
| modified_base | 933..934 | |
| | mod_base = OTHER | |
| | note = thymine | |
| modified_base | 939 | |
| | mod_base = OTHER | |
| | note = thymine | |
| modified_base | 943 | |
| | mod_base = OTHER | |
| | note = thymine | |
| modified_base | 949 | |

-continued

```
                                mod_base = OTHER
                                note = thymine
modified_base   951..952
                                mod_base = OTHER
                                note = thymine
modified_base   954
                                mod_base = OTHER
                                note = thymine
modified_base   957
                                mod_base = OTHER
                                note = thymine
modified_base   960..962
                                mod_base = OTHER
                                note = thymine
modified_base   964
                                mod_base = OTHER
                                note = thymine
modified_base   972
                                mod_base = OTHER
                                note = thymine
modified_base   977
                                mod_base = OTHER
                                note = thymine
modified_base   981
                                mod_base = OTHER
                                note = thymine
modified_base   985
                                mod_base = OTHER
                                note = thymine
modified_base   998
                                mod_base = OTHER
                                note = thymine
modified_base   1002
                                mod_base = OTHER
                                note = thymine
modified_base   1009
                                mod_base = OTHER
                                note = thymine
modified_base   1011
                                mod_base = OTHER
                                note = thymine
modified_base   1014
                                mod_base = OTHER
                                note = thymine
modified_base   1019
                                mod_base = OTHER
                                note = thymine
modified_base   1021
                                mod_base = OTHER
                                note = thymine
modified_base   1028
                                mod_base = OTHER
                                note = thymine
modified_base   1031
                                mod_base = OTHER
                                note = thymine
modified_base   1036
                                mod_base = OTHER
                                note = thymine
modified_base   1042
                                mod_base = OTHER
                                note = thymine
modified_base   1049
                                mod_base = OTHER
                                note = thymine
modified_base   1056
                                mod_base = OTHER
                                note = thymine
modified_base   1064
                                mod_base = OTHER
                                note = thymine
modified_base   1068
                                mod_base = OTHER
                                note = thymine
modified_base   1072..1073
                                mod_base = OTHER
                                note = thymine
modified_base   1077
                                mod_base = OTHER
```

-continued

```
                    note = thymine
modified_base       1094..1095
                    mod_base = OTHER
                    note = thymine
modified_base       1099
                    mod_base = OTHER
                    note = thymine
modified_base       1102..1103
                    mod_base = OTHER
                    note = thymine
modified_base       1107
                    mod_base = OTHER
                    note = thymine
modified_base       1113..1114
                    mod_base = OTHER
                    note = thymine
modified_base       1119
                    mod_base = OTHER
                    note = thymine
modified_base       1121
                    mod_base = OTHER
                    note = thymine
modified_base       1124..1125
                    mod_base = OTHER
                    note = thymine
modified_base       1132
                    mod_base = OTHER
                    note = thymine
modified_base       1140
                    mod_base = OTHER
                    note = thymine
modified_base       1143
                    mod_base = OTHER
                    note = thymine
modified_base       1148
                    mod_base = OTHER
                    note = thymine
modified_base       1151
                    mod_base = OTHER
                    note = thymine
modified_base       1154
                    mod_base = OTHER
                    note = thymine
modified_base       1159
                    mod_base = OTHER
                    note = thymine
modified_base       1165
                    mod_base = OTHER
                    note = thymine
modified_base       1168
                    mod_base = OTHER
                    note = thymine
modified_base       1170
                    mod_base = OTHER
                    note = thymine
modified_base       1174
                    mod_base = OTHER
                    note = thymine
modified_base       1176
                    mod_base = OTHER
                    note = thymine
modified_base       1183
                    mod_base = OTHER
                    note = thymine
modified_base       1185..1187
                    mod_base = OTHER
                    note = thymine
modified_base       1189..1190
                    mod_base = OTHER
                    note = thymine
modified_base       1192
                    mod_base = OTHER
                    note = thymine
modified_base       1196..1198
                    mod_base = OTHER
                    note = thymine
modified_base       1202..1205
                    mod_base = OTHER
                    note = thymine
```

| | | |
|---|---|---|
| modified_base | 1207 | |
| | mod_base = OTHER | |
| | note = thymine | |
| modified_base | 1214 | |
| | mod_base = OTHER | |
| | note = thymine | |
| modified_base | 1217 | |
| | mod_base = OTHER | |
| | note = thymine | |
| modified_base | 1219 | |
| | mod_base = OTHER | |
| | note = thymine | |
| modified_base | 1221 | |
| | mod_base = OTHER | |
| | note = thymine | |
| modified_base | 1223..1224 | |
| | mod_base = OTHER | |
| | note = thymine | |
| modified_base | 1226 | |
| | mod_base = OTHER | |
| | note = thymine | |
| modified_base | 1229..1230 | |
| | mod_base = OTHER | |
| | note = thymine | |
| modified_base | 1234 | |
| | mod_base = OTHER | |
| | note = thymine | |
| modified_base | 1237 | |
| | mod_base = OTHER | |
| | note = thymine | |
| modified_base | 1241..1244 | |
| | mod_base = OTHER | |
| | note = thymine | |
| modified_base | 1247..1249 | |
| | mod_base = OTHER | |
| | note = thymine | |
| modified_base | 1256..1257 | |
| | mod_base = OTHER | |
| | note = thymine | |
| modified_base | 1259..1260 | |
| | mod_base = OTHER | |
| | note = thymine | |
| modified_base | 1272..1273 | |
| | mod_base = OTHER | |
| | note = thymine | |
| modified_base | 1285 | |
| | mod_base = OTHER | |
| | note = thymine | |
| modified_base | 1287 | |
| | mod_base = OTHER | |
| | note = thymine | |
| modified_base | 1293 | |
| | mod_base = OTHER | |
| | note = thymine | |
| modified_base | 1297 | |
| | mod_base = OTHER | |
| | note = thymine | |
| modified_base | 1300 | |
| | mod_base = OTHER | |
| | note = thymine | |
| modified_base | 1302 | |
| | mod_base = OTHER | |
| | note = thymine | |
| modified_base | 1304..1305 | |
| | mod_base = OTHER | |
| | note = thymine | |
| modified_base | 1308 | |
| | mod_base = OTHER | |
| | note = thymine | |
| modified_base | 1324 | |
| | mod_base = OTHER | |
| | note = thymine | |
| modified_base | 1326..1327 | |
| | mod_base = OTHER | |
| | note = thymine | |
| modified_base | 1329 | |
| | mod_base = OTHER | |
| | note = thymine | |
| modified_base | 1344 | |

-continued

```
                              mod_base = OTHER
                              note = thymine
modified_base    1356..1357
                              mod_base = OTHER
                              note = thymine
modified_base    1360
                              mod_base = OTHER
                              note = thymine
modified_base    1362..1363
                              mod_base = OTHER
                              note = thymine
modified_base    1365
                              mod_base = OTHER
                              note = thymine
modified_base    1372
                              mod_base = OTHER
                              note = thymine
modified_base    1379
                              mod_base = OTHER
                              note = thymine
modified_base    1383
                              mod_base = OTHER
                              note = thymine
modified_base    1390..1391
                              mod_base = OTHER
                              note = thymine
modified_base    1396
                              mod_base = OTHER
                              note = thymine
modified_base    1398
                              mod_base = OTHER
                              note = thymine
modified_base    1400..1401
                              mod_base = OTHER
                              note = thymine
modified_base    1411..1412
                              mod_base = OTHER
                              note = thymine
modified_base    1415
                              mod_base = OTHER
                              note = thymine
modified_base    1417..1418
                              mod_base = OTHER
                              note = thymine
modified_base    1421
                              mod_base = OTHER
                              note = thymine
modified_base    1424..1426
                              mod_base = OTHER
                              note = thymine
modified_base    1428..1429
                              mod_base = OTHER
                              note = thymine
modified_base    1431..1432
                              mod_base = OTHER
                              note = thymine
modified_base    1435
                              mod_base = OTHER
                              note = thymine
modified_base    1439
                              mod_base = OTHER
                              note = thymine
modified_base    1447
                              mod_base = OTHER
                              note = thymine
modified_base    1452
                              mod_base = OTHER
                              note = thymine
modified_base    1454
                              mod_base = OTHER
                              note = thymine
modified_base    1456
                              mod_base = OTHER
                              note = thymine
modified_base    1460..1461
                              mod_base = OTHER
                              note = thymine
modified_base    1466
                              mod_base = OTHER
```

-continued

| | | |
|---|---|---|
| modified_base | 1470 | |
| | mod_base = OTHER | |
| | note = thymine | |
| modified_base | 1472 | |
| | mod_base = OTHER | |
| | note = thymine | |
| modified_base | 1475..1476 | |
| | mod_base = OTHER | |
| | note = thymine | |
| modified_base | 1480 | |
| | mod_base = OTHER | |
| | note = thymine | |
| modified_base | 1482 | |
| | mod_base = OTHER | |
| | note = thymine | |
| modified_base | 1485 | |
| | mod_base = OTHER | |
| | note = thymine | |
| modified_base | 1487..1488 | |
| | mod_base = OTHER | |
| | note = thymine | |
| modified_base | 1490 | |
| | mod_base = OTHER | |
| | note = thymine | |
| modified_base | 1494 | |
| | mod_base = OTHER | |
| | note = thymine | |
| modified_base | 1496 | |
| | mod_base = OTHER | |
| | note = thymine | |
| modified_base | 1502..1503 | |
| | mod_base = OTHER | |
| | note = thymine | |
| modified_base | 1506..1507 | |
| | mod_base = OTHER | |
| | note = thymine | |
| modified_base | 1523..1525 | |
| | mod_base = OTHER | |
| | note = thymine | |
| modified_base | 1535 | |
| | mod_base = OTHER | |
| | note = thymine | |
| modified_base | 1537..1538 | |
| | mod_base = OTHER | |
| | note = thymine | |
| modified_base | 1543 | |
| | mod_base = OTHER | |
| | note = thymine | |
| modified_base | 1547 | |
| | mod_base = OTHER | |
| | note = thymine | |
| modified_base | 1550 | |
| | mod_base = OTHER | |
| | note = thymine | |
| modified_base | 1554..1556 | |
| | mod_base = OTHER | |
| | note = thymine | |
| modified_base | 1558 | |
| | mod_base = OTHER | |
| | note = thymine | |
| modified_base | 1561 | |
| | mod_base = OTHER | |
| | note = thymine | |
| modified_base | 1568 | |
| | mod_base = OTHER | |
| | note = thymine | |
| modified_base | 1577..1578 | |
| | mod_base = OTHER | |
| | note = thymine | |
| modified_base | 1585 | |
| | mod_base = OTHER | |
| | note = thymine | |
| modified_base | 1590..1591 | |
| | mod_base = OTHER | |
| | note = thymine | |
| modified_base | 1594 | |
| | mod_base = OTHER | |
| | note = thymine | |

| | |
|---|---|
| modified_base | 1601..1602<br>mod_base = OTHER<br>note = thymine |
| modified_base | 1605<br>mod_base = OTHER<br>note = thymine |
| modified_base | 1607<br>mod_base = OTHER<br>note = thymine |
| modified_base | 1612<br>mod_base = OTHER<br>note = thymine |
| modified_base | 1615<br>mod_base = OTHER<br>note = thymine |
| modified_base | 1622..1623<br>mod_base = OTHER<br>note = thymine |
| modified_base | 1629..1631<br>mod_base = OTHER<br>note = thymine |
| modified_base | 1633<br>mod_base = OTHER<br>note = thymine |
| modified_base | 1635<br>mod_base = OTHER<br>note = thymine |
| modified_base | 1638<br>mod_base = OTHER<br>note = thymine |
| modified_base | 1640<br>mod_base = OTHER<br>note = thymine |
| modified_base | 1644<br>mod_base = OTHER<br>note = thymine |
| modified_base | 1646<br>mod_base = OTHER<br>note = thymine |
| modified_base | 1648<br>mod_base = OTHER<br>note = thymine |
| modified_base | 1653<br>mod_base = OTHER<br>note = thymine |
| modified_base | 1658<br>mod_base = OTHER<br>note = thymine |
| modified_base | 1668<br>mod_base = OTHER<br>note = thymine |
| modified_base | 1672<br>mod_base = OTHER<br>note = thymine |
| modified_base | 1674<br>mod_base = OTHER<br>note = thymine |
| modified_base | 1676..1678<br>mod_base = OTHER<br>note = thymine |
| modified_base | 1684<br>mod_base = OTHER<br>note = thymine |
| modified_base | 1686<br>mod_base = OTHER<br>note = thymine |
| modified_base | 1692..1693<br>mod_base = OTHER<br>note = thymine |
| modified_base | 1695..1696<br>mod_base = OTHER<br>note = thymine |
| modified_base | 1698<br>mod_base = OTHER<br>note = thymine |
| modified_base | 1700<br>mod_base = OTHER<br>note = thymine |
| modified_base | 1702..1703 |

-continued

```
                         mod_base = OTHER
                         note = thymine
modified_base   1706..1708
                         mod_base = OTHER
                         note = thymine
modified_base   1712
                         mod_base = OTHER
                         note = thymine
modified_base   1716
                         mod_base = OTHER
                         note = thymine
modified_base   1720..1721
                         mod_base = OTHER
                         note = thymine
modified_base   1723
                         mod_base = OTHER
                         note = thymine
modified_base   1726
                         mod_base = OTHER
                         note = thymine
modified_base   1730
                         mod_base = OTHER
                         note = thymine
modified_base   1734..1737
                         mod_base = OTHER
                         note = thymine
modified_base   1740..1741
                         mod_base = OTHER
                         note = thymine
modified_base   1744
                         mod_base = OTHER
                         note = thymine
modified_base   1747
                         mod_base = OTHER
                         note = thymine
modified_base   1749
                         mod_base = OTHER
                         note = thymine
modified_base   1751
                         mod_base = OTHER
                         note = thymine
modified_base   1767
                         mod_base = OTHER
                         note = thymine
modified_base   1769
                         mod_base = OTHER
                         note = thymine
modified_base   1776..1777
                         mod_base = OTHER
                         note = thymine
modified_base   1781
                         mod_base = OTHER
                         note = thymine
modified_base   1783..1784
                         mod_base = OTHER
                         note = thymine
modified_base   1789
                         mod_base = OTHER
                         note = thymine
modified_base   1791
                         mod_base = OTHER
                         note = thymine
modified_base   1799
                         mod_base = OTHER
                         note = thymine
modified_base   1801
                         mod_base = OTHER
                         note = thymine
modified_base   1803..1804
                         mod_base = OTHER
                         note = thymine
modified_base   1808..1809
                         mod_base = OTHER
                         note = thymine
modified_base   1815
                         mod_base = OTHER
                         note = thymine
modified_base   1818..1819
                         mod_base = OTHER
```

| | | |
|---|---|---|
| | | note = thymine |
| modified_base | 1822 | |
| | | mod_base = OTHER |
| | | note = thymine |
| modified_base | 1829 | |
| | | mod_base = OTHER |
| | | note = thymine |
| modified_base | 1836 | |
| | | mod_base = OTHER |
| | | note = thymine |
| modified_base | 1838..1839 | |
| | | mod_base = OTHER |
| | | note = thymine |
| modified_base | 1841..1842 | |
| | | mod_base = OTHER |
| | | note = thymine |
| modified_base | 1847 | |
| | | mod_base = OTHER |
| | | note = thymine |
| modified_base | 1850..1852 | |
| | | mod_base = OTHER |
| | | note = thymine |
| modified_base | 1857 | |
| | | mod_base = OTHER |
| | | note = thymine |
| modified_base | 1860..1862 | |
| | | mod_base = OTHER |
| | | note = thymine |
| modified_base | 1864..1865 | |
| | | mod_base = OTHER |
| | | note = thymine |
| modified_base | 1868 | |
| | | mod_base = OTHER |
| | | note = thymine |
| modified_base | 1870 | |
| | | mod_base = OTHER |
| | | note = thymine |
| modified_base | 1875 | |
| | | mod_base = OTHER |
| | | note = thymine |
| modified_base | 1880 | |
| | | mod_base = OTHER |
| | | note = thymine |
| modified_base | 1884 | |
| | | mod_base = OTHER |
| | | note = thymine |
| modified_base | 1887..1888 | |
| | | mod_base = OTHER |
| | | note = thymine |
| modified_base | 1891 | |
| | | mod_base = OTHER |
| | | note = thymine |
| modified_base | 1895 | |
| | | mod_base = OTHER |
| | | note = thymine |
| modified_base | 1898..1899 | |
| | | mod_base = OTHER |
| | | note = thymine |
| modified_base | 1902 | |
| | | mod_base = OTHER |
| | | note = thymine |
| modified_base | 1904..1905 | |
| | | mod_base = OTHER |
| | | note = thymine |
| modified_base | 1907 | |
| | | mod_base = OTHER |
| | | note = thymine |
| modified_base | 1909 | |
| | | mod_base = OTHER |
| | | note = thymine |
| modified_base | 1911 | |
| | | mod_base = OTHER |
| | | note = thymine |
| modified_base | 1913 | |
| | | mod_base = OTHER |
| | | note = thymine |
| modified_base | 1916 | |
| | | mod_base = OTHER |
| | | note = thymine |

| | |
|---|---|
| modified_base | 1919<br>mod_base = OTHER<br>note = thymine |
| modified_base | 1922..1924<br>mod_base = OTHER<br>note = thymine |
| modified_base | 1928..1930<br>mod_base = OTHER<br>note = thymine |
| modified_base | 1947..1948<br>mod_base = OTHER<br>note = thymine |
| modified_base | 1950..1951<br>mod_base = OTHER<br>note = thymine |
| modified_base | 1953..1954<br>mod_base = OTHER<br>note = thymine |
| modified_base | 1958<br>mod_base = OTHER<br>note = thymine |
| modified_base | 1974<br>mod_base = OTHER<br>note = thymine |
| modified_base | 1976<br>mod_base = OTHER<br>note = thymine |
| modified_base | 1981<br>mod_base = OTHER<br>note = thymine |
| modified_base | 1983..1984<br>mod_base = OTHER<br>note = thymine |
| modified_base | 1987<br>mod_base = OTHER<br>note = thymine |
| modified_base | 2004<br>mod_base = OTHER<br>note = thymine |
| modified_base | 2009<br>mod_base = OTHER<br>note = thymine |
| modified_base | 2013<br>mod_base = OTHER<br>note = thymine |
| modified_base | 2022..2024<br>mod_base = OTHER<br>note = thymine |
| modified_base | 2026<br>mod_base = OTHER<br>note = thymine |
| modified_base | 2043<br>mod_base = OTHER<br>note = thymine |
| modified_base | 2046<br>mod_base = OTHER<br>note = thymine |
| modified_base | 2056..2057<br>mod_base = OTHER<br>note = thymine |
| modified_base | 2060..2062<br>mod_base = OTHER<br>note = thymine |
| modified_base | 2069..2070<br>mod_base = OTHER<br>note = thymine |
| modified_base | 2073..2074<br>mod_base = OTHER<br>note = thymine |
| modified_base | 2078..2079<br>mod_base = OTHER<br>note = thymine |
| modified_base | 2081..2083<br>mod_base = OTHER<br>note = thymine |
| modified_base | 2087<br>mod_base = OTHER<br>note = thymine |
| modified_base | 2090..2094 |

-continued

|   |   |
|---|---|
|   | mod_base = OTHER |
|   | note = thymine |
| modified_base | 2100 |
|   | mod_base = OTHER |
|   | note = thymine |
| modified_base | 2104 |
|   | mod_base = OTHER |
|   | note = thymine |
| modified_base | 2108..2110 |
|   | mod_base = OTHER |
|   | note = thymine |
| modified_base | 2115..2117 |
|   | mod_base = OTHER |
|   | note = thymine |
| modified_base | 2119 |
|   | mod_base = OTHER |
|   | note = thymine |
| modified_base | 2121 |
|   | mod_base = OTHER |
|   | note = thymine |
| modified_base | 2128..2129 |
|   | mod_base = OTHER |
|   | note = thymine |
| modified_base | 2141 |
|   | mod_base = OTHER |
|   | note = thymine |
| modified_base | 2146..2147 |
|   | mod_base = OTHER |
|   | note = thymine |
| modified_base | 2149..2150 |
|   | mod_base = OTHER |
|   | note = thymine |
| modified_base | 2155 |
|   | mod_base = OTHER |
|   | note = thymine |
| modified_base | 2159 |
|   | mod_base = OTHER |
|   | note = thymine |
| modified_base | 2161 |
|   | mod_base = OTHER |
|   | note = thymine |
| modified_base | 2163 |
|   | mod_base = OTHER |
|   | note = thymine |
| modified_base | 2166..2168 |
|   | mod_base = OTHER |
|   | note = thymine |
| modified_base | 2170 |
|   | mod_base = OTHER |
|   | note = thymine |
| modified_base | 2172 |
|   | mod_base = OTHER |
|   | note = thymine |
| modified_base | 2180 |
|   | mod_base = OTHER |
|   | note = thymine |
| modified_base | 2186..2188 |
|   | mod_base = OTHER |
|   | note = thymine |
| modified_base | 2193 |
|   | mod_base = OTHER |
|   | note = thymine |
| modified_base | 2197 |
|   | mod_base = OTHER |
|   | note = thymine |
| modified_base | 2205..2206 |
|   | mod_base = OTHER |
|   | note = thymine |
| modified_base | 2209 |
|   | mod_base = OTHER |
|   | note = thymine |
| modified_base | 2215 |
|   | mod_base = OTHER |
|   | note = thymine |
| modified_base | 2218 |
|   | mod_base = OTHER |
|   | note = thymine |
| modified_base | 2220..2221 |
|   | mod_base = OTHER |

| | | |
|---|---|---|
| | | note = thymine |
| modified_base | 2233 | |
| | | mod_base = OTHER |
| | | note = thymine |
| modified_base | 2240 | |
| | | mod_base = OTHER |
| | | note = thymine |
| modified_base | 2256 | |
| | | mod_base = OTHER |
| | | note = thymine |
| modified_base | 2261 | |
| | | mod_base = OTHER |
| | | note = thymine |
| modified_base | 2267..2269 | |
| | | mod_base = OTHER |
| | | note = thymine |
| modified_base | 2271..2272 | |
| | | mod_base = OTHER |
| | | note = thymine |
| modified_base | 2275..2276 | |
| | | mod_base = OTHER |
| | | note = thymine |
| modified_base | 2280 | |
| | | mod_base = OTHER |
| | | note = thymine |
| modified_base | 2282 | |
| | | mod_base = OTHER |
| | | note = thymine |
| modified_base | 2290 | |
| | | mod_base = OTHER |
| | | note = thymine |
| modified_base | 2292..2293 | |
| | | mod_base = OTHER |
| | | note = thymine |
| modified_base | 2295..2296 | |
| | | mod_base = OTHER |
| | | note = thymine |
| modified_base | 2303..2306 | |
| | | mod_base = OTHER |
| | | note = thymine |
| modified_base | 2308 | |
| | | mod_base = OTHER |
| | | note = thymine |
| modified_base | 2313..2315 | |
| | | mod_base = OTHER |
| | | note = thymine |
| modified_base | 2317..2318 | |
| | | mod_base = OTHER |
| | | note = thymine |
| modified_base | 2326 | |
| | | mod_base = OTHER |
| | | note = thymine |
| modified_base | 2331 | |
| | | mod_base = OTHER |
| | | note = thymine |
| modified_base | 2333 | |
| | | mod_base = OTHER |
| | | note = thymine |
| modified_base | 2335..2336 | |
| | | mod_base = OTHER |
| | | note = thymine |
| modified_base | 2338 | |
| | | mod_base = OTHER |
| | | note = thymine |
| modified_base | 2341..2342 | |
| | | mod_base = OTHER |
| | | note = thymine |
| modified_base | 2344 | |
| | | mod_base = OTHER |
| | | note = thymine |
| modified_base | 2348 | |
| | | mod_base = OTHER |
| | | note = thymine |
| modified_base | 2350..2351 | |
| | | mod_base = OTHER |
| | | note = thymine |
| modified_base | 2356 | |
| | | mod_base = OTHER |
| | | note = thymine |

-continued

| | |
|---|---|
| modified_base | 2358<br>mod_base = OTHER<br>note = thymine |
| modified_base | 2360..2361<br>mod_base = OTHER<br>note = thymine |
| modified_base | 2363..2365<br>mod_base = OTHER<br>note = thymine |
| modified_base | 2367<br>mod_base = OTHER<br>note = thymine |
| modified_base | 2369<br>mod_base = OTHER<br>note = thymine |
| modified_base | 2375<br>mod_base = OTHER<br>note = thymine |
| modified_base | 2377..2378<br>mod_base = OTHER<br>note = thymine |
| modified_base | 2383..2384<br>mod_base = OTHER<br>note = thymine |
| modified_base | 2386<br>mod_base = OTHER<br>note = thymine |
| modified_base | 2389<br>mod_base = OTHER<br>note = thymine |
| modified_base | 2393..2395<br>mod_base = OTHER<br>note = thymine |
| modified_base | 2398<br>mod_base = OTHER<br>note = thymine |
| modified_base | 2401<br>mod_base = OTHER<br>note = thymine |
| modified_base | 2413<br>mod_base = OTHER<br>note = thymine |
| modified_base | 2418<br>mod_base = OTHER<br>note = thymine |
| modified_base | 2428<br>mod_base = OTHER<br>note = thymine |
| modified_base | 2432<br>mod_base = OTHER<br>note = thymine |
| modified_base | 2436..2437<br>mod_base = OTHER<br>note = thymine |
| modified_base | 2444<br>mod_base = OTHER<br>note = thymine |
| modified_base | 2446<br>mod_base = OTHER<br>note = thymine |
| modified_base | 2448<br>mod_base = OTHER<br>note = thymine |
| modified_base | 2451<br>mod_base = OTHER<br>note = thymine |
| modified_base | 2453<br>mod_base = OTHER<br>note = thymine |
| modified_base | 2458..2460<br>mod_base = OTHER<br>note = thymine |
| modified_base | 2462<br>mod_base = OTHER<br>note = thymine |
| modified_base | 2464<br>mod_base = OTHER<br>note = thymine |
| modified_base | 2467..2469 |

|                |                    |
|----------------|--------------------|
|                | mod_base = OTHER   |
|                | note = thymine     |
| modified_base  | 2472               |
|                | mod_base = OTHER   |
|                | note = thymine     |
| modified_base  | 2474..2475         |
|                | mod_base = OTHER   |
|                | note = thymine     |
| modified_base  | 2479               |
|                | mod_base = OTHER   |
|                | note = thymine     |
| modified_base  | 2490               |
|                | mod_base = OTHER   |
|                | note = thymine     |
| modified_base  | 2492..2493         |
|                | mod_base = OTHER   |
|                | note = thymine     |
| modified_base  | 2501               |
|                | mod_base = OTHER   |
|                | note = thymine     |
| modified_base  | 2507               |
|                | mod_base = OTHER   |
|                | note = thymine     |
| modified_base  | 2514               |
|                | mod_base = OTHER   |
|                | note = thymine     |
| modified_base  | 2517               |
|                | mod_base = OTHER   |
|                | note = thymine     |
| modified_base  | 2522               |
|                | mod_base = OTHER   |
|                | note = thymine     |
| modified_base  | 2527               |
|                | mod_base = OTHER   |
|                | note = thymine     |
| modified_base  | 2530..2531         |
|                | mod_base = OTHER   |
|                | note = thymine     |
| modified_base  | 2533               |
|                | mod_base = OTHER   |
|                | note = thymine     |
| modified_base  | 2538..2539         |
|                | mod_base = OTHER   |
|                | note = thymine     |
| modified_base  | 2542               |
|                | mod_base = OTHER   |
|                | note = thymine     |
| modified_base  | 2547..2550         |
|                | mod_base = OTHER   |
|                | note = thymine     |
| modified_base  | 2553               |
|                | mod_base = OTHER   |
|                | note = thymine     |
| modified_base  | 2560..2563         |
|                | mod_base = OTHER   |
|                | note = thymine     |
| modified_base  | 2567               |
|                | mod_base = OTHER   |
|                | note = thymine     |
| modified_base  | 2569               |
|                | mod_base = OTHER   |
|                | note = thymine     |
| modified_base  | 2571..2572         |
|                | mod_base = OTHER   |
|                | note = thymine     |
| modified_base  | 2575               |
|                | mod_base = OTHER   |
|                | note = thymine     |
| modified_base  | 2577               |
|                | mod_base = OTHER   |
|                | note = thymine     |
| modified_base  | 2580..2581         |
|                | mod_base = OTHER   |
|                | note = thymine     |
| modified_base  | 2588..2590         |
|                | mod_base = OTHER   |
|                | note = thymine     |
| modified_base  | 2593               |
|                | mod_base = OTHER   |

-continued

| | | |
|---|---|---|
| | | note = thymine |
| modified_base | 2601..2602 | |
| | | mod_base = OTHER |
| | | note = thymine |
| modified_base | 2605..2606 | |
| | | mod_base = OTHER |
| | | note = thymine |
| modified_base | 2608 | |
| | | mod_base = OTHER |
| | | note = thymine |
| modified_base | 2614..2615 | |
| | | mod_base = OTHER |
| | | note = thymine |
| modified_base | 2617 | |
| | | mod_base = OTHER |
| | | note = thymine |
| modified_base | 2619 | |
| | | mod_base = OTHER |
| | | note = thymine |
| modified_base | 2622..2623 | |
| | | mod_base = OTHER |
| | | note = thymine |
| modified_base | 2625 | |
| | | mod_base = OTHER |
| | | note = thymine |
| modified_base | 2628 | |
| | | mod_base = OTHER |
| | | note = thymine |
| modified_base | 2638 | |
| | | mod_base = OTHER |
| | | note = thymine |
| modified_base | 2642..2643 | |
| | | mod_base = OTHER |
| | | note = thymine |
| modified_base | 2647..2650 | |
| | | mod_base = OTHER |
| | | note = thymine |
| modified_base | 2653 | |
| | | mod_base = OTHER |
| | | note = thymine |
| modified_base | 2655 | |
| | | mod_base = OTHER |
| | | note = thymine |
| modified_base | 2657 | |
| | | mod_base = OTHER |
| | | note = thymine |
| modified_base | 2664 | |
| | | mod_base = OTHER |
| | | note = thymine |
| modified_base | 2669 | |
| | | mod_base = OTHER |
| | | note = thymine |
| modified_base | 2671 | |
| | | mod_base = OTHER |
| | | note = thymine |
| modified_base | 2679 | |
| | | mod_base = OTHER |
| | | note = thymine |
| modified_base | 2688 | |
| | | mod_base = OTHER |
| | | note = thymine |
| modified_base | 2690..2692 | |
| | | mod_base = OTHER |
| | | note = thymine |
| modified_base | 2697 | |
| | | mod_base = OTHER |
| | | note = thymine |
| modified_base | 2699..2700 | |
| | | mod_base = OTHER |
| | | note = thymine |
| modified_base | 2702..2703 | |
| | | mod_base = OTHER |
| | | note = thymine |
| modified_base | 2705..2706 | |
| | | mod_base = OTHER |
| | | note = thymine |
| modified_base | 2710 | |
| | | mod_base = OTHER |
| | | note = thymine |

| | | |
|---|---|---|
| modified_base | 2714 mod_base = OTHER note = thymine | |
| modified_base | 2725 mod_base = OTHER note = thymine | |
| modified_base | 2727 mod_base = OTHER note = thymine | |
| modified_base | 2729 mod_base = OTHER note = thymine | |
| modified_base | 2731 mod_base = OTHER note = thymine | |
| modified_base | 2733 mod_base = OTHER note = thymine | |
| modified_base | 2735 mod_base = OTHER note = thymine | |
| modified_base | 2742 mod_base = OTHER note = thymine | |
| modified_base | 2744 mod_base = OTHER note = thymine | |
| modified_base | 2746 mod_base = OTHER note = thymine | |
| modified_base | 2749 mod_base = OTHER note = thymine | |
| modified_base | 2753..2754 mod_base = OTHER note = thymine | |
| modified_base | 2757..2758 mod_base = OTHER note = thymine | |
| modified_base | 2762 mod_base = OTHER note = thymine | |
| modified_base | 2764 mod_base = OTHER note = thymine | |
| modified_base | 2767 mod_base = OTHER note = thymine | |
| modified_base | 2773 mod_base = OTHER note = thymine | |
| modified_base | 2775..2777 mod_base = OTHER note = thymine | |
| modified_base | 2783 mod_base = OTHER note = thymine | |
| modified_base | 2785 mod_base = OTHER note = thymine | |
| modified_base | 2787 mod_base = OTHER note = thymine | |
| modified_base | 2791 mod_base = OTHER note = thymine | |
| modified_base | 2794 mod_base = OTHER note = thymine | |
| modified_base | 2802..2803 mod_base = OTHER note = thymine | |
| modified_base | 2809 mod_base = OTHER note = thymine | |
| modified_base | 2813..2814 mod_base = OTHER note = thymine | |
| modified_base | 2817 | |

-continued

|                |                                      |
|----------------|--------------------------------------|
|                | mod_base = OTHER                     |
|                | note = thymine                       |
| modified_base  | 2824..2825                           |
|                | mod_base = OTHER                     |
|                | note = thymine                       |
| modified_base  | 2827                                 |
|                | mod_base = OTHER                     |
|                | note = thymine                       |
| modified_base  | 2829                                 |
|                | mod_base = OTHER                     |
|                | note = thymine                       |
| modified_base  | 2831                                 |
|                | mod_base = OTHER                     |
|                | note = thymine                       |
| modified_base  | 2833                                 |
|                | mod_base = OTHER                     |
|                | note = thymine                       |
| modified_base  | 2836                                 |
|                | mod_base = OTHER                     |
|                | note = thymine                       |
| modified_base  | 2838                                 |
|                | mod_base = OTHER                     |
|                | note = thymine                       |
| modified_base  | 2840                                 |
|                | mod_base = OTHER                     |
|                | note = thymine                       |
| modified_base  | 2846..2847                           |
|                | mod_base = OTHER                     |
|                | note = thymine                       |
| modified_base  | 2849                                 |
|                | mod_base = OTHER                     |
|                | note = thymine                       |
| modified_base  | 2851..2852                           |
|                | mod_base = OTHER                     |
|                | note = thymine                       |
| modified_base  | 2857..2860                           |
|                | mod_base = OTHER                     |
|                | note = thymine                       |
| modified_base  | 2865..2866                           |
|                | mod_base = OTHER                     |
|                | note = thymine                       |
| modified_base  | 2871..2872                           |
|                | mod_base = OTHER                     |
|                | note = thymine                       |
| modified_base  | 2874                                 |
|                | mod_base = OTHER                     |
|                | note = thymine                       |
| modified_base  | 2876                                 |
|                | mod_base = OTHER                     |
|                | note = thymine                       |
| modified_base  | 2895..2896                           |
|                | mod_base = OTHER                     |
|                | note = thymine                       |
| modified_base  | 2899                                 |
|                | mod_base = OTHER                     |
|                | note = thymine                       |
| modified_base  | 2903                                 |
|                | mod_base = OTHER                     |
|                | note = thymine                       |
| modified_base  | 2911                                 |
|                | mod_base = OTHER                     |
|                | note = thymine                       |
| modified_base  | 2913                                 |
|                | mod_base = OTHER                     |
|                | note = thymine                       |
| modified_base  | 2915..2916                           |
|                | mod_base = OTHER                     |
|                | note = thymine                       |
| modified_base  | 2923                                 |
|                | mod_base = OTHER                     |
|                | note = thymine                       |
| modified_base  | 2933                                 |
|                | mod_base = OTHER                     |
|                | note = thymine                       |
| modified_base  | 2935..2936                           |
|                | mod_base = OTHER                     |
|                | note = thymine                       |
| modified_base  | 2940..2941                           |
|                | mod_base = OTHER                     |

| | | |
|---|---|---|
| | | note = thymine |
| modified_base | 2946 | |
| | | mod_base = OTHER |
| | | note = thymine |
| modified_base | 2959..2960 | |
| | | mod_base = OTHER |
| | | note = thymine |
| modified_base | 2963 | |
| | | mod_base = OTHER |
| | | note = thymine |
| modified_base | 2965 | |
| | | mod_base = OTHER |
| | | note = thymine |
| modified_base | 2971 | |
| | | mod_base = OTHER |
| | | note = thymine |
| modified_base | 2973..2975 | |
| | | mod_base = OTHER |
| | | note = thymine |
| modified_base | 2980 | |
| | | mod_base = OTHER |
| | | note = thymine |
| modified_base | 2983 | |
| | | mod_base = OTHER |
| | | note = thymine |
| modified_base | 2988..2989 | |
| | | mod_base = OTHER |
| | | note = thymine |
| modified_base | 2991..2993 | |
| | | mod_base = OTHER |
| | | note = thymine |
| modified_base | 2996..2998 | |
| | | mod_base = OTHER |
| | | note = thymine |
| modified_base | 3005 | |
| | | mod_base = OTHER |
| | | note = thymine |
| modified_base | 3011..3012 | |
| | | mod_base = OTHER |
| | | note = thymine |
| modified_base | 3015 | |
| | | mod_base = OTHER |
| | | note = thymine |
| modified_base | 3028..3030 | |
| | | mod_base = OTHER |
| | | note = thymine |
| modified_base | 3038..3039 | |
| | | mod_base = OTHER |
| | | note = thymine |
| modified_base | 3041 | |
| | | mod_base = OTHER |
| | | note = thymine |
| modified_base | 3043 | |
| | | mod_base = OTHER |
| | | note = thymine |
| modified_base | 3046 | |
| | | mod_base = OTHER |
| | | note = thymine |
| modified_base | 3048 | |
| | | mod_base = OTHER |
| | | note = thymine |
| modified_base | 3050..3051 | |
| | | mod_base = OTHER |
| | | note = thymine |
| modified_base | 3057..3060 | |
| | | mod_base = OTHER |
| | | note = thymine |
| modified_base | 3063 | |
| | | mod_base = OTHER |
| | | note = thymine |
| modified_base | 3067 | |
| | | mod_base = OTHER |
| | | note = thymine |
| modified_base | 3079..3083 | |
| | | mod_base = OTHER |
| | | note = thymine |
| modified_base | 3085 | |
| | | mod_base = OTHER |
| | | note = thymine |

-continued

| | |
|---|---|
| modified_base | 3091<br>mod_base = OTHER<br>note = thymine |
| modified_base | 3096<br>mod_base = OTHER<br>note = thymine |
| modified_base | 3099<br>mod_base = OTHER<br>note = thymine |
| modified_base | 3102<br>mod_base = OTHER<br>note = thymine |
| modified_base | 3106<br>mod_base = OTHER<br>note = thymine |
| modified_base | 3112<br>mod_base = OTHER<br>note = thymine |
| modified_base | 3114<br>mod_base = OTHER<br>note = thymine |
| modified_base | 3118<br>mod_base = OTHER<br>note = thymine |
| modified_base | 3125<br>mod_base = OTHER<br>note = thymine |
| modified_base | 3127<br>mod_base = OTHER<br>note = thymine |
| modified_base | 3132<br>mod_base = OTHER<br>note = thymine |
| modified_base | 3135<br>mod_base = OTHER<br>note = thymine |
| modified_base | 3140<br>mod_base = OTHER<br>note = thymine |
| modified_base | 3144<br>mod_base = OTHER<br>note = thymine |
| modified_base | 3149<br>mod_base = OTHER<br>note = thymine |
| modified_base | 3153<br>mod_base = OTHER<br>note = thymine |
| modified_base | 3164..3165<br>mod_base = OTHER<br>note = thymine |
| modified_base | 3167..3168<br>mod_base = OTHER<br>note = thymine |
| modified_base | 3172<br>mod_base = OTHER<br>note = thymine |
| modified_base | 3175..3176<br>mod_base = OTHER<br>note = thymine |
| modified_base | 3183<br>mod_base = OTHER<br>note = thymine |
| modified_base | 3185<br>mod_base = OTHER<br>note = thymine |
| modified_base | 3189<br>mod_base = OTHER<br>note = thymine |
| modified_base | 3191<br>mod_base = OTHER<br>note = thymine |
| modified_base | 3194<br>mod_base = OTHER<br>note = thymine |
| modified_base | 3196<br>mod_base = OTHER<br>note = thymine |
| modified_base | 3198..3199 |

-continued

```
                               mod_base = OTHER
                               note = thymine
modified_base       3201
                    mod_base = OTHER
                    note = thymine
modified_base       3208..3209
                    mod_base = OTHER
                    note = thymine
modified_base       3213
                    mod_base = OTHER
                    note = thymine
modified_base       3220
                    mod_base = OTHER
                    note = thymine
modified_base       3222
                    mod_base = OTHER
                    note = thymine
modified_base       3235..3236
                    mod_base = OTHER
                    note = thymine
modified_base       3238
                    mod_base = OTHER
                    note = thymine
modified_base       3240
                    mod_base = OTHER
                    note = thymine
modified_base       3244
                    mod_base = OTHER
                    note = thymine
modified_base       3252
                    mod_base = OTHER
                    note = thymine
modified_base       3255
                    mod_base = OTHER
                    note = thymine
modified_base       3259..3260
                    mod_base = OTHER
                    note = thymine
modified_base       3264
                    mod_base = OTHER
                    note = thymine
modified_base       3270
                    mod_base = OTHER
                    note = thymine
modified_base       3273
                    mod_base = OTHER
                    note = thymine
modified_base       3276
                    mod_base = OTHER
                    note = thymine
modified_base       3285
                    mod_base = OTHER
                    note = thymine
modified_base       3287..3288
                    mod_base = OTHER
                    note = thymine
modified_base       3298
                    mod_base = OTHER
                    note = thymine
modified_base       3301
                    mod_base = OTHER
                    note = thymine
modified_base       3306
                    mod_base = OTHER
                    note = thymine
modified_base       3316..3317
                    mod_base = OTHER
                    note = thymine
modified_base       3323
                    mod_base = OTHER
                    note = thymine
modified_base       3329
                    mod_base = OTHER
                    note = thymine
modified_base       3331
                    mod_base = OTHER
                    note = thymine
modified_base       3333..3334
                    mod_base = OTHER
```

```
modified_base    3338..3340
                 mod_base = OTHER
                 note = thymine
modified_base    3344
                 mod_base = OTHER
                 note = thymine
modified_base    3351
                 mod_base = OTHER
                 note = thymine
modified_base    3356..3357
                 mod_base = OTHER
                 note = thymine
modified_base    3359
                 mod_base = OTHER
                 note = thymine
modified_base    3366..3367
                 mod_base = OTHER
                 note = thymine
modified_base    3370..3371
                 mod_base = OTHER
                 note = thymine
modified_base    3377..3378
                 mod_base = OTHER
                 note = thymine
modified_base    3387..3388
                 mod_base = OTHER
                 note = thymine
modified_base    3390
                 mod_base = OTHER
                 note = thymine
modified_base    3396
                 mod_base = OTHER
                 note = thymine
modified_base    3401..3403
                 mod_base = OTHER
                 note = thymine
modified_base    3409
                 mod_base = OTHER
                 note = thymine
modified_base    3411..3412
                 mod_base = OTHER
                 note = thymine
modified_base    3415..3416
                 mod_base = OTHER
                 note = thymine
modified_base    3419
                 mod_base = OTHER
                 note = thymine
modified_base    3422..3423
                 mod_base = OTHER
                 note = thymine
modified_base    3429..3430
                 mod_base = OTHER
                 note = thymine
modified_base    3435..3437
                 mod_base = OTHER
                 note = thymine
modified_base    3439..3440
                 mod_base = OTHER
                 note = thymine
modified_base    3442
                 mod_base = OTHER
                 note = thymine
modified_base    3444
                 mod_base = OTHER
                 note = thymine
modified_base    3446
                 mod_base = OTHER
                 note = thymine
modified_base    3448
                 mod_base = OTHER
                 note = thymine
modified_base    3453..3454
                 mod_base = OTHER
                 note = thymine
modified_base    3456..3457
                 mod_base = OTHER
                 note = thymine
```

-continued

| | | |
|---|---|---|
| modified_base | 3461..3462<br>mod_base = OTHER<br>note = thymine | |
| modified_base | 3464<br>mod_base = OTHER<br>note = thymine | |
| modified_base | 3467<br>mod_base = OTHER<br>note = thymine | |
| modified_base | 3469<br>mod_base = OTHER<br>note = thymine | |
| modified_base | 3471<br>mod_base = OTHER<br>note = thymine | |
| modified_base | 3491<br>mod_base = OTHER<br>note = thymine | |
| modified_base | 3494<br>mod_base = OTHER<br>note = thymine | |
| modified_base | 3499<br>mod_base = OTHER<br>note = thymine | |
| modified_base | 3502<br>mod_base = OTHER<br>note = thymine | |
| modified_base | 3505..3506<br>mod_base = OTHER<br>note = thymine | |
| modified_base | 3509<br>mod_base = OTHER<br>note = thymine | |
| modified_base | 3515..3517<br>mod_base = OTHER<br>note = thymine | |
| modified_base | 3522<br>mod_base = OTHER<br>note = thymine | |
| modified_base | 3525<br>mod_base = OTHER<br>note = thymine | |
| modified_base | 3528<br>mod_base = OTHER<br>note = thymine | |
| modified_base | 3530<br>mod_base = OTHER<br>note = thymine | |
| modified_base | 3543<br>mod_base = OTHER<br>note = thymine | |
| modified_base | 3549..3550<br>mod_base = OTHER<br>note = thymine | |
| modified_base | 3552..3553<br>mod_base = OTHER<br>note = thymine | |
| modified_base | 3562..3565<br>mod_base = OTHER<br>note = thymine | |
| modified_base | 3568<br>mod_base = OTHER<br>note = thymine | |
| modified_base | 3570<br>mod_base = OTHER<br>note = thymine | |
| modified_base | 3577..3578<br>mod_base = OTHER<br>note = thymine | |
| modified_base | 3584..3585<br>mod_base = OTHER<br>note = thymine | |
| modified_base | 3590..3591<br>mod_base = OTHER<br>note = thymine | |
| modified_base | 3594..3597<br>mod_base = OTHER<br>note = thymine | |
| modified_base | 3599 | |

-continued

| | | |
|---|---|---|
| | | mod_base = OTHER |
| | | note = thymine |
| modified_base | 3603..3604 | |
| | | mod_base = OTHER |
| | | note = thymine |
| modified_base | 3611 | |
| | | mod_base = OTHER |
| | | note = thymine |
| modified_base | 3613 | |
| | | mod_base = OTHER |
| | | note = thymine |
| modified_base | 3615 | |
| | | mod_base = OTHER |
| | | note = thymine |
| modified_base | 3617..3619 | |
| | | mod_base = OTHER |
| | | note = thymine |
| modified_base | 3622..3623 | |
| | | mod_base = OTHER |
| | | note = thymine |
| modified_base | 3628 | |
| | | mod_base = OTHER |
| | | note = thymine |
| modified_base | 3638..3639 | |
| | | mod_base = OTHER |
| | | note = thymine |
| modified_base | 3641 | |
| | | mod_base = OTHER |
| | | note = thymine |
| modified_base | 3648 | |
| | | mod_base = OTHER |
| | | note = thymine |
| modified_base | 3650..3651 | |
| | | mod_base = OTHER |
| | | note = thymine |
| modified_base | 3656 | |
| | | mod_base = OTHER |
| | | note = thymine |
| modified_base | 3661 | |
| | | mod_base = OTHER |
| | | note = thymine |
| modified_base | 3664 | |
| | | mod_base = OTHER |
| | | note = thymine |
| modified_base | 3667 | |
| | | mod_base = OTHER |
| | | note = thymine |
| modified_base | 3672..3673 | |
| | | mod_base = OTHER |
| | | note = thymine |
| modified_base | 3676 | |
| | | mod_base = OTHER |
| | | note = thymine |
| modified_base | 3678..3679 | |
| | | mod_base = OTHER |
| | | note = thymine |
| modified_base | 3684 | |
| | | mod_base = OTHER |
| | | note = thymine |
| modified_base | 3686 | |
| | | mod_base = OTHER |
| | | note = thymine |
| modified_base | 3693 | |
| | | mod_base = OTHER |
| | | note = thymine |
| modified_base | 3698..3699 | |
| | | mod_base = OTHER |
| | | note = thymine |
| modified_base | 3701 | |
| | | mod_base = OTHER |
| | | note = thymine |
| modified_base | 3703 | |
| | | mod_base = OTHER |
| | | note = thymine |
| modified_base | 3705..3707 | |
| | | mod_base = OTHER |
| | | note = thymine |
| modified_base | 3717 | |
| | | mod_base = OTHER |

| | | |
|---|---|---|
| | | note = thymine |
| modified_base | 3720 | |
| | | mod_base = OTHER |
| | | note = thymine |
| modified_base | 3723..3724 | |
| | | mod_base = OTHER |
| | | note = thymine |
| modified_base | 3726 | |
| | | mod_base = OTHER |
| | | note = thymine |
| modified_base | 3730..3731 | |
| | | mod_base = OTHER |
| | | note = thymine |
| modified_base | 3734 | |
| | | mod_base = OTHER |
| | | note = thymine |
| modified_base | 3740..3742 | |
| | | mod_base = OTHER |
| | | note = thymine |
| modified_base | 3747..3748 | |
| | | mod_base = OTHER |
| | | note = thymine |
| modified_base | 3752 | |
| | | mod_base = OTHER |
| | | note = thymine |
| modified_base | 3754 | |
| | | mod_base = OTHER |
| | | note = thymine |
| modified_base | 3756..3758 | |
| | | mod_base = OTHER |
| | | note = thymine |
| modified_base | 3763 | |
| | | mod_base = OTHER |
| | | note = thymine |
| modified_base | 3766 | |
| | | mod_base = OTHER |
| | | note = thymine |
| modified_base | 3769..3770 | |
| | | mod_base = OTHER |
| | | note = thymine |
| modified_base | 3772 | |
| | | mod_base = OTHER |
| | | note = thymine |
| modified_base | 3777 | |
| | | mod_base = OTHER |
| | | note = thymine |
| modified_base | 3779 | |
| | | mod_base = OTHER |
| | | note = thymine |
| modified_base | 3781 | |
| | | mod_base = OTHER |
| | | note = thymine |
| modified_base | 3789 | |
| | | mod_base = OTHER |
| | | note = thymine |
| modified_base | 3792 | |
| | | mod_base = OTHER |
| | | note = thymine |
| modified_base | 3794 | |
| | | mod_base = OTHER |
| | | note = thymine |
| modified_base | 3798 | |
| | | mod_base = OTHER |
| | | note = thymine |
| modified_base | 3806 | |
| | | mod_base = OTHER |
| | | note = thymine |
| modified_base | 3810..3811 | |
| | | mod_base = OTHER |
| | | note = thymine |
| modified_base | 3815 | |
| | | mod_base = OTHER |
| | | note = thymine |
| modified_base | 3821 | |
| | | mod_base = OTHER |
| | | note = thymine |
| modified_base | 3825..3827 | |
| | | mod_base = OTHER |
| | | note = thymine |

| | | |
|---|---|---|
| modified_base | 3829 | |
| | mod_base = OTHER | |
| | note = thymine | |
| modified_base | 3834 | |
| | mod_base = OTHER | |
| | note = thymine | |
| modified_base | 3838..3841 | |
| | mod_base = OTHER | |
| | note = thymine | |
| modified_base | 3843 | |
| | mod_base = OTHER | |
| | note = thymine | |
| modified_base | 3845 | |
| | mod_base = OTHER | |
| | note = thymine | |
| modified_base | 3849..3850 | |
| | mod_base = OTHER | |
| | note = thymine | |
| modified_base | 3852 | |
| | mod_base = OTHER | |
| | note = thymine | |
| modified_base | 3859 | |
| | mod_base = OTHER | |
| | note = thymine | |
| modified_base | 3863..3864 | |
| | mod_base = OTHER | |
| | note = thymine | |
| modified_base | 3870..3871 | |
| | mod_base = OTHER | |
| | note = thymine | |
| modified_base | 3874..3876 | |
| | mod_base = OTHER | |
| | note = thymine | |
| modified_base | 3880 | |
| | mod_base = OTHER | |
| | note = thymine | |
| modified_base | 3883 | |
| | mod_base = OTHER | |
| | note = thymine | |
| modified_base | 3886 | |
| | mod_base = OTHER | |
| | note = thymine | |
| modified_base | 3897 | |
| | mod_base = OTHER | |
| | note = thymine | |
| modified_base | 3900 | |
| | mod_base = OTHER | |
| | note = thymine | |
| modified_base | 3903..3905 | |
| | mod_base = OTHER | |
| | note = thymine | |
| modified_base | 3908 | |
| | mod_base = OTHER | |
| | note = thymine | |
| modified_base | 3910 | |
| | mod_base = OTHER | |
| | note = thymine | |
| modified_base | 3917..3918 | |
| | mod_base = OTHER | |
| | note = thymine | |
| modified_base | 3922 | |
| | mod_base = OTHER | |
| | note = thymine | |
| modified_base | 3935 | |
| | mod_base = OTHER | |
| | note = thymine | |
| modified_base | 3937 | |
| | mod_base = OTHER | |
| | note = thymine | |
| modified_base | 3941 | |
| | mod_base = OTHER | |
| | note = thymine | |
| modified_base | 3943 | |
| | mod_base = OTHER | |
| | note = thymine | |
| modified_base | 3946..3947 | |
| | mod_base = OTHER | |
| | note = thymine | |
| modified_base | 3949 | |

-continued

```
                              mod_base = OTHER
                              note = thymine
modified_base    3951
                              mod_base = OTHER
                              note = thymine
modified_base    3954
                              mod_base = OTHER
                              note = thymine
modified_base    3957
                              mod_base = OTHER
                              note = thymine
modified_base    3961
                              mod_base = OTHER
                              note = thymine
modified_base    3968..3970
                              mod_base = OTHER
                              note = thymine
modified_base    3972
                              mod_base = OTHER
                              note = thymine
modified_base    3975
                              mod_base = OTHER
                              note = thymine
modified_base    3978
                              mod_base = OTHER
                              note = thymine
modified_base    3981
                              mod_base = OTHER
                              note = thymine
modified_base    3983
                              mod_base = OTHER
                              note = thymine
modified_base    3986..3987
                              mod_base = OTHER
                              note = thymine
modified_base    3991..3992
                              mod_base = OTHER
                              note = thymine
modified_base    3999
                              mod_base = OTHER
                              note = thymine
modified_base    4002..4003
                              mod_base = OTHER
                              note = thymine
modified_base    4010..4011
                              mod_base = OTHER
                              note = thymine
modified_base    4019..4020
                              mod_base = OTHER
                              note = thymine
modified_base    4023
                              mod_base = OTHER
                              note = thymine
modified_base    4025..4026
                              mod_base = OTHER
                              note = thymine
modified_base    4028..4029
                              mod_base = OTHER
                              note = thymine
modified_base    4032
                              mod_base = OTHER
                              note = thymine
modified_base    4037
                              mod_base = OTHER
                              note = thymine
modified_base    4039..4040
                              mod_base = OTHER
                              note = thymine
modified_base    4042..4043
                              mod_base = OTHER
                              note = thymine
modified_base    4045
                              mod_base = OTHER
                              note = thymine
modified_base    4050..4055
                              mod_base = OTHER
                              note = thymine
modified_base    4058
                              mod_base = OTHER
```

| | | |
|---|---|---|
| | | note = thymine |
| modified_base | 4078 | |
| | | mod_base = OTHER |
| | | note = thymine |
| modified_base | 4080 | |
| | | mod_base = OTHER |
| | | note = thymine |
| modified_base | 4083 | |
| | | mod_base = OTHER |
| | | note = thymine |
| modified_base | 4088 | |
| | | mod_base = OTHER |
| | | note = thymine |
| modified_base | 4091..4092 | |
| | | mod_base = OTHER |
| | | note = thymine |
| modified_base | 4101 | |
| | | mod_base = OTHER |
| | | note = thymine |
| modified_base | 4105 | |
| | | mod_base = OTHER |
| | | note = thymine |
| modified_base | 4109..4111 | |
| | | mod_base = OTHER |
| | | note = thymine |
| modified_base | 4115 | |
| | | mod_base = OTHER |
| | | note = thymine |
| modified_base | 4121 | |
| | | mod_base = OTHER |
| | | note = thymine |
| modified_base | 4125 | |
| | | mod_base = OTHER |
| | | note = thymine |
| modified_base | 4134 | |
| | | mod_base = OTHER |
| | | note = thymine |
| modified_base | 4139 | |
| | | mod_base = OTHER |
| | | note = thymine |
| modified_base | 4143 | |
| | | mod_base = OTHER |
| | | note = thymine |
| modified_base | 4145..4147 | |
| | | mod_base = OTHER |
| | | note = thymine |
| modified_base | 4149 | |
| | | mod_base = OTHER |
| | | note = thymine |
| modified_base | 4155 | |
| | | mod_base = OTHER |
| | | note = thymine |
| modified_base | 4162 | |
| | | mod_base = OTHER |
| | | note = thymine |
| modified_base | 4170 | |
| | | mod_base = OTHER |
| | | note = thymine |
| modified_base | 4172 | |
| | | mod_base = OTHER |
| | | note = thymine |
| modified_base | 4176 | |
| | | mod_base = OTHER |
| | | note = thymine |
| modified_base | 4182 | |
| | | mod_base = OTHER |
| | | note = thymine |
| modified_base | 4185..4186 | |
| | | mod_base = OTHER |
| | | note = thymine |
| modified_base | 4191 | |
| | | mod_base = OTHER |
| | | note = thymine |
| modified_base | 4194 | |
| | | mod_base = OTHER |
| | | note = thymine |
| modified_base | 4198..4199 | |
| | | mod_base = OTHER |
| | | note = thymine |

-continued

| | | |
|---|---|---|
| modified_base | 4206 | |
| | mod_base = OTHER | |
| | note = thymine | |
| modified_base | 4208 | |
| | mod_base = OTHER | |
| | note = thymine | |
| modified_base | 4211..4213 | |
| | mod_base = OTHER | |
| | note = thymine | |
| modified_base | 4216 | |
| | mod_base = OTHER | |
| | note = thymine | |
| modified_base | 4218 | |
| | mod_base = OTHER | |
| | note = thymine | |
| modified_base | 4220 | |
| | mod_base = OTHER | |
| | note = thymine | |
| modified_base | 4222 | |
| | mod_base = OTHER | |
| | note = thymine | |
| modified_base | 4229 | |
| | mod_base = OTHER | |
| | note = thymine | |
| modified_base | 4247 | |
| | mod_base = OTHER | |
| | note = thymine | |
| modified_base | 4251 | |
| | mod_base = OTHER | |
| | note = thymine | |
| modified_base | 4260 | |
| | mod_base = OTHER | |
| | note = thymine | |
| modified_base | 4262 | |
| | mod_base = OTHER | |
| | note = thymine | |
| modified_base | 4266 | |
| | mod_base = OTHER | |
| | note = thymine | |
| modified_base | 4269 | |
| | mod_base = OTHER | |
| | note = thymine | |
| modified_base | 4277 | |
| | mod_base = OTHER | |
| | note = thymine | |
| modified_base | 4281..4286 | |
| | mod_base = OTHER | |
| | note = thymine | |
| modified_base | 4289..4291 | |
| | mod_base = OTHER | |
| | note = thymine | |
| modified_base | 4296..4297 | |
| | mod_base = OTHER | |
| | note = thymine | |
| modified_base | 4300 | |
| | mod_base = OTHER | |
| | note = thymine | |
| modified_base | 4303 | |
| | mod_base = OTHER | |
| | note = thymine | |
| modified_base | 4305 | |
| | mod_base = OTHER | |
| | note = thymine | |
| modified_base | 4310..4313 | |
| | mod_base = OTHER | |
| | note = thymine | |
| modified_base | 4315 | |
| | mod_base = OTHER | |
| | note = thymine | |
| modified_base | 4320 | |
| | mod_base = OTHER | |
| | note = thymine | |
| modified_base | 4324 | |
| | mod_base = OTHER | |
| | note = thymine | |
| modified_base | 4326..4327 | |
| | mod_base = OTHER | |
| | note = thymine | |
| modified_base | 4333 | |

-continued

```
                              mod_base = OTHER
                              note = thymine
modified_base      4335..4336
                              mod_base = OTHER
                              note = thymine
modified_base      4340
                              mod_base = OTHER
                              note = thymine
modified_base      4343
                              mod_base = OTHER
                              note = thymine
modified_base      4345
                              mod_base = OTHER
                              note = thymine
modified_base      4348..4350
                              mod_base = OTHER
                              note = thymine
modified_base      4352
                              mod_base = OTHER
                              note = thymine
modified_base      4356
                              mod_base = OTHER
                              note = thymine
modified_base      4359..4361
                              mod_base = OTHER
                              note = thymine
modified_base      4363
                              mod_base = OTHER
                              note = thymine
modified_base      4366
                              mod_base = OTHER
                              note = thymine
modified_base      4371
                              mod_base = OTHER
                              note = thymine
modified_base      4381..4382
                              mod_base = OTHER
                              note = thymine
modified_base      4385..4386
                              mod_base = OTHER
                              note = thymine
modified_base      4389
                              mod_base = OTHER
                              note = thymine
modified_base      4392
                              mod_base = OTHER
                              note = thymine
modified_base      4394
                              mod_base = OTHER
                              note = thymine
modified_base      4396..4397
                              mod_base = OTHER
                              note = thymine
modified_base      4402
                              mod_base = OTHER
                              note = thymine
modified_base      4404
                              mod_base = OTHER
                              note = thymine
modified_base      4407
                              mod_base = OTHER
                              note = thymine
modified_base      4411
                              mod_base = OTHER
                              note = thymine
modified_base      4415
                              mod_base = OTHER
                              note = thymine
modified_base      4418
                              mod_base = OTHER
                              note = thymine
modified_base      4421..4422
                              mod_base = OTHER
                              note = thymine
modified_base      4424..4425
                              mod_base = OTHER
                              note = thymine
modified_base      4427..4428
                              mod_base = OTHER
```

-continued

| | | |
|---|---|---|
| | note = thymine | |
| modified_base | 4431..4432 | |
| | mod_base = OTHER | |
| | note = thymine | |
| modified_base | 4435..4436 | |
| | mod_base = OTHER | |
| | note = thymine | |
| modified_base | 4438 | |
| | mod_base = OTHER | |
| | note = thymine | |
| modified_base | 4441..4442 | |
| | mod_base = OTHER | |
| | note = thymine | |
| modified_base | 4444..4445 | |
| | mod_base = OTHER | |
| | note = thymine | |
| modified_base | 4453 | |
| | mod_base = OTHER | |
| | note = thymine | |
| modified_base | 4456 | |
| | mod_base = OTHER | |
| | note = thymine | |
| modified_base | 4466 | |
| | mod_base = OTHER | |
| | note = thymine | |
| modified_base | 4468..4469 | |
| | mod_base = OTHER | |
| | note = thymine | |
| modified_base | 4473..4478 | |
| | mod_base = OTHER | |
| | note = thymine | |
| modified_base | 4481 | |
| | mod_base = OTHER | |
| | note = thymine | |
| modified_base | 4483..4484 | |
| | mod_base = OTHER | |
| | note = thymine | |
| modified_base | 4488 | |
| | mod_base = OTHER | |
| | note = thymine | |
| modified_base | 4491 | |
| | mod_base = OTHER | |
| | note = thymine | |
| modified_base | 4495 | |
| | mod_base = OTHER | |
| | note = thymine | |
| modified_base | 4500 | |
| | mod_base = OTHER | |
| | note = thymine | |
| modified_base | 4506 | |
| | mod_base = OTHER | |
| | note = thymine | |
| modified_base | 4512..4513 | |
| | mod_base = OTHER | |
| | note = thymine | |
| modified_base | 4515 | |
| | mod_base = OTHER | |
| | note = thymine | |
| modified_base | 4519 | |
| | mod_base = OTHER | |
| | note = thymine | |
| modified_base | 4523..4526 | |
| | mod_base = OTHER | |
| | note = thymine | |
| modified_base | 4528..4531 | |
| | mod_base = OTHER | |
| | note = thymine | |
| modified_base | 4537 | |
| | mod_base = OTHER | |
| | note = thymine | |
| modified_base | 4539 | |
| | mod_base = OTHER | |
| | note = thymine | |
| modified_base | 4546 | |
| | mod_base = OTHER | |
| | note = thymine | |
| modified_base | 4549 | |
| | mod_base = OTHER | |
| | note = thymine | |

| | | |
|---|---|---|
| modified_base | 4559 mod_base = OTHER note = thymine | |
| modified_base | 4561..4562 mod_base = OTHER note = thymine | |
| modified_base | 4571..4573 mod_base = OTHER note = thymine | |
| modified_base | 4575 mod_base = OTHER note = thymine | |
| modified_base | 4578..4579 mod_base = OTHER note = thymine | |
| modified_base | 4581 mod_base = OTHER note = thymine | |
| modified_base | 4584 mod_base = OTHER note = thymine | |
| modified_base | 4597 mod_base = OTHER note = thymine | |
| modified_base | 4599..4601 mod_base = OTHER note = thymine | |
| modified_base | 4607..4608 mod_base = OTHER note = thymine | |
| modified_base | 4611 mod_base = OTHER note = thymine | |
| modified_base | 4617..4618 mod_base = OTHER note = thymine | |
| modified_base | 4624..4625 mod_base = OTHER note = thymine | |
| modified_base | 4633..4636 mod_base = OTHER note = thymine | |
| modified_base | 4638..4639 mod_base = OTHER note = thymine | |
| modified_base | 4642..4643 mod_base = OTHER note = thymine | |
| modified_base | 4650 mod_base = OTHER note = thymine | |
| modified_base | 4658 mod_base = OTHER note = thymine | |
| modified_base | 4660 mod_base = OTHER note = thymine | |
| modified_base | 4663 mod_base = OTHER note = thymine | |
| modified_base | 4666 mod_base = OTHER note = thymine | |
| modified_base | 4669 mod_base = OTHER note = thymine | |
| modified_base | 4671..4672 mod_base = OTHER note = thymine | |
| modified_base | 4678 mod_base = OTHER note = thymine | |
| modified_base | 4680 mod_base = OTHER note = thymine | |
| modified_base | 4686..4687 mod_base = OTHER note = thymine | |
| modified_base | 4690..4693 | |

-continued

| | |
|---|---|
| | mod_base = OTHER |
| | note = thymine |
| modified_base | 4697..4698 |
| | mod_base = OTHER |
| | note = thymine |
| modified_base | 4703 |
| | mod_base = OTHER |
| | note = thymine |
| modified_base | 4705 |
| | mod_base = OTHER |
| | note = thymine |
| modified_base | 4709..4711 |
| | mod_base = OTHER |
| | note = thymine |
| modified_base | 4715 |
| | mod_base = OTHER |
| | note = thymine |
| modified_base | 4717..4718 |
| | mod_base = OTHER |
| | note = thymine |
| modified_base | 4721 |
| | mod_base = OTHER |
| | note = thymine |
| modified_base | 4723 |
| | mod_base = OTHER |
| | note = thymine |
| modified_base | 4725..4726 |
| | mod_base = OTHER |
| | note = thymine |
| modified_base | 4738 |
| | mod_base = OTHER |
| | note = thymine |
| modified_base | 4753 |
| | mod_base = OTHER |
| | note = thymine |
| modified_base | 4755 |
| | mod_base = OTHER |
| | note = thymine |
| modified_base | 4757..4759 |
| | mod_base = OTHER |
| | note = thymine |
| modified_base | 4766 |
| | mod_base = OTHER |
| | note = thymine |
| modified_base | 4769 |
| | mod_base = OTHER |
| | note = thymine |
| modified_base | 4774..4776 |
| | mod_base = OTHER |
| | note = thymine |
| modified_base | 4780 |
| | mod_base = OTHER |
| | note = thymine |
| modified_base | 4782 |
| | mod_base = OTHER |
| | note = thymine |
| modified_base | 4784 |
| | mod_base = OTHER |
| | note = thymine |
| modified_base | 4792 |
| | mod_base = OTHER |
| | note = thymine |
| modified_base | 4794..4795 |
| | mod_base = OTHER |
| | note = thymine |
| modified_base | 4800 |
| | mod_base = OTHER |
| | note = thymine |
| modified_base | 4802..4804 |
| | mod_base = OTHER |
| | note = thymine |
| source | 1..7114 |
| | mol_type = other RNA |
| | organism = unidentified |

SEQUENCE: 2
```
cgcacagtgg atcctaggcg taacttcatc attaaaatct cagattctgc tctgagtgtg    60
acttactgcg aagaggcaga caaatgggca actgcaacgg ggcatccaag tctaaccagc   120
cagactcctc aagagccaca cagccagccg cagaatttag gagggtagct cacagcagtc   180
tatatggtag atataactgt aagtgctgct ggtttgctga taccaatttg ataacctgta   240
```

```
atgatcacta cctttgttta aggtgccatc agggtatgtt aaggaattca gatctctgca   300
atatctgctg gaagccsctg cccaccacaa tcacagtacc ggtggagcca acagcaccac   360
caccataggc agactgcaca gggtcagacc cgaccccccg ggggggccccc atggggaccc   420
cccgtggggg aaccccgggg gtgatgcgcc attagtcaat gtctttgatc tcgactttgt   480
gcttcagtgg cctgcatgtc accccttca atctgaactg cccttgggga tctgatatca   540
gcaggtcatt taaagatctg ctgaatgcca ccttgaaatt tgagaattcc aaccagtcac   600
caaatttatc aagtgaacgg atcaactgct ctttgtgtag atcataaacg aggacaaagt   660
cctcttgctg aaataatatt gtttgtgatg ttgtttttag ataaggccat agttggctta   720
ataaggtttc cacactatca atgtcctcta gtgctccaat tgccttgact atgacatccc   780
cagacaactc aactctatat gttgacaacc tttcattacc tctgtaaaag atacctctt   840
tcaagacaag aggttctcct gggttatctg gcccaatgag gtcatatgca tacttgttac   900
ttagttcaga ataaaagtca ccaaagttga acttaacatg gctcagaata ttgtcatcat   960
ttgtcgcagc gtagcctgca tcaataaaca agccagctag gtcaaagctc tcatggcctg  1020
tgaacaatgg taggctagcg ataaccagtg caccatccaa caatgagtgg cttccctcag  1080
acccagaaac acattgactc attgcatcca cattcagctc taattcaggg gtaccgacat  1140
catccactcc tagtgaactg acaatggtgt aactgtacac catctttctt ctaagtttaa  1200
attttgtcga aactcgtgtg tgttctactt gaatgatcaa ttttagtttc acagcttctt  1260
ggcaagcaac attgcgcaac acagtgtgca ggtccatcat gtcttcctga ggcaacaagg  1320
agatgttgtc aacagagaca ccctcaagga aaaccttgat attatcaaag ctagaaacta  1380
cataacccat tgcaatgtct tcaacaaaca ttgctcttga tactttatta ttcctaactg  1440
acaaggtaaa atctgtgagt tcagctagat ctacttgact gtcatcttct agatctagaa  1500
cttcattgaa ccaaaagaag gatttgagac acgatgttga catgactagt gggttttatca  1560
tcgaagataa gacaacttgc accatgaagt tcctgcaaac ttgctgtggg ctgatgccaa  1620
cttcccaatt tgtatactct gactgtctaa catgggctga agcgcaatca ctctgtttca  1680
caatataaac attattatct cttactttca ataagtgact tataatccct aagttttcat  1740
tcatcatgtc tagagccaca cagacatcta gaaacttgac tcttccacta tccaaagatc  1800
tgttcacttg aagatcattc ataaagggtg ccaaatgttc ttcaaatagt ttggggtaat  1860
ttcttcgtat agaatgcaat acatggttca tgcctaattg gtcttctatc tgtcgtactg  1920
ctttgggttt aacagcccag aagaaattct tattacataa gaccagaggg gcctgtggac  1980
tcttaatagc aaaaaacacc cactccccta actcacaggc atttgtcagc accaaagaga  2040
agtaatccca caaaattggt ttagaaaatt ggttaacttc tttaagtgat ttttagacagt  2100
aaataacttt aggctttctc tcacaaattc cacaaagaca tggcattatt cgagtaaata  2160
tgtcctttat atacagaaat ccgcctttac catccctaac acacttactc cccatactct  2220
tacaaaaccc aatgaagcct gaggcaacag aagactgaaa tgcagatttg ttgattgact  2280
ctgccaagat cttcttcacg ccttttgtga aatttcttga cagcctggac tgtattgtcc  2340
ttatcaatgt tggcatctct tctttctcta acactcttcg acttgtcatg agtttggtcc  2400
tcaagaccaa cctcaagtcc ccaaagctcg ctaaattgac ccatctgtag tctagagttt  2460
gtctgatttc atcttcacta cacccggcat attgcaggaa tccggataaa gcctcatccc  2520
ctcccctgct tatcaagttg ataaggtttt cctcaaagat tttgcctctc ttaatgtcat  2580
tgaacacttt cctcgcgcag ttccttataa acattgtctc cttatcatca gaaaaaatag  2640
cttcaattt cctctgtaga cggtaccctc tagacccatc aacccagtct tgacatctt  2700
gttcttcaat agctccaaac ggagtctctc tgtatccaga gtatctaatc aattggttga  2760
ctctaatgaa aatctttgac actatatgag tgctaaccac attagcaata cattgatcac  2820
aaattgtgtc tatggtctct gacagttgtg ttggagtttt acacttaacg ttgtgtagag  2880
cagcagacac aaacttggtg agtaaaggag tctcttcacc catgacaaaa atcttgact  2940
taaactcagc aacaaaagtt cctatcacac tctttgggct gataaacttg tttaatttag  3000
aagataagaa ttcatggaag cacaccattt ccagcagttc tgtcctgtct tgaaactttt  3060
catcactaag gcaaggaatt tttataaggc taacctggtc atcgctggag gtataagtga  3120
caggtatcac atcatacaat aagtcaagtg cataacacag aaattgttca gtaattagcc  3180
catataaatc tgatgtgttg tgcaagattc cctggcccat gtccaagaca gacattatat  3240
ggctggggac ctggtccctt gactgcagat actggtgaaa aaactcttca ccaacactag  3300
tacagtcaca acccattaaa cctaaagatc tcttcaattt ccctacacag taggcttctg  3360
caacattaat tggaacttca acgacttat gaagatgcca tttgagaatg ttcattactg  3420
gttcaagatt caccttgtt ctatctctgg gattcttcaa ttctaatgtg tacaaaaaag  3480
aaaggaaag tgctggggctc atagttggtc cccatttgga gtggtcatat gaacaggaca  3540
agtcaccatt gttaacagcc attttcatat cacagattgc acgttcgaat tcctttttctg  3600
aattcaagca tgtgtatttc attgaactac ccacagcttc tgagaagtct tcaactaacc  3660
tggtcatcag cttagtgttg aggtctccca catacagttc tctatttgag ccaacctgct  3720
ccttataact tagtccaaat ttcaagttcc ctgtatttga gctgatgctt gtgaactctg  3780
taggagagtc gtctgaatag aaacataaat tccgtagggc tgcatttgta aataaacttt  3840
tgtctagctt atcagcaatg gcttcagaat tgctttccct ggtactaagc cgaacctcat  3900
cctttagtct cagaacttca ctggaaaagc ccaatctaga tctacttcta tgctcataac  3960
tacccaattt ctgatcataa tgtccttgaa ttaaagata cttgaagcat tcaaagaatt  4020
catcttcttg gtaggctatt gttgtcaaat tttttaataa caaacccaaa gggcagatgt  4080
cctgcggtgc ttcaagaaaa taagtcaatt taaatggaga tagataaaca gcatcacata  4140
actctttata cacatcagac ctgagcacat ctggatcaaa atcttcacc tcatgcattg  4200
acacctctgc tttaatctct ctcaacactc caaaggggc ccacaatgac tcaagagact  4260
ctcgctcatc aacagatgga tttttgatt tcaacttggt gatctcaact tttgtcccct  4320
cactattagc catccttggct agtgtcattt gtacgtcatt tctaatacee tcaaaggcc  4380
ttacttgatc ctctgttaaa ctctcataca tcactgataa ttcttcttga ttggttctgg  4440
ttcttgaacc ggtgctcaca agacctgtta gattttttaa tattaagtag tccatggaat  4500
caggatcaag attatacctg cctttgtttt taaacctctc agccatagta gaaacgcatg  4560
ttgaaacaag tttctcctta tcataaacag aaagaatatt tccaagttcg tcgagcttgg  4620
ggattaccac acttttattg cttgacagat cgtagtgatg ttaggcctgt  4680
agggattgct tttcagttca cctgtaactt taagtcttcc tctattgaag agagaaatgc  4740
agaaggacaa aatctcttta cacactcctg gaatttgagt atctgaggaa gtcttagcct  4800
ctttggaaaa gaatctgtcc aatcctctta tcatggtgtc ctcttgttcc agtgttagac  4860
tcccacttag agggggggttt acaacaacac aatcaaactt gactttgggc tcaataaact  4920
tctcaaaaca cttgatttga tctgtcaggc gatcaggtgt ctctttggtt accaagtgac  4980
```

```
acagataact aacatttaat agatatttaa accttcttgc aaagtaaaga tctgcatctt  5040
ccccttcacc caaaattgtc tggaaaagtt ccacagccat cctctgaatc agcacctctg  5100
atccagacat gcagtcgacc cttaactttg acatcaaatc cacatgatgg atttgatttg  5160
catatgccat caagaaatat cttagacctt gtaaaaatgt ctggttcctt ttggaagggg  5220
aacagagtac agctaaacact aacaatctta atattggcct tgtcattgtc atgagttcgt  5280
ggctaaaatc caaccagctg gtcatttcct cacacatttc aattaacaca tcctccgaaa  5340
atataggcag gaaaaatctc tttggatcac agtaaaaaga gccttgttct tccaatacccc  5400
cattgatgga tagatagata gaatagcacc ttgacttctc acctgttttt tggtaaaaca  5460
agagaccaaa tgtattcttt gtcagatgaa atctttgtac ataacactct cttagtctaa  5520
cattcccaaa atatctagaa tactctcttt cattgattaa caatcgggag gaaaatgatg  5580
tcttcatcga gttgaccaat gcaagggaaa tggaggacaa aatcctaaat aatttcttct  5640
gctcaccttc cactaagctg ctgaatggct gatgtctaca gatttctca aattccttgt  5700
taatagtata tctcatcact ggtctgtcag aaacaagtgc ctgagctaaa atcatcaagc  5760
tatccatatc agggtgtttt attagttttt ccagctgtga ccagagatct tgatgagagt  5820
tcttcaatgt tctggaacac gcttgaaccc acttggggct ggtcatcaat ttcttccgtta  5880
ttagtttaat cgcctccaga atatctagaa gtctgtcatt gactaacatt aacatttgtc  5940
caacaactat tcccgcattt cttaacctta caattgcatc atcatgcgtt ttgaaaagat  6000
cacaaagtaa attgagtaaa actaagtcca gaaacagtaa agtgtttctc ctggtgttga  6060
aaactttttag acctttcact ttgttacaca cggaaagggc ttgaagataa cacctctcta  6120
cagcatcaat agatatagaa ttctcatctg actggctttc catgttgact tcatctattg  6180
gatgcaatgc gatagagtag actacatcca tcaacttgtt tgcacaaaaa gggcagctgg  6240
gcacatcact gtctttgtgg cttcctaata agatcaagtc atttataagc ttagacttt  6300
gtgaaaattt gaatttcccc aactgcttgt caaaaatctc cttcttaaac caaaaccttta  6360
acttatgag ttcttctctt atgacagatt ctctaatgtc tcctaaccc ccaacaaaga  6420
gggattcatt taacctctca tcataaccca aagaattctt tttcaagcat tcgatgtttt  6480
ctaatcccaa gctctggttt tttgtgttgg acaaactatg gatcaatcgc tggtattctt  6540
gttcttcaat attaatctct tgcataaatt ttgatttctt taggatgtcg atcagcaacc  6600
accgaactct ttcaacaacc caatcagcaa ggaatctatt gctgtagcta gatctgccat  6660
caaccacagg aaccaacgta atccctgccc ttagtaggtc ggactttagg tttaagagct  6720
ttgacatgtc actcttccat ttctctcaa actcatcagg attgaccccta acaaaggttt  6780
ccaataggat gagtgttttc cctgtgagtt tgaagccatc cggaatgact tttgggaaggg  6840
tgggacatag tatgccatag tcagacagga tcacatcaac aaacttctga tctgaattga  6900
tctgacaggc gtgtgcctca caggactcaa gctctactaa acttgacaga agtttgaacc  6960
cttccaacaa cagagagctg gggtgatgtt gagataaaaa gatgtcccctt tggtatgcta  7020
gctcctgtct ttctggaaaa tgctttctaa taaggctttt tatttcattt actgattcct  7080
ccatgctcaa gtgccgccta ggatccactg tgcg                              7114
```

| SEQ ID NO: 3 | moltype = RNA  length = 3410 |
|---|---|
| FEATURE | Location/Qualifiers |
| modified_base | 8 |
| | mod_base = OTHER |
| | note = thymine |
| modified_base | 12 |
| | mod_base = OTHER |
| | note = thymine |
| modified_base | 15 |
| | mod_base = OTHER |
| | note = thymine |
| modified_base | 22..25 |
| | mod_base = OTHER |
| | note = thymine |
| modified_base | 28..29 |
| | mod_base = OTHER |
| | note = thymine |
| modified_base | 34 |
| | mod_base = OTHER |
| | note = thymine |
| modified_base | 36 |
| | mod_base = OTHER |
| | note = thymine |
| modified_base | 39..40 |
| | mod_base = OTHER |
| | note = thymine |
| modified_base | 42 |
| | mod_base = OTHER |
| | note = thymine |
| modified_base | 46 |
| | mod_base = OTHER |
| | note = thymine |
| modified_base | 48..51 |
| | mod_base = OTHER |
| | note = thymine |
| modified_base | 53 |
| | mod_base = OTHER |
| | note = thymine |
| modified_base | 55..57 |
| | mod_base = OTHER |
| | note = thymine |
| modified_base | 66 |

-continued

| | | |
|---|---|---|
| | | mod_base = OTHER |
| | | note = thymine |
| modified_base | 75 | |
| | | mod_base = OTHER |
| | | note = thymine |
| modified_base | 79..80 | |
| | | mod_base = OTHER |
| | | note = thymine |
| modified_base | 87 | |
| | | mod_base = OTHER |
| | | note = thymine |
| modified_base | 95..96 | |
| | | mod_base = OTHER |
| | | note = thymine |
| modified_base | 99..100 | |
| | | mod_base = OTHER |
| | | note = thymine |
| modified_base | 104..105 | |
| | | mod_base = OTHER |
| | | note = thymine |
| modified_base | 108 | |
| | | mod_base = OTHER |
| | | note = thymine |
| modified_base | 117 | |
| | | mod_base = OTHER |
| | | note = thymine |
| modified_base | 125..129 | |
| | | mod_base = OTHER |
| | | note = thymine |
| modified_base | 139 | |
| | | mod_base = OTHER |
| | | note = thymine |
| modified_base | 141 | |
| | | mod_base = OTHER |
| | | note = thymine |
| modified_base | 147..148 | |
| | | mod_base = OTHER |
| | | note = thymine |
| modified_base | 151 | |
| | | mod_base = OTHER |
| | | note = thymine |
| modified_base | 153..154 | |
| | | mod_base = OTHER |
| | | note = thymine |
| modified_base | 156..157 | |
| | | mod_base = OTHER |
| | | note = thymine |
| modified_base | 162 | |
| | | mod_base = OTHER |
| | | note = thymine |
| modified_base | 166 | |
| | | mod_base = OTHER |
| | | note = thymine |
| modified_base | 168 | |
| | | mod_base = OTHER |
| | | note = thymine |
| modified_base | 171..172 | |
| | | mod_base = OTHER |
| | | note = thymine |
| modified_base | 177 | |
| | | mod_base = OTHER |
| | | note = thymine |
| modified_base | 180..181 | |
| | | mod_base = OTHER |
| | | note = thymine |
| modified_base | 187 | |
| | | mod_base = OTHER |
| | | note = thymine |
| modified_base | 189 | |
| | | mod_base = OTHER |
| | | note = thymine |
| modified_base | 192 | |
| | | mod_base = OTHER |
| | | note = thymine |
| modified_base | 198 | |
| | | mod_base = OTHER |
| | | note = thymine |
| modified_base | 200 | |
| | | mod_base = OTHER |

```
                              note = thymine
modified_base                 208
                              mod_base = OTHER
                              note = thymine
modified_base                 211..213
                              mod_base = OTHER
                              note = thymine
modified_base                 215..216
                              mod_base = OTHER
                              note = thymine
modified_base                 221..222
                              mod_base = OTHER
                              note = thymine
modified_base                 224..226
                              mod_base = OTHER
                              note = thymine
modified_base                 228
                              mod_base = OTHER
                              note = thymine
modified_base                 230..231
                              mod_base = OTHER
                              note = thymine
modified_base                 234
                              mod_base = OTHER
                              note = thymine
modified_base                 240
                              mod_base = OTHER
                              note = thymine
modified_base                 251
                              mod_base = OTHER
                              note = thymine
modified_base                 254
                              mod_base = OTHER
                              note = thymine
modified_base                 268..271
                              mod_base = OTHER
                              note = thymine
modified_base                 276
                              mod_base = OTHER
                              note = thymine
modified_base                 282
                              mod_base = OTHER
                              note = thymine
modified_base                 293..294
                              mod_base = OTHER
                              note = thymine
modified_base                 301
                              mod_base = OTHER
                              note = thymine
modified_base                 303
                              mod_base = OTHER
                              note = thymine
modified_base                 305
                              mod_base = OTHER
                              note = thymine
modified_base                 308..309
                              mod_base = OTHER
                              note = thymine
modified_base                 311
                              mod_base = OTHER
                              note = thymine
modified_base                 315
                              mod_base = OTHER
                              note = thymine
modified_base                 318
                              mod_base = OTHER
                              note = thymine
modified_base                 322
                              mod_base = OTHER
                              note = thymine
modified_base                 324
                              mod_base = OTHER
                              note = thymine
modified_base                 326..329
                              mod_base = OTHER
                              note = thymine
modified_base                 337
                              mod_base = OTHER
                              note = thymine
```

| | |
|---|---|
| modified_base | 343<br>mod_base = OTHER<br>note = thymine |
| modified_base | 348<br>mod_base = OTHER<br>note = thymine |
| modified_base | 352<br>mod_base = OTHER<br>note = thymine |
| modified_base | 354<br>mod_base = OTHER<br>note = thymine |
| modified_base | 356..357<br>mod_base = OTHER<br>note = thymine |
| modified_base | 359<br>mod_base = OTHER<br>note = thymine |
| modified_base | 361<br>mod_base = OTHER<br>note = thymine |
| modified_base | 365..366<br>mod_base = OTHER<br>note = thymine |
| modified_base | 379<br>mod_base = OTHER<br>note = thymine |
| modified_base | 381..383<br>mod_base = OTHER<br>note = thymine |
| modified_base | 387..388<br>mod_base = OTHER<br>note = thymine |
| modified_base | 400<br>mod_base = OTHER<br>note = thymine |
| modified_base | 403..404<br>mod_base = OTHER<br>note = thymine |
| modified_base | 407..409<br>mod_base = OTHER<br>note = thymine |
| modified_base | 414<br>mod_base = OTHER<br>note = thymine |
| modified_base | 419..421<br>mod_base = OTHER<br>note = thymine |
| modified_base | 424<br>mod_base = OTHER<br>note = thymine |
| modified_base | 427<br>mod_base = OTHER<br>note = thymine |
| modified_base | 429..430<br>mod_base = OTHER<br>note = thymine |
| modified_base | 435<br>mod_base = OTHER<br>note = thymine |
| modified_base | 437..438<br>mod_base = OTHER<br>note = thymine |
| modified_base | 440..441<br>mod_base = OTHER<br>note = thymine |
| modified_base | 449<br>mod_base = OTHER<br>note = thymine |
| modified_base | 451<br>mod_base = OTHER<br>note = thymine |
| modified_base | 454<br>mod_base = OTHER<br>note = thymine |
| modified_base | 456..457<br>mod_base = OTHER<br>note = thymine |
| modified_base | 459 |

-continued

```
                         mod_base = OTHER
                         note = thymine
modified_base   462
                         mod_base = OTHER
                         note = thymine
modified_base   469
                         mod_base = OTHER
                         note = thymine
modified_base   478
                         mod_base = OTHER
                         note = thymine
modified_base   480
                         mod_base = OTHER
                         note = thymine
modified_base   485
                         mod_base = OTHER
                         note = thymine
modified_base   488
                         mod_base = OTHER
                         note = thymine
modified_base   490..491
                         mod_base = OTHER
                         note = thymine
modified_base   499
                         mod_base = OTHER
                         note = thymine
modified_base   502
                         mod_base = OTHER
                         note = thymine
modified_base   505
                         mod_base = OTHER
                         note = thymine
modified_base   510..512
                         mod_base = OTHER
                         note = thymine
modified_base   515..516
                         mod_base = OTHER
                         note = thymine
modified_base   518
                         mod_base = OTHER
                         note = thymine
modified_base   520
                         mod_base = OTHER
                         note = thymine
modified_base   524
                         mod_base = OTHER
                         note = thymine
modified_base   527..528
                         mod_base = OTHER
                         note = thymine
modified_base   531
                         mod_base = OTHER
                         note = thymine
modified_base   535
                         mod_base = OTHER
                         note = thymine
modified_base   538
                         mod_base = OTHER
                         note = thymine
modified_base   540
                         mod_base = OTHER
                         note = thymine
modified_base   547
                         mod_base = OTHER
                         note = thymine
modified_base   550..551
                         mod_base = OTHER
                         note = thymine
modified_base   556
                         mod_base = OTHER
                         note = thymine
modified_base   558
                         mod_base = OTHER
                         note = thymine
modified_base   569..571
                         mod_base = OTHER
                         note = thymine
modified_base   573
                         mod_base = OTHER
```

| | | |
|---|---|---|
| | | -continued |
| | | note = thymine |
| modified_base | 575 | |
| | | mod_base = OTHER |
| | | note = thymine |
| modified_base | 577 | |
| | | mod_base = OTHER |
| | | note = thymine |
| modified_base | 586 | |
| | | mod_base = OTHER |
| | | note = thymine |
| modified_base | 602..603 | |
| | | mod_base = OTHER |
| | | note = thymine |
| modified_base | 606 | |
| | | mod_base = OTHER |
| | | note = thymine |
| modified_base | 608..610 | |
| | | mod_base = OTHER |
| | | note = thymine |
| modified_base | 615 | |
| | | mod_base = OTHER |
| | | note = thymine |
| modified_base | 623 | |
| | | mod_base = OTHER |
| | | note = thymine |
| modified_base | 631 | |
| | | mod_base = OTHER |
| | | note = thymine |
| modified_base | 634 | |
| | | mod_base = OTHER |
| | | note = thymine |
| modified_base | 636 | |
| | | mod_base = OTHER |
| | | note = thymine |
| modified_base | 640 | |
| | | mod_base = OTHER |
| | | note = thymine |
| modified_base | 646..647 | |
| | | mod_base = OTHER |
| | | note = thymine |
| modified_base | 649 | |
| | | mod_base = OTHER |
| | | note = thymine |
| modified_base | 652 | |
| | | mod_base = OTHER |
| | | note = thymine |
| modified_base | 659..661 | |
| | | mod_base = OTHER |
| | | note = thymine |
| modified_base | 667 | |
| | | mod_base = OTHER |
| | | note = thymine |
| modified_base | 672 | |
| | | mod_base = OTHER |
| | | note = thymine |
| modified_base | 676 | |
| | | mod_base = OTHER |
| | | note = thymine |
| modified_base | 679..681 | |
| | | mod_base = OTHER |
| | | note = thymine |
| modified_base | 683 | |
| | | mod_base = OTHER |
| | | note = thymine |
| modified_base | 685 | |
| | | mod_base = OTHER |
| | | note = thymine |
| modified_base | 692 | |
| | | mod_base = OTHER |
| | | note = thymine |
| modified_base | 694 | |
| | | mod_base = OTHER |
| | | note = thymine |
| modified_base | 697 | |
| | | mod_base = OTHER |
| | | note = thymine |
| modified_base | 703..704 | |
| | | mod_base = OTHER |
| | | note = thymine |

| | | |
|---|---|---|
| modified_base | 707..708 mod_base = OTHER note = thymine | |
| modified_base | 712 mod_base = OTHER note = thymine | |
| modified_base | 720 mod_base = OTHER note = thymine | |
| modified_base | 722 mod_base = OTHER note = thymine | |
| modified_base | 725..726 mod_base = OTHER note = thymine | |
| modified_base | 729 mod_base = OTHER note = thymine | |
| modified_base | 742 mod_base = OTHER note = thymine | |
| modified_base | 748..749 mod_base = OTHER note = thymine | |
| modified_base | 754 mod_base = OTHER note = thymine | |
| modified_base | 756 mod_base = OTHER note = thymine | |
| modified_base | 761 mod_base = OTHER note = thymine | |
| modified_base | 763 mod_base = OTHER note = thymine | |
| modified_base | 768 mod_base = OTHER note = thymine | |
| modified_base | 777..778 mod_base = OTHER note = thymine | |
| modified_base | 785..786 mod_base = OTHER note = thymine | |
| modified_base | 791..792 mod_base = OTHER note = thymine | |
| modified_base | 795..796 mod_base = OTHER note = thymine | |
| modified_base | 805 mod_base = OTHER note = thymine | |
| modified_base | 813..814 mod_base = OTHER note = thymine | |
| modified_base | 819..820 mod_base = OTHER note = thymine | |
| modified_base | 830 mod_base = OTHER note = thymine | |
| modified_base | 833..834 mod_base = OTHER note = thymine | |
| modified_base | 842..843 mod_base = OTHER note = thymine | |
| modified_base | 845..846 mod_base = OTHER note = thymine | |
| modified_base | 848 mod_base = OTHER note = thymine | |
| modified_base | 851 mod_base = OTHER note = thymine | |
| modified_base | 854 | |

-continued

```
                         mod_base = OTHER
                         note = thymine
modified_base   856..858
                         mod_base = OTHER
                         note = thymine
modified_base   866
                         mod_base = OTHER
                         note = thymine
modified_base   869
                         mod_base = OTHER
                         note = thymine
modified_base   880
                         mod_base = OTHER
                         note = thymine
modified_base   886
                         mod_base = OTHER
                         note = thymine
modified_base   893
                         mod_base = OTHER
                         note = thymine
modified_base   895..896
                         mod_base = OTHER
                         note = thymine
modified_base   898
                         mod_base = OTHER
                         note = thymine
modified_base   900
                         mod_base = OTHER
                         note = thymine
modified_base   908
                         mod_base = OTHER
                         note = thymine
modified_base   912
                         mod_base = OTHER
                         note = thymine
modified_base   915
                         mod_base = OTHER
                         note = thymine
modified_base   918..919
                         mod_base = OTHER
                         note = thymine
modified_base   930
                         mod_base = OTHER
                         note = thymine
modified_base   935
                         mod_base = OTHER
                         note = thymine
modified_base   937..940
                         mod_base = OTHER
                         note = thymine
modified_base   946
                         mod_base = OTHER
                         note = thymine
modified_base   949
                         mod_base = OTHER
                         note = thymine
modified_base   952
                         mod_base = OTHER
                         note = thymine
modified_base   954
                         mod_base = OTHER
                         note = thymine
modified_base   962
                         mod_base = OTHER
                         note = thymine
modified_base   967
                         mod_base = OTHER
                         note = thymine
modified_base   969
                         mod_base = OTHER
                         note = thymine
modified_base   973
                         mod_base = OTHER
                         note = thymine
modified_base   976
                         mod_base = OTHER
                         note = thymine
modified_base   980
                         mod_base = OTHER
```

-continued

| | | |
|---|---|---|
| | | note = thymine |
| modified_base | 982 | |
| | | mod_base = OTHER |
| | | note = thymine |
| modified_base | 986..987 | |
| | | mod_base = OTHER |
| | | note = thymine |
| modified_base | 989 | |
| | | mod_base = OTHER |
| | | note = thymine |
| modified_base | 991 | |
| | | mod_base = OTHER |
| | | note = thymine |
| modified_base | 996 | |
| | | mod_base = OTHER |
| | | note = thymine |
| modified_base | 999 | |
| | | mod_base = OTHER |
| | | note = thymine |
| modified_base | 1005..1009 | |
| | | mod_base = OTHER |
| | | note = thymine |
| modified_base | 1012..1013 | |
| | | mod_base = OTHER |
| | | note = thymine |
| modified_base | 1024 | |
| | | mod_base = OTHER |
| | | note = thymine |
| modified_base | 1027 | |
| | | mod_base = OTHER |
| | | note = thymine |
| modified_base | 1029 | |
| | | mod_base = OTHER |
| | | note = thymine |
| modified_base | 1037..1038 | |
| | | mod_base = OTHER |
| | | note = thymine |
| modified_base | 1042 | |
| | | mod_base = OTHER |
| | | note = thymine |
| modified_base | 1045 | |
| | | mod_base = OTHER |
| | | note = thymine |
| modified_base | 1051 | |
| | | mod_base = OTHER |
| | | note = thymine |
| modified_base | 1062 | |
| | | mod_base = OTHER |
| | | note = thymine |
| modified_base | 1066 | |
| | | mod_base = OTHER |
| | | note = thymine |
| modified_base | 1068 | |
| | | mod_base = OTHER |
| | | note = thymine |
| modified_base | 1071 | |
| | | mod_base = OTHER |
| | | note = thymine |
| modified_base | 1083 | |
| | | mod_base = OTHER |
| | | note = thymine |
| modified_base | 1087 | |
| | | mod_base = OTHER |
| | | note = thymine |
| modified_base | 1092 | |
| | | mod_base = OTHER |
| | | note = thymine |
| modified_base | 1095 | |
| | | mod_base = OTHER |
| | | note = thymine |
| modified_base | 1097 | |
| | | mod_base = OTHER |
| | | note = thymine |
| modified_base | 1099 | |
| | | mod_base = OTHER |
| | | note = thymine |
| modified_base | 1105..1107 | |
| | | mod_base = OTHER |
| | | note = thymine |

-continued

| | | |
|---|---|---|
| modified_base | 1109..1110 | |
| | mod_base = OTHER | |
| | note = thymine | |
| modified_base | 1113 | |
| | mod_base = OTHER | |
| | note = thymine | |
| modified_base | 1125..1126 | |
| | mod_base = OTHER | |
| | note = thymine | |
| modified_base | 1134 | |
| | mod_base = OTHER | |
| | note = thymine | |
| modified_base | 1137 | |
| | mod_base = OTHER | |
| | note = thymine | |
| modified_base | 1141 | |
| | mod_base = OTHER | |
| | note = thymine | |
| modified_base | 1143 | |
| | mod_base = OTHER | |
| | note = thymine | |
| modified_base | 1147..1148 | |
| | mod_base = OTHER | |
| | note = thymine | |
| modified_base | 1151 | |
| | mod_base = OTHER | |
| | note = thymine | |
| modified_base | 1156..1157 | |
| | mod_base = OTHER | |
| | note = thymine | |
| modified_base | 1166..1169 | |
| | mod_base = OTHER | |
| | note = thymine | |
| modified_base | 1172 | |
| | mod_base = OTHER | |
| | note = thymine | |
| modified_base | 1174 | |
| | mod_base = OTHER | |
| | note = thymine | |
| modified_base | 1176 | |
| | mod_base = OTHER | |
| | note = thymine | |
| modified_base | 1188..1190 | |
| | mod_base = OTHER | |
| | note = thymine | |
| modified_base | 1202 | |
| | mod_base = OTHER | |
| | note = thymine | |
| modified_base | 1205..1206 | |
| | mod_base = OTHER | |
| | note = thymine | |
| modified_base | 1214 | |
| | mod_base = OTHER | |
| | note = thymine | |
| modified_base | 1217 | |
| | mod_base = OTHER | |
| | note = thymine | |
| modified_base | 1220..1221 | |
| | mod_base = OTHER | |
| | note = thymine | |
| modified_base | 1224 | |
| | mod_base = OTHER | |
| | note = thymine | |
| modified_base | 1238 | |
| | mod_base = OTHER | |
| | note = thymine | |
| modified_base | 1240..1242 | |
| | mod_base = OTHER | |
| | note = thymine | |
| modified_base | 1248 | |
| | mod_base = OTHER | |
| | note = thymine | |
| modified_base | 1250 | |
| | mod_base = OTHER | |
| | note = thymine | |
| modified_base | 1252 | |
| | mod_base = OTHER | |
| | note = thymine | |
| modified_base | 1256..1257 | |

-continued

|   |   |
|---|---|
| | mod_base = OTHER |
| | note = thymine |
| modified_base | 1261 |
| | mod_base = OTHER |
| | note = thymine |
| modified_base | 1264 |
| | mod_base = OTHER |
| | note = thymine |
| modified_base | 1268 |
| | mod_base = OTHER |
| | note = thymine |
| modified_base | 1272 |
| | mod_base = OTHER |
| | note = thymine |
| modified_base | 1274..1275 |
| | mod_base = OTHER |
| | note = thymine |
| modified_base | 1282 |
| | mod_base = OTHER |
| | note = thymine |
| modified_base | 1286..1287 |
| | mod_base = OTHER |
| | note = thymine |
| modified_base | 1289..1290 |
| | mod_base = OTHER |
| | note = thymine |
| modified_base | 1293..1295 |
| | mod_base = OTHER |
| | note = thymine |
| modified_base | 1297 |
| | mod_base = OTHER |
| | note = thymine |
| modified_base | 1302 |
| | mod_base = OTHER |
| | note = thymine |
| modified_base | 1305 |
| | mod_base = OTHER |
| | note = thymine |
| modified_base | 1316 |
| | mod_base = OTHER |
| | note = thymine |
| modified_base | 1318..1319 |
| | mod_base = OTHER |
| | note = thymine |
| modified_base | 1333 |
| | mod_base = OTHER |
| | note = thymine |
| modified_base | 1339 |
| | mod_base = OTHER |
| | note = thymine |
| modified_base | 1342..1344 |
| | mod_base = OTHER |
| | note = thymine |
| modified_base | 1348..1350 |
| | mod_base = OTHER |
| | note = thymine |
| modified_base | 1353..1354 |
| | mod_base = OTHER |
| | note = thymine |
| modified_base | 1359 |
| | mod_base = OTHER |
| | note = thymine |
| modified_base | 1361 |
| | mod_base = OTHER |
| | note = thymine |
| modified_base | 1363 |
| | mod_base = OTHER |
| | note = thymine |
| modified_base | 1365..1367 |
| | mod_base = OTHER |
| | note = thymine |
| modified_base | 1377 |
| | mod_base = OTHER |
| | note = thymine |
| modified_base | 1379..1380 |
| | mod_base = OTHER |
| | note = thymine |
| modified_base | 1382..1383 |
| | mod_base = OTHER |

-continued

| | | |
|---|---|---|
| modified_base | 1391 | |
| | mod_base = OTHER | |
| | note = thymine | |
| modified_base | 1395 | |
| | mod_base = OTHER | |
| | note = thymine | |
| modified_base | 1397..1398 | |
| | mod_base = OTHER | |
| | note = thymine | |
| modified_base | 1401..1402 | |
| | mod_base = OTHER | |
| | note = thymine | |
| modified_base | 1406..1407 | |
| | mod_base = OTHER | |
| | note = thymine | |
| modified_base | 1410 | |
| | mod_base = OTHER | |
| | note = thymine | |
| modified_base | 1414 | |
| | mod_base = OTHER | |
| | note = thymine | |
| modified_base | 1416 | |
| | mod_base = OTHER | |
| | note = thymine | |
| modified_base | 1421 | |
| | mod_base = OTHER | |
| | note = thymine | |
| modified_base | 1434 | |
| | mod_base = OTHER | |
| | note = thymine | |
| modified_base | 1448 | |
| | mod_base = OTHER | |
| | note = thymine | |
| modified_base | 1453..1455 | |
| | mod_base = OTHER | |
| | note = thymine | |
| modified_base | 1466..1467 | |
| | mod_base = OTHER | |
| | note = thymine | |
| modified_base | 1475..1476 | |
| | mod_base = OTHER | |
| | note = thymine | |
| modified_base | 1480 | |
| | mod_base = OTHER | |
| | note = thymine | |
| modified_base | 1483..1484 | |
| | mod_base = OTHER | |
| | note = thymine | |
| modified_base | 1490 | |
| | mod_base = OTHER | |
| | note = thymine | |
| modified_base | 1492 | |
| | mod_base = OTHER | |
| | note = thymine | |
| modified_base | 1495 | |
| | mod_base = OTHER | |
| | note = thymine | |
| modified_base | 1499 | |
| | mod_base = OTHER | |
| | note = thymine | |
| modified_base | 1507 | |
| | mod_base = OTHER | |
| | note = thymine | |
| modified_base | 1509 | |
| | mod_base = OTHER | |
| | note = thymine | |
| modified_base | 1524..1526 | |
| | mod_base = OTHER | |
| | note = thymine | |
| modified_base | 1531 | |
| | mod_base = OTHER | |
| | note = thymine | |
| modified_base | 1541 | |
| | mod_base = OTHER | |
| | note = thymine | |
| modified_base | 1548 | |
| | mod_base = OTHER | |
| | note = thymine | |

-continued

| | |
|---|---|
| modified_base | 1551<br>mod_base = OTHER<br>note = thymine |
| modified_base | 1557<br>mod_base = OTHER<br>note = thymine |
| modified_base | 1576<br>mod_base = OTHER<br>note = thymine |
| modified_base | 1585<br>mod_base = OTHER<br>note = thymine |
| modified_base | 1588<br>mod_base = OTHER<br>note = thymine |
| modified_base | 1590<br>mod_base = OTHER<br>note = thymine |
| modified_base | 1601<br>mod_base = OTHER<br>note = thymine |
| modified_base | 1610<br>mod_base = OTHER<br>note = thymine |
| modified_base | 1621<br>mod_base = OTHER<br>note = thymine |
| modified_base | 1632<br>mod_base = OTHER<br>note = thymine |
| modified_base | 1635..1636<br>mod_base = OTHER<br>note = thymine |
| modified_base | 1641<br>mod_base = OTHER<br>note = thymine |
| modified_base | 1645<br>mod_base = OTHER<br>note = thymine |
| modified_base | 1650<br>mod_base = OTHER<br>note = thymine |
| modified_base | 1654..1655<br>mod_base = OTHER<br>note = thymine |
| modified_base | 1673<br>mod_base = OTHER<br>note = thymine |
| modified_base | 1677<br>mod_base = OTHER<br>note = thymine |
| modified_base | 1680<br>mod_base = OTHER<br>note = thymine |
| modified_base | 1683<br>mod_base = OTHER<br>note = thymine |
| modified_base | 1689<br>mod_base = OTHER<br>note = thymine |
| modified_base | 1691<br>mod_base = OTHER<br>note = thymine |
| modified_base | 1695..1696<br>mod_base = OTHER<br>note = thymine |
| modified_base | 1699<br>mod_base = OTHER<br>note = thymine |
| modified_base | 1702<br>mod_base = OTHER<br>note = thymine |
| modified_base | 1705<br>mod_base = OTHER<br>note = thymine |
| modified_base | 1711..1712<br>mod_base = OTHER<br>note = thymine |
| modified_base | 1717 |

-continued

| | | |
|---|---|---|
| | mod_base = OTHER | |
| | note = thymine | |
| modified_base | 1719 | |
| | mod_base = OTHER | |
| | note = thymine | |
| modified_base | 1725 | |
| | mod_base = OTHER | |
| | note = thymine | |
| modified_base | 1729 | |
| | mod_base = OTHER | |
| | note = thymine | |
| modified_base | 1736..1737 | |
| | mod_base = OTHER | |
| | note = thymine | |
| modified_base | 1739 | |
| | mod_base = OTHER | |
| | note = thymine | |
| modified_base | 1744 | |
| | mod_base = OTHER | |
| | note = thymine | |
| modified_base | 1746 | |
| | mod_base = OTHER | |
| | note = thymine | |
| modified_base | 1759 | |
| | mod_base = OTHER | |
| | note = thymine | |
| modified_base | 1761 | |
| | mod_base = OTHER | |
| | note = thymine | |
| modified_base | 1764..1765 | |
| | mod_base = OTHER | |
| | note = thymine | |
| modified_base | 1769 | |
| | mod_base = OTHER | |
| | note = thymine | |
| modified_base | 1780..1781 | |
| | mod_base = OTHER | |
| | note = thymine | |
| modified_base | 1790 | |
| | mod_base = OTHER | |
| | note = thymine | |
| modified_base | 1792 | |
| | mod_base = OTHER | |
| | note = thymine | |
| modified_base | 1795..1798 | |
| | mod_base = OTHER | |
| | note = thymine | |
| modified_base | 1802 | |
| | mod_base = OTHER | |
| | note = thymine | |
| modified_base | 1804..1808 | |
| | mod_base = OTHER | |
| | note = thymine | |
| modified_base | 1810..1811 | |
| | mod_base = OTHER | |
| | note = thymine | |
| modified_base | 1813..1814 | |
| | mod_base = OTHER | |
| | note = thymine | |
| modified_base | 1824 | |
| | mod_base = OTHER | |
| | note = thymine | |
| modified_base | 1828..1829 | |
| | mod_base = OTHER | |
| | note = thymine | |
| modified_base | 1831 | |
| | mod_base = OTHER | |
| | note = thymine | |
| modified_base | 1834 | |
| | mod_base = OTHER | |
| | note = thymine | |
| modified_base | 1836..1838 | |
| | mod_base = OTHER | |
| | note = thymine | |
| modified_base | 1842 | |
| | mod_base = OTHER | |
| | note = thymine | |
| modified_base | 1846 | |
| | mod_base = OTHER | |

-continued

```
                            note = thymine
modified_base               1852
                            mod_base = OTHER
                            note = thymine
modified_base               1854..1856
                            mod_base = OTHER
                            note = thymine
modified_base               1858
                            mod_base = OTHER
                            note = thymine
modified_base               1867
                            mod_base = OTHER
                            note = thymine
modified_base               1869..1870
                            mod_base = OTHER
                            note = thymine
modified_base               1873
                            mod_base = OTHER
                            note = thymine
modified_base               1879
                            mod_base = OTHER
                            note = thymine
modified_base               1883
                            mod_base = OTHER
                            note = thymine
modified_base               1887..1888
                            mod_base = OTHER
                            note = thymine
modified_base               1890..1891
                            mod_base = OTHER
                            note = thymine
modified_base               1896
                            mod_base = OTHER
                            note = thymine
modified_base               1898
                            mod_base = OTHER
                            note = thymine
modified_base               1903..1904
                            mod_base = OTHER
                            note = thymine
modified_base               1909
                            mod_base = OTHER
                            note = thymine
modified_base               1917..1919
                            mod_base = OTHER
                            note = thymine
modified_base               1924
                            mod_base = OTHER
                            note = thymine
modified_base               1926
                            mod_base = OTHER
                            note = thymine
modified_base               1928..1929
                            mod_base = OTHER
                            note = thymine
modified_base               1931..1932
                            mod_base = OTHER
                            note = thymine
modified_base               1936
                            mod_base = OTHER
                            note = thymine
modified_base               1942
                            mod_base = OTHER
                            note = thymine
modified_base               1951..1952
                            mod_base = OTHER
                            note = thymine
modified_base               1955
                            mod_base = OTHER
                            note = thymine
modified_base               1958
                            mod_base = OTHER
                            note = thymine
modified_base               1960
                            mod_base = OTHER
                            note = thymine
modified_base               1963
                            mod_base = OTHER
                            note = thymine
```

-continued

| | | |
|---|---|---|
| modified_base | 1968 | |
| | mod_base = OTHER | |
| | note = thymine | |
| modified_base | 1971..1972 | |
| | mod_base = OTHER | |
| | note = thymine | |
| modified_base | 1976 | |
| | mod_base = OTHER | |
| | note = thymine | |
| modified_base | 1979 | |
| | mod_base = OTHER | |
| | note = thymine | |
| modified_base | 1988 | |
| | mod_base = OTHER | |
| | note = thymine | |
| modified_base | 1990 | |
| | mod_base = OTHER | |
| | note = thymine | |
| modified_base | 1992 | |
| | mod_base = OTHER | |
| | note = thymine | |
| modified_base | 2009 | |
| | mod_base = OTHER | |
| | note = thymine | |
| modified_base | 2014 | |
| | mod_base = OTHER | |
| | note = thymine | |
| modified_base | 2018 | |
| | mod_base = OTHER | |
| | note = thymine | |
| modified_base | 2025 | |
| | mod_base = OTHER | |
| | note = thymine | |
| modified_base | 2028 | |
| | mod_base = OTHER | |
| | note = thymine | |
| modified_base | 2033..2034 | |
| | mod_base = OTHER | |
| | note = thymine | |
| modified_base | 2038 | |
| | mod_base = OTHER | |
| | note = thymine | |
| modified_base | 2040..2041 | |
| | mod_base = OTHER | |
| | note = thymine | |
| modified_base | 2043 | |
| | mod_base = OTHER | |
| | note = thymine | |
| modified_base | 2045 | |
| | mod_base = OTHER | |
| | note = thymine | |
| modified_base | 2047 | |
| | mod_base = OTHER | |
| | note = thymine | |
| modified_base | 2049..2051 | |
| | mod_base = OTHER | |
| | note = thymine | |
| modified_base | 2054..2055 | |
| | mod_base = OTHER | |
| | note = thymine | |
| modified_base | 2060 | |
| | mod_base = OTHER | |
| | note = thymine | |
| modified_base | 2065 | |
| | mod_base = OTHER | |
| | note = thymine | |
| modified_base | 2071 | |
| | mod_base = OTHER | |
| | note = thymine | |
| modified_base | 2073 | |
| | mod_base = OTHER | |
| | note = thymine | |
| modified_base | 2075 | |
| | mod_base = OTHER | |
| | note = thymine | |
| modified_base | 2078 | |
| | mod_base = OTHER | |
| | note = thymine | |
| modified_base | 2083..2087 | |

|               |           |
|---------------|-----------|
|               | mod_base = OTHER |
|               | note = thymine |
| modified_base | 2094..2096 |
|               | mod_base = OTHER |
|               | note = thymine |
| modified_base | 2098 |
|               | mod_base = OTHER |
|               | note = thymine |
| modified_base | 2101 |
|               | mod_base = OTHER |
|               | note = thymine |
| modified_base | 2104 |
|               | mod_base = OTHER |
|               | note = thymine |
| modified_base | 2106 |
|               | mod_base = OTHER |
|               | note = thymine |
| modified_base | 2109..2112 |
|               | mod_base = OTHER |
|               | note = thymine |
| modified_base | 2114 |
|               | mod_base = OTHER |
|               | note = thymine |
| modified_base | 2122 |
|               | mod_base = OTHER |
|               | note = thymine |
| modified_base | 2126 |
|               | mod_base = OTHER |
|               | note = thymine |
| modified_base | 2128 |
|               | mod_base = OTHER |
|               | note = thymine |
| modified_base | 2131 |
|               | mod_base = OTHER |
|               | note = thymine |
| modified_base | 2134..2135 |
|               | mod_base = OTHER |
|               | note = thymine |
| modified_base | 2139 |
|               | mod_base = OTHER |
|               | note = thymine |
| modified_base | 2146 |
|               | mod_base = OTHER |
|               | note = thymine |
| modified_base | 2159 |
|               | mod_base = OTHER |
|               | note = thymine |
| modified_base | 2161 |
|               | mod_base = OTHER |
|               | note = thymine |
| modified_base | 2170 |
|               | mod_base = OTHER |
|               | note = thymine |
| modified_base | 2174 |
|               | mod_base = OTHER |
|               | note = thymine |
| modified_base | 2178 |
|               | mod_base = OTHER |
|               | note = thymine |
| modified_base | 2181 |
|               | mod_base = OTHER |
|               | note = thymine |
| modified_base | 2184..2185 |
|               | mod_base = OTHER |
|               | note = thymine |
| modified_base | 2189 |
|               | mod_base = OTHER |
|               | note = thymine |
| modified_base | 2191 |
|               | mod_base = OTHER |
|               | note = thymine |
| modified_base | 2204 |
|               | mod_base = OTHER |
|               | note = thymine |
| modified_base | 2206..2207 |
|               | mod_base = OTHER |
|               | note = thymine |
| modified_base | 2210 |
|               | mod_base = OTHER |

-continued

| | | |
|---|---|---|
| modified_base | 2215 mod_base = OTHER note = thymine | |
| modified_base | 2220..2222 mod_base = OTHER note = thymine | |
| modified_base | 2229 mod_base = OTHER note = thymine | |
| modified_base | 2233 mod_base = OTHER note = thymine | |
| modified_base | 2235 mod_base = OTHER note = thymine | |
| modified_base | 2237 mod_base = OTHER note = thymine | |
| modified_base | 2240 mod_base = OTHER note = thymine | |
| modified_base | 2247..2248 mod_base = OTHER note = thymine | |
| modified_base | 2250..2251 mod_base = OTHER note = thymine | |
| modified_base | 2253 mod_base = OTHER note = thymine | |
| modified_base | 2255 mod_base = OTHER note = thymine | |
| modified_base | 2257 mod_base = OTHER note = thymine | |
| modified_base | 2259 mod_base = OTHER note = thymine | |
| modified_base | 2261 mod_base = OTHER note = thymine | |
| modified_base | 2266..2267 mod_base = OTHER note = thymine | |
| modified_base | 2274 mod_base = OTHER note = thymine | |
| modified_base | 2276 mod_base = OTHER note = thymine | |
| modified_base | 2281..2282 mod_base = OTHER note = thymine | |
| modified_base | 2284 mod_base = OTHER note = thymine | |
| modified_base | 2290..2291 mod_base = OTHER note = thymine | |
| modified_base | 2293..2296 mod_base = OTHER note = thymine | |
| modified_base | 2301..2302 mod_base = OTHER note = thymine | |
| modified_base | 2304 mod_base = OTHER note = thymine | |
| modified_base | 2306 mod_base = OTHER note = thymine | |
| modified_base | 2310 mod_base = OTHER note = thymine | |
| modified_base | 2319 mod_base = OTHER note = thymine | |

-continued

| | |
|---|---|
| modified_base | 2322..2324<br>mod_base = OTHER<br>note = thymine |
| modified_base | 2327..2328<br>mod_base = OTHER<br>note = thymine |
| modified_base | 2330<br>mod_base = OTHER<br>note = thymine |
| modified_base | 2335<br>mod_base = OTHER<br>note = thymine |
| modified_base | 2339<br>mod_base = OTHER<br>note = thymine |
| modified_base | 2342..2343<br>mod_base = OTHER<br>note = thymine |
| modified_base | 2345<br>mod_base = OTHER<br>note = thymine |
| modified_base | 2347..2348<br>mod_base = OTHER<br>note = thymine |
| modified_base | 2350<br>mod_base = OTHER<br>note = thymine |
| modified_base | 2355<br>mod_base = OTHER<br>note = thymine |
| modified_base | 2360<br>mod_base = OTHER<br>note = thymine |
| modified_base | 2364<br>mod_base = OTHER<br>note = thymine |
| modified_base | 2366<br>mod_base = OTHER<br>note = thymine |
| modified_base | 2369..2371<br>mod_base = OTHER<br>note = thymine |
| modified_base | 2373<br>mod_base = OTHER<br>note = thymine |
| modified_base | 2376<br>mod_base = OTHER<br>note = thymine |
| modified_base | 2378<br>mod_base = OTHER<br>note = thymine |
| modified_base | 2387<br>mod_base = OTHER<br>note = thymine |
| modified_base | 2389<br>mod_base = OTHER<br>note = thymine |
| modified_base | 2401<br>mod_base = OTHER<br>note = thymine |
| modified_base | 2418..2420<br>mod_base = OTHER<br>note = thymine |
| modified_base | 2422<br>mod_base = OTHER<br>note = thymine |
| modified_base | 2431..2434<br>mod_base = OTHER<br>note = thymine |
| modified_base | 2437<br>mod_base = OTHER<br>note = thymine |
| modified_base | 2443..2445<br>mod_base = OTHER<br>note = thymine |
| modified_base | 2447<br>mod_base = OTHER<br>note = thymine |
| modified_base | 2449..2450 |

-continued

|  |  |
|---|---|
|  | mod_base = OTHER |
|  | note = thymine |
| modified_base | 2454 |
|  | mod_base = OTHER |
|  | note = thymine |
| modified_base | 2457..2459 |
|  | mod_base = OTHER |
|  | note = thymine |
| modified_base | 2461 |
|  | mod_base = OTHER |
|  | note = thymine |
| modified_base | 2464 |
|  | mod_base = OTHER |
|  | note = thymine |
| modified_base | 2468 |
|  | mod_base = OTHER |
|  | note = thymine |
| modified_base | 2474 |
|  | mod_base = OTHER |
|  | note = thymine |
| modified_base | 2478..2479 |
|  | mod_base = OTHER |
|  | note = thymine |
| modified_base | 2481 |
|  | mod_base = OTHER |
|  | note = thymine |
| modified_base | 2483..2484 |
|  | mod_base = OTHER |
|  | note = thymine |
| modified_base | 2487..2489 |
|  | mod_base = OTHER |
|  | note = thymine |
| modified_base | 2494 |
|  | mod_base = OTHER |
|  | note = thymine |
| modified_base | 2498 |
|  | mod_base = OTHER |
|  | note = thymine |
| modified_base | 2501..2502 |
|  | mod_base = OTHER |
|  | note = thymine |
| modified_base | 2505..2508 |
|  | mod_base = OTHER |
|  | note = thymine |
| modified_base | 2510 |
|  | mod_base = OTHER |
|  | note = thymine |
| modified_base | 2524..2525 |
|  | mod_base = OTHER |
|  | note = thymine |
| modified_base | 2527 |
|  | mod_base = OTHER |
|  | note = thymine |
| modified_base | 2529 |
|  | mod_base = OTHER |
|  | note = thymine |
| modified_base | 2534 |
|  | mod_base = OTHER |
|  | note = thymine |
| modified_base | 2538 |
|  | mod_base = OTHER |
|  | note = thymine |
| modified_base | 2540 |
|  | mod_base = OTHER |
|  | note = thymine |
| modified_base | 2543..2544 |
|  | mod_base = OTHER |
|  | note = thymine |
| modified_base | 2546 |
|  | mod_base = OTHER |
|  | note = thymine |
| modified_base | 2548 |
|  | mod_base = OTHER |
|  | note = thymine |
| modified_base | 2555 |
|  | mod_base = OTHER |
|  | note = thymine |
| modified_base | 2557..2559 |
|  | mod_base = OTHER |

-continued

```
                           note = thymine
modified_base              2566
                           mod_base = OTHER
                           note = thymine
modified_base              2573
                           mod_base = OTHER
                           note = thymine
modified_base              2577
                           mod_base = OTHER
                           note = thymine
modified_base              2587..2589
                           mod_base = OTHER
                           note = thymine
modified_base              2592
                           mod_base = OTHER
                           note = thymine
modified_base              2598
                           mod_base = OTHER
                           note = thymine
modified_base              2606
                           mod_base = OTHER
                           note = thymine
modified_base              2611..2612
                           mod_base = OTHER
                           note = thymine
modified_base              2614
                           mod_base = OTHER
                           note = thymine
modified_base              2624
                           mod_base = OTHER
                           note = thymine
modified_base              2626..2627
                           mod_base = OTHER
                           note = thymine
modified_base              2630
                           mod_base = OTHER
                           note = thymine
modified_base              2636..2638
                           mod_base = OTHER
                           note = thymine
modified_base              2641
                           mod_base = OTHER
                           note = thymine
modified_base              2644..2645
                           mod_base = OTHER
                           note = thymine
modified_base              2648
                           mod_base = OTHER
                           note = thymine
modified_base              2654
                           mod_base = OTHER
                           note = thymine
modified_base              2656
                           mod_base = OTHER
                           note = thymine
modified_base              2665
                           mod_base = OTHER
                           note = thymine
modified_base              2668
                           mod_base = OTHER
                           note = thymine
modified_base              2670..2671
                           mod_base = OTHER
                           note = thymine
modified_base              2674
                           mod_base = OTHER
                           note = thymine
modified_base              2678
                           mod_base = OTHER
                           note = thymine
modified_base              2682
                           mod_base = OTHER
                           note = thymine
modified_base              2684
                           mod_base = OTHER
                           note = thymine
modified_base              2686
                           mod_base = OTHER
                           note = thymine
```

-continued

| | | |
|---|---|---|
| modified_base | 2692 | |
| | mod_base = OTHER | |
| | note = thymine | |
| modified_base | 2696 | |
| | mod_base = OTHER | |
| | note = thymine | |
| modified_base | 2701..2703 | |
| | mod_base = OTHER | |
| | note = thymine | |
| modified_base | 2707 | |
| | mod_base = OTHER | |
| | note = thymine | |
| modified_base | 2710..2711 | |
| | mod_base = OTHER | |
| | note = thymine | |
| modified_base | 2717 | |
| | mod_base = OTHER | |
| | note = thymine | |
| modified_base | 2719 | |
| | mod_base = OTHER | |
| | note = thymine | |
| modified_base | 2721 | |
| | mod_base = OTHER | |
| | note = thymine | |
| modified_base | 2738..2739 | |
| | mod_base = OTHER | |
| | note = thymine | |
| modified_base | 2746 | |
| | mod_base = OTHER | |
| | note = thymine | |
| modified_base | 2748 | |
| | mod_base = OTHER | |
| | note = thymine | |
| modified_base | 2750 | |
| | mod_base = OTHER | |
| | note = thymine | |
| modified_base | 2756 | |
| | mod_base = OTHER | |
| | note = thymine | |
| modified_base | 2758..2759 | |
| | mod_base = OTHER | |
| | note = thymine | |
| modified_base | 2762..2763 | |
| | mod_base = OTHER | |
| | note = thymine | |
| modified_base | 2765 | |
| | mod_base = OTHER | |
| | note = thymine | |
| modified_base | 2767 | |
| | mod_base = OTHER | |
| | note = thymine | |
| modified_base | 2772 | |
| | mod_base = OTHER | |
| | note = thymine | |
| modified_base | 2775..2776 | |
| | mod_base = OTHER | |
| | note = thymine | |
| modified_base | 2783 | |
| | mod_base = OTHER | |
| | note = thymine | |
| modified_base | 2786 | |
| | mod_base = OTHER | |
| | note = thymine | |
| modified_base | 2790 | |
| | mod_base = OTHER | |
| | note = thymine | |
| modified_base | 2795..2796 | |
| | mod_base = OTHER | |
| | note = thymine | |
| modified_base | 2798 | |
| | mod_base = OTHER | |
| | note = thymine | |
| modified_base | 2802 | |
| | mod_base = OTHER | |
| | note = thymine | |
| modified_base | 2821 | |
| | mod_base = OTHER | |
| | note = thymine | |
| modified_base | 2824..2825 | |

```
                        mod_base = OTHER
                        note = thymine
modified_base           2827..2828
                        mod_base = OTHER
                        note = thymine
modified_base           2832..2835
                        mod_base = OTHER
                        note = thymine
modified_base           2842
                        mod_base = OTHER
                        note = thymine
modified_base           2844..2846
                        mod_base = OTHER
                        note = thymine
modified_base           2851
                        mod_base = OTHER
                        note = thymine
modified_base           2856
                        mod_base = OTHER
                        note = thymine
modified_base           2861
                        mod_base = OTHER
                        note = thymine
modified_base           2872..2874
                        mod_base = OTHER
                        note = thymine
modified_base           2882..2883
                        mod_base = OTHER
                        note = thymine
modified_base           2886..2887
                        mod_base = OTHER
                        note = thymine
modified_base           2890
                        mod_base = OTHER
                        note = thymine
modified_base           2892..2893
                        mod_base = OTHER
                        note = thymine
modified_base           2898
                        mod_base = OTHER
                        note = thymine
modified_base           2904
                        mod_base = OTHER
                        note = thymine
modified_base           2906..2907
                        mod_base = OTHER
                        note = thymine
modified_base           2909
                        mod_base = OTHER
                        note = thymine
modified_base           2913
                        mod_base = OTHER
                        note = thymine
modified_base           2915
                        mod_base = OTHER
                        note = thymine
modified_base           2917
                        mod_base = OTHER
                        note = thymine
modified_base           2919
                        mod_base = OTHER
                        note = thymine
modified_base           2922
                        mod_base = OTHER
                        note = thymine
modified_base           2924
                        mod_base = OTHER
                        note = thymine
modified_base           2926..2927
                        mod_base = OTHER
                        note = thymine
modified_base           2934..2935
                        mod_base = OTHER
                        note = thymine
modified_base           2937
                        mod_base = OTHER
                        note = thymine
modified_base           2940..2941
                        mod_base = OTHER
```

-continued

| | |
|---|---|
| | note = thymine |
| modified_base | 2950..2951 |
| | mod_base = OTHER |
| | note = thymine |
| modified_base | 2957 |
| | mod_base = OTHER |
| | note = thymine |
| modified_base | 2959 |
| | mod_base = OTHER |
| | note = thymine |
| modified_base | 2967..2968 |
| | mod_base = OTHER |
| | note = thymine |
| modified_base | 2976 |
| | mod_base = OTHER |
| | note = thymine |
| modified_base | 2978 |
| | mod_base = OTHER |
| | note = thymine |
| modified_base | 2980 |
| | mod_base = OTHER |
| | note = thymine |
| modified_base | 2982 |
| | mod_base = OTHER |
| | note = thymine |
| modified_base | 2985 |
| | mod_base = OTHER |
| | note = thymine |
| modified_base | 2987..2988 |
| | mod_base = OTHER |
| | note = thymine |
| modified_base | 2990 |
| | mod_base = OTHER |
| | note = thymine |
| modified_base | 2993 |
| | mod_base = OTHER |
| | note = thymine |
| modified_base | 2995..2996 |
| | mod_base = OTHER |
| | note = thymine |
| modified_base | 2998..3003 |
| | mod_base = OTHER |
| | note = thymine |
| modified_base | 3006..3008 |
| | mod_base = OTHER |
| | note = thymine |
| modified_base | 3010 |
| | mod_base = OTHER |
| | note = thymine |
| modified_base | 3016 |
| | mod_base = OTHER |
| | note = thymine |
| modified_base | 3028 |
| | mod_base = OTHER |
| | note = thymine |
| modified_base | 3032 |
| | mod_base = OTHER |
| | note = thymine |
| modified_base | 3036..3037 |
| | mod_base = OTHER |
| | note = thymine |
| modified_base | 3040 |
| | mod_base = OTHER |
| | note = thymine |
| modified_base | 3044 |
| | mod_base = OTHER |
| | note = thymine |
| modified_base | 3052 |
| | mod_base = OTHER |
| | note = thymine |
| modified_base | 3054 |
| | mod_base = OTHER |
| | note = thymine |
| modified_base | 3061..3062 |
| | mod_base = OTHER |
| | note = thymine |
| modified_base | 3069 |
| | mod_base = OTHER |
| | note = thymine |

-continued

| | |
|---|---|
| modified_base | 3071<br>mod_base = OTHER<br>note = thymine |
| modified_base | 3073..3075<br>mod_base = OTHER<br>note = thymine |
| modified_base | 3078..3079<br>mod_base = OTHER<br>note = thymine |
| modified_base | 3086<br>mod_base = OTHER<br>note = thymine |
| modified_base | 3089<br>mod_base = OTHER<br>note = thymine |
| modified_base | 3092<br>mod_base = OTHER<br>note = thymine |
| modified_base | 3098<br>mod_base = OTHER<br>note = thymine |
| modified_base | 3102<br>mod_base = OTHER<br>note = thymine |
| modified_base | 3104<br>mod_base = OTHER<br>note = thymine |
| modified_base | 3106<br>mod_base = OTHER<br>note = thymine |
| modified_base | 3112<br>mod_base = OTHER<br>note = thymine |
| modified_base | 3114..3116<br>mod_base = OTHER<br>note = thymine |
| modified_base | 3118..3119<br>mod_base = OTHER<br>note = thymine |
| modified_base | 3124<br>mod_base = OTHER<br>note = thymine |
| modified_base | 3128<br>mod_base = OTHER<br>note = thymine |
| modified_base | 3133..3134<br>mod_base = OTHER<br>note = thymine |
| modified_base | 3136..3137<br>mod_base = OTHER<br>note = thymine |
| modified_base | 3142<br>mod_base = OTHER<br>note = thymine |
| modified_base | 3144..3145<br>mod_base = OTHER<br>note = thymine |
| modified_base | 3147..3148<br>mod_base = OTHER<br>note = thymine |
| modified_base | 3155..3158<br>mod_base = OTHER<br>note = thymine |
| modified_base | 3161<br>mod_base = OTHER<br>note = thymine |
| modified_base | 3163..3165<br>mod_base = OTHER<br>note = thymine |
| modified_base | 3167<br>mod_base = OTHER<br>note = thymine |
| modified_base | 3171<br>mod_base = OTHER<br>note = thymine |
| modified_base | 3178<br>mod_base = OTHER<br>note = thymine |
| modified_base | 3184 |

|                |                           |
|----------------|---------------------------|
|                | mod_base = OTHER          |
|                | note = thymine            |
| modified_base  | 3186                      |
|                | mod_base = OTHER          |
|                | note = thymine            |
| modified_base  | 3190                      |
|                | mod_base = OTHER          |
|                | note = thymine            |
| modified_base  | 3192..3193                |
|                | mod_base = OTHER          |
|                | note = thymine            |
| modified_base  | 3196..3197                |
|                | mod_base = OTHER          |
|                | note = thymine            |
| modified_base  | 3202                      |
|                | mod_base = OTHER          |
|                | note = thymine            |
| modified_base  | 3206                      |
|                | mod_base = OTHER          |
|                | note = thymine            |
| modified_base  | 3209                      |
|                | mod_base = OTHER          |
|                | note = thymine            |
| modified_base  | 3211                      |
|                | mod_base = OTHER          |
|                | note = thymine            |
| modified_base  | 3218..3219                |
|                | mod_base = OTHER          |
|                | note = thymine            |
| modified_base  | 3223..3224                |
|                | mod_base = OTHER          |
|                | note = thymine            |
| modified_base  | 3229                      |
|                | mod_base = OTHER          |
|                | note = thymine            |
| modified_base  | 3232..3233                |
|                | mod_base = OTHER          |
|                | note = thymine            |
| modified_base  | 3241                      |
|                | mod_base = OTHER          |
|                | note = thymine            |
| modified_base  | 3247..3248                |
|                | mod_base = OTHER          |
|                | note = thymine            |
| modified_base  | 3254                      |
|                | mod_base = OTHER          |
|                | note = thymine            |
| modified_base  | 3256                      |
|                | mod_base = OTHER          |
|                | note = thymine            |
| modified_base  | 3260                      |
|                | mod_base = OTHER          |
|                | note = thymine            |
| modified_base  | 3264..3265                |
|                | mod_base = OTHER          |
|                | note = thymine            |
| modified_base  | 3269                      |
|                | mod_base = OTHER          |
|                | note = thymine            |
| modified_base  | 3276                      |
|                | mod_base = OTHER          |
|                | note = thymine            |
| modified_base  | 3278                      |
|                | mod_base = OTHER          |
|                | note = thymine            |
| modified_base  | 3281..3282                |
|                | mod_base = OTHER          |
|                | note = thymine            |
| modified_base  | 3289                      |
|                | mod_base = OTHER          |
|                | note = thymine            |
| modified_base  | 3293                      |
|                | mod_base = OTHER          |
|                | note = thymine            |
| modified_base  | 3297                      |
|                | mod_base = OTHER          |
|                | note = thymine            |
| modified_base  | 3299                      |
|                | mod_base = OTHER          |

-continued

```
                        note = thymine
modified_base           3305..3306
                        mod_base = OTHER
                        note = thymine
modified_base           3313
                        mod_base = OTHER
                        note = thymine
modified_base           3315..3317
                        mod_base = OTHER
                        note = thymine
modified_base           3322
                        mod_base = OTHER
                        note = thymine
modified_base           3324
                        mod_base = OTHER
                        note = thymine
modified_base           3329
                        mod_base = OTHER
                        note = thymine
modified_base           3338..3339
                        mod_base = OTHER
                        note = thymine
modified_base           3341
                        mod_base = OTHER
                        note = thymine
modified_base           3344
                        mod_base = OTHER
                        note = thymine
modified_base           3347..3350
                        mod_base = OTHER
                        note = thymine
modified_base           3353
                        mod_base = OTHER
                        note = thymine
modified_base           3355
                        mod_base = OTHER
                        note = thymine
modified_base           3360
                        mod_base = OTHER
                        note = thymine
modified_base           3365..3366
                        mod_base = OTHER
                        note = thymine
modified_base           3369
                        mod_base = OTHER
                        note = thymine
modified_base           3373
                        mod_base = OTHER
                        note = thymine
modified_base           3379
                        mod_base = OTHER
                        note = thymine
modified_base           3381..3382
                        mod_base = OTHER
                        note = thymine
modified_base           3389
                        mod_base = OTHER
                        note = thymine
modified_base           3391
                        mod_base = OTHER
                        note = thymine
modified_base           3395
                        mod_base = OTHER
                        note = thymine
modified_base           3400
                        mod_base = OTHER
                        note = thymine
modified_base           3405
                        mod_base = OTHER
                        note = thymine
modified_base           3407
                        mod_base = OTHER
                        note = thymine
misc_feature            1..3410
                        note = Junin virus strain Candid #1 segment S,
                         completesequence.-ACCESSION FJ969442-VERSION
                         FJ969442.1-GI:264665554 - Viruses; ssRNA viruses; ssRNA
                         negative-strand viruses; Arenaviridae; Mammarenavirus.
source                  1..3410
```

```
                    mol_type = other RNA
                    organism = unidentified
SEQUENCE: 3
cgcacagtgg atcctaggcg attttggtta cgctataatt gtaactgttt tctgtttgga    60
caacatcaaa aacatccatt gcacaatggg gcagttcatt agcttcatgc aagaaatacc   120
aaccttttg caggaggctc tgaacattgc tcttgttgca gtcagtctca ttgccatcat    180
taagggtgta gtgaacctgt acaaaagtgg tttgttccaa ttctttgtat tcctagcact   240
cgcaggaaga tcctgcacag aagaagcttt taaaatcgga ctgcacacag agttccagac   300
tgtgtccttc tcaatggtgg gtctcttttc caacaatcca catgacctgc ctctgttgtg   360
taccttaaac aagagccatc tttacattaa gggggggcaat gcttcatttc agatcagctt   420
tgatgatatt gcagtattgt tgccacagta tgatgttata atacaacatc cagcagatat   480
gagctggtgt tccaaaagtg atgatcaaat ttggttgtct cagtggttca tgaatgctgt   540
gggacatgat tggcatctag acccaccatt tctgtgtagg aaccgtgcaa agacagaagg   600
cttcatcttt caagtcaaca cctccaagac tggtgtcaat ggaaatttatg ctaagaagtt   660
taagactggc atgcatcatt tatatagaga atatcctgac ccttgcttga atggcaaact   720
gtgcttaatg aaggcacaac ctaccagttg gcctctccaa tgtccactcg accacgttaa   780
cacattacac ttccttacaa gaggtaaaaa cattcaactt ccaaggaggt ccttgaaagc   840
attcttctcc tggtctttga cagactcatc cggcaaggat acccctggag gctattgtct   900
agaagagtgg atgctcgttg cagccaaaat gaagtgtttt ggcaatactg ctgtagcaaa   960
atgcaatctg aatcatgact ctgaattctg tgacatgctg aggctttttg attacaacaa  1020
aaatgctatc aaaaccttaa atgatgaaac taagaaacaa gtaaatctga tgggacagac  1080
aatcaatgcg ctgatatctg acaatttatt gatgaaaaac aaaattaggg aactgatgag  1140
tgtcccttac tgcaattaca caaaattttg gtatgtcaac cacacacttt caggacaaca  1200
ctcattacca aggtgctggt taataaaaaa caacagctat ttgaacatct ctgacttccg  1260
taatgactgg atattagaaa gtgacttctt aatttctgaa atgctaagca aagagtattc  1320
ggacaggcag ggtaaaactc cttttgacttt agttgacatc tgtatttgga gcacagtatt  1380
cttcacagcg tcactcttcc ttcacttggt gggtataccc tcccacagac acatcagggg  1440
cgaagcatgc cctttgccac acaggttgaa cagcttgggt ggttgcagat gtggtaagta  1500
ccccaatcta aagaaaccaa cagtttggcg tagaggacac taagacctcc tgagggtccc  1560
caccagccg ggcactgccc gggctggtgt ggcccccag tccgcgggcct ggccgcgac   1620
tgggaggca ctgcttacag tgcataggct gccttcggga ggaacagcaa gctcggtggt  1680
aatagaggtg taggttcctc ctcatagagc ttcccatcta gcactgactg aaacattatg  1740
cagtctagca gagcacagtg tggttcactg gaggccaact tgaagggagt atcctttcc   1800
ctcttttct tattgacaac cactccattg tgatatttgc ataagtgcc atatttcctc    1860
cagacctgtt gatcaaactg cctggcttgt tcagtgtga gcttaacatc aaccagttta  1920
agatctcttc ttccatggag gtcaaacaac ttcctgatgt catcggatcc ttgagtagtc  1980
acaaccatgt ctgaggcag caagccgatc acgtaactaa gaactcctgg cattgcatct   2040
tctatgtctt tcattaagat gccgtgagag tgtctgctac cattttttaaa cccttctca   2100
tcatgtggtt ttctgaagca gtgaatatac tgcttacctg caggctgaca caacgccatc  2160
tcaacagggt cagtagctgg tccttcaatg tcgagccaaa gggtattggt ggggtcgagt  2220
ttccccactg cctctctgat gacagcttct tgtatctctg tcaagttagc caatctcaaa  2280
ttctgaccgt tcttttccgg ttgtctaggt ccagcaactg gttcttgt cagatcaata   2340
cttgtgttgt cccatgacct gcctatgatt tgtgatctgg aaccaataa aggccaacca  2400
tcgccagaaa ggcaaagttt gtacagaagg ttttcataag gtttctatt gcctggttc    2460
tcatcaataa acatgccttc tcttcgttta acctgaatgg ttgattttat gagggaagaa  2520
aagttatctg gggtgactct gattgtctcc aacatatttc caccatcaag aatggatgca  2580
ccagccttta ctgcagctga aagactaaag ttgtagccag aaatgttgat ggagctttca  2640
tccttagtca caatctggag gcagtcatgt tcctgagtca atctgtcaag gtcactcaag  2700
tttggatact tcagagtgta tagaagccca agagaggtta aagcctgtat gacactgttc  2760
attgtctcac ctccttgaac agtcatgcat gcaattgtca atgcaggaac agaaccaaac  2820
tgattgttaa gttttgaagg atctttaaca tcccataccc tcaccacac atttcccca    2880
gttccttgct gttgaaatcc cagtgttctc aatatctctg atctcttggc cagttgtgat  2940
tgagacaagt tacccatgta aacccttga gagcctgtct ctgctcttct aatcttgttt   3000
tttaatttct caaggtcaga cgccaactcc atcagttcat ccctcccag atctcccacc   3060
ttgaaaactg tgttcgttg aacactcctc atggacatga gtctgtcaac ctctttattc   3120
aggtccctca acttattgag gtcttcttcc cccctttag tctttctgag tgcccgctgt   3180
acctgtgcct cttggttgaa gtcaatgctg tcagcaatta gcttggcatc cttcagaaca  3240
tccgacttga cagtctgagt aaattgactc aaacctctcc ttaaggactg agtccatcta  3300
aagcttggaa cctctttgga gtgtgccatg ccagaagttc tggtgatttt gatctagaat  3360
agagttgctc agtgaaagtg ttagacacta tgcctaggat ccactgtgcg              3410

SEQ ID NO: 4           moltype = RNA   length = 7114
FEATURE                Location/Qualifiers
modified_base          8
                       mod_base = OTHER
                       note = thymine
modified_base          12
                       mod_base = OTHER
                       note = thymine
modified_base          15
                       mod_base = OTHER
                       note = thymine
modified_base          21
                       mod_base = OTHER
                       note = thymine
modified_base          25..26
                       mod_base = OTHER
                       note = thymine
modified_base          29
```

-continued

```
                                mod_base = OTHER
                                note = thymine
modified_base   32..33
                                mod_base = OTHER
                                note = thymine
modified_base   38
                                mod_base = OTHER
                                note = thymine
modified_base   40
                                mod_base = OTHER
                                note = thymine
modified_base   45..46
                                mod_base = OTHER
                                note = thymine
modified_base   48
                                mod_base = OTHER
                                note = thymine
modified_base   51
                                mod_base = OTHER
                                note = thymine
modified_base   53
                                mod_base = OTHER
                                note = thymine
modified_base   57
                                mod_base = OTHER
                                note = thymine
modified_base   59
                                mod_base = OTHER
                                note = thymine
modified_base   63..64
                                mod_base = OTHER
                                note = thymine
modified_base   67
                                mod_base = OTHER
                                note = thymine
modified_base   85
                                mod_base = OTHER
                                note = thymine
modified_base   93
                                mod_base = OTHER
                                note = thymine
modified_base   105
                                mod_base = OTHER
                                note = thymine
modified_base   111
                                mod_base = OTHER
                                note = thymine
modified_base   113
                                mod_base = OTHER
                                note = thymine
modified_base   126
                                mod_base = OTHER
                                note = thymine
modified_base   129
                                mod_base = OTHER
                                note = thymine
modified_base   156..158
                                mod_base = OTHER
                                note = thymine
modified_base   166
                                mod_base = OTHER
                                note = thymine
modified_base   170
                                mod_base = OTHER
                                note = thymine
modified_base   179
                                mod_base = OTHER
                                note = thymine
modified_base   181
                                mod_base = OTHER
                                note = thymine
modified_base   183
                                mod_base = OTHER
                                note = thymine
modified_base   185
                                mod_base = OTHER
                                note = thymine
modified_base   188
                                mod_base = OTHER
```

-continued

| | | |
|---|---|---|
| | | note = thymine |
| modified_base | 192 | |
| | | mod_base = OTHER |
| | | note = thymine |
| modified_base | 194 | |
| | | mod_base = OTHER |
| | | note = thymine |
| modified_base | 198 | |
| | | mod_base = OTHER |
| | | note = thymine |
| modified_base | 200 | |
| | | mod_base = OTHER |
| | | note = thymine |
| modified_base | 204 | |
| | | mod_base = OTHER |
| | | note = thymine |
| modified_base | 207 | |
| | | mod_base = OTHER |
| | | note = thymine |
| modified_base | 210 | |
| | | mod_base = OTHER |
| | | note = thymine |
| modified_base | 213..215 | |
| | | mod_base = OTHER |
| | | note = thymine |
| modified_base | 218 | |
| | | mod_base = OTHER |
| | | note = thymine |
| modified_base | 221 | |
| | | mod_base = OTHER |
| | | note = thymine |
| modified_base | 227..229 | |
| | | mod_base = OTHER |
| | | note = thymine |
| modified_base | 232 | |
| | | mod_base = OTHER |
| | | note = thymine |
| modified_base | 237 | |
| | | mod_base = OTHER |
| | | note = thymine |
| modified_base | 239 | |
| | | mod_base = OTHER |
| | | note = thymine |
| modified_base | 242 | |
| | | mod_base = OTHER |
| | | note = thymine |
| modified_base | 245 | |
| | | mod_base = OTHER |
| | | note = thymine |
| modified_base | 249 | |
| | | mod_base = OTHER |
| | | note = thymine |
| modified_base | 253..255 | |
| | | mod_base = OTHER |
| | | note = thymine |
| modified_base | 257..259 | |
| | | mod_base = OTHER |
| | | note = thymine |
| modified_base | 264 | |
| | | mod_base = OTHER |
| | | note = thymine |
| modified_base | 269 | |
| | | mod_base = OTHER |
| | | note = thymine |
| modified_base | 275 | |
| | | mod_base = OTHER |
| | | note = thymine |
| modified_base | 277 | |
| | | mod_base = OTHER |
| | | note = thymine |
| modified_base | 279..280 | |
| | | mod_base = OTHER |
| | | note = thymine |
| modified_base | 287..288 | |
| | | mod_base = OTHER |
| | | note = thymine |
| modified_base | 293 | |
| | | mod_base = OTHER |
| | | note = thymine |

-continued

| | | |
|---|---|---|
| modified_base | 295 | |
| | mod_base = OTHER | |
| | note = thymine | |
| modified_base | 297 | |
| | mod_base = OTHER | |
| | note = thymine | |
| modified_base | 302 | |
| | mod_base = OTHER | |
| | note = thymine | |
| modified_base | 304 | |
| | mod_base = OTHER | |
| | note = thymine | |
| modified_base | 306 | |
| | mod_base = OTHER | |
| | note = thymine | |
| modified_base | 309 | |
| | mod_base = OTHER | |
| | note = thymine | |
| modified_base | 319 | |
| | mod_base = OTHER | |
| | note = thymine | |
| modified_base | 331 | |
| | mod_base = OTHER | |
| | note = thymine | |
| modified_base | 337 | |
| | mod_base = OTHER | |
| | note = thymine | |
| modified_base | 343 | |
| | mod_base = OTHER | |
| | note = thymine | |
| modified_base | 366 | |
| | mod_base = OTHER | |
| | note = thymine | |
| modified_base | 375 | |
| | mod_base = OTHER | |
| | note = thymine | |
| modified_base | 384 | |
| | mod_base = OTHER | |
| | note = thymine | |
| modified_base | 412 | |
| | mod_base = OTHER | |
| | note = thymine | |
| modified_base | 425 | |
| | mod_base = OTHER | |
| | note = thymine | |
| modified_base | 442 | |
| | mod_base = OTHER | |
| | note = thymine | |
| modified_base | 445 | |
| | mod_base = OTHER | |
| | note = thymine | |
| modified_base | 452..453 | |
| | mod_base = OTHER | |
| | note = thymine | |
| modified_base | 456 | |
| | mod_base = OTHER | |
| | note = thymine | |
| modified_base | 460 | |
| | mod_base = OTHER | |
| | note = thymine | |
| modified_base | 462 | |
| | mod_base = OTHER | |
| | note = thymine | |
| modified_base | 464..466 | |
| | mod_base = OTHER | |
| | note = thymine | |
| modified_base | 469 | |
| | mod_base = OTHER | |
| | note = thymine | |
| modified_base | 471 | |
| | mod_base = OTHER | |
| | note = thymine | |
| modified_base | 476..478 | |
| | mod_base = OTHER | |
| | note = thymine | |
| modified_base | 480 | |
| | mod_base = OTHER | |
| | note = thymine | |
| modified_base | 483..484 | |

-continued

```
                         mod_base = OTHER
                         note = thymine
modified_base   488
                         mod_base = OTHER
                         note = thymine
modified_base   493
                         mod_base = OTHER
                         note = thymine
modified_base   497
                         mod_base = OTHER
                         note = thymine
modified_base   499
                         mod_base = OTHER
                         note = thymine
modified_base   506..508
                         mod_base = OTHER
                         note = thymine
modified_base   512
                         mod_base = OTHER
                         note = thymine
modified_base   514
                         mod_base = OTHER
                         note = thymine
modified_base   519
                         mod_base = OTHER
                         note = thymine
modified_base   524..525
                         mod_base = OTHER
                         note = thymine
modified_base   531
                         mod_base = OTHER
                         note = thymine
modified_base   533
                         mod_base = OTHER
                         note = thymine
modified_base   536
                         mod_base = OTHER
                         note = thymine
modified_base   538
                         mod_base = OTHER
                         note = thymine
modified_base   546
                         mod_base = OTHER
                         note = thymine
modified_base   549..551
                         mod_base = OTHER
                         note = thymine
modified_base   557
                         mod_base = OTHER
                         note = thymine
modified_base   559
                         mod_base = OTHER
                         note = thymine
modified_base   562
                         mod_base = OTHER
                         note = thymine
modified_base   566
                         mod_base = OTHER
                         note = thymine
modified_base   573..574
                         mod_base = OTHER
                         note = thymine
modified_base   579..581
                         mod_base = OTHER
                         note = thymine
modified_base   587..588
                         mod_base = OTHER
                         note = thymine
modified_base   597
                         mod_base = OTHER
                         note = thymine
modified_base   605..607
                         mod_base = OTHER
                         note = thymine
modified_base   609
                         mod_base = OTHER
                         note = thymine
modified_base   614
                         mod_base = OTHER
```

| | | |
|---|---|---|
| | note = thymine | |
| modified_base | 622 | |
| | mod_base = OTHER | |
| | note = thymine | |
| modified_base | 627 | |
| | mod_base = OTHER | |
| | note = thymine | |
| modified_base | 630 | |
| | mod_base = OTHER | |
| | note = thymine | |
| modified_base | 632..634 | |
| | mod_base = OTHER | |
| | note = thymine | |
| modified_base | 636 | |
| | mod_base = OTHER | |
| | note = thymine | |
| modified_base | 638 | |
| | mod_base = OTHER | |
| | note = thymine | |
| modified_base | 642 | |
| | mod_base = OTHER | |
| | note = thymine | |
| modified_base | 645 | |
| | mod_base = OTHER | |
| | note = thymine | |
| modified_base | 660 | |
| | mod_base = OTHER | |
| | note = thymine | |
| modified_base | 663 | |
| | mod_base = OTHER | |
| | note = thymine | |
| modified_base | 665..666 | |
| | mod_base = OTHER | |
| | note = thymine | |
| modified_base | 669 | |
| | mod_base = OTHER | |
| | note = thymine | |
| modified_base | 674 | |
| | mod_base = OTHER | |
| | note = thymine | |
| modified_base | 677 | |
| | mod_base = OTHER | |
| | note = thymine | |
| modified_base | 679..680 | |
| | mod_base = OTHER | |
| | note = thymine | |
| modified_base | 682..684 | |
| | mod_base = OTHER | |
| | note = thymine | |
| modified_base | 686 | |
| | mod_base = OTHER | |
| | note = thymine | |
| modified_base | 689 | |
| | mod_base = OTHER | |
| | note = thymine | |
| modified_base | 691..692 | |
| | mod_base = OTHER | |
| | note = thymine | |
| modified_base | 694..698 | |
| | mod_base = OTHER | |
| | note = thymine | |
| modified_base | 702 | |
| | mod_base = OTHER | |
| | note = thymine | |
| modified_base | 710 | |
| | mod_base = OTHER | |
| | note = thymine | |
| modified_base | 713..714 | |
| | mod_base = OTHER | |
| | note = thymine | |
| modified_base | 718..719 | |
| | mod_base = OTHER | |
| | note = thymine | |
| modified_base | 722 | |
| | mod_base = OTHER | |
| | note = thymine | |
| modified_base | 727..729 | |
| | mod_base = OTHER | |
| | note = thymine | |

-continued

| | | |
|---|---|---|
| modified_base | 736 | |
| | mod_base = OTHER | |
| | note = thymine | |
| modified_base | 738 | |
| | mod_base = OTHER | |
| | note = thymine | |
| modified_base | 742 | |
| | mod_base = OTHER | |
| | note = thymine | |
| modified_base | 744 | |
| | mod_base = OTHER | |
| | note = thymine | |
| modified_base | 747 | |
| | mod_base = OTHER | |
| | note = thymine | |
| modified_base | 749 | |
| | mod_base = OTHER | |
| | note = thymine | |
| modified_base | 752 | |
| | mod_base = OTHER | |
| | note = thymine | |
| modified_base | 755 | |
| | mod_base = OTHER | |
| | note = thymine | |
| modified_base | 760..761 | |
| | mod_base = OTHER | |
| | note = thymine | |
| modified_base | 765..766 | |
| | mod_base = OTHER | |
| | note = thymine | |
| modified_base | 770 | |
| | mod_base = OTHER | |
| | note = thymine | |
| modified_base | 772 | |
| | mod_base = OTHER | |
| | note = thymine | |
| modified_base | 777 | |
| | mod_base = OTHER | |
| | note = thymine | |
| modified_base | 789 | |
| | mod_base = OTHER | |
| | note = thymine | |
| modified_base | 794 | |
| | mod_base = OTHER | |
| | note = thymine | |
| modified_base | 796 | |
| | mod_base = OTHER | |
| | note = thymine | |
| modified_base | 798 | |
| | mod_base = OTHER | |
| | note = thymine | |
| modified_base | 800 | |
| | mod_base = OTHER | |
| | note = thymine | |
| modified_base | 802..803 | |
| | mod_base = OTHER | |
| | note = thymine | |
| modified_base | 811..813 | |
| | mod_base = OTHER | |
| | note = thymine | |
| modified_base | 816..817 | |
| | mod_base = OTHER | |
| | note = thymine | |
| modified_base | 821 | |
| | mod_base = OTHER | |
| | note = thymine | |
| modified_base | 823 | |
| | mod_base = OTHER | |
| | note = thymine | |
| modified_base | 825 | |
| | mod_base = OTHER | |
| | note = thymine | |
| modified_base | 832 | |
| | mod_base = OTHER | |
| | note = thymine | |
| modified_base | 837 | |
| | mod_base = OTHER | |
| | note = thymine | |
| modified_base | 839..841 | |

-continued

```
                             mod_base = OTHER
                             note = thymine
modified_base    854..855
                             mod_base = OTHER
                             note = thymine
modified_base    857
                             mod_base = OTHER
                             note = thymine
modified_base    860
                             mod_base = OTHER
                             note = thymine
modified_base    864..865
                             mod_base = OTHER
                             note = thymine
modified_base    867
                             mod_base = OTHER
                             note = thymine
modified_base    869
                             mod_base = OTHER
                             note = thymine
modified_base    877
                             mod_base = OTHER
                             note = thymine
modified_base    882
                             mod_base = OTHER
                             note = thymine
modified_base    885
                             mod_base = OTHER
                             note = thymine
modified_base    887
                             mod_base = OTHER
                             note = thymine
modified_base    891
                             mod_base = OTHER
                             note = thymine
modified_base    894..895
                             mod_base = OTHER
                             note = thymine
modified_base    897..898
                             mod_base = OTHER
                             note = thymine
modified_base    901..902
                             mod_base = OTHER
                             note = thymine
modified_base    905..906
                             mod_base = OTHER
                             note = thymine
modified_base    912
                             mod_base = OTHER
                             note = thymine
modified_base    918
                             mod_base = OTHER
                             note = thymine
modified_base    927..928
                             mod_base = OTHER
                             note = thymine
modified_base    933..934
                             mod_base = OTHER
                             note = thymine
modified_base    939
                             mod_base = OTHER
                             note = thymine
modified_base    943
                             mod_base = OTHER
                             note = thymine
modified_base    949
                             mod_base = OTHER
                             note = thymine
modified_base    951..952
                             mod_base = OTHER
                             note = thymine
modified_base    954
                             mod_base = OTHER
                             note = thymine
modified_base    957
                             mod_base = OTHER
                             note = thymine
modified_base    960..962
                             mod_base = OTHER
```

```
                     note = thymine
modified_base        964
                     mod_base = OTHER
                     note = thymine
modified_base        972
                     mod_base = OTHER
                     note = thymine
modified_base        977
                     mod_base = OTHER
                     note = thymine
modified_base        981
                     mod_base = OTHER
                     note = thymine
modified_base        985
                     mod_base = OTHER
                     note = thymine
modified_base        998
                     mod_base = OTHER
                     note = thymine
modified_base        1002
                     mod_base = OTHER
                     note = thymine
modified_base        1009
                     mod_base = OTHER
                     note = thymine
modified_base        1011
                     mod_base = OTHER
                     note = thymine
modified_base        1014
                     mod_base = OTHER
                     note = thymine
modified_base        1019
                     mod_base = OTHER
                     note = thymine
modified_base        1021
                     mod_base = OTHER
                     note = thymine
modified_base        1028
                     mod_base = OTHER
                     note = thymine
modified_base        1031
                     mod_base = OTHER
                     note = thymine
modified_base        1036
                     mod_base = OTHER
                     note = thymine
modified_base        1042
                     mod_base = OTHER
                     note = thymine
modified_base        1049
                     mod_base = OTHER
                     note = thymine
modified_base        1056
                     mod_base = OTHER
                     note = thymine
modified_base        1064
                     mod_base = OTHER
                     note = thymine
modified_base        1068
                     mod_base = OTHER
                     note = thymine
modified_base        1072..1073
                     mod_base = OTHER
                     note = thymine
modified_base        1077
                     mod_base = OTHER
                     note = thymine
modified_base        1094..1095
                     mod_base = OTHER
                     note = thymine
modified_base        1099
                     mod_base = OTHER
                     note = thymine
modified_base        1102..1103
                     mod_base = OTHER
                     note = thymine
modified_base        1107
                     mod_base = OTHER
                     note = thymine
```

-continued

| | | |
|---|---|---|
| modified_base | 1113..1114 | |
| | mod_base = OTHER | |
| | note = thymine | |
| modified_base | 1119 | |
| | mod_base = OTHER | |
| | note = thymine | |
| modified_base | 1121 | |
| | mod_base = OTHER | |
| | note = thymine | |
| modified_base | 1124..1125 | |
| | mod_base = OTHER | |
| | note = thymine | |
| modified_base | 1132 | |
| | mod_base = OTHER | |
| | note = thymine | |
| modified_base | 1140 | |
| | mod_base = OTHER | |
| | note = thymine | |
| modified_base | 1143 | |
| | mod_base = OTHER | |
| | note = thymine | |
| modified_base | 1148 | |
| | mod_base = OTHER | |
| | note = thymine | |
| modified_base | 1151 | |
| | mod_base = OTHER | |
| | note = thymine | |
| modified_base | 1154 | |
| | mod_base = OTHER | |
| | note = thymine | |
| modified_base | 1159 | |
| | mod_base = OTHER | |
| | note = thymine | |
| modified_base | 1165 | |
| | mod_base = OTHER | |
| | note = thymine | |
| modified_base | 1168 | |
| | mod_base = OTHER | |
| | note = thymine | |
| modified_base | 1170 | |
| | mod_base = OTHER | |
| | note = thymine | |
| modified_base | 1174 | |
| | mod_base = OTHER | |
| | note = thymine | |
| modified_base | 1176 | |
| | mod_base = OTHER | |
| | note = thymine | |
| modified_base | 1183 | |
| | mod_base = OTHER | |
| | note = thymine | |
| modified_base | 1185..1187 | |
| | mod_base = OTHER | |
| | note = thymine | |
| modified_base | 1189..1190 | |
| | mod_base = OTHER | |
| | note = thymine | |
| modified_base | 1192 | |
| | mod_base = OTHER | |
| | note = thymine | |
| modified_base | 1196..1198 | |
| | mod_base = OTHER | |
| | note = thymine | |
| modified_base | 1202..1205 | |
| | mod_base = OTHER | |
| | note = thymine | |
| modified_base | 1207 | |
| | mod_base = OTHER | |
| | note = thymine | |
| modified_base | 1214 | |
| | mod_base = OTHER | |
| | note = thymine | |
| modified_base | 1217 | |
| | mod_base = OTHER | |
| | note = thymine | |
| modified_base | 1219 | |
| | mod_base = OTHER | |
| | note = thymine | |
| modified_base | 1221 | |

```
                              mod_base = OTHER
                              note = thymine
modified_base   1223..1224
                              mod_base = OTHER
                              note = thymine
modified_base   1226
                              mod_base = OTHER
                              note = thymine
modified_base   1229..1230
                              mod_base = OTHER
                              note = thymine
modified_base   1234
                              mod_base = OTHER
                              note = thymine
modified_base   1237
                              mod_base = OTHER
                              note = thymine
modified_base   1241..1244
                              mod_base = OTHER
                              note = thymine
modified_base   1247..1249
                              mod_base = OTHER
                              note = thymine
modified_base   1256..1257
                              mod_base = OTHER
                              note = thymine
modified_base   1259..1260
                              mod_base = OTHER
                              note = thymine
modified_base   1272..1273
                              mod_base = OTHER
                              note = thymine
modified_base   1285
                              mod_base = OTHER
                              note = thymine
modified_base   1287
                              mod_base = OTHER
                              note = thymine
modified_base   1293
                              mod_base = OTHER
                              note = thymine
modified_base   1297
                              mod_base = OTHER
                              note = thymine
modified_base   1300
                              mod_base = OTHER
                              note = thymine
modified_base   1302
                              mod_base = OTHER
                              note = thymine
modified_base   1304..1305
                              mod_base = OTHER
                              note = thymine
modified_base   1308
                              mod_base = OTHER
                              note = thymine
modified_base   1324
                              mod_base = OTHER
                              note = thymine
modified_base   1326..1327
                              mod_base = OTHER
                              note = thymine
modified_base   1329
                              mod_base = OTHER
                              note = thymine
modified_base   1344
                              mod_base = OTHER
                              note = thymine
modified_base   1356..1357
                              mod_base = OTHER
                              note = thymine
modified_base   1360
                              mod_base = OTHER
                              note = thymine
modified_base   1362..1363
                              mod_base = OTHER
                              note = thymine
modified_base   1365
                              mod_base = OTHER
```

-continued

```
                        note = thymine
modified_base           1372
                        mod_base = OTHER
                        note = thymine
modified_base           1379
                        mod_base = OTHER
                        note = thymine
modified_base           1383
                        mod_base = OTHER
                        note = thymine
modified_base           1390..1391
                        mod_base = OTHER
                        note = thymine
modified_base           1396
                        mod_base = OTHER
                        note = thymine
modified_base           1398
                        mod_base = OTHER
                        note = thymine
modified_base           1400..1401
                        mod_base = OTHER
                        note = thymine
modified_base           1411..1412
                        mod_base = OTHER
                        note = thymine
modified_base           1415
                        mod_base = OTHER
                        note = thymine
modified_base           1417..1418
                        mod_base = OTHER
                        note = thymine
modified_base           1421
                        mod_base = OTHER
                        note = thymine
modified_base           1424..1426
                        mod_base = OTHER
                        note = thymine
modified_base           1428..1429
                        mod_base = OTHER
                        note = thymine
modified_base           1431..1432
                        mod_base = OTHER
                        note = thymine
modified_base           1435
                        mod_base = OTHER
                        note = thymine
modified_base           1439
                        mod_base = OTHER
                        note = thymine
modified_base           1447
                        mod_base = OTHER
                        note = thymine
modified_base           1452
                        mod_base = OTHER
                        note = thymine
modified_base           1454
                        mod_base = OTHER
                        note = thymine
modified_base           1456
                        mod_base = OTHER
                        note = thymine
modified_base           1460..1461
                        mod_base = OTHER
                        note = thymine
modified_base           1466
                        mod_base = OTHER
                        note = thymine
modified_base           1470
                        mod_base = OTHER
                        note = thymine
modified_base           1472
                        mod_base = OTHER
                        note = thymine
modified_base           1475..1476
                        mod_base = OTHER
                        note = thymine
modified_base           1480
                        mod_base = OTHER
                        note = thymine
```

-continued

| | | |
|---|---|---|
| modified_base | 1482 | |
| | mod_base = OTHER | |
| | note = thymine | |
| modified_base | 1485 | |
| | mod_base = OTHER | |
| | note = thymine | |
| modified_base | 1487..1488 | |
| | mod_base = OTHER | |
| | note = thymine | |
| modified_base | 1490 | |
| | mod_base = OTHER | |
| | note = thymine | |
| modified_base | 1494 | |
| | mod_base = OTHER | |
| | note = thymine | |
| modified_base | 1496 | |
| | mod_base = OTHER | |
| | note = thymine | |
| modified_base | 1502..1503 | |
| | mod_base = OTHER | |
| | note = thymine | |
| modified_base | 1506..1507 | |
| | mod_base = OTHER | |
| | note = thymine | |
| modified_base | 1523..1525 | |
| | mod_base = OTHER | |
| | note = thymine | |
| modified_base | 1535 | |
| | mod_base = OTHER | |
| | note = thymine | |
| modified_base | 1537..1538 | |
| | mod_base = OTHER | |
| | note = thymine | |
| modified_base | 1543 | |
| | mod_base = OTHER | |
| | note = thymine | |
| modified_base | 1547 | |
| | mod_base = OTHER | |
| | note = thymine | |
| modified_base | 1550 | |
| | mod_base = OTHER | |
| | note = thymine | |
| modified_base | 1554..1556 | |
| | mod_base = OTHER | |
| | note = thymine | |
| modified_base | 1558 | |
| | mod_base = OTHER | |
| | note = thymine | |
| modified_base | 1561 | |
| | mod_base = OTHER | |
| | note = thymine | |
| modified_base | 1568 | |
| | mod_base = OTHER | |
| | note = thymine | |
| modified_base | 1577..1578 | |
| | mod_base = OTHER | |
| | note = thymine | |
| modified_base | 1585 | |
| | mod_base = OTHER | |
| | note = thymine | |
| modified_base | 1590..1591 | |
| | mod_base = OTHER | |
| | note = thymine | |
| modified_base | 1594 | |
| | mod_base = OTHER | |
| | note = thymine | |
| modified_base | 1601..1602 | |
| | mod_base = OTHER | |
| | note = thymine | |
| modified_base | 1605 | |
| | mod_base = OTHER | |
| | note = thymine | |
| modified_base | 1607 | |
| | mod_base = OTHER | |
| | note = thymine | |
| modified_base | 1612 | |
| | mod_base = OTHER | |
| | note = thymine | |
| modified_base | 1615 | |

```
                              mod_base = OTHER
                              note = thymine
modified_base                 1622..1623
                              mod_base = OTHER
                              note = thymine
modified_base                 1629..1631
                              mod_base = OTHER
                              note = thymine
modified_base                 1633
                              mod_base = OTHER
                              note = thymine
modified_base                 1635
                              mod_base = OTHER
                              note = thymine
modified_base                 1638
                              mod_base = OTHER
                              note = thymine
modified_base                 1640
                              mod_base = OTHER
                              note = thymine
modified_base                 1644
                              mod_base = OTHER
                              note = thymine
modified_base                 1646
                              mod_base = OTHER
                              note = thymine
modified_base                 1648
                              mod_base = OTHER
                              note = thymine
modified_base                 1653
                              mod_base = OTHER
                              note = thymine
modified_base                 1658
                              mod_base = OTHER
                              note = thymine
modified_base                 1668
                              mod_base = OTHER
                              note = thymine
modified_base                 1672
                              mod_base = OTHER
                              note = thymine
modified_base                 1674
                              mod_base = OTHER
                              note = thymine
modified_base                 1676..1678
                              mod_base = OTHER
                              note = thymine
modified_base                 1684
                              mod_base = OTHER
                              note = thymine
modified_base                 1686
                              mod_base = OTHER
                              note = thymine
modified_base                 1692..1693
                              mod_base = OTHER
                              note = thymine
modified_base                 1695..1696
                              mod_base = OTHER
                              note = thymine
modified_base                 1698
                              mod_base = OTHER
                              note = thymine
modified_base                 1700
                              mod_base = OTHER
                              note = thymine
modified_base                 1702..1703
                              mod_base = OTHER
                              note = thymine
modified_base                 1706..1708
                              mod_base = OTHER
                              note = thymine
modified_base                 1712
                              mod_base = OTHER
                              note = thymine
modified_base                 1716
                              mod_base = OTHER
                              note = thymine
modified_base                 1720..1721
                              mod_base = OTHER
```

-continued

| | | |
|---|---|---|
| modified_base | 1723 | |
| | mod_base = OTHER | |
| | note = thymine | |
| modified_base | 1726 | |
| | mod_base = OTHER | |
| | note = thymine | |
| modified_base | 1730 | |
| | mod_base = OTHER | |
| | note = thymine | |
| modified_base | 1734..1737 | |
| | mod_base = OTHER | |
| | note = thymine | |
| modified_base | 1740..1741 | |
| | mod_base = OTHER | |
| | note = thymine | |
| modified_base | 1744 | |
| | mod_base = OTHER | |
| | note = thymine | |
| modified_base | 1747 | |
| | mod_base = OTHER | |
| | note = thymine | |
| modified_base | 1749 | |
| | mod_base = OTHER | |
| | note = thymine | |
| modified_base | 1751 | |
| | mod_base = OTHER | |
| | note = thymine | |
| modified_base | 1767 | |
| | mod_base = OTHER | |
| | note = thymine | |
| modified_base | 1769 | |
| | mod_base = OTHER | |
| | note = thymine | |
| modified_base | 1776..1777 | |
| | mod_base = OTHER | |
| | note = thymine | |
| modified_base | 1781 | |
| | mod_base = OTHER | |
| | note = thymine | |
| modified_base | 1783..1784 | |
| | mod_base = OTHER | |
| | note = thymine | |
| modified_base | 1789 | |
| | mod_base = OTHER | |
| | note = thymine | |
| modified_base | 1791 | |
| | mod_base = OTHER | |
| | note = thymine | |
| modified_base | 1799 | |
| | mod_base = OTHER | |
| | note = thymine | |
| modified_base | 1801 | |
| | mod_base = OTHER | |
| | note = thymine | |
| modified_base | 1803..1804 | |
| | mod_base = OTHER | |
| | note = thymine | |
| modified_base | 1808..1809 | |
| | mod_base = OTHER | |
| | note = thymine | |
| modified_base | 1815 | |
| | mod_base = OTHER | |
| | note = thymine | |
| modified_base | 1818..1819 | |
| | mod_base = OTHER | |
| | note = thymine | |
| modified_base | 1822 | |
| | mod_base = OTHER | |
| | note = thymine | |
| modified_base | 1829 | |
| | mod_base = OTHER | |
| | note = thymine | |
| modified_base | 1836 | |
| | mod_base = OTHER | |
| | note = thymine | |
| modified_base | 1838..1839 | |
| | mod_base = OTHER | |
| | note = thymine | |

-continued

| | | |
|---|---|---|
| modified_base | 1841..1842<br>mod_base = OTHER<br>note = thymine | |
| modified_base | 1847<br>mod_base = OTHER<br>note = thymine | |
| modified_base | 1850..1852<br>mod_base = OTHER<br>note = thymine | |
| modified_base | 1857<br>mod_base = OTHER<br>note = thymine | |
| modified_base | 1860..1862<br>mod_base = OTHER<br>note = thymine | |
| modified_base | 1864..1865<br>mod_base = OTHER<br>note = thymine | |
| modified_base | 1868<br>mod_base = OTHER<br>note = thymine | |
| modified_base | 1870<br>mod_base = OTHER<br>note = thymine | |
| modified_base | 1875<br>mod_base = OTHER<br>note = thymine | |
| modified_base | 1880<br>mod_base = OTHER<br>note = thymine | |
| modified_base | 1884<br>mod_base = OTHER<br>note = thymine | |
| modified_base | 1887..1888<br>mod_base = OTHER<br>note = thymine | |
| modified_base | 1891<br>mod_base = OTHER<br>note = thymine | |
| modified_base | 1895<br>mod_base = OTHER<br>note = thymine | |
| modified_base | 1898..1899<br>mod_base = OTHER<br>note = thymine | |
| modified_base | 1902<br>mod_base = OTHER<br>note = thymine | |
| modified_base | 1904..1905<br>mod_base = OTHER<br>note = thymine | |
| modified_base | 1907<br>mod_base = OTHER<br>note = thymine | |
| modified_base | 1909<br>mod_base = OTHER<br>note = thymine | |
| modified_base | 1911<br>mod_base = OTHER<br>note = thymine | |
| modified_base | 1913<br>mod_base = OTHER<br>note = thymine | |
| modified_base | 1916<br>mod_base = OTHER<br>note = thymine | |
| modified_base | 1919<br>mod_base = OTHER<br>note = thymine | |
| modified_base | 1922..1924<br>mod_base = OTHER<br>note = thymine | |
| modified_base | 1928..1930<br>mod_base = OTHER<br>note = thymine | |
| modified_base | 1947..1948<br>mod_base = OTHER<br>note = thymine | |
| modified_base | 1950..1951 | |

-continued

|  |  |
|---|---|
|  | mod_base = OTHER<br>note = thymine |
| modified_base | 1953..1954<br>mod_base = OTHER<br>note = thymine |
| modified_base | 1958<br>mod_base = OTHER<br>note = thymine |
| modified_base | 1974<br>mod_base = OTHER<br>note = thymine |
| modified_base | 1976<br>mod_base = OTHER<br>note = thymine |
| modified_base | 1981<br>mod_base = OTHER<br>note = thymine |
| modified_base | 1983..1984<br>mod_base = OTHER<br>note = thymine |
| modified_base | 1987<br>mod_base = OTHER<br>note = thymine |
| modified_base | 2004<br>mod_base = OTHER<br>note = thymine |
| modified_base | 2009<br>mod_base = OTHER<br>note = thymine |
| modified_base | 2013<br>mod_base = OTHER<br>note = thymine |
| modified_base | 2022..2024<br>mod_base = OTHER<br>note = thymine |
| modified_base | 2026<br>mod_base = OTHER<br>note = thymine |
| modified_base | 2043<br>mod_base = OTHER<br>note = thymine |
| modified_base | 2046<br>mod_base = OTHER<br>note = thymine |
| modified_base | 2056..2057<br>mod_base = OTHER<br>note = thymine |
| modified_base | 2060..2062<br>mod_base = OTHER<br>note = thymine |
| modified_base | 2069..2070<br>mod_base = OTHER<br>note = thymine |
| modified_base | 2073..2074<br>mod_base = OTHER<br>note = thymine |
| modified_base | 2078..2079<br>mod_base = OTHER<br>note = thymine |
| modified_base | 2081..2083<br>mod_base = OTHER<br>note = thymine |
| modified_base | 2087<br>mod_base = OTHER<br>note = thymine |
| modified_base | 2090..2094<br>mod_base = OTHER<br>note = thymine |
| modified_base | 2100<br>mod_base = OTHER<br>note = thymine |
| modified_base | 2104<br>mod_base = OTHER<br>note = thymine |
| modified_base | 2108..2110<br>mod_base = OTHER<br>note = thymine |
| modified_base | 2115..2117<br>mod_base = OTHER |

-continued

| | | |
|---|---|---|
| modified_base | 2119 mod_base = OTHER note = thymine | |
| modified_base | 2121 mod_base = OTHER note = thymine | |
| modified_base | 2128..2129 mod_base = OTHER note = thymine | |
| modified_base | 2141 mod_base = OTHER note = thymine | |
| modified_base | 2146..2147 mod_base = OTHER note = thymine | |
| modified_base | 2149..2150 mod_base = OTHER note = thymine | |
| modified_base | 2155 mod_base = OTHER note = thymine | |
| modified_base | 2159 mod_base = OTHER note = thymine | |
| modified_base | 2161 mod_base = OTHER note = thymine | |
| modified_base | 2163 mod_base = OTHER note = thymine | |
| modified_base | 2166..2168 mod_base = OTHER note = thymine | |
| modified_base | 2170 mod_base = OTHER note = thymine | |
| modified_base | 2172 mod_base = OTHER note = thymine | |
| modified_base | 2180 mod_base = OTHER note = thymine | |
| modified_base | 2186..2188 mod_base = OTHER note = thymine | |
| modified_base | 2193 mod_base = OTHER note = thymine | |
| modified_base | 2197 mod_base = OTHER note = thymine | |
| modified_base | 2205..2206 mod_base = OTHER note = thymine | |
| modified_base | 2209 mod_base = OTHER note = thymine | |
| modified_base | 2215 mod_base = OTHER note = thymine | |
| modified_base | 2218 mod_base = OTHER note = thymine | |
| modified_base | 2220..2221 mod_base = OTHER note = thymine | |
| modified_base | 2233 mod_base = OTHER note = thymine | |
| modified_base | 2240 mod_base = OTHER note = thymine | |
| modified_base | 2256 mod_base = OTHER note = thymine | |
| modified_base | 2261 mod_base = OTHER note = thymine | |

| | | |
|---|---|---|
| modified_base | 2267..2269 mod_base = OTHER note = thymine | |
| modified_base | 2271..2272 mod_base = OTHER note = thymine | |
| modified_base | 2275..2276 mod_base = OTHER note = thymine | |
| modified_base | 2280 mod_base = OTHER note = thymine | |
| modified_base | 2282 mod_base = OTHER note = thymine | |
| modified_base | 2290 mod_base = OTHER note = thymine | |
| modified_base | 2292..2293 mod_base = OTHER note = thymine | |
| modified_base | 2295..2296 mod_base = OTHER note = thymine | |
| modified_base | 2303..2306 mod_base = OTHER note = thymine | |
| modified_base | 2308 mod_base = OTHER note = thymine | |
| modified_base | 2313..2315 mod_base = OTHER note = thymine | |
| modified_base | 2317..2318 mod_base = OTHER note = thymine | |
| modified_base | 2326 mod_base = OTHER note = thymine | |
| modified_base | 2331 mod_base = OTHER note = thymine | |
| modified_base | 2333 mod_base = OTHER note = thymine | |
| modified_base | 2335..2336 mod_base = OTHER note = thymine | |
| modified_base | 2338 mod_base = OTHER note = thymine | |
| modified_base | 2341..2342 mod_base = OTHER note = thymine | |
| modified_base | 2344 mod_base = OTHER note = thymine | |
| modified_base | 2348 mod_base = OTHER note = thymine | |
| modified_base | 2350..2351 mod_base = OTHER note = thymine | |
| modified_base | 2356 mod_base = OTHER note = thymine | |
| modified_base | 2358 mod_base = OTHER note = thymine | |
| modified_base | 2360..2361 mod_base = OTHER note = thymine | |
| modified_base | 2363..2365 mod_base = OTHER note = thymine | |
| modified_base | 2367 mod_base = OTHER note = thymine | |
| modified_base | 2369 | |

```
                                mod_base = OTHER
                                note = thymine
modified_base    2375
                                mod_base = OTHER
                                note = thymine
modified_base    2377..2378
                                mod_base = OTHER
                                note = thymine
modified_base    2383..2384
                                mod_base = OTHER
                                note = thymine
modified_base    2386
                                mod_base = OTHER
                                note = thymine
modified_base    2389
                                mod_base = OTHER
                                note = thymine
modified_base    2393..2395
                                mod_base = OTHER
                                note = thymine
modified_base    2398
                                mod_base = OTHER
                                note = thymine
modified_base    2401
                                mod_base = OTHER
                                note = thymine
modified_base    2413
                                mod_base = OTHER
                                note = thymine
modified_base    2418
                                mod_base = OTHER
                                note = thymine
modified_base    2428
                                mod_base = OTHER
                                note = thymine
modified_base    2432
                                mod_base = OTHER
                                note = thymine
modified_base    2436..2437
                                mod_base = OTHER
                                note = thymine
modified_base    2444
                                mod_base = OTHER
                                note = thymine
modified_base    2446
                                mod_base = OTHER
                                note = thymine
modified_base    2448
                                mod_base = OTHER
                                note = thymine
modified_base    2451
                                mod_base = OTHER
                                note = thymine
modified_base    2453
                                mod_base = OTHER
                                note = thymine
modified_base    2458..2460
                                mod_base = OTHER
                                note = thymine
modified_base    2462
                                mod_base = OTHER
                                note = thymine
modified_base    2464
                                mod_base = OTHER
                                note = thymine
modified_base    2467..2469
                                mod_base = OTHER
                                note = thymine
modified_base    2472
                                mod_base = OTHER
                                note = thymine
modified_base    2474..2475
                                mod_base = OTHER
                                note = thymine
modified_base    2479
                                mod_base = OTHER
                                note = thymine
modified_base    2490
                                mod_base = OTHER
```

| | |
|---|---|
| | note = thymine |
| modified_base | 2492..2493<br>mod_base = OTHER<br>note = thymine |
| modified_base | 2501<br>mod_base = OTHER<br>note = thymine |
| modified_base | 2507<br>mod_base = OTHER<br>note = thymine |
| modified_base | 2514<br>mod_base = OTHER<br>note = thymine |
| modified_base | 2517<br>mod_base = OTHER<br>note = thymine |
| modified_base | 2522<br>mod_base = OTHER<br>note = thymine |
| modified_base | 2527<br>mod_base = OTHER<br>note = thymine |
| modified_base | 2530..2531<br>mod_base = OTHER<br>note = thymine |
| modified_base | 2533<br>mod_base = OTHER<br>note = thymine |
| modified_base | 2538..2539<br>mod_base = OTHER<br>note = thymine |
| modified_base | 2542<br>mod_base = OTHER<br>note = thymine |
| modified_base | 2547..2550<br>mod_base = OTHER<br>note = thymine |
| modified_base | 2553<br>mod_base = OTHER<br>note = thymine |
| modified_base | 2560..2563<br>mod_base = OTHER<br>note = thymine |
| modified_base | 2567<br>mod_base = OTHER<br>note = thymine |
| modified_base | 2569<br>mod_base = OTHER<br>note = thymine |
| modified_base | 2571..2572<br>mod_base = OTHER<br>note = thymine |
| modified_base | 2575<br>mod_base = OTHER<br>note = thymine |
| modified_base | 2577<br>mod_base = OTHER<br>note = thymine |
| modified_base | 2580..2581<br>mod_base = OTHER<br>note = thymine |
| modified_base | 2588..2590<br>mod_base = OTHER<br>note = thymine |
| modified_base | 2593<br>mod_base = OTHER<br>note = thymine |
| modified_base | 2601..2602<br>mod_base = OTHER<br>note = thymine |
| modified_base | 2605..2606<br>mod_base = OTHER<br>note = thymine |
| modified_base | 2608<br>mod_base = OTHER<br>note = thymine |
| modified_base | 2614..2615<br>mod_base = OTHER<br>note = thymine |

| | | |
|---|---|---|
| modified_base | 2617 mod_base = OTHER note = thymine | |
| modified_base | 2619 mod_base = OTHER note = thymine | |
| modified_base | 2622..2623 mod_base = OTHER note = thymine | |
| modified_base | 2625 mod_base = OTHER note = thymine | |
| modified_base | 2628 mod_base = OTHER note = thymine | |
| modified_base | 2638 mod_base = OTHER note = thymine | |
| modified_base | 2642..2643 mod_base = OTHER note = thymine | |
| modified_base | 2647..2650 mod_base = OTHER note = thymine | |
| modified_base | 2653 mod_base = OTHER note = thymine | |
| modified_base | 2655 mod_base = OTHER note = thymine | |
| modified_base | 2657 mod_base = OTHER note = thymine | |
| modified_base | 2664 mod_base = OTHER note = thymine | |
| modified_base | 2669 mod_base = OTHER note = thymine | |
| modified_base | 2671 mod_base = OTHER note = thymine | |
| modified_base | 2679 mod_base = OTHER note = thymine | |
| modified_base | 2688 mod_base = OTHER note = thymine | |
| modified_base | 2690..2692 mod_base = OTHER note = thymine | |
| modified_base | 2697 mod_base = OTHER note = thymine | |
| modified_base | 2699..2700 mod_base = OTHER note = thymine | |
| modified_base | 2702..2703 mod_base = OTHER note = thymine | |
| modified_base | 2705..2706 mod_base = OTHER note = thymine | |
| modified_base | 2710 mod_base = OTHER note = thymine | |
| modified_base | 2714 mod_base = OTHER note = thymine | |
| modified_base | 2725 mod_base = OTHER note = thymine | |
| modified_base | 2727 mod_base = OTHER note = thymine | |
| modified_base | 2729 mod_base = OTHER note = thymine | |
| modified_base | 2731 | |

|                |               |
|----------------|---------------|
|                | mod_base = OTHER |
|                | note = thymine |
| modified_base  | 2733 |
|                | mod_base = OTHER |
|                | note = thymine |
| modified_base  | 2735 |
|                | mod_base = OTHER |
|                | note = thymine |
| modified_base  | 2742 |
|                | mod_base = OTHER |
|                | note = thymine |
| modified_base  | 2744 |
|                | mod_base = OTHER |
|                | note = thymine |
| modified_base  | 2746 |
|                | mod_base = OTHER |
|                | note = thymine |
| modified_base  | 2749 |
|                | mod_base = OTHER |
|                | note = thymine |
| modified_base  | 2753..2754 |
|                | mod_base = OTHER |
|                | note = thymine |
| modified_base  | 2757..2758 |
|                | mod_base = OTHER |
|                | note = thymine |
| modified_base  | 2762 |
|                | mod_base = OTHER |
|                | note = thymine |
| modified_base  | 2764 |
|                | mod_base = OTHER |
|                | note = thymine |
| modified_base  | 2767 |
|                | mod_base = OTHER |
|                | note = thymine |
| modified_base  | 2773 |
|                | mod_base = OTHER |
|                | note = thymine |
| modified_base  | 2775..2777 |
|                | mod_base = OTHER |
|                | note = thymine |
| modified_base  | 2783 |
|                | mod_base = OTHER |
|                | note = thymine |
| modified_base  | 2785 |
|                | mod_base = OTHER |
|                | note = thymine |
| modified_base  | 2787 |
|                | mod_base = OTHER |
|                | note = thymine |
| modified_base  | 2791 |
|                | mod_base = OTHER |
|                | note = thymine |
| modified_base  | 2794 |
|                | mod_base = OTHER |
|                | note = thymine |
| modified_base  | 2802..2803 |
|                | mod_base = OTHER |
|                | note = thymine |
| modified_base  | 2809 |
|                | mod_base = OTHER |
|                | note = thymine |
| modified_base  | 2813..2814 |
|                | mod_base = OTHER |
|                | note = thymine |
| modified_base  | 2817 |
|                | mod_base = OTHER |
|                | note = thymine |
| modified_base  | 2824..2825 |
|                | mod_base = OTHER |
|                | note = thymine |
| modified_base  | 2827 |
|                | mod_base = OTHER |
|                | note = thymine |
| modified_base  | 2829 |
|                | mod_base = OTHER |
|                | note = thymine |
| modified_base  | 2831 |
|                | mod_base = OTHER |

| | | |
|---|---|---|
| | | note = thymine |
| modified_base | 2833 | |
| | | mod_base = OTHER |
| | | note = thymine |
| modified_base | 2836 | |
| | | mod_base = OTHER |
| | | note = thymine |
| modified_base | 2838 | |
| | | mod_base = OTHER |
| | | note = thymine |
| modified_base | 2840 | |
| | | mod_base = OTHER |
| | | note = thymine |
| modified_base | 2846..2847 | |
| | | mod_base = OTHER |
| | | note = thymine |
| modified_base | 2849 | |
| | | mod_base = OTHER |
| | | note = thymine |
| modified_base | 2851..2852 | |
| | | mod_base = OTHER |
| | | note = thymine |
| modified_base | 2857..2860 | |
| | | mod_base = OTHER |
| | | note = thymine |
| modified_base | 2865..2866 | |
| | | mod_base = OTHER |
| | | note = thymine |
| modified_base | 2871..2872 | |
| | | mod_base = OTHER |
| | | note = thymine |
| modified_base | 2874 | |
| | | mod_base = OTHER |
| | | note = thymine |
| modified_base | 2876 | |
| | | mod_base = OTHER |
| | | note = thymine |
| modified_base | 2895..2896 | |
| | | mod_base = OTHER |
| | | note = thymine |
| modified_base | 2899 | |
| | | mod_base = OTHER |
| | | note = thymine |
| modified_base | 2903 | |
| | | mod_base = OTHER |
| | | note = thymine |
| modified_base | 2911 | |
| | | mod_base = OTHER |
| | | note = thymine |
| modified_base | 2913 | |
| | | mod_base = OTHER |
| | | note = thymine |
| modified_base | 2915..2916 | |
| | | mod_base = OTHER |
| | | note = thymine |
| modified_base | 2923 | |
| | | mod_base = OTHER |
| | | note = thymine |
| modified_base | 2933 | |
| | | mod_base = OTHER |
| | | note = thymine |
| modified_base | 2935..2936 | |
| | | mod_base = OTHER |
| | | note = thymine |
| modified_base | 2940..2941 | |
| | | mod_base = OTHER |
| | | note = thymine |
| modified_base | 2946 | |
| | | mod_base = OTHER |
| | | note = thymine |
| modified_base | 2959..2960 | |
| | | mod_base = OTHER |
| | | note = thymine |
| modified_base | 2963 | |
| | | mod_base = OTHER |
| | | note = thymine |
| modified_base | 2965 | |
| | | mod_base = OTHER |
| | | note = thymine |

-continued

| | | |
|---|---|---|
| modified_base | 2971 | |
| | mod_base = OTHER | |
| | note = thymine | |
| modified_base | 2973..2975 | |
| | mod_base = OTHER | |
| | note = thymine | |
| modified_base | 2980 | |
| | mod_base = OTHER | |
| | note = thymine | |
| modified_base | 2983 | |
| | mod_base = OTHER | |
| | note = thymine | |
| modified_base | 2988..2989 | |
| | mod_base = OTHER | |
| | note = thymine | |
| modified_base | 2991..2993 | |
| | mod_base = OTHER | |
| | note = thymine | |
| modified_base | 2996..2998 | |
| | mod_base = OTHER | |
| | note = thymine | |
| modified_base | 3005 | |
| | mod_base = OTHER | |
| | note = thymine | |
| modified_base | 3011..3012 | |
| | mod_base = OTHER | |
| | note = thymine | |
| modified_base | 3015 | |
| | mod_base = OTHER | |
| | note = thymine | |
| modified_base | 3028..3030 | |
| | mod_base = OTHER | |
| | note = thymine | |
| modified_base | 3038..3039 | |
| | mod_base = OTHER | |
| | note = thymine | |
| modified_base | 3041 | |
| | mod_base = OTHER | |
| | note = thymine | |
| modified_base | 3043 | |
| | mod_base = OTHER | |
| | note = thymine | |
| modified_base | 3046 | |
| | mod_base = OTHER | |
| | note = thymine | |
| modified_base | 3048 | |
| | mod_base = OTHER | |
| | note = thymine | |
| modified_base | 3050..3051 | |
| | mod_base = OTHER | |
| | note = thymine | |
| modified_base | 3057..3060 | |
| | mod_base = OTHER | |
| | note = thymine | |
| modified_base | 3063 | |
| | mod_base = OTHER | |
| | note = thymine | |
| modified_base | 3067 | |
| | mod_base = OTHER | |
| | note = thymine | |
| modified_base | 3079..3083 | |
| | mod_base = OTHER | |
| | note = thymine | |
| modified_base | 3085 | |
| | mod_base = OTHER | |
| | note = thymine | |
| modified_base | 3091 | |
| | mod_base = OTHER | |
| | note = thymine | |
| modified_base | 3096 | |
| | mod_base = OTHER | |
| | note = thymine | |
| modified_base | 3099 | |
| | mod_base = OTHER | |
| | note = thymine | |
| modified_base | 3102 | |
| | mod_base = OTHER | |
| | note = thymine | |
| modified_base | 3106 | |

-continued

```
                           mod_base = OTHER
                           note = thymine
modified_base              3112
                           mod_base = OTHER
                           note = thymine
modified_base              3114
                           mod_base = OTHER
                           note = thymine
modified_base              3118
                           mod_base = OTHER
                           note = thymine
modified_base              3125
                           mod_base = OTHER
                           note = thymine
modified_base              3127
                           mod_base = OTHER
                           note = thymine
modified_base              3132
                           mod_base = OTHER
                           note = thymine
modified_base              3135
                           mod_base = OTHER
                           note = thymine
modified_base              3140
                           mod_base = OTHER
                           note = thymine
modified_base              3144
                           mod_base = OTHER
                           note = thymine
modified_base              3149
                           mod_base = OTHER
                           note = thymine
modified_base              3153
                           mod_base = OTHER
                           note = thymine
modified_base              3164..3165
                           mod_base = OTHER
                           note = thymine
modified_base              3167..3168
                           mod_base = OTHER
                           note = thymine
modified_base              3172
                           mod_base = OTHER
                           note = thymine
modified_base              3175..3176
                           mod_base = OTHER
                           note = thymine
modified_base              3183
                           mod_base = OTHER
                           note = thymine
modified_base              3185
                           mod_base = OTHER
                           note = thymine
modified_base              3189
                           mod_base = OTHER
                           note = thymine
modified_base              3191
                           mod_base = OTHER
                           note = thymine
modified_base              3194
                           mod_base = OTHER
                           note = thymine
modified_base              3196
                           mod_base = OTHER
                           note = thymine
modified_base              3198..3199
                           mod_base = OTHER
                           note = thymine
modified_base              3201
                           mod_base = OTHER
                           note = thymine
modified_base              3208..3209
                           mod_base = OTHER
                           note = thymine
modified_base              3213
                           mod_base = OTHER
                           note = thymine
modified_base              3220
                           mod_base = OTHER
```

| | | |
|---|---|---|
| | note = thymine | |
| modified_base | 3222 | |
| | mod_base = OTHER | |
| | note = thymine | |
| modified_base | 3235..3236 | |
| | mod_base = OTHER | |
| | note = thymine | |
| modified_base | 3238 | |
| | mod_base = OTHER | |
| | note = thymine | |
| modified_base | 3240 | |
| | mod_base = OTHER | |
| | note = thymine | |
| modified_base | 3244 | |
| | mod_base = OTHER | |
| | note = thymine | |
| modified_base | 3252 | |
| | mod_base = OTHER | |
| | note = thymine | |
| modified_base | 3255 | |
| | mod_base = OTHER | |
| | note = thymine | |
| modified_base | 3259..3260 | |
| | mod_base = OTHER | |
| | note = thymine | |
| modified_base | 3264 | |
| | mod_base = OTHER | |
| | note = thymine | |
| modified_base | 3270 | |
| | mod_base = OTHER | |
| | note = thymine | |
| modified_base | 3273 | |
| | mod_base = OTHER | |
| | note = thymine | |
| modified_base | 3276 | |
| | mod_base = OTHER | |
| | note = thymine | |
| modified_base | 3285 | |
| | mod_base = OTHER | |
| | note = thymine | |
| modified_base | 3287..3288 | |
| | mod_base = OTHER | |
| | note = thymine | |
| modified_base | 3298 | |
| | mod_base = OTHER | |
| | note = thymine | |
| modified_base | 3301 | |
| | mod_base = OTHER | |
| | note = thymine | |
| modified_base | 3306 | |
| | mod_base = OTHER | |
| | note = thymine | |
| modified_base | 3316..3317 | |
| | mod_base = OTHER | |
| | note = thymine | |
| modified_base | 3323 | |
| | mod_base = OTHER | |
| | note = thymine | |
| modified_base | 3329 | |
| | mod_base = OTHER | |
| | note = thymine | |
| modified_base | 3331 | |
| | mod_base = OTHER | |
| | note = thymine | |
| modified_base | 3333..3334 | |
| | mod_base = OTHER | |
| | note = thymine | |
| modified_base | 3338..3340 | |
| | mod_base = OTHER | |
| | note = thymine | |
| modified_base | 3344 | |
| | mod_base = OTHER | |
| | note = thymine | |
| modified_base | 3351 | |
| | mod_base = OTHER | |
| | note = thymine | |
| modified_base | 3356..3357 | |
| | mod_base = OTHER | |
| | note = thymine | |

-continued

| | | |
|---|---|---|
| modified_base | 3359 | |
| | mod_base = OTHER | |
| | note = thymine | |
| modified_base | 3366..3367 | |
| | mod_base = OTHER | |
| | note = thymine | |
| modified_base | 3370..3371 | |
| | mod_base = OTHER | |
| | note = thymine | |
| modified_base | 3377..3378 | |
| | mod_base = OTHER | |
| | note = thymine | |
| modified_base | 3387..3388 | |
| | mod_base = OTHER | |
| | note = thymine | |
| modified_base | 3390 | |
| | mod_base = OTHER | |
| | note = thymine | |
| modified_base | 3396 | |
| | mod_base = OTHER | |
| | note = thymine | |
| modified_base | 3401..3403 | |
| | mod_base = OTHER | |
| | note = thymine | |
| modified_base | 3409 | |
| | mod_base = OTHER | |
| | note = thymine | |
| modified_base | 3411..3412 | |
| | mod_base = OTHER | |
| | note = thymine | |
| modified_base | 3415..3416 | |
| | mod_base = OTHER | |
| | note = thymine | |
| modified_base | 3419 | |
| | mod_base = OTHER | |
| | note = thymine | |
| modified_base | 3422..3423 | |
| | mod_base = OTHER | |
| | note = thymine | |
| modified_base | 3429..3430 | |
| | mod_base = OTHER | |
| | note = thymine | |
| modified_base | 3435..3437 | |
| | mod_base = OTHER | |
| | note = thymine | |
| modified_base | 3439..3440 | |
| | mod_base = OTHER | |
| | note = thymine | |
| modified_base | 3442 | |
| | mod_base = OTHER | |
| | note = thymine | |
| modified_base | 3444 | |
| | mod_base = OTHER | |
| | note = thymine | |
| modified_base | 3446 | |
| | mod_base = OTHER | |
| | note = thymine | |
| modified_base | 3448 | |
| | mod_base = OTHER | |
| | note = thymine | |
| modified_base | 3453..3454 | |
| | mod_base = OTHER | |
| | note = thymine | |
| modified_base | 3456..3457 | |
| | mod_base = OTHER | |
| | note = thymine | |
| modified_base | 3461..3462 | |
| | mod_base = OTHER | |
| | note = thymine | |
| modified_base | 3464 | |
| | mod_base = OTHER | |
| | note = thymine | |
| modified_base | 3467 | |
| | mod_base = OTHER | |
| | note = thymine | |
| modified_base | 3469 | |
| | mod_base = OTHER | |
| | note = thymine | |
| modified_base | 3471 | |

|  |  |
|---|---|
|  | mod_base = OTHER |
|  | note = thymine |
| modified_base | 3491 |
|  | mod_base = OTHER |
|  | note = thymine |
| modified_base | 3494 |
|  | mod_base = OTHER |
|  | note = thymine |
| modified_base | 3499 |
|  | mod_base = OTHER |
|  | note = thymine |
| modified_base | 3502 |
|  | mod_base = OTHER |
|  | note = thymine |
| modified_base | 3505..3506 |
|  | mod_base = OTHER |
|  | note = thymine |
| modified_base | 3509 |
|  | mod_base = OTHER |
|  | note = thymine |
| modified_base | 3515..3517 |
|  | mod_base = OTHER |
|  | note = thymine |
| modified_base | 3522 |
|  | mod_base = OTHER |
|  | note = thymine |
| modified_base | 3525 |
|  | mod_base = OTHER |
|  | note = thymine |
| modified_base | 3528 |
|  | mod_base = OTHER |
|  | note = thymine |
| modified_base | 3530 |
|  | mod_base = OTHER |
|  | note = thymine |
| modified_base | 3543 |
|  | mod_base = OTHER |
|  | note = thymine |
| modified_base | 3549..3550 |
|  | mod_base = OTHER |
|  | note = thymine |
| modified_base | 3552..3553 |
|  | mod_base = OTHER |
|  | note = thymine |
| modified_base | 3562..3565 |
|  | mod_base = OTHER |
|  | note = thymine |
| modified_base | 3568 |
|  | mod_base = OTHER |
|  | note = thymine |
| modified_base | 3570 |
|  | mod_base = OTHER |
|  | note = thymine |
| modified_base | 3577..3578 |
|  | mod_base = OTHER |
|  | note = thymine |
| modified_base | 3584..3585 |
|  | mod_base = OTHER |
|  | note = thymine |
| modified_base | 3590..3591 |
|  | mod_base = OTHER |
|  | note = thymine |
| modified_base | 3594..3597 |
|  | mod_base = OTHER |
|  | note = thymine |
| modified_base | 3599 |
|  | mod_base = OTHER |
|  | note = thymine |
| modified_base | 3603..3604 |
|  | mod_base = OTHER |
|  | note = thymine |
| modified_base | 3611 |
|  | mod_base = OTHER |
|  | note = thymine |
| modified_base | 3613 |
|  | mod_base = OTHER |
|  | note = thymine |
| modified_base | 3615 |
|  | mod_base = OTHER |

| | | |
|---|---|---|
| | | note = thymine |
| modified_base | 3617..3619 | |
| | mod_base = OTHER | |
| | note = thymine | |
| modified_base | 3622..3623 | |
| | mod_base = OTHER | |
| | note = thymine | |
| modified_base | 3628 | |
| | mod_base = OTHER | |
| | note = thymine | |
| modified_base | 3638..3639 | |
| | mod_base = OTHER | |
| | note = thymine | |
| modified_base | 3641 | |
| | mod_base = OTHER | |
| | note = thymine | |
| modified_base | 3648 | |
| | mod_base = OTHER | |
| | note = thymine | |
| modified_base | 3650..3651 | |
| | mod_base = OTHER | |
| | note = thymine | |
| modified_base | 3656 | |
| | mod_base = OTHER | |
| | note = thymine | |
| modified_base | 3661 | |
| | mod_base = OTHER | |
| | note = thymine | |
| modified_base | 3664 | |
| | mod_base = OTHER | |
| | note = thymine | |
| modified_base | 3667 | |
| | mod_base = OTHER | |
| | note = thymine | |
| modified_base | 3672..3673 | |
| | mod_base = OTHER | |
| | note = thymine | |
| modified_base | 3676 | |
| | mod_base = OTHER | |
| | note = thymine | |
| modified_base | 3678..3679 | |
| | mod_base = OTHER | |
| | note = thymine | |
| modified_base | 3684 | |
| | mod_base = OTHER | |
| | note = thymine | |
| modified_base | 3686 | |
| | mod_base = OTHER | |
| | note = thymine | |
| modified_base | 3693 | |
| | mod_base = OTHER | |
| | note = thymine | |
| modified_base | 3698..3699 | |
| | mod_base = OTHER | |
| | note = thymine | |
| modified_base | 3701 | |
| | mod_base = OTHER | |
| | note = thymine | |
| modified_base | 3703 | |
| | mod_base = OTHER | |
| | note = thymine | |
| modified_base | 3705..3707 | |
| | mod_base = OTHER | |
| | note = thymine | |
| modified_base | 3717 | |
| | mod_base = OTHER | |
| | note = thymine | |
| modified_base | 3720 | |
| | mod_base = OTHER | |
| | note = thymine | |
| modified_base | 3723..3724 | |
| | mod_base = OTHER | |
| | note = thymine | |
| modified_base | 3726 | |
| | mod_base = OTHER | |
| | note = thymine | |
| modified_base | 3730..3731 | |
| | mod_base = OTHER | |
| | note = thymine | |

-continued

| | | |
|---|---|---|
| modified_base | 3734 | |
| | mod_base = OTHER | |
| | note = thymine | |
| modified_base | 3740..3742 | |
| | mod_base = OTHER | |
| | note = thymine | |
| modified_base | 3747..3748 | |
| | mod_base = OTHER | |
| | note = thymine | |
| modified_base | 3752 | |
| | mod_base = OTHER | |
| | note = thymine | |
| modified_base | 3754 | |
| | mod_base = OTHER | |
| | note = thymine | |
| modified_base | 3756..3758 | |
| | mod_base = OTHER | |
| | note = thymine | |
| modified_base | 3763 | |
| | mod_base = OTHER | |
| | note = thymine | |
| modified_base | 3766 | |
| | mod_base = OTHER | |
| | note = thymine | |
| modified_base | 3769..3770 | |
| | mod_base = OTHER | |
| | note = thymine | |
| modified_base | 3772 | |
| | mod_base = OTHER | |
| | note = thymine | |
| modified_base | 3777 | |
| | mod_base = OTHER | |
| | note = thymine | |
| modified_base | 3779 | |
| | mod_base = OTHER | |
| | note = thymine | |
| modified_base | 3781 | |
| | mod_base = OTHER | |
| | note = thymine | |
| modified_base | 3789 | |
| | mod_base = OTHER | |
| | note = thymine | |
| modified_base | 3792 | |
| | mod_base = OTHER | |
| | note = thymine | |
| modified_base | 3794 | |
| | mod_base = OTHER | |
| | note = thymine | |
| modified_base | 3798 | |
| | mod_base = OTHER | |
| | note = thymine | |
| modified_base | 3806 | |
| | mod_base = OTHER | |
| | note = thymine | |
| modified_base | 3810..3811 | |
| | mod_base = OTHER | |
| | note = thymine | |
| modified_base | 3815 | |
| | mod_base = OTHER | |
| | note = thymine | |
| modified_base | 3821 | |
| | mod_base = OTHER | |
| | note = thymine | |
| modified_base | 3825..3827 | |
| | mod_base = OTHER | |
| | note = thymine | |
| modified_base | 3829 | |
| | mod_base = OTHER | |
| | note = thymine | |
| modified_base | 3834 | |
| | mod_base = OTHER | |
| | note = thymine | |
| modified_base | 3838..3841 | |
| | mod_base = OTHER | |
| | note = thymine | |
| modified_base | 3843 | |
| | mod_base = OTHER | |
| | note = thymine | |
| modified_base | 3845 | |

-continued

| | | |
|---|---|---|
| | mod_base = OTHER | |
| | note = thymine | |
| modified_base | 3849..3850 | |
| | mod_base = OTHER | |
| | note = thymine | |
| modified_base | 3852 | |
| | mod_base = OTHER | |
| | note = thymine | |
| modified_base | 3859 | |
| | mod_base = OTHER | |
| | note = thymine | |
| modified_base | 3863..3864 | |
| | mod_base = OTHER | |
| | note = thymine | |
| modified_base | 3870..3871 | |
| | mod_base = OTHER | |
| | note = thymine | |
| modified_base | 3874..3876 | |
| | mod_base = OTHER | |
| | note = thymine | |
| modified_base | 3880 | |
| | mod_base = OTHER | |
| | note = thymine | |
| modified_base | 3883 | |
| | mod_base = OTHER | |
| | note = thymine | |
| modified_base | 3886 | |
| | mod_base = OTHER | |
| | note = thymine | |
| modified_base | 3897 | |
| | mod_base = OTHER | |
| | note = thymine | |
| modified_base | 3900 | |
| | mod_base = OTHER | |
| | note = thymine | |
| modified_base | 3903..3905 | |
| | mod_base = OTHER | |
| | note = thymine | |
| modified_base | 3908 | |
| | mod_base = OTHER | |
| | note = thymine | |
| modified_base | 3910 | |
| | mod_base = OTHER | |
| | note = thymine | |
| modified_base | 3917..3918 | |
| | mod_base = OTHER | |
| | note = thymine | |
| modified_base | 3922 | |
| | mod_base = OTHER | |
| | note = thymine | |
| modified_base | 3935 | |
| | mod_base = OTHER | |
| | note = thymine | |
| modified_base | 3937 | |
| | mod_base = OTHER | |
| | note = thymine | |
| modified_base | 3941 | |
| | mod_base = OTHER | |
| | note = thymine | |
| modified_base | 3943 | |
| | mod_base = OTHER | |
| | note = thymine | |
| modified_base | 3946..3947 | |
| | mod_base = OTHER | |
| | note = thymine | |
| modified_base | 3949 | |
| | mod_base = OTHER | |
| | note = thymine | |
| modified_base | 3951 | |
| | mod_base = OTHER | |
| | note = thymine | |
| modified_base | 3954 | |
| | mod_base = OTHER | |
| | note = thymine | |
| modified_base | 3957 | |
| | mod_base = OTHER | |
| | note = thymine | |
| modified_base | 3961 | |
| | mod_base = OTHER | |

-continued

```
                             note = thymine
modified_base                3968..3970
                             mod_base = OTHER
                             note = thymine
modified_base                3972
                             mod_base = OTHER
                             note = thymine
modified_base                3975
                             mod_base = OTHER
                             note = thymine
modified_base                3978
                             mod_base = OTHER
                             note = thymine
modified_base                3981
                             mod_base = OTHER
                             note = thymine
modified_base                3983
                             mod_base = OTHER
                             note = thymine
modified_base                3986..3987
                             mod_base = OTHER
                             note = thymine
modified_base                3991..3992
                             mod_base = OTHER
                             note = thymine
modified_base                3999
                             mod_base = OTHER
                             note = thymine
modified_base                4002..4003
                             mod_base = OTHER
                             note = thymine
modified_base                4010..4011
                             mod_base = OTHER
                             note = thymine
modified_base                4019..4020
                             mod_base = OTHER
                             note = thymine
modified_base                4023
                             mod_base = OTHER
                             note = thymine
modified_base                4025..4026
                             mod_base = OTHER
                             note = thymine
modified_base                4028..4029
                             mod_base = OTHER
                             note = thymine
modified_base                4032
                             mod_base = OTHER
                             note = thymine
modified_base                4037
                             mod_base = OTHER
                             note = thymine
modified_base                4039..4040
                             mod_base = OTHER
                             note = thymine
modified_base                4042..4043
                             mod_base = OTHER
                             note = thymine
modified_base                4045
                             mod_base = OTHER
                             note = thymine
modified_base                4050..4055
                             mod_base = OTHER
                             note = thymine
modified_base                4058
                             mod_base = OTHER
                             note = thymine
modified_base                4078
                             mod_base = OTHER
                             note = thymine
modified_base                4080
                             mod_base = OTHER
                             note = thymine
modified_base                4083
                             mod_base = OTHER
                             note = thymine
modified_base                4088
                             mod_base = OTHER
                             note = thymine
```

| | |
|---|---|
| modified_base | 4091..4092<br>mod_base = OTHER<br>note = thymine |
| modified_base | 4101<br>mod_base = OTHER<br>note = thymine |
| modified_base | 4105<br>mod_base = OTHER<br>note = thymine |
| modified_base | 4109..4111<br>mod_base = OTHER<br>note = thymine |
| modified_base | 4115<br>mod_base = OTHER<br>note = thymine |
| modified_base | 4121<br>mod_base = OTHER<br>note = thymine |
| modified_base | 4125<br>mod_base = OTHER<br>note = thymine |
| modified_base | 4134<br>mod_base = OTHER<br>note = thymine |
| modified_base | 4139<br>mod_base = OTHER<br>note = thymine |
| modified_base | 4143<br>mod_base = OTHER<br>note = thymine |
| modified_base | 4145..4147<br>mod_base = OTHER<br>note = thymine |
| modified_base | 4149<br>mod_base = OTHER<br>note = thymine |
| modified_base | 4155<br>mod_base = OTHER<br>note = thymine |
| modified_base | 4162<br>mod_base = OTHER<br>note = thymine |
| modified_base | 4170<br>mod_base = OTHER<br>note = thymine |
| modified_base | 4172<br>mod_base = OTHER<br>note = thymine |
| modified_base | 4176<br>mod_base = OTHER<br>note = thymine |
| modified_base | 4182<br>mod_base = OTHER<br>note = thymine |
| modified_base | 4185..4186<br>mod_base = OTHER<br>note = thymine |
| modified_base | 4191<br>mod_base = OTHER<br>note = thymine |
| modified_base | 4194<br>mod_base = OTHER<br>note = thymine |
| modified_base | 4198..4199<br>mod_base = OTHER<br>note = thymine |
| modified_base | 4206<br>mod_base = OTHER<br>note = thymine |
| modified_base | 4208<br>mod_base = OTHER<br>note = thymine |
| modified_base | 4211..4213<br>mod_base = OTHER<br>note = thymine |
| modified_base | 4216<br>mod_base = OTHER<br>note = thymine |
| modified_base | 4218 |

-continued

```
                         mod_base = OTHER
                         note = thymine
modified_base            4220
                         mod_base = OTHER
                         note = thymine
modified_base            4222
                         mod_base = OTHER
                         note = thymine
modified_base            4229
                         mod_base = OTHER
                         note = thymine
modified_base            4247
                         mod_base = OTHER
                         note = thymine
modified_base            4251
                         mod_base = OTHER
                         note = thymine
modified_base            4260
                         mod_base = OTHER
                         note = thymine
modified_base            4262
                         mod_base = OTHER
                         note = thymine
modified_base            4266
                         mod_base = OTHER
                         note = thymine
modified_base            4269
                         mod_base = OTHER
                         note = thymine
modified_base            4277
                         mod_base = OTHER
                         note = thymine
modified_base            4281..4286
                         mod_base = OTHER
                         note = thymine
modified_base            4289..4291
                         mod_base = OTHER
                         note = thymine
modified_base            4296..4297
                         mod_base = OTHER
                         note = thymine
modified_base            4300
                         mod_base = OTHER
                         note = thymine
modified_base            4303
                         mod_base = OTHER
                         note = thymine
modified_base            4305
                         mod_base = OTHER
                         note = thymine
modified_base            4310..4313
                         mod_base = OTHER
                         note = thymine
modified_base            4315
                         mod_base = OTHER
                         note = thymine
modified_base            4320
                         mod_base = OTHER
                         note = thymine
modified_base            4324
                         mod_base = OTHER
                         note = thymine
modified_base            4326..4327
                         mod_base = OTHER
                         note = thymine
modified_base            4333
                         mod_base = OTHER
                         note = thymine
modified_base            4335..4336
                         mod_base = OTHER
                         note = thymine
modified_base            4340
                         mod_base = OTHER
                         note = thymine
modified_base            4343
                         mod_base = OTHER
                         note = thymine
modified_base            4345
                         mod_base = OTHER
```

| | | |
|---|---|---|
| | | note = thymine |
| modified_base | 4348..4350 | |
| | mod_base = OTHER | |
| | note = thymine | |
| modified_base | 4352 | |
| | mod_base = OTHER | |
| | note = thymine | |
| modified_base | 4356 | |
| | mod_base = OTHER | |
| | note = thymine | |
| modified_base | 4359..4361 | |
| | mod_base = OTHER | |
| | note = thymine | |
| modified_base | 4363 | |
| | mod_base = OTHER | |
| | note = thymine | |
| modified_base | 4366 | |
| | mod_base = OTHER | |
| | note = thymine | |
| modified_base | 4371 | |
| | mod_base = OTHER | |
| | note = thymine | |
| modified_base | 4381..4382 | |
| | mod_base = OTHER | |
| | note = thymine | |
| modified_base | 4385..4386 | |
| | mod_base = OTHER | |
| | note = thymine | |
| modified_base | 4389 | |
| | mod_base = OTHER | |
| | note = thymine | |
| modified_base | 4392 | |
| | mod_base = OTHER | |
| | note = thymine | |
| modified_base | 4394 | |
| | mod_base = OTHER | |
| | note = thymine | |
| modified_base | 4396..4397 | |
| | mod_base = OTHER | |
| | note = thymine | |
| modified_base | 4402 | |
| | mod_base = OTHER | |
| | note = thymine | |
| modified_base | 4404 | |
| | mod_base = OTHER | |
| | note = thymine | |
| modified_base | 4407 | |
| | mod_base = OTHER | |
| | note = thymine | |
| modified_base | 4411 | |
| | mod_base = OTHER | |
| | note = thymine | |
| modified_base | 4415 | |
| | mod_base = OTHER | |
| | note = thymine | |
| modified_base | 4418 | |
| | mod_base = OTHER | |
| | note = thymine | |
| modified_base | 4421..4422 | |
| | mod_base = OTHER | |
| | note = thymine | |
| modified_base | 4424..4425 | |
| | mod_base = OTHER | |
| | note = thymine | |
| modified_base | 4427..4428 | |
| | mod_base = OTHER | |
| | note = thymine | |
| modified_base | 4431..4432 | |
| | mod_base = OTHER | |
| | note = thymine | |
| modified_base | 4435..4436 | |
| | mod_base = OTHER | |
| | note = thymine | |
| modified_base | 4438 | |
| | mod_base = OTHER | |
| | note = thymine | |
| modified_base | 4441..4442 | |
| | mod_base = OTHER | |
| | note = thymine | |

| | |
|---|---|
| modified_base | 4444..4445<br>mod_base = OTHER<br>note = thymine |
| modified_base | 4453<br>mod_base = OTHER<br>note = thymine |
| modified_base | 4456<br>mod_base = OTHER<br>note = thymine |
| modified_base | 4466<br>mod_base = OTHER<br>note = thymine |
| modified_base | 4468..4469<br>mod_base = OTHER<br>note = thymine |
| modified_base | 4473..4478<br>mod_base = OTHER<br>note = thymine |
| modified_base | 4481<br>mod_base = OTHER<br>note = thymine |
| modified_base | 4483..4484<br>mod_base = OTHER<br>note = thymine |
| modified_base | 4488<br>mod_base = OTHER<br>note = thymine |
| modified_base | 4491<br>mod_base = OTHER<br>note = thymine |
| modified_base | 4495<br>mod_base = OTHER<br>note = thymine |
| modified_base | 4500<br>mod_base = OTHER<br>note = thymine |
| modified_base | 4506<br>mod_base = OTHER<br>note = thymine |
| modified_base | 4512..4513<br>mod_base = OTHER<br>note = thymine |
| modified_base | 4515<br>mod_base = OTHER<br>note = thymine |
| modified_base | 4519<br>mod_base = OTHER<br>note = thymine |
| modified_base | 4523..4526<br>mod_base = OTHER<br>note = thymine |
| modified_base | 4528..4531<br>mod_base = OTHER<br>note = thymine |
| modified_base | 4537<br>mod_base = OTHER<br>note = thymine |
| modified_base | 4539<br>mod_base = OTHER<br>note = thymine |
| modified_base | 4546<br>mod_base = OTHER<br>note = thymine |
| modified_base | 4549<br>mod_base = OTHER<br>note = thymine |
| modified_base | 4559<br>mod_base = OTHER<br>note = thymine |
| modified_base | 4561..4562<br>mod_base = OTHER<br>note = thymine |
| modified_base | 4571..4573<br>mod_base = OTHER<br>note = thymine |
| modified_base | 4575<br>mod_base = OTHER<br>note = thymine |
| modified_base | 4578..4579 |

|               |         |
|---------------|---------|
| | mod_base = OTHER |
| | note = thymine |
| modified_base | 4581 |
| | mod_base = OTHER |
| | note = thymine |
| modified_base | 4584 |
| | mod_base = OTHER |
| | note = thymine |
| modified_base | 4597 |
| | mod_base = OTHER |
| | note = thymine |
| modified_base | 4599..4601 |
| | mod_base = OTHER |
| | note = thymine |
| modified_base | 4607..4608 |
| | mod_base = OTHER |
| | note = thymine |
| modified_base | 4611 |
| | mod_base = OTHER |
| | note = thymine |
| modified_base | 4617..4618 |
| | mod_base = OTHER |
| | note = thymine |
| modified_base | 4624..4625 |
| | mod_base = OTHER |
| | note = thymine |
| modified_base | 4633..4636 |
| | mod_base = OTHER |
| | note = thymine |
| modified_base | 4638..4639 |
| | mod_base = OTHER |
| | note = thymine |
| modified_base | 4642..4643 |
| | mod_base = OTHER |
| | note = thymine |
| modified_base | 4650 |
| | mod_base = OTHER |
| | note = thymine |
| modified_base | 4658 |
| | mod_base = OTHER |
| | note = thymine |
| modified_base | 4660 |
| | mod_base = OTHER |
| | note = thymine |
| modified_base | 4663 |
| | mod_base = OTHER |
| | note = thymine |
| modified_base | 4666 |
| | mod_base = OTHER |
| | note = thymine |
| modified_base | 4669 |
| | mod_base = OTHER |
| | note = thymine |
| modified_base | 4671..4672 |
| | mod_base = OTHER |
| | note = thymine |
| modified_base | 4678 |
| | mod_base = OTHER |
| | note = thymine |
| modified_base | 4680 |
| | mod_base = OTHER |
| | note = thymine |
| modified_base | 4686..4687 |
| | mod_base = OTHER |
| | note = thymine |
| modified_base | 4690..4693 |
| | mod_base = OTHER |
| | note = thymine |
| modified_base | 4697..4698 |
| | mod_base = OTHER |
| | note = thymine |
| modified_base | 4703 |
| | mod_base = OTHER |
| | note = thymine |
| modified_base | 4705 |
| | mod_base = OTHER |
| | note = thymine |
| modified_base | 4709..4711 |
| | mod_base = OTHER |

|   |   |
|---|---|
| | note = thymine |
| modified_base | 4715 |
| | mod_base = OTHER |
| | note = thymine |
| modified_base | 4717..4718 |
| | mod_base = OTHER |
| | note = thymine |
| modified_base | 4721 |
| | mod_base = OTHER |
| | note = thymine |
| modified_base | 4723 |
| | mod_base = OTHER |
| | note = thymine |
| modified_base | 4725..4726 |
| | mod_base = OTHER |
| | note = thymine |
| modified_base | 4738 |
| | mod_base = OTHER |
| | note = thymine |
| modified_base | 4753 |
| | mod_base = OTHER |
| | note = thymine |
| modified_base | 4755 |
| | mod_base = OTHER |
| | note = thymine |
| modified_base | 4757..4759 |
| | mod_base = OTHER |
| | note = thymine |
| modified_base | 4766 |
| | mod_base = OTHER |
| | note = thymine |
| modified_base | 4769 |
| | mod_base = OTHER |
| | note = thymine |
| modified_base | 4774..4776 |
| | mod_base = OTHER |
| | note = thymine |
| modified_base | 4780 |
| | mod_base = OTHER |
| | note = thymine |
| modified_base | 4782 |
| | mod_base = OTHER |
| | note = thymine |
| modified_base | 4784 |
| | mod_base = OTHER |
| | note = thymine |
| modified_base | 4792 |
| | mod_base = OTHER |
| | note = thymine |
| modified_base | 4794..4795 |
| | mod_base = OTHER |
| | note = thymine |
| modified_base | 4800 |
| | mod_base = OTHER |
| | note = thymine |
| modified_base | 4802..4804 |
| | mod_base = OTHER |
| | note = thymine |
| source | 1..7114 |
| | mol_type = other RNA |
| | organism = unidentified |

SEQUENCE: 4

```
cgcacagtgg atcctaggcg taacttcatc attaaaatct cagattctgc tctgagtgtg   60
acttactgcg aagaggcaga caaatgggca actgcaacgg ggcatccaag tctaaccagc  120
cagactcctc aagagccaca cagccagccg cagaatttag gagggtagct cacagcagtc  180
tatatggtag atataactgt aagtgctgct ggtttgctga taccaatttg ataacctgta  240
atgatcacta cctttgttta aggtgccatc agggtatgtt aaggaattca gatctctgca  300
atatctgctg gaagcccctg cccaccacaa tcacagtacc ggtggagcca acagcaccac  360
caccataggc agactgcaca gggtcagacc cgaccccccg gggggccccc atgggaccc  420
cccgtggggg aaccccgggg gtgatgcgcc attagtcaat gtctttgatc tcgactttgt  480
gcttcagtgg cctgcatgtc accccttttca atctgaactg cccttgggga tctgatatca  540
gcaggtcatt taaagatctg ctgaatgcca ccttgaaatt tgagaattcc aaccagtcac  600
caaatttatc aagtgaacgg atcaactgct ctttgtgtag atcataaacg aggacaaagt  660
cctcttgctg aaataatatt gtttgtgatg ttgttttag ataaggccat agttggctta  720
ataaggtttc cacactatca atgtcctcta gtgctccaat tgccttgact atgacatccc  780
cagacaactc aactctatat gttgacaacc tttcattacc tctgtaaaag ataccctctt  840
tcaagacaag aggttctcct gggttatctg gcccaatgag gtcatatgca tacttgttac  900
ttagttcaga ataaaagtca ccaaagttga acttaacatg gctcagaata ttgtcatcat  960
ttgtcgcagc gtagcctgca tcaataaaca agccagctag gtcaaagctc tcatggcctg 1020
```

```
tgaacaatgg taggctagcg ataaccagtg caccatccaa caatgagtgg cttccctcag   1080
acccagaaac acattgactc attgcatcca cattcagctc taattcaggg gtaccgacat   1140
catccactcc tagtgaactg acaatggtgt aactgtacac catctttctt ctaagtttaa   1200
attttgtcga aactcgtgtg tgttctactt gaatgatcaa ttttagtttc acagcttctt   1260
ggcaagcaac attgcgcaac acagtgcaa ggtccatcat gtcttcctga ggcaacaagg    1320
agatgttgtc aacagagaca ccctcaagga aaaccttgat attatcaaag ctagaaacta   1380
cataacccat tgcaatgtct tcaacaaaca ttgctcttga tactttatta ttcctaactg   1440
acaaggtaaa atctgtgagt tcagctagat ctacttgact gtcatcttct agatctagaa   1500
cttcattgaa ccaaaagaag gatttgagac acgatgttga catgactagt gggtttatca   1560
tcgaagataa gacaacttgc accatgaagt tcctgcaaac ttgctgtggg ctgatgccaa   1620
cttcccaatt tgtatactct gactgtctaa catgggctga agcgcaatca ctctgtttca   1680
caatataaac attattatct cttactttca ataagtgact tataatccct aagttttcat   1740
tcatcatgtc tagagccaca cagacatcta gaaacttgag tcttccacta tccaaagatc   1800
tgttcacttg aagatcattc ataaagggtg ccaaatgttc ttcaaatagt ttgggggtaat  1860
ttcttcgtat agaatgcaat acatggttca tgcctaattg gtcttctatc tgtcgtactg   1920
ctttgggttt aacagcccag aagaaattct tattacataa gaccagaggg gcctgtggac   1980
tcttaatagc aaaaaacacc cactccccta actcacaggc atttgtcagc accaaagaga   2040
agtaatccca caaaattggt ttagaaaatt ggttaacttc tttaagtgat ttttgacagt   2100
aaataacttt aggctttctc tcacaaattc cacaaagaca tggcattatt cgagtaaata   2160
tgtccttatt atacagaaat ccgcctttac catccctaac acacttactc cccatactct   2220
tacaaaaccc aatgaagcct gaggcaacag aagactgaaa tgcagatttg ttgattgact   2280
ctgccaagat cttcttcacg cctttttgtga aatttcttga cagcctgac tgtattgtcc   2340
ttatcaatgt tggcatctct tctttctcta acactcttcg acttgtcatg agtttggtcc   2400
tcaagaccaa cctcaagtcc ccaaagctcg ctaaattgac ccatctgtag tctagagttt   2460
gtctgatttc atcttcacta cacccggcat attgcaggaa tccggataaa gcctcatccc   2520
ctccctgct tatcaagtt ataaggtttt cctcaaagat tttgcctctc ttaatgtcat    2580
tgaacacttt cctcgcgcag ttccttataa acattgtctc cttatcatca gaaaaaatag   2640
cttcaatttt cctctgtaga cggtaccctc tagacccatc aacccagtct ttgacatctt   2700
gttcttcaat agctccaaac ggagtctctc tgtatccaga gtatctaatc aattggttga   2760
ctctaatgga aatcttttgac actatatgag tgctaacccc attagcaata cattgatcac   2820
aaattgtgtc tatggtctct gacagttgtg ttggagtttt acacttaacg ttgtgtagag   2880
cagcagacac aaacttggtg agtaaggag tctcttcacc catgacaaaa aatcttgact    2940
taaactcagc aacaaaagtt cctatcacac tctttgggct gataaacttg tttaatttag   3000
aagataagaa ttcatggaag cacaccattt ccagcagttc tgtcctgtct tgaaacttt    3060
catcactaag gcaaggaatt tttataaggc taacctggtc atcgctggag gtataagtga   3120
caggtatcac atcatacaat aagtcaagtg cataacacag aaattgttca gtaattagcc   3180
catataaatc tgatgtgttg tgcaagattc cctggcccat gtccaagaca gacattatat   3240
ggctgggggac ctggtccctt gactgcagat actggtgaaa aaactcttca ccaacactag   3300
tacagtcaca acccattaaa cctaaagatc tcttcaattt ccctacacag taggcttctg   3360
caacattaat tggaacttca acgacctat gaagatgcca tttgagaatg ttcattactg    3420
gttcaagatt caccttgtt ctatctctgg gattcttcaa ttctaatgtg tacaaaaaag    3480
aaaggaaaag tgctgggctc atagttggtc cccatttgga gtggtcatat gaacaggaca   3540
agtcaccatt gttaacagcc attttcatat cacagattgc acgttcgaat tccttttctg   3600
aattcaagca tgtgtatttc attgaactac ccacagcttc tgagaagtct tcaactaacc   3660
tggtcatcag cttagtgttg aggtctccca catacagttc tctatttgag ccaacctgct   3720
ccttataact tagtccaaat ttcaagttcc ctgtatttga gctgatgctt gtgaactctg   3780
taggagagtc gtctgaatag aaacataaat tccgtaggtc tgcattttgta aataacttt   3840
tgtctagctt atcagcaatg gcttcagaat tgctttccct ggtactaagc cgaacctcat   3900
cctttagtct cagaacttca ctggaaaagc ccaatctaga tctacttcta tgctcataac   3960
tacccaattt ctgatcataa tgtccttgaa ttaaaagata cttgaagcat tcaaagaatt   4020
catcttcttg gtaggctatt gttgtcaaat ttttaataa caaacccaaa gggcagatgt   4080
cctgcggtgc ttcaagaaaa taagtcaatt taaatggaga tagataaaca gcatcacata   4140
actcttata cacatcagac ctgagcacat ctggatcaaa atccttcacc tcatgcattg    4200
acacctctgc tttaatctct ctcaacactc caaaggggc ccacaatgac tcaagagact    4260
ctcgctcatc aacagatgga ttttttgatt tcaacttggt gatctcaact tttgtcccct   4320
cactattagc catcttggct agtgtcattt gtacgtcatt tctaatccc tcaaaggccc    4380
ttacttgatc ctctgttaaa ctctcataca tcactgataa ttcttcttga ttggttctgg   4440
ttcttgaacc ggtgctcaca agacctgtta gattttttaa tattaagtag tccatggaat   4500
caggataag attatacctg cctttttgtt taaacctctc agccatagta gaaacgcatg    4560
ttgaaacaag tttctcctta tcataaacag aaagaatatt tccaagttcg tcgagctttg   4620
ggattaccac acttttattg cttgacagat ccagagctgt gctagtgatg ttaggcctgt   4680
agggattgct tttcagttca cctgtaactt taagtcttcc tctattgaag agagaaatgc   4740
agaaggacaa aatctcttta cacactcctg gaatttgagt atctgaggaa gtcttagcct   4800
ctttggaaaa gaatctgtcc aatcctctta tcatgtgtc ctcttgttcc agtgttagac    4860
tcccacttag aggggggttt acaacaacac aatcaaactt gactttgggc tcaataaact   4920
tctcaaaaca cttgatttga tctgtcaggc gatcaggtgt ctcttggtt accaagtgac    4980
acagataact aacatttaat agatatttaa accttcttgc aaagtaaaga tctgcatctt   5040
cccttcacc caaaattgtc tggaaaagtt ccacagccat cctctgaatc agcacctctg   5100
atccagacat gcagtcgacc cttaactttg acatcaaatc cacatgatgg atttgatttg   5160
catatgccat caagaaatat cttagacctt gtaaaaatgt ctggttcctt ttggaagggg   5220
aacagagtac agctaaacact aacaatctta atattgccct tgtcattgtc atgagttcgt  5280
ggctaaaatc caaccagctg gtcatttcct cacacatttc aattaacaca tcctccgaaa   5340
atataggcag gaaaaatctc tttggatcac agtaaaaaga gccttgttct tccaatccc    5400
cattgatgga tagatagata gaatagcacc ttgacttctc acctgttttt tggtaaaaca   5460
agagaccaaa tgtattcttt gtcagatgaa atctttgtac ataacactct cttagtctaa   5520
cattcccaaa atatctagaa tactctcttt cattgattaa caatcgggag gaaaatgatg   5580
tcttcatcga gttgaccaat gcaagggaaa tggaggacaa aatcctaaat aatttcttct   5640
gctcaccttc cactaagctg ctgaatggct gatgtctaca gattttctca aattccttgt   5700
taatagtata tctcatcact ggtctgtcag aaacaagtgc ctgagctaaa atcatcaagc   5760
```

```
tatccatatc agggtgtttt attagttttt ccagctgtga ccagagatct tgatgagagt    5820
tcttcaatgt tctggaacac gcttgaaccc acttggggct ggtcatcaat ttcttcctta    5880
ttagtttaat cgcctccaga atatctagaa gtctgtcatt gactaacatt aacatttgtc    5940
caacaactat tcccgcattt cttaacctta caattgcatc atcatgcgtt ttgaaaagat    6000
cacaaagtaa attgagtaaa actaagtcca gaaacagtaa agtgttctc ctggtgttga     6060
aaacttttag accttccact ttgttacaca cggaaagggc ttgaagataa cacctctcta    6120
cagcatcaat agatatagaa ttctcatctg actggctttc catgttgact tcatctattg    6180
gatgcaatgc gatagagtag actacatcca tcaacttgtt tgcacaaaaa gggcagctgg    6240
gcacatcact gtctttgtgg cttcctaata agatcaagtc atttataagc ttagacttt     6300
gtgaaaattt gaattcccc aactgcttgt caaaaatctc cttcttaaac caaaaccta      6360
acttatgag ttcttctctt atgacagatt ctctaatgtc tcctctaacc ccaacaaaga     6420
gggattcatt taacctctca tcataaccca aagaattctt tttcaagcat cgatgttt      6480
ctaatcccaa gctctggttt tttgtgttgg acaaactatg gatcaatcgc tggtattctt    6540
gttcttcaat attaatctct tgcataaatt ttgatttctt taggatgtcg atcagcaacc    6600
accgaactct ttcaacaacc caatcagcaa ggaatctatt gctgtagcta gatctgccat    6660
caaccacagg aaccaacgta atccctgccc ttagtaggtc ggactttagg tttaagagct    6720
ttgacatgtc actcttccat tttctctcaa actcatcagg attgaccta acaaaggttt     6780
ccaataggat gagtgttttc cctgtgagtt tgaagccatc cggaatgact ttttggaaggg   6840
tgggacatag tatgccatag tcagacagga tcacatcaac aaacttctga tctgaattga    6900
tctgacaggc gtgtgcctca caggactcaa gctctactaa acttgacaga agtttgaacc    6960
cttccaacaa cagagagctg gggtgatgtt gagataaaaa gatgtcctt tggtatgcta     7020
gctcctgtct ttctggaaaa tgctttctaa taaggctttt tattcattt actgattcct     7080
ccatgctcaa gtgccgccta ggatccactg tgcg                                7114

SEQ ID NO: 5           moltype = RNA  length = 3377
FEATURE                Location/Qualifiers
modified_base          13
                       mod_base = OTHER
                       note = thymine
modified_base          16
                       mod_base = OTHER
                       note = thymine
modified_base          21..25
                       mod_base = OTHER
                       note = thymine
modified_base          29..30
                       mod_base = OTHER
                       note = thymine
modified_base          35..37
                       mod_base = OTHER
                       note = thymine
modified_base          40
                       mod_base = OTHER
                       note = thymine
modified_base          42
                       mod_base = OTHER
                       note = thymine
modified_base          46
                       mod_base = OTHER
                       note = thymine
modified_base          51
                       mod_base = OTHER
                       note = thymine
modified_base          55
                       mod_base = OTHER
                       note = thymine
modified_base          57
                       mod_base = OTHER
                       note = thymine
modified_base          65
                       mod_base = OTHER
                       note = thymine
modified_base          67
                       mod_base = OTHER
                       note = thymine
modified_base          70
                       mod_base = OTHER
                       note = thymine
modified_base          80
                       mod_base = OTHER
                       note = thymine
modified_base          84
                       mod_base = OTHER
                       note = thymine
modified_base          89..90
                       mod_base = OTHER
                       note = thymine
modified_base          92
                       mod_base = OTHER
```

```
                              note = thymine
modified_base                 98
                              mod_base = OTHER
                              note = thymine
modified_base                 100..102
                              mod_base = OTHER
                              note = thymine
modified_base                 108
                              mod_base = OTHER
                              note = thymine
modified_base                 110
                              mod_base = OTHER
                              note = thymine
modified_base                 114
                              mod_base = OTHER
                              note = thymine
modified_base                 119
                              mod_base = OTHER
                              note = thymine
modified_base                 122
                              mod_base = OTHER
                              note = thymine
modified_base                 126
                              mod_base = OTHER
                              note = thymine
modified_base                 131
                              mod_base = OTHER
                              note = thymine
modified_base                 134
                              mod_base = OTHER
                              note = thymine
modified_base                 140..141
                              mod_base = OTHER
                              note = thymine
modified_base                 143
                              mod_base = OTHER
                              note = thymine
modified_base                 146..147
                              mod_base = OTHER
                              note = thymine
modified_base                 149..150
                              mod_base = OTHER
                              note = thymine
modified_base                 152
                              mod_base = OTHER
                              note = thymine
modified_base                 155..156
                              mod_base = OTHER
                              note = thymine
modified_base                 158
                              mod_base = OTHER
                              note = thymine
modified_base                 161
                              mod_base = OTHER
                              note = thymine
modified_base                 164
                              mod_base = OTHER
                              note = thymine
modified_base                 171
                              mod_base = OTHER
                              note = thymine
modified_base                 173
                              mod_base = OTHER
                              note = thymine
modified_base                 180
                              mod_base = OTHER
                              note = thymine
modified_base                 182
                              mod_base = OTHER
                              note = thymine
modified_base                 184
                              mod_base = OTHER
                              note = thymine
modified_base                 189..192
                              mod_base = OTHER
                              note = thymine
modified_base                 199
                              mod_base = OTHER
                              note = thymine
```

| | |
|---|---|
| modified_base | 201<br>mod_base = OTHER<br>note = thymine |
| modified_base | 206<br>mod_base = OTHER<br>note = thymine |
| modified_base | 208..209<br>mod_base = OTHER<br>note = thymine |
| modified_base | 214..215<br>mod_base = OTHER<br>note = thymine |
| modified_base | 218<br>mod_base = OTHER<br>note = thymine |
| modified_base | 222..224<br>mod_base = OTHER<br>note = thymine |
| modified_base | 227<br>mod_base = OTHER<br>note = thymine |
| modified_base | 230..231<br>mod_base = OTHER<br>note = thymine |
| modified_base | 233<br>mod_base = OTHER<br>note = thymine |
| modified_base | 237<br>mod_base = OTHER<br>note = thymine |
| modified_base | 244<br>mod_base = OTHER<br>note = thymine |
| modified_base | 247<br>mod_base = OTHER<br>note = thymine |
| modified_base | 249<br>mod_base = OTHER<br>note = thymine |
| modified_base | 254<br>mod_base = OTHER<br>note = thymine |
| modified_base | 256<br>mod_base = OTHER<br>note = thymine |
| modified_base | 261<br>mod_base = OTHER<br>note = thymine |
| modified_base | 263..264<br>mod_base = OTHER<br>note = thymine |
| modified_base | 278..280<br>mod_base = OTHER<br>note = thymine |
| modified_base | 290..292<br>mod_base = OTHER<br>note = thymine |
| modified_base | 298..300<br>mod_base = OTHER<br>note = thymine |
| modified_base | 304<br>mod_base = OTHER<br>note = thymine |
| modified_base | 308<br>mod_base = OTHER<br>note = thymine |
| modified_base | 313..315<br>mod_base = OTHER<br>note = thymine |
| modified_base | 318<br>mod_base = OTHER<br>note = thymine |
| modified_base | 320<br>mod_base = OTHER<br>note = thymine |
| modified_base | 322<br>mod_base = OTHER<br>note = thymine |
| modified_base | 327 |

| | | |
|---|---|---|
| | | mod_base = OTHER |
| | | note = thymine |
| modified_base | 329 | |
| | | mod_base = OTHER |
| | | note = thymine |
| modified_base | 335 | |
| | | mod_base = OTHER |
| | | note = thymine |
| modified_base | 341 | |
| | | mod_base = OTHER |
| | | note = thymine |
| modified_base | 352 | |
| | | mod_base = OTHER |
| | | note = thymine |
| modified_base | 354..355 | |
| | | mod_base = OTHER |
| | | note = thymine |
| modified_base | 367 | |
| | | mod_base = OTHER |
| | | note = thymine |
| modified_base | 375..376 | |
| | | mod_base = OTHER |
| | | note = thymine |
| modified_base | 380 | |
| | | mod_base = OTHER |
| | | note = thymine |
| modified_base | 384 | |
| | | mod_base = OTHER |
| | | note = thymine |
| modified_base | 386 | |
| | | mod_base = OTHER |
| | | note = thymine |
| modified_base | 393..394 | |
| | | mod_base = OTHER |
| | | note = thymine |
| modified_base | 396 | |
| | | mod_base = OTHER |
| | | note = thymine |
| modified_base | 401 | |
| | | mod_base = OTHER |
| | | note = thymine |
| modified_base | 406..407 | |
| | | mod_base = OTHER |
| | | note = thymine |
| modified_base | 412..413 | |
| | | mod_base = OTHER |
| | | note = thymine |
| modified_base | 420 | |
| | | mod_base = OTHER |
| | | note = thymine |
| modified_base | 423..424 | |
| | | mod_base = OTHER |
| | | note = thymine |
| modified_base | 428 | |
| | | mod_base = OTHER |
| | | note = thymine |
| modified_base | 431 | |
| | | mod_base = OTHER |
| | | note = thymine |
| modified_base | 435 | |
| | | mod_base = OTHER |
| | | note = thymine |
| modified_base | 442..445 | |
| | | mod_base = OTHER |
| | | note = thymine |
| modified_base | 450 | |
| | | mod_base = OTHER |
| | | note = thymine |
| modified_base | 452 | |
| | | mod_base = OTHER |
| | | note = thymine |
| modified_base | 457 | |
| | | mod_base = OTHER |
| | | note = thymine |
| modified_base | 459 | |
| | | mod_base = OTHER |
| | | note = thymine |
| modified_base | 463..464 | |
| | | mod_base = OTHER |

```
                        note = thymine
modified_base           478..480
                        mod_base = OTHER
                        note = thymine
modified_base           491
                        mod_base = OTHER
                        note = thymine
modified_base           494
                        mod_base = OTHER
                        note = thymine
modified_base           498
                        mod_base = OTHER
                        note = thymine
modified_base           500
                        mod_base = OTHER
                        note = thymine
modified_base           503..505
                        mod_base = OTHER
                        note = thymine
modified_base           512
                        mod_base = OTHER
                        note = thymine
modified_base           518
                        mod_base = OTHER
                        note = thymine
modified_base           522
                        mod_base = OTHER
                        note = thymine
modified_base           524
                        mod_base = OTHER
                        note = thymine
modified_base           535
                        mod_base = OTHER
                        note = thymine
modified_base           541
                        mod_base = OTHER
                        note = thymine
modified_base           543
                        mod_base = OTHER
                        note = thymine
modified_base           551
                        mod_base = OTHER
                        note = thymine
modified_base           553
                        mod_base = OTHER
                        note = thymine
modified_base           556
                        mod_base = OTHER
                        note = thymine
modified_base           562..563
                        mod_base = OTHER
                        note = thymine
modified_base           570
                        mod_base = OTHER
                        note = thymine
modified_base           575
                        mod_base = OTHER
                        note = thymine
modified_base           581
                        mod_base = OTHER
                        note = thymine
modified_base           586
                        mod_base = OTHER
                        note = thymine
modified_base           592..593
                        mod_base = OTHER
                        note = thymine
modified_base           598..599
                        mod_base = OTHER
                        note = thymine
modified_base           601
                        mod_base = OTHER
                        note = thymine
modified_base           606
                        mod_base = OTHER
                        note = thymine
modified_base           615
                        mod_base = OTHER
                        note = thymine
```

-continued

| | | |
|---|---|---|
| modified_base | 618 | |
| | mod_base = OTHER | |
| | note = thymine | |
| modified_base | 628 | |
| | mod_base = OTHER | |
| | note = thymine | |
| modified_base | 630 | |
| | mod_base = OTHER | |
| | note = thymine | |
| modified_base | 637..638 | |
| | mod_base = OTHER | |
| | note = thymine | |
| modified_base | 645 | |
| | mod_base = OTHER | |
| | note = thymine | |
| modified_base | 650 | |
| | mod_base = OTHER | |
| | note = thymine | |
| modified_base | 653 | |
| | mod_base = OTHER | |
| | note = thymine | |
| modified_base | 657 | |
| | mod_base = OTHER | |
| | note = thymine | |
| modified_base | 659 | |
| | mod_base = OTHER | |
| | note = thymine | |
| modified_base | 661..663 | |
| | mod_base = OTHER | |
| | note = thymine | |
| modified_base | 669 | |
| | mod_base = OTHER | |
| | note = thymine | |
| modified_base | 673..674 | |
| | mod_base = OTHER | |
| | note = thymine | |
| modified_base | 685 | |
| | mod_base = OTHER | |
| | note = thymine | |
| modified_base | 689 | |
| | mod_base = OTHER | |
| | note = thymine | |
| modified_base | 696 | |
| | mod_base = OTHER | |
| | note = thymine | |
| modified_base | 700 | |
| | mod_base = OTHER | |
| | note = thymine | |
| modified_base | 706 | |
| | mod_base = OTHER | |
| | note = thymine | |
| modified_base | 715 | |
| | mod_base = OTHER | |
| | note = thymine | |
| modified_base | 720 | |
| | mod_base = OTHER | |
| | note = thymine | |
| modified_base | 733 | |
| | mod_base = OTHER | |
| | note = thymine | |
| modified_base | 736 | |
| | mod_base = OTHER | |
| | note = thymine | |
| modified_base | 738 | |
| | mod_base = OTHER | |
| | note = thymine | |
| modified_base | 750..751 | |
| | mod_base = OTHER | |
| | note = thymine | |
| modified_base | 757 | |
| | mod_base = OTHER | |
| | note = thymine | |
| modified_base | 761 | |
| | mod_base = OTHER | |
| | note = thymine | |
| modified_base | 764..765 | |
| | mod_base = OTHER | |
| | note = thymine | |
| modified_base | 767 | |

|  |  |
|---|---|
|  | mod_base = OTHER |
|  | note = thymine |
| modified_base | 774 |
|  | mod_base = OTHER |
|  | note = thymine |
| modified_base | 781 |
|  | mod_base = OTHER |
|  | note = thymine |
| modified_base | 793 |
|  | mod_base = OTHER |
|  | note = thymine |
| modified_base | 799 |
|  | mod_base = OTHER |
|  | note = thymine |
| modified_base | 801 |
|  | mod_base = OTHER |
|  | note = thymine |
| modified_base | 807 |
|  | mod_base = OTHER |
|  | note = thymine |
| modified_base | 810..813 |
|  | mod_base = OTHER |
|  | note = thymine |
| modified_base | 818 |
|  | mod_base = OTHER |
|  | note = thymine |
| modified_base | 820 |
|  | mod_base = OTHER |
|  | note = thymine |
| modified_base | 827..828 |
|  | mod_base = OTHER |
|  | note = thymine |
| modified_base | 830 |
|  | mod_base = OTHER |
|  | note = thymine |
| modified_base | 833..835 |
|  | mod_base = OTHER |
|  | note = thymine |
| modified_base | 849 |
|  | mod_base = OTHER |
|  | note = thymine |
| modified_base | 853..854 |
|  | mod_base = OTHER |
|  | note = thymine |
| modified_base | 857 |
|  | mod_base = OTHER |
|  | note = thymine |
| modified_base | 861 |
|  | mod_base = OTHER |
|  | note = thymine |
| modified_base | 869 |
|  | mod_base = OTHER |
|  | note = thymine |
| modified_base | 880..881 |
|  | mod_base = OTHER |
|  | note = thymine |
| modified_base | 886 |
|  | mod_base = OTHER |
|  | note = thymine |
| modified_base | 891..893 |
|  | mod_base = OTHER |
|  | note = thymine |
| modified_base | 895 |
|  | mod_base = OTHER |
|  | note = thymine |
| modified_base | 901 |
|  | mod_base = OTHER |
|  | note = thymine |
| modified_base | 903..904 |
|  | mod_base = OTHER |
|  | note = thymine |
| modified_base | 911 |
|  | mod_base = OTHER |
|  | note = thymine |
| modified_base | 918 |
|  | mod_base = OTHER |
|  | note = thymine |
| modified_base | 924 |
|  | mod_base = OTHER |

```
modified_base      927..928
                   mod_base = OTHER
                   note = thymine
modified_base      930..931
                   mod_base = OTHER
                   note = thymine
modified_base      935
                   mod_base = OTHER
                   note = thymine
modified_base      943
                   mod_base = OTHER
                   note = thymine
modified_base      947
                   mod_base = OTHER
                   note = thymine
modified_base      950..951
                   mod_base = OTHER
                   note = thymine
modified_base      953..954
                   mod_base = OTHER
                   note = thymine
modified_base      957
                   mod_base = OTHER
                   note = thymine
modified_base      965..966
                   mod_base = OTHER
                   note = thymine
modified_base      970
                   mod_base = OTHER
                   note = thymine
modified_base      972..974
                   mod_base = OTHER
                   note = thymine
modified_base      989..990
                   mod_base = OTHER
                   note = thymine
modified_base      997
                   mod_base = OTHER
                   note = thymine
modified_base      1002
                   mod_base = OTHER
                   note = thymine
modified_base      1004
                   mod_base = OTHER
                   note = thymine
modified_base      1008
                   mod_base = OTHER
                   note = thymine
modified_base      1011
                   mod_base = OTHER
                   note = thymine
modified_base      1014
                   mod_base = OTHER
                   note = thymine
modified_base      1021..1022
                   mod_base = OTHER
                   note = thymine
modified_base      1024
                   mod_base = OTHER
                   note = thymine
modified_base      1026
                   mod_base = OTHER
                   note = thymine
modified_base      1031
                   mod_base = OTHER
                   note = thymine
modified_base      1034
                   mod_base = OTHER
                   note = thymine
modified_base      1040
                   mod_base = OTHER
                   note = thymine
modified_base      1043..1044
                   mod_base = OTHER
                   note = thymine
modified_base      1048
                   mod_base = OTHER
                   note = thymine
```

-continued

| | | |
|---|---|---|
| modified_base | 1059 | |
| | mod_base = OTHER | |
| | note = thymine | |
| modified_base | 1062..1064 | |
| | mod_base = OTHER | |
| | note = thymine | |
| modified_base | 1068 | |
| | mod_base = OTHER | |
| | note = thymine | |
| modified_base | 1072..1073 | |
| | mod_base = OTHER | |
| | note = thymine | |
| modified_base | 1085 | |
| | mod_base = OTHER | |
| | note = thymine | |
| modified_base | 1090 | |
| | mod_base = OTHER | |
| | note = thymine | |
| modified_base | 1092 | |
| | mod_base = OTHER | |
| | note = thymine | |
| modified_base | 1096..1097 | |
| | mod_base = OTHER | |
| | note = thymine | |
| modified_base | 1102..1103 | |
| | mod_base = OTHER | |
| | note = thymine | |
| modified_base | 1105..1106 | |
| | mod_base = OTHER | |
| | note = thymine | |
| modified_base | 1118 | |
| | mod_base = OTHER | |
| | note = thymine | |
| modified_base | 1122..1123 | |
| | mod_base = OTHER | |
| | note = thymine | |
| modified_base | 1125..1127 | |
| | mod_base = OTHER | |
| | note = thymine | |
| modified_base | 1130..1132 | |
| | mod_base = OTHER | |
| | note = thymine | |
| modified_base | 1137 | |
| | mod_base = OTHER | |
| | note = thymine | |
| modified_base | 1142 | |
| | mod_base = OTHER | |
| | note = thymine | |
| modified_base | 1145 | |
| | mod_base = OTHER | |
| | note = thymine | |
| modified_base | 1148 | |
| | mod_base = OTHER | |
| | note = thymine | |
| modified_base | 1159..1160 | |
| | mod_base = OTHER | |
| | note = thymine | |
| modified_base | 1167 | |
| | mod_base = OTHER | |
| | note = thymine | |
| modified_base | 1169 | |
| | mod_base = OTHER | |
| | note = thymine | |
| modified_base | 1172 | |
| | mod_base = OTHER | |
| | note = thymine | |
| modified_base | 1178 | |
| | mod_base = OTHER | |
| | note = thymine | |
| modified_base | 1183 | |
| | mod_base = OTHER | |
| | note = thymine | |
| modified_base | 1185..1186 | |
| | mod_base = OTHER | |
| | note = thymine | |
| modified_base | 1191..1192 | |
| | mod_base = OTHER | |
| | note = thymine | |
| modified_base | 1195 | |

```
                        mod_base = OTHER
                        note = thymine
modified_base           1201..1204
                        mod_base = OTHER
                        note = thymine
modified_base           1207
                        mod_base = OTHER
                        note = thymine
modified_base           1211
                        mod_base = OTHER
                        note = thymine
modified_base           1218
                        mod_base = OTHER
                        note = thymine
modified_base           1236
                        mod_base = OTHER
                        note = thymine
modified_base           1239
                        mod_base = OTHER
                        note = thymine
modified_base           1241
                        mod_base = OTHER
                        note = thymine
modified_base           1249
                        mod_base = OTHER
                        note = thymine
modified_base           1252
                        mod_base = OTHER
                        note = thymine
modified_base           1256..1257
                        mod_base = OTHER
                        note = thymine
modified_base           1259
                        mod_base = OTHER
                        note = thymine
modified_base           1266
                        mod_base = OTHER
                        note = thymine
modified_base           1269..1270
                        mod_base = OTHER
                        note = thymine
modified_base           1272..1273
                        mod_base = OTHER
                        note = thymine
modified_base           1276..1277
                        mod_base = OTHER
                        note = thymine
modified_base           1281
                        mod_base = OTHER
                        note = thymine
modified_base           1291..1292
                        mod_base = OTHER
                        note = thymine
modified_base           1296
                        mod_base = OTHER
                        note = thymine
modified_base           1304
                        mod_base = OTHER
                        note = thymine
modified_base           1320
                        mod_base = OTHER
                        note = thymine
modified_base           1325
                        mod_base = OTHER
                        note = thymine
modified_base           1328..1329
                        mod_base = OTHER
                        note = thymine
modified_base           1337
                        mod_base = OTHER
                        note = thymine
modified_base           1339..1340
                        mod_base = OTHER
                        note = thymine
modified_base           1350..1351
                        mod_base = OTHER
                        note = thymine
modified_base           1355
                        mod_base = OTHER
```

```
modified_base    1371
                 mod_base = OTHER
                 note = thymine
modified_base    1379
                 mod_base = OTHER
                 note = thymine
modified_base    1384..1385
                 mod_base = OTHER
                 note = thymine
modified_base    1388
                 mod_base = OTHER
                 note = thymine
modified_base    1394..1395
                 mod_base = OTHER
                 note = thymine
modified_base    1397
                 mod_base = OTHER
                 note = thymine
modified_base    1400
                 mod_base = OTHER
                 note = thymine
modified_base    1402..1405
                 mod_base = OTHER
                 note = thymine
modified_base    1411
                 mod_base = OTHER
                 note = thymine
modified_base    1413
                 mod_base = OTHER
                 note = thymine
modified_base    1417
                 mod_base = OTHER
                 note = thymine
modified_base    1419
                 mod_base = OTHER
                 note = thymine
modified_base    1421
                 mod_base = OTHER
                 note = thymine
modified_base    1424
                 mod_base = OTHER
                 note = thymine
modified_base    1430
                 mod_base = OTHER
                 note = thymine
modified_base    1432..1433
                 mod_base = OTHER
                 note = thymine
modified_base    1436
                 mod_base = OTHER
                 note = thymine
modified_base    1442..1443
                 mod_base = OTHER
                 note = thymine
modified_base    1445
                 mod_base = OTHER
                 note = thymine
modified_base    1451
                 mod_base = OTHER
                 note = thymine
modified_base    1469
                 mod_base = OTHER
                 note = thymine
modified_base    1476
                 mod_base = OTHER
                 note = thymine
modified_base    1480
                 mod_base = OTHER
                 note = thymine
modified_base    1483
                 mod_base = OTHER
                 note = thymine
modified_base    1485
                 mod_base = OTHER
                 note = thymine
modified_base    1501..1502
                 mod_base = OTHER
                 note = thymine
```

-continued

| | | |
|---|---|---|
| modified_base | 1517..1519 | |
| | mod_base = OTHER | |
| | note = thymine | |
| modified_base | 1521 | |
| | mod_base = OTHER | |
| | note = thymine | |
| modified_base | 1524..1525 | |
| | mod_base = OTHER | |
| | note = thymine | |
| modified_base | 1527 | |
| | mod_base = OTHER | |
| | note = thymine | |
| modified_base | 1530 | |
| | mod_base = OTHER | |
| | note = thymine | |
| modified_base | 1534..1536 | |
| | mod_base = OTHER | |
| | note = thymine | |
| modified_base | 1541 | |
| | mod_base = OTHER | |
| | note = thymine | |
| modified_base | 1545 | |
| | mod_base = OTHER | |
| | note = thymine | |
| modified_base | 1548 | |
| | mod_base = OTHER | |
| | note = thymine | |
| modified_base | 1550 | |
| | mod_base = OTHER | |
| | note = thymine | |
| modified_base | 1559 | |
| | mod_base = OTHER | |
| | note = thymine | |
| modified_base | 1561 | |
| | mod_base = OTHER | |
| | note = thymine | |
| modified_base | 1573 | |
| | mod_base = OTHER | |
| | note = thymine | |
| modified_base | 1587 | |
| | mod_base = OTHER | |
| | note = thymine | |
| modified_base | 1591 | |
| | mod_base = OTHER | |
| | note = thymine | |
| modified_base | 1595 | |
| | mod_base = OTHER | |
| | note = thymine | |
| modified_base | 1597 | |
| | mod_base = OTHER | |
| | note = thymine | |
| modified_base | 1603 | |
| | mod_base = OTHER | |
| | note = thymine | |
| modified_base | 1613 | |
| | mod_base = OTHER | |
| | note = thymine | |
| modified_base | 1620 | |
| | mod_base = OTHER | |
| | note = thymine | |
| modified_base | 1638 | |
| | mod_base = OTHER | |
| | note = thymine | |
| modified_base | 1640..1641 | |
| | mod_base = OTHER | |
| | note = thymine | |
| modified_base | 1646 | |
| | mod_base = OTHER | |
| | note = thymine | |
| modified_base | 1648 | |
| | mod_base = OTHER | |
| | note = thymine | |
| modified_base | 1656..1658 | |
| | mod_base = OTHER | |
| | note = thymine | |
| modified_base | 1664 | |
| | mod_base = OTHER | |
| | note = thymine | |
| modified_base | 1666 | |

```
                              mod_base = OTHER
                              note = thymine
modified_base                 1672..1673
                              mod_base = OTHER
                              note = thymine
modified_base                 1677
                              mod_base = OTHER
                              note = thymine
modified_base                 1680
                              mod_base = OTHER
                              note = thymine
modified_base                 1682
                              mod_base = OTHER
                              note = thymine
modified_base                 1690
                              mod_base = OTHER
                              note = thymine
modified_base                 1692..1693
                              mod_base = OTHER
                              note = thymine
modified_base                 1695
                              mod_base = OTHER
                              note = thymine
modified_base                 1702..1705
                              mod_base = OTHER
                              note = thymine
modified_base                 1710
                              mod_base = OTHER
                              note = thymine
modified_base                 1712
                              mod_base = OTHER
                              note = thymine
modified_base                 1720..1721
                              mod_base = OTHER
                              note = thymine
modified_base                 1724..1726
                              mod_base = OTHER
                              note = thymine
modified_base                 1735..1737
                              mod_base = OTHER
                              note = thymine
modified_base                 1744
                              mod_base = OTHER
                              note = thymine
modified_base                 1747
                              mod_base = OTHER
                              note = thymine
modified_base                 1752
                              mod_base = OTHER
                              note = thymine
modified_base                 1756
                              mod_base = OTHER
                              note = thymine
modified_base                 1760
                              mod_base = OTHER
                              note = thymine
modified_base                 1767
                              mod_base = OTHER
                              note = thymine
modified_base                 1774
                              mod_base = OTHER
                              note = thymine
modified_base                 1777
                              mod_base = OTHER
                              note = thymine
modified_base                 1779
                              mod_base = OTHER
                              note = thymine
modified_base                 1781..1783
                              mod_base = OTHER
                              note = thymine
modified_base                 1785..1786
                              mod_base = OTHER
                              note = thymine
modified_base                 1788..1792
                              mod_base = OTHER
                              note = thymine
modified_base                 1794
                              mod_base = OTHER
```

| | | |
|---|---|---|
| | | note = thymine |
| modified_base | 1798..1799 | |
| | | mod_base = OTHER |
| | | note = thymine |
| modified_base | 1802 | |
| | | mod_base = OTHER |
| | | note = thymine |
| modified_base | 1804..1805 | |
| | | mod_base = OTHER |
| | | note = thymine |
| modified_base | 1810 | |
| | | mod_base = OTHER |
| | | note = thymine |
| modified_base | 1812 | |
| | | mod_base = OTHER |
| | | note = thymine |
| modified_base | 1816 | |
| | | mod_base = OTHER |
| | | note = thymine |
| modified_base | 1818..1819 | |
| | | mod_base = OTHER |
| | | note = thymine |
| modified_base | 1833 | |
| | | mod_base = OTHER |
| | | note = thymine |
| modified_base | 1835..1837 | |
| | | mod_base = OTHER |
| | | note = thymine |
| modified_base | 1839 | |
| | | mod_base = OTHER |
| | | note = thymine |
| modified_base | 1847..1849 | |
| | | mod_base = OTHER |
| | | note = thymine |
| modified_base | 1851 | |
| | | mod_base = OTHER |
| | | note = thymine |
| modified_base | 1853..1854 | |
| | | mod_base = OTHER |
| | | note = thymine |
| modified_base | 1857 | |
| | | mod_base = OTHER |
| | | note = thymine |
| modified_base | 1860 | |
| | | mod_base = OTHER |
| | | note = thymine |
| modified_base | 1864 | |
| | | mod_base = OTHER |
| | | note = thymine |
| modified_base | 1871..1872 | |
| | | mod_base = OTHER |
| | | note = thymine |
| modified_base | 1876 | |
| | | mod_base = OTHER |
| | | note = thymine |
| modified_base | 1879 | |
| | | mod_base = OTHER |
| | | note = thymine |
| modified_base | 1882..1884 | |
| | | mod_base = OTHER |
| | | note = thymine |
| modified_base | 1890 | |
| | | mod_base = OTHER |
| | | note = thymine |
| modified_base | 1894 | |
| | | mod_base = OTHER |
| | | note = thymine |
| modified_base | 1899..1900 | |
| | | mod_base = OTHER |
| | | note = thymine |
| modified_base | 1903 | |
| | | mod_base = OTHER |
| | | note = thymine |
| modified_base | 1905 | |
| | | mod_base = OTHER |
| | | note = thymine |
| modified_base | 1908..1909 | |
| | | mod_base = OTHER |
| | | note = thymine |

-continued

| | | |
|---|---|---|
| modified_base | 1912 | |
| | mod_base = OTHER | |
| | note = thymine | |
| modified_base | 1914..1915 | |
| | mod_base = OTHER | |
| | note = thymine | |
| modified_base | 1917 | |
| | mod_base = OTHER | |
| | note = thymine | |
| modified_base | 1919 | |
| | mod_base = OTHER | |
| | note = thymine | |
| modified_base | 1923 | |
| | mod_base = OTHER | |
| | note = thymine | |
| modified_base | 1932..1934 | |
| | mod_base = OTHER | |
| | note = thymine | |
| modified_base | 1936 | |
| | mod_base = OTHER | |
| | note = thymine | |
| modified_base | 1939 | |
| | mod_base = OTHER | |
| | note = thymine | |
| modified_base | 1941 | |
| | mod_base = OTHER | |
| | note = thymine | |
| modified_base | 1944 | |
| | mod_base = OTHER | |
| | note = thymine | |
| modified_base | 1952..1953 | |
| | mod_base = OTHER | |
| | note = thymine | |
| modified_base | 1960..1961 | |
| | mod_base = OTHER | |
| | note = thymine | |
| modified_base | 1969 | |
| | mod_base = OTHER | |
| | note = thymine | |
| modified_base | 1974 | |
| | mod_base = OTHER | |
| | note = thymine | |
| modified_base | 1988 | |
| | mod_base = OTHER | |
| | note = thymine | |
| modified_base | 1990 | |
| | mod_base = OTHER | |
| | note = thymine | |
| modified_base | 1994 | |
| | mod_base = OTHER | |
| | note = thymine | |
| modified_base | 2002 | |
| | mod_base = OTHER | |
| | note = thymine | |
| modified_base | 2012..2013 | |
| | mod_base = OTHER | |
| | note = thymine | |
| modified_base | 2019..2020 | |
| | mod_base = OTHER | |
| | note = thymine | |
| modified_base | 2028 | |
| | mod_base = OTHER | |
| | note = thymine | |
| modified_base | 2037 | |
| | mod_base = OTHER | |
| | note = thymine | |
| modified_base | 2041 | |
| | mod_base = OTHER | |
| | note = thymine | |
| modified_base | 2046 | |
| | mod_base = OTHER | |
| | note = thymine | |
| modified_base | 2048 | |
| | mod_base = OTHER | |
| | note = thymine | |
| modified_base | 2052 | |
| | mod_base = OTHER | |
| | note = thymine | |
| modified_base | 2055..2056 | |

```
                          mod_base = OTHER
                          note = thymine
modified_base             2061
                          mod_base = OTHER
                          note = thymine
modified_base             2063..2064
                          mod_base = OTHER
                          note = thymine
modified_base             2067..2068
                          mod_base = OTHER
                          note = thymine
modified_base             2072..2073
                          mod_base = OTHER
                          note = thymine
modified_base             2075..2079
                          mod_base = OTHER
                          note = thymine
modified_base             2082
                          mod_base = OTHER
                          note = thymine
modified_base             2090..2091
                          mod_base = OTHER
                          note = thymine
modified_base             2095
                          mod_base = OTHER
                          note = thymine
modified_base             2097
                          mod_base = OTHER
                          note = thymine
modified_base             2103
                          mod_base = OTHER
                          note = thymine
modified_base             2105
                          mod_base = OTHER
                          note = thymine
modified_base             2107
                          mod_base = OTHER
                          note = thymine
modified_base             2112
                          mod_base = OTHER
                          note = thymine
modified_base             2118..2119
                          mod_base = OTHER
                          note = thymine
modified_base             2121
                          mod_base = OTHER
                          note = thymine
modified_base             2123
                          mod_base = OTHER
                          note = thymine
modified_base             2126..2127
                          mod_base = OTHER
                          note = thymine
modified_base             2134..2135
                          mod_base = OTHER
                          note = thymine
modified_base             2138
                          mod_base = OTHER
                          note = thymine
modified_base             2140..2142
                          mod_base = OTHER
                          note = thymine
modified_base             2147
                          mod_base = OTHER
                          note = thymine
modified_base             2151
                          mod_base = OTHER
                          note = thymine
modified_base             2154..2155
                          mod_base = OTHER
                          note = thymine
modified_base             2159
                          mod_base = OTHER
                          note = thymine
modified_base             2161
                          mod_base = OTHER
                          note = thymine
modified_base             2166
                          mod_base = OTHER
```

```
                         note = thymine
modified_base            2170
                         mod_base = OTHER
                         note = thymine
modified_base            2172
                         mod_base = OTHER
                         note = thymine
modified_base            2176
                         mod_base = OTHER
                         note = thymine
modified_base            2180
                         mod_base = OTHER
                         note = thymine
modified_base            2182
                         mod_base = OTHER
                         note = thymine
modified_base            2190..2191
                         mod_base = OTHER
                         note = thymine
modified_base            2196
                         mod_base = OTHER
                         note = thymine
modified_base            2200..2201
                         mod_base = OTHER
                         note = thymine
modified_base            2204
                         mod_base = OTHER
                         note = thymine
modified_base            2209
                         mod_base = OTHER
                         note = thymine
modified_base            2214
                         mod_base = OTHER
                         note = thymine
modified_base            2216..2219
                         mod_base = OTHER
                         note = thymine
modified_base            2227..2228
                         mod_base = OTHER
                         note = thymine
modified_base            2230
                         mod_base = OTHER
                         note = thymine
modified_base            2232
                         mod_base = OTHER
                         note = thymine
modified_base            2236
                         mod_base = OTHER
                         note = thymine
modified_base            2238
                         mod_base = OTHER
                         note = thymine
modified_base            2242..2243
                         mod_base = OTHER
                         note = thymine
modified_base            2253
                         mod_base = OTHER
                         note = thymine
modified_base            2258
                         mod_base = OTHER
                         note = thymine
modified_base            2264
                         mod_base = OTHER
                         note = thymine
modified_base            2267
                         mod_base = OTHER
                         note = thymine
modified_base            2270
                         mod_base = OTHER
                         note = thymine
modified_base            2279
                         mod_base = OTHER
                         note = thymine
modified_base            2284
                         mod_base = OTHER
                         note = thymine
modified_base            2288
                         mod_base = OTHER
                         note = thymine
```

-continued

| | |
|---|---|
| modified_base | 2292..2293<br>mod_base = OTHER<br>note = thymine |
| modified_base | 2297<br>mod_base = OTHER<br>note = thymine |
| modified_base | 2303..2305<br>mod_base = OTHER<br>note = thymine |
| modified_base | 2307<br>mod_base = OTHER<br>note = thymine |
| modified_base | 2311..2312<br>mod_base = OTHER<br>note = thymine |
| modified_base | 2314<br>mod_base = OTHER<br>note = thymine |
| modified_base | 2319<br>mod_base = OTHER<br>note = thymine |
| modified_base | 2323..2324<br>mod_base = OTHER<br>note = thymine |
| modified_base | 2326..2327<br>mod_base = OTHER<br>note = thymine |
| modified_base | 2329<br>mod_base = OTHER<br>note = thymine |
| modified_base | 2331..2334<br>mod_base = OTHER<br>note = thymine |
| modified_base | 2339<br>mod_base = OTHER<br>note = thymine |
| modified_base | 2342<br>mod_base = OTHER<br>note = thymine |
| modified_base | 2344<br>mod_base = OTHER<br>note = thymine |
| modified_base | 2353<br>mod_base = OTHER<br>note = thymine |
| modified_base | 2357<br>mod_base = OTHER<br>note = thymine |
| modified_base | 2359..2360<br>mod_base = OTHER<br>note = thymine |
| modified_base | 2362<br>mod_base = OTHER<br>note = thymine |
| modified_base | 2369<br>mod_base = OTHER<br>note = thymine |
| modified_base | 2371<br>mod_base = OTHER<br>note = thymine |
| modified_base | 2373<br>mod_base = OTHER<br>note = thymine |
| modified_base | 2375<br>mod_base = OTHER<br>note = thymine |
| modified_base | 2381<br>mod_base = OTHER<br>note = thymine |
| modified_base | 2384..2385<br>mod_base = OTHER<br>note = thymine |
| modified_base | 2390<br>mod_base = OTHER<br>note = thymine |
| modified_base | 2402..2404<br>mod_base = OTHER<br>note = thymine |
| modified_base | 2406 |

-continued

|               |           |
|---------------|-----------|
|               | mod_base = OTHER |
|               | note = thymine |
| modified_base | 2413 |
|               | mod_base = OTHER |
|               | note = thymine |
| modified_base | 2415..2418 |
|               | mod_base = OTHER |
|               | note = thymine |
| modified_base | 2421 |
|               | mod_base = OTHER |
|               | note = thymine |
| modified_base | 2427..2428 |
|               | mod_base = OTHER |
|               | note = thymine |
| modified_base | 2431 |
|               | mod_base = OTHER |
|               | note = thymine |
| modified_base | 2433 |
|               | mod_base = OTHER |
|               | note = thymine |
| modified_base | 2441..2442 |
|               | mod_base = OTHER |
|               | note = thymine |
| modified_base | 2445 |
|               | mod_base = OTHER |
|               | note = thymine |
| modified_base | 2447 |
|               | mod_base = OTHER |
|               | note = thymine |
| modified_base | 2458 |
|               | mod_base = OTHER |
|               | note = thymine |
| modified_base | 2460..2461 |
|               | mod_base = OTHER |
|               | note = thymine |
| modified_base | 2465..2468 |
|               | mod_base = OTHER |
|               | note = thymine |
| modified_base | 2470 |
|               | mod_base = OTHER |
|               | note = thymine |
| modified_base | 2472..2473 |
|               | mod_base = OTHER |
|               | note = thymine |
| modified_base | 2486 |
|               | mod_base = OTHER |
|               | note = thymine |
| modified_base | 2490..2491 |
|               | mod_base = OTHER |
|               | note = thymine |
| modified_base | 2499 |
|               | mod_base = OTHER |
|               | note = thymine |
| modified_base | 2502 |
|               | mod_base = OTHER |
|               | note = thymine |
| modified_base | 2506 |
|               | mod_base = OTHER |
|               | note = thymine |
| modified_base | 2508..2509 |
|               | mod_base = OTHER |
|               | note = thymine |
| modified_base | 2512..2513 |
|               | mod_base = OTHER |
|               | note = thymine |
| modified_base | 2517..2518 |
|               | mod_base = OTHER |
|               | note = thymine |
| modified_base | 2521 |
|               | mod_base = OTHER |
|               | note = thymine |
| modified_base | 2527..2528 |
|               | mod_base = OTHER |
|               | note = thymine |
| modified_base | 2532 |
|               | mod_base = OTHER |
|               | note = thymine |
| modified_base | 2534 |
|               | mod_base = OTHER |

-continued

| | | |
|---|---|---|
| modified_base | 2539 | |
| | mod_base = OTHER | |
| | note = thymine | |
| modified_base | 2541..2542 | |
| | mod_base = OTHER | |
| | note = thymine | |
| modified_base | 2550 | |
| | mod_base = OTHER | |
| | note = thymine | |
| modified_base | 2561 | |
| | mod_base = OTHER | |
| | note = thymine | |
| modified_base | 2567 | |
| | mod_base = OTHER | |
| | note = thymine | |
| modified_base | 2571..2572 | |
| | mod_base = OTHER | |
| | note = thymine | |
| modified_base | 2590 | |
| | mod_base = OTHER | |
| | note = thymine | |
| modified_base | 2595..2596 | |
| | mod_base = OTHER | |
| | note = thymine | |
| modified_base | 2598 | |
| | mod_base = OTHER | |
| | note = thymine | |
| modified_base | 2608 | |
| | mod_base = OTHER | |
| | note = thymine | |
| modified_base | 2610..2611 | |
| | mod_base = OTHER | |
| | note = thymine | |
| modified_base | 2614 | |
| | mod_base = OTHER | |
| | note = thymine | |
| modified_base | 2617 | |
| | mod_base = OTHER | |
| | note = thymine | |
| modified_base | 2622 | |
| | mod_base = OTHER | |
| | note = thymine | |
| modified_base | 2625 | |
| | mod_base = OTHER | |
| | note = thymine | |
| modified_base | 2627..2628 | |
| | mod_base = OTHER | |
| | note = thymine | |
| modified_base | 2632 | |
| | mod_base = OTHER | |
| | note = thymine | |
| modified_base | 2635 | |
| | mod_base = OTHER | |
| | note = thymine | |
| modified_base | 2648 | |
| | mod_base = OTHER | |
| | note = thymine | |
| modified_base | 2652 | |
| | mod_base = OTHER | |
| | note = thymine | |
| modified_base | 2655..2656 | |
| | mod_base = OTHER | |
| | note = thymine | |
| modified_base | 2658 | |
| | mod_base = OTHER | |
| | note = thymine | |
| modified_base | 2660..2662 | |
| | mod_base = OTHER | |
| | note = thymine | |
| modified_base | 2668..2670 | |
| | mod_base = OTHER | |
| | note = thymine | |
| modified_base | 2676 | |
| | mod_base = OTHER | |
| | note = thymine | |
| modified_base | 2679..2680 | |
| | mod_base = OTHER | |
| | note = thymine | |

-continued

| | |
|---|---|
| modified_base | 2685..2687<br>mod_base = OTHER<br>note = thymine |
| modified_base | 2691<br>mod_base = OTHER<br>note = thymine |
| modified_base | 2694..2695<br>mod_base = OTHER<br>note = thymine |
| modified_base | 2699<br>mod_base = OTHER<br>note = thymine |
| modified_base | 2701<br>mod_base = OTHER<br>note = thymine |
| modified_base | 2703<br>mod_base = OTHER<br>note = thymine |
| modified_base | 2718<br>mod_base = OTHER<br>note = thymine |
| modified_base | 2720<br>mod_base = OTHER<br>note = thymine |
| modified_base | 2722<br>mod_base = OTHER<br>note = thymine |
| modified_base | 2729..2730<br>mod_base = OTHER<br>note = thymine |
| modified_base | 2732<br>mod_base = OTHER<br>note = thymine |
| modified_base | 2739<br>mod_base = OTHER<br>note = thymine |
| modified_base | 2742..2743<br>mod_base = OTHER<br>note = thymine |
| modified_base | 2752<br>mod_base = OTHER<br>note = thymine |
| modified_base | 2754<br>mod_base = OTHER<br>note = thymine |
| modified_base | 2756<br>mod_base = OTHER<br>note = thymine |
| modified_base | 2760<br>mod_base = OTHER<br>note = thymine |
| modified_base | 2762..2764<br>mod_base = OTHER<br>note = thymine |
| modified_base | 2770<br>mod_base = OTHER<br>note = thymine |
| modified_base | 2779<br>mod_base = OTHER<br>note = thymine |
| modified_base | 2782..2783<br>mod_base = OTHER<br>note = thymine |
| modified_base | 2788..2789<br>mod_base = OTHER<br>note = thymine |
| modified_base | 2794..2795<br>mod_base = OTHER<br>note = thymine |
| modified_base | 2797<br>mod_base = OTHER<br>note = thymine |
| modified_base | 2804..2805<br>mod_base = OTHER<br>note = thymine |
| modified_base | 2808..2809<br>mod_base = OTHER<br>note = thymine |
| modified_base | 2811..2812 |

-continued

| | | |
|---|---|---|
| | | mod_base = OTHER |
| | | note = thymine |
| modified_base | 2819 | |
| | | mod_base = OTHER |
| | | note = thymine |
| modified_base | 2822 | |
| | | mod_base = OTHER |
| | | note = thymine |
| modified_base | 2826 | |
| | | mod_base = OTHER |
| | | note = thymine |
| modified_base | 2828..2830 | |
| | | mod_base = OTHER |
| | | note = thymine |
| modified_base | 2835 | |
| | | mod_base = OTHER |
| | | note = thymine |
| modified_base | 2843 | |
| | | mod_base = OTHER |
| | | note = thymine |
| modified_base | 2845..2846 | |
| | | mod_base = OTHER |
| | | note = thymine |
| modified_base | 2857..2858 | |
| | | mod_base = OTHER |
| | | note = thymine |
| modified_base | 2865 | |
| | | mod_base = OTHER |
| | | note = thymine |
| modified_base | 2868 | |
| | | mod_base = OTHER |
| | | note = thymine |
| modified_base | 2874..2876 | |
| | | mod_base = OTHER |
| | | note = thymine |
| modified_base | 2878 | |
| | | mod_base = OTHER |
| | | note = thymine |
| modified_base | 2881 | |
| | | mod_base = OTHER |
| | | note = thymine |
| modified_base | 2888 | |
| | | mod_base = OTHER |
| | | note = thymine |
| modified_base | 2890 | |
| | | mod_base = OTHER |
| | | note = thymine |
| modified_base | 2892 | |
| | | mod_base = OTHER |
| | | note = thymine |
| modified_base | 2894 | |
| | | mod_base = OTHER |
| | | note = thymine |
| modified_base | 2899 | |
| | | mod_base = OTHER |
| | | note = thymine |
| modified_base | 2901 | |
| | | mod_base = OTHER |
| | | note = thymine |
| modified_base | 2906 | |
| | | mod_base = OTHER |
| | | note = thymine |
| modified_base | 2908..2910 | |
| | | mod_base = OTHER |
| | | note = thymine |
| modified_base | 2913 | |
| | | mod_base = OTHER |
| | | note = thymine |
| modified_base | 2915 | |
| | | mod_base = OTHER |
| | | note = thymine |
| modified_base | 2918..2919 | |
| | | mod_base = OTHER |
| | | note = thymine |
| modified_base | 2922 | |
| | | mod_base = OTHER |
| | | note = thymine |
| modified_base | 2924 | |
| | | mod_base = OTHER |

```
                       note = thymine
modified_base          2926..2927
                       mod_base = OTHER
                       note = thymine
modified_base          2929..2930
                       mod_base = OTHER
                       note = thymine
modified_base          2934..2935
                       mod_base = OTHER
                       note = thymine
modified_base          2941
                       mod_base = OTHER
                       note = thymine
modified_base          2943
                       mod_base = OTHER
                       note = thymine
modified_base          2945
                       mod_base = OTHER
                       note = thymine
modified_base          2951
                       mod_base = OTHER
                       note = thymine
modified_base          2958
                       mod_base = OTHER
                       note = thymine
modified_base          2965..2967
                       mod_base = OTHER
                       note = thymine
modified_base          2974
                       mod_base = OTHER
                       note = thymine
modified_base          2977
                       mod_base = OTHER
                       note = thymine
modified_base          2980
                       mod_base = OTHER
                       note = thymine
modified_base          2982..2983
                       mod_base = OTHER
                       note = thymine
modified_base          2988..2989
                       mod_base = OTHER
                       note = thymine
modified_base          2994..2995
                       mod_base = OTHER
                       note = thymine
modified_base          2997
                       mod_base = OTHER
                       note = thymine
modified_base          3003
                       mod_base = OTHER
                       note = thymine
modified_base          3019
                       mod_base = OTHER
                       note = thymine
modified_base          3023..3024
                       mod_base = OTHER
                       note = thymine
modified_base          3026..3027
                       mod_base = OTHER
                       note = thymine
modified_base          3029
                       mod_base = OTHER
                       note = thymine
modified_base          3034
                       mod_base = OTHER
                       note = thymine
modified_base          3040
                       mod_base = OTHER
                       note = thymine
modified_base          3047..3049
                       mod_base = OTHER
                       note = thymine
modified_base          3057..3058
                       mod_base = OTHER
                       note = thymine
modified_base          3060..3061
                       mod_base = OTHER
                       note = thymine
```

| | | |
|---|---|---|
| modified_base | 3063..3065<br>mod_base = OTHER<br>note = thymine | |
| modified_base | 3068<br>mod_base = OTHER<br>note = thymine | |
| modified_base | 3070..3071<br>mod_base = OTHER<br>note = thymine | |
| modified_base | 3075..3077<br>mod_base = OTHER<br>note = thymine | |
| modified_base | 3081<br>mod_base = OTHER<br>note = thymine | |
| modified_base | 3093<br>mod_base = OTHER<br>note = thymine | |
| modified_base | 3095<br>mod_base = OTHER<br>note = thymine | |
| modified_base | 3100<br>mod_base = OTHER<br>note = thymine | |
| modified_base | 3102<br>mod_base = OTHER<br>note = thymine | |
| modified_base | 3105..3106<br>mod_base = OTHER<br>note = thymine | |
| modified_base | 3112..3113<br>mod_base = OTHER<br>note = thymine | |
| modified_base | 3115<br>mod_base = OTHER<br>note = thymine | |
| modified_base | 3119<br>mod_base = OTHER<br>note = thymine | |
| modified_base | 3121<br>mod_base = OTHER<br>note = thymine | |
| modified_base | 3123<br>mod_base = OTHER<br>note = thymine | |
| modified_base | 3125<br>mod_base = OTHER<br>note = thymine | |
| modified_base | 3129<br>mod_base = OTHER<br>note = thymine | |
| modified_base | 3131..3133<br>mod_base = OTHER<br>note = thymine | |
| modified_base | 3135<br>mod_base = OTHER<br>note = thymine | |
| modified_base | 3138<br>mod_base = OTHER<br>note = thymine | |
| modified_base | 3140<br>mod_base = OTHER<br>note = thymine | |
| modified_base | 3142<br>mod_base = OTHER<br>note = thymine | |
| modified_base | 3144..3147<br>mod_base = OTHER<br>note = thymine | |
| modified_base | 3150..3151<br>mod_base = OTHER<br>note = thymine | |
| modified_base | 3154<br>mod_base = OTHER<br>note = thymine | |
| modified_base | 3157<br>mod_base = OTHER<br>note = thymine | |
| modified_base | 3160 | |

-continued

| | | |
|---|---|---|
| | | mod_base = OTHER |
| | | note = thymine |
| modified_base | 3163 | |
| | | mod_base = OTHER |
| | | note = thymine |
| modified_base | 3165 | |
| | | mod_base = OTHER |
| | | note = thymine |
| modified_base | 3171..3172 | |
| | | mod_base = OTHER |
| | | note = thymine |
| modified_base | 3175 | |
| | | mod_base = OTHER |
| | | note = thymine |
| modified_base | 3180 | |
| | | mod_base = OTHER |
| | | note = thymine |
| modified_base | 3189 | |
| | | mod_base = OTHER |
| | | note = thymine |
| modified_base | 3198..3199 | |
| | | mod_base = OTHER |
| | | note = thymine |
| modified_base | 3207..3208 | |
| | | mod_base = OTHER |
| | | note = thymine |
| modified_base | 3211..3212 | |
| | | mod_base = OTHER |
| | | note = thymine |
| modified_base | 3216 | |
| | | mod_base = OTHER |
| | | note = thymine |
| modified_base | 3219..3220 | |
| | | mod_base = OTHER |
| | | note = thymine |
| modified_base | 3223 | |
| | | mod_base = OTHER |
| | | note = thymine |
| modified_base | 3234..3235 | |
| | | mod_base = OTHER |
| | | note = thymine |
| modified_base | 3240 | |
| | | mod_base = OTHER |
| | | note = thymine |
| modified_base | 3242 | |
| | | mod_base = OTHER |
| | | note = thymine |
| modified_base | 3245 | |
| | | mod_base = OTHER |
| | | note = thymine |
| modified_base | 3247 | |
| | | mod_base = OTHER |
| | | note = thymine |
| modified_base | 3253 | |
| | | mod_base = OTHER |
| | | note = thymine |
| modified_base | 3255 | |
| | | mod_base = OTHER |
| | | note = thymine |
| modified_base | 3260..3261 | |
| | | mod_base = OTHER |
| | | note = thymine |
| modified_base | 3263 | |
| | | mod_base = OTHER |
| | | note = thymine |
| modified_base | 3265..3266 | |
| | | mod_base = OTHER |
| | | note = thymine |
| modified_base | 3268 | |
| | | mod_base = OTHER |
| | | note = thymine |
| modified_base | 3272 | |
| | | mod_base = OTHER |
| | | note = thymine |
| modified_base | 3275..3276 | |
| | | mod_base = OTHER |
| | | note = thymine |
| modified_base | 3280 | |
| | | mod_base = OTHER |

|   |   |
|---|---|
| | note = thymine |
| modified_base | 3284..3285 |
| | mod_base = OTHER |
| | note = thymine |
| modified_base | 3292 |
| | mod_base = OTHER |
| | note = thymine |
| modified_base | 3294..3295 |
| | mod_base = OTHER |
| | note = thymine |
| modified_base | 3299..3300 |
| | mod_base = OTHER |
| | note = thymine |
| modified_base | 3303..3304 |
| | mod_base = OTHER |
| | note = thymine |
| modified_base | 3316 |
| | mod_base = OTHER |
| | note = thymine |
| modified_base | 3318..3319 |
| | mod_base = OTHER |
| | note = thymine |
| modified_base | 3321..3322 |
| | mod_base = OTHER |
| | note = thymine |
| modified_base | 3325 |
| | mod_base = OTHER |
| | note = thymine |
| modified_base | 3329 |
| | mod_base = OTHER |
| | note = thymine |
| modified_base | 3332..3334 |
| | mod_base = OTHER |
| | note = thymine |
| modified_base | 3336 |
| | mod_base = OTHER |
| | note = thymine |
| modified_base | 3346 |
| | mod_base = OTHER |
| | note = thymine |
| modified_base | 3353 |
| | mod_base = OTHER |
| | note = thymine |
| modified_base | 3358 |
| | mod_base = OTHER |
| | note = thymine |
| modified_base | 3362 |
| | mod_base = OTHER |
| | note = thymine |
| modified_base | 3367 |
| | mod_base = OTHER |
| | note = thymine |
| modified_base | 3372 |
| | mod_base = OTHER |
| | note = thymine |
| modified_base | 3374 |
| | mod_base = OTHER |
| | note = thymine |
| misc_feature | 1..3377 |
| | note = Lymphocytic choriomeningitis mammarenavirus Viruses (LCMV); Lymphocytic choriomeningitis virus clone 13 segment S, complete sequence.ACCESSION DQ361065-VERSION DQ361065.2-GI:116563461.-ssRNA viruses; ssRNA negative-strand viruses; Arenaviridae; Mammarenavirus. |
| source | 1..3377 |
| | mol_type = other RNA |
| | organism = unidentified |

SEQUENCE: 5

```
gcgcaccggg gatcctaggc tttttggatt gcgctttcct ctagatcaac tgggtgtcag   60
gccctatcct acagaaggat gggtcagatt gtgacaatgt ttgaggctct gcctcacatc  120
atcgatgagg tgatcaacat tgtcattatt gtgcttatcg tgatcacggg tatcaaggct  180
gtctacaatt ttgccacctg tgggatattc gcattgatca gtttcctact tctggctggc  240
aggtcctgtg gcatgtacgg tcttaaggga cccgacattt acaaaggagt ttaccaattt  300
aagtcagtgg agtttgatat gtcacatctg aacctgacca tgcccaacgc atgttcagcc  360
aacaactccc accattacat cagtatgggg acttctggac tagaattgac cttcaccaat  420
gattccatca tcagtcacaa cttttgcaat ctgacctctg ccttcaacaa aaagaccttt  480
gaccacacac tcatgagtat agtttcgagc ctacacctca gtatcagagg gaactccaac  540
tataaggcag tatcctgcga cttcaacaat ggcataacca tccaatacaa cttgacattc  600
tcagatgcac aaagtgctca gagccagtgt agaaccttca gaggtagagt cctagatatg  660
```

-continued

```
tttagaactg ccttcggggg gaaatacatg aggagtggct ggggctggac aggctcagat    720
ggcaagacca cctggtgtag ccagacgagt taccaatacc tgattataca aaatagaacc    780
tgggaaaacc actgcacata tgcaggtcct tttgggatgt ccaggattct cctttcccaa    840
gagaagacta agttcctcac taggagacta gcgggcacat tcacctggac tttgtcagac    900
tcttcagggg tggagaatcc aggtggttat tgcctgacca aatggatgat tcttgctgca    960
gagcttaagt gtttcgggaa cacagcagtt gcgaaatgca atgtaaatca tgatgaagaa   1020
ttctgtgaca tgctgcgact aattgactac aacaaggctg ctttgagtaa gttcaaagag   1080
gacgtagaat ctgccttgca cttattcaaa acaacagtga attctttgat ttcagatcaa   1140
ctactgatga ggaaccactt gagagatctg atggggggtgc catattgcaa ttactcaaag   1200
ttttggtacc tagaacatgc aaagaccggc gaaactagtg tccccaagtg ctggcttgtc   1260
accaatggtt cttacttaaa tgagacccac ttcagtgacc aaatcgaaca ggaagccgat   1320
aacatgatta cagagatgtt gaggaaggat tacataaaga ggcagggag tacccccccta   1380
gcattgatgg accttctgat gttttccaca tctgcatatc tagtcagcat cttcctgcac   1440
cttgtcaaaa taccaacaca caggcacata aaaggtggct catgtccaaa gccacaccga   1500
ttaaccaaca aaggaatttg tagttgtggt gcatttaagg tgcctggtgt aaaaaccgtc   1560
tggaaaagac gctgaagaac agcgcctccc tgactctcca cctcgaaaga ggtggagagt   1620
cagggaggcc cagagggtct tagagtgtca aacatttgg gcctctaaaa attaggtcat   1680
gtggcagaat gttgtgaaca gttttcagat ctgggagcct tgctttggag gcgcttttcaa   1740
aaatgatgca gtccatgagt gcacagtgcg gggtgatctc tttcttctt ttgtcccctta   1800
ctattccagt atgcatctta cacaaccagc catatttgtc ccacactttg tcttcatact   1860
ccctcgaagc ttccctggtc atttcaacat cgataagctt aatgtccttc ctattctgtg   1920
agtccagaag cttctgatg tcatcggagc cttgacagct tagaaccatc ccctgcggaa   1980
gagcacctat aactgacgag gtcaaccccgg gttgcgcatt gaagaggtcg gcaagatcca   2040
tgccgtgtga gtacttggaa tcttgcttga attgttttg atcaacgggt tccctgtaaa   2100
agtgtatgaa ctgcccgttc tgtggttgga aaattgctat ttccactgga tcattaaatc   2160
tacctcaat gtcaatccat gtaggagcgt tggggtcaat tcctcccatg aggtcttta   2220
aaagcattgt ctggctgtag cttaagccca cctgaggtgg acctgctgct ccaggcgctg   2280
gcctgggtga attgactgca ggtttctcgc ttgtgagatc aattgttgtg ttttcccatg   2340
ctctccccac aatcgatgtt ctacaagcta tgtatggcca tccttcacct gaaaggcaaa   2400
ctttatagag gatgttttca taagggttcc tgtccccaac ttggtctgaa acaaacatgt   2460
tgagttttct cttggccccg agaactgcct tcaagaggtc ctcgctgttg cttggcttga   2520
tcaaaattga ctctaacatg ttaccccccat ccaacagggc tgcccctgcc ttcacggcag   2580
caccaagact aaagttatag ccagaaatgt tgatgctgga ctgctgttca gtgatgaccc   2640
ccagaagtgc gtgcttgtct ttcagccttt caagatcatt aagattgga tacttgactg   2700
tgtaaagcaa gccaaggtct gtgagcgctt gtacaacgtc attgagcgga gtctgtgact   2760
gtttggccat acaagccata gttagacttg gcattgtgcc aaattgattg ttcaaaagtg   2820
atgagtcttt cacatcccaa actcttacca caccacttgc accctgctga ggctttctca   2880
tcccaactat ctgtaggatc tgagatcttt ggtctagttg ctgtgttgtt aagttcccca   2940
tatataccccc tgaagcctgg ggcctttcag acctcatgat cttggccttc agcttctcaa   3000
ggtcagccgc aagagacatc agttcttctg cactgagcct ccccactttc aaaacattct   3060
tctttgatgt tgactttaaa tccacaagag aatgtacagt ctggttgaga cttctgagtc   3120
tctgtaggtc tttgtcatct ctcttttcct tcctcatgat cctctgaaca ttgctgacct   3180
cagagaagtc caacccattc agaaggttgg ttgcatcctt aatgacagca gcctttcacat   3240
ctgatgtgaa gctctgcaat tctcttctca atgcttgcgt ccattggaag ctcttaactt   3300
ccttagacaa ggacatcttg ttgctcaatg gtttctcaag acaaatgcgc aatcaaatgc   3360
ctaggatcca ctgtgcg                                                   3377
```

```
SEQ ID NO: 6          moltype = RNA   length = 7229
FEATURE               Location/Qualifiers
misc_feature          1..7229
                      note = Lymphocytic choriomeningitis mammarenavirus Viruses
                      (LCMV); Lymphocytic choriomeningitis virus clone 13
                      segment L, complete sequence.-ACCESSION DQ361066-VERSION
                      DQ361066.1-GI:86440167.-ssRNA viruses; ssRNA
                      negative-strand viruses; Arenaviridae; Mammarenavirus
source                1..7229
                      mol_type = other RNA
                      organism = unidentified
modified_base         13
                      mod_base = OTHER
                      note = thymine
modified_base         16
                      mod_base = OTHER
                      note = thymine
modified_base         22..24
                      mod_base = OTHER
                      note = thymine
modified_base         27..28
                      mod_base = OTHER
                      note = thymine
modified_base         33
                      mod_base = OTHER
                      note = thymine
modified_base         35..37
                      mod_base = OTHER
                      note = thymine
modified_base         40..41
                      mod_base = OTHER
                      note = thymine
```

| | |
|---|---|
| modified_base | 49..51<br>mod_base = OTHER<br>note = thymine |
| modified_base | 53..54<br>mod_base = OTHER<br>note = thymine |
| modified_base | 57<br>mod_base = OTHER<br>note = thymine |
| modified_base | 63<br>mod_base = OTHER<br>note = thymine |
| modified_base | 65<br>mod_base = OTHER<br>note = thymine |
| modified_base | 72<br>mod_base = OTHER<br>note = thymine |
| modified_base | 78<br>mod_base = OTHER<br>note = thymine |
| modified_base | 82<br>mod_base = OTHER<br>note = thymine |
| modified_base | 85<br>mod_base = OTHER<br>note = thymine |
| modified_base | 91<br>mod_base = OTHER<br>note = thymine |
| modified_base | 95<br>mod_base = OTHER<br>note = thymine |
| modified_base | 105<br>mod_base = OTHER<br>note = thymine |
| modified_base | 128<br>mod_base = OTHER<br>note = thymine |
| modified_base | 131<br>mod_base = OTHER<br>note = thymine |
| modified_base | 148<br>mod_base = OTHER<br>note = thymine |
| modified_base | 151<br>mod_base = OTHER<br>note = thymine |
| modified_base | 158<br>mod_base = OTHER<br>note = thymine |
| modified_base | 165<br>mod_base = OTHER<br>note = thymine |
| modified_base | 167<br>mod_base = OTHER<br>note = thymine |
| modified_base | 169..170<br>mod_base = OTHER<br>note = thymine |
| modified_base | 176..178<br>mod_base = OTHER<br>note = thymine |
| modified_base | 183<br>mod_base = OTHER<br>note = thymine |
| modified_base | 189<br>mod_base = OTHER<br>note = thymine |
| modified_base | 191..192<br>mod_base = OTHER<br>note = thymine |
| modified_base | 195<br>mod_base = OTHER<br>note = thymine |
| modified_base | 204..206<br>mod_base = OTHER<br>note = thymine |
| modified_base | 213..214 |

-continued

```
                         mod_base = OTHER
                         note = thymine
modified_base            217
                         mod_base = OTHER
                         note = thymine
modified_base            222
                         mod_base = OTHER
                         note = thymine
modified_base            227
                         mod_base = OTHER
                         note = thymine
modified_base            234
                         mod_base = OTHER
                         note = thymine
modified_base            238..240
                         mod_base = OTHER
                         note = thymine
modified_base            249
                         mod_base = OTHER
                         note = thymine
modified_base            251..253
                         mod_base = OTHER
                         note = thymine
modified_base            259..260
                         mod_base = OTHER
                         note = thymine
modified_base            262
                         mod_base = OTHER
                         note = thymine
modified_base            265
                         mod_base = OTHER
                         note = thymine
modified_base            267
                         mod_base = OTHER
                         note = thymine
modified_base            271
                         mod_base = OTHER
                         note = thymine
modified_base            273
                         mod_base = OTHER
                         note = thymine
modified_base            282
                         mod_base = OTHER
                         note = thymine
modified_base            284
                         mod_base = OTHER
                         note = thymine
modified_base            287
                         mod_base = OTHER
                         note = thymine
modified_base            289..291
                         mod_base = OTHER
                         note = thymine
modified_base            293
                         mod_base = OTHER
                         note = thymine
modified_base            297
                         mod_base = OTHER
                         note = thymine
modified_base            299
                         mod_base = OTHER
                         note = thymine
modified_base            303..304
                         mod_base = OTHER
                         note = thymine
modified_base            315..316
                         mod_base = OTHER
                         note = thymine
modified_base            322
                         mod_base = OTHER
                         note = thymine
modified_base            324
                         mod_base = OTHER
                         note = thymine
modified_base            339
                         mod_base = OTHER
                         note = thymine
modified_base            341
                         mod_base = OTHER
```

```
                            note = thymine
modified_base               347
                            mod_base = OTHER
                            note = thymine
modified_base               351
                            mod_base = OTHER
                            note = thymine
modified_base               360
                            mod_base = OTHER
                            note = thymine
modified_base               368
                            mod_base = OTHER
                            note = thymine
modified_base               414
                            mod_base = OTHER
                            note = thymine
modified_base               559
                            mod_base = OTHER
                            note = thymine
modified_base               565
                            mod_base = OTHER
                            note = thymine
modified_base               569
                            mod_base = OTHER
                            note = thymine
modified_base               573
                            mod_base = OTHER
                            note = thymine
modified_base               575
                            mod_base = OTHER
                            note = thymine
modified_base               578
                            mod_base = OTHER
                            note = thymine
modified_base               602
                            mod_base = OTHER
                            note = thymine
modified_base               605
                            mod_base = OTHER
                            note = thymine
modified_base               615
                            mod_base = OTHER
                            note = thymine
modified_base               620..621
                            mod_base = OTHER
                            note = thymine
modified_base               625
                            mod_base = OTHER
                            note = thymine
modified_base               627
                            mod_base = OTHER
                            note = thymine
modified_base               633
                            mod_base = OTHER
                            note = thymine
modified_base               643
                            mod_base = OTHER
                            note = thymine
modified_base               645..647
                            mod_base = OTHER
                            note = thymine
modified_base               650
                            mod_base = OTHER
                            note = thymine
modified_base               654
                            mod_base = OTHER
                            note = thymine
modified_base               660
                            mod_base = OTHER
                            note = thymine
modified_base               663
                            mod_base = OTHER
                            note = thymine
modified_base               666
                            mod_base = OTHER
                            note = thymine
modified_base               670..672
                            mod_base = OTHER
                            note = thymine
```

-continued

| | | |
|---|---|---|
| modified_base | 675 | |
| | mod_base = OTHER | |
| | note = thymine | |
| modified_base | 685 | |
| | mod_base = OTHER | |
| | note = thymine | |
| modified_base | 687 | |
| | mod_base = OTHER | |
| | note = thymine | |
| modified_base | 692 | |
| | mod_base = OTHER | |
| | note = thymine | |
| modified_base | 695..696 | |
| | mod_base = OTHER | |
| | note = thymine | |
| modified_base | 710 | |
| | mod_base = OTHER | |
| | note = thymine | |
| modified_base | 712 | |
| | mod_base = OTHER | |
| | note = thymine | |
| modified_base | 727 | |
| | mod_base = OTHER | |
| | note = thymine | |
| modified_base | 732 | |
| | mod_base = OTHER | |
| | note = thymine | |
| modified_base | 741 | |
| | mod_base = OTHER | |
| | note = thymine | |
| modified_base | 745 | |
| | mod_base = OTHER | |
| | note = thymine | |
| modified_base | 747 | |
| | mod_base = OTHER | |
| | note = thymine | |
| modified_base | 749 | |
| | mod_base = OTHER | |
| | note = thymine | |
| modified_base | 751 | |
| | mod_base = OTHER | |
| | note = thymine | |
| modified_base | 753 | |
| | mod_base = OTHER | |
| | note = thymine | |
| modified_base | 757 | |
| | mod_base = OTHER | |
| | note = thymine | |
| modified_base | 760..761 | |
| | mod_base = OTHER | |
| | note = thymine | |
| modified_base | 764 | |
| | mod_base = OTHER | |
| | note = thymine | |
| modified_base | 771..772 | |
| | mod_base = OTHER | |
| | note = thymine | |
| modified_base | 777..778 | |
| | mod_base = OTHER | |
| | note = thymine | |
| modified_base | 780 | |
| | mod_base = OTHER | |
| | note = thymine | |
| modified_base | 782 | |
| | mod_base = OTHER | |
| | note = thymine | |
| modified_base | 784 | |
| | mod_base = OTHER | |
| | note = thymine | |
| modified_base | 797 | |
| | mod_base = OTHER | |
| | note = thymine | |
| modified_base | 799..800 | |
| | mod_base = OTHER | |
| | note = thymine | |
| modified_base | 807..808 | |
| | mod_base = OTHER | |
| | note = thymine | |
| modified_base | 810 | |

-continued

|                |                                             |
|----------------|---------------------------------------------|
|                | mod_base = OTHER                            |
|                | note = thymine                              |
| modified_base  | 814                                         |
|                | mod_base = OTHER                            |
|                | note = thymine                              |
| modified_base  | 818                                         |
|                | mod_base = OTHER                            |
|                | note = thymine                              |
| modified_base  | 830..831                                    |
|                | mod_base = OTHER                            |
|                | note = thymine                              |
| modified_base  | 842                                         |
|                | mod_base = OTHER                            |
|                | note = thymine                              |
| modified_base  | 846                                         |
|                | mod_base = OTHER                            |
|                | note = thymine                              |
| modified_base  | 849                                         |
|                | mod_base = OTHER                            |
|                | note = thymine                              |
| modified_base  | 851..854                                    |
|                | mod_base = OTHER                            |
|                | note = thymine                              |
| modified_base  | 857                                         |
|                | mod_base = OTHER                            |
|                | note = thymine                              |
| modified_base  | 863                                         |
|                | mod_base = OTHER                            |
|                | note = thymine                              |
| modified_base  | 868                                         |
|                | mod_base = OTHER                            |
|                | note = thymine                              |
| modified_base  | 871                                         |
|                | mod_base = OTHER                            |
|                | note = thymine                              |
| modified_base  | 874                                         |
|                | mod_base = OTHER                            |
|                | note = thymine                              |
| modified_base  | 883..885                                    |
|                | mod_base = OTHER                            |
|                | note = thymine                              |
| modified_base  | 888                                         |
|                | mod_base = OTHER                            |
|                | note = thymine                              |
| modified_base  | 890                                         |
|                | mod_base = OTHER                            |
|                | note = thymine                              |
| modified_base  | 893..894                                    |
|                | mod_base = OTHER                            |
|                | note = thymine                              |
| modified_base  | 897                                         |
|                | mod_base = OTHER                            |
|                | note = thymine                              |
| modified_base  | 899                                         |
|                | mod_base = OTHER                            |
|                | note = thymine                              |
| modified_base  | 905..906                                    |
|                | mod_base = OTHER                            |
|                | note = thymine                              |
| modified_base  | 912                                         |
|                | mod_base = OTHER                            |
|                | note = thymine                              |
| modified_base  | 915                                         |
|                | mod_base = OTHER                            |
|                | note = thymine                              |
| modified_base  | 917..920                                    |
|                | mod_base = OTHER                            |
|                | note = thymine                              |
| modified_base  | 929..931                                    |
|                | mod_base = OTHER                            |
|                | note = thymine                              |
| modified_base  | 933..934                                    |
|                | mod_base = OTHER                            |
|                | note = thymine                              |
| modified_base  | 937..938                                    |
|                | mod_base = OTHER                            |
|                | note = thymine                              |
| modified_base  | 954                                         |
|                | mod_base = OTHER                            |

-continued

| | |
|---|---|
| modified_base | 956..958<br>mod_base = OTHER<br>note = thymine |
| modified_base | 963<br>mod_base = OTHER<br>note = thymine |
| modified_base | 967<br>mod_base = OTHER<br>note = thymine |
| modified_base | 977<br>mod_base = OTHER<br>note = thymine |
| modified_base | 983<br>mod_base = OTHER<br>note = thymine |
| modified_base | 988<br>mod_base = OTHER<br>note = thymine |
| modified_base | 994<br>mod_base = OTHER<br>note = thymine |
| modified_base | 996<br>mod_base = OTHER<br>note = thymine |
| modified_base | 998<br>mod_base = OTHER<br>note = thymine |
| modified_base | 1004<br>mod_base = OTHER<br>note = thymine |
| modified_base | 1008<br>mod_base = OTHER<br>note = thymine |
| modified_base | 1012<br>mod_base = OTHER<br>note = thymine |
| modified_base | 1014<br>mod_base = OTHER<br>note = thymine |
| modified_base | 1017<br>mod_base = OTHER<br>note = thymine |
| modified_base | 1022<br>mod_base = OTHER<br>note = thymine |
| modified_base | 1027<br>mod_base = OTHER<br>note = thymine |
| modified_base | 1029..1030<br>mod_base = OTHER<br>note = thymine |
| modified_base | 1032..1035<br>mod_base = OTHER<br>note = thymine |
| modified_base | 1049<br>mod_base = OTHER<br>note = thymine |
| modified_base | 1055<br>mod_base = OTHER<br>note = thymine |
| modified_base | 1064<br>mod_base = OTHER<br>note = thymine |
| modified_base | 1072<br>mod_base = OTHER<br>note = thymine |
| modified_base | 1074<br>mod_base = OTHER<br>note = thymine |
| modified_base | 1082<br>mod_base = OTHER<br>note = thymine |
| modified_base | 1084..1085<br>mod_base = OTHER<br>note = thymine |
| modified_base | 1089<br>mod_base = OTHER<br>note = thymine |

| | |
|---|---|
| modified_base | 1091<br>mod_base = OTHER<br>note = thymine |
| modified_base | 1094<br>mod_base = OTHER<br>note = thymine |
| modified_base | 1097<br>mod_base = OTHER<br>note = thymine |
| modified_base | 1103<br>mod_base = OTHER<br>note = thymine |
| modified_base | 1105..1106<br>mod_base = OTHER<br>note = thymine |
| modified_base | 1111<br>mod_base = OTHER<br>note = thymine |
| modified_base | 1113<br>mod_base = OTHER<br>note = thymine |
| modified_base | 1116<br>mod_base = OTHER<br>note = thymine |
| modified_base | 1118<br>mod_base = OTHER<br>note = thymine |
| modified_base | 1130<br>mod_base = OTHER<br>note = thymine |
| modified_base | 1133..1134<br>mod_base = OTHER<br>note = thymine |
| modified_base | 1139..1140<br>mod_base = OTHER<br>note = thymine |
| modified_base | 1151<br>mod_base = OTHER<br>note = thymine |
| modified_base | 1153<br>mod_base = OTHER<br>note = thymine |
| modified_base | 1155<br>mod_base = OTHER<br>note = thymine |
| modified_base | 1158<br>mod_base = OTHER<br>note = thymine |
| modified_base | 1162<br>mod_base = OTHER<br>note = thymine |
| modified_base | 1166<br>mod_base = OTHER<br>note = thymine |
| modified_base | 1174..1175<br>mod_base = OTHER<br>note = thymine |
| modified_base | 1178<br>mod_base = OTHER<br>note = thymine |
| modified_base | 1185..1186<br>mod_base = OTHER<br>note = thymine |
| modified_base | 1188..1189<br>mod_base = OTHER<br>note = thymine |
| modified_base | 1191<br>mod_base = OTHER<br>note = thymine |
| modified_base | 1193<br>mod_base = OTHER<br>note = thymine |
| modified_base | 1195<br>mod_base = OTHER<br>note = thymine |
| modified_base | 1197<br>mod_base = OTHER<br>note = thymine |
| modified_base | 1199 |

-continued

```
                              mod_base = OTHER
                              note = thymine
modified_base    1205..1206
                              mod_base = OTHER
                              note = thymine
modified_base    1214
                              mod_base = OTHER
                              note = thymine
modified_base    1222
                              mod_base = OTHER
                              note = thymine
modified_base    1225
                              mod_base = OTHER
                              note = thymine
modified_base    1231..1232
                              mod_base = OTHER
                              note = thymine
modified_base    1243
                              mod_base = OTHER
                              note = thymine
modified_base    1247..1248
                              mod_base = OTHER
                              note = thymine
modified_base    1250
                              mod_base = OTHER
                              note = thymine
modified_base    1252
                              mod_base = OTHER
                              note = thymine
modified_base    1255..1256
                              mod_base = OTHER
                              note = thymine
modified_base    1263
                              mod_base = OTHER
                              note = thymine
modified_base    1273
                              mod_base = OTHER
                              note = thymine
modified_base    1275
                              mod_base = OTHER
                              note = thymine
modified_base    1279
                              mod_base = OTHER
                              note = thymine
modified_base    1285..1287
                              mod_base = OTHER
                              note = thymine
modified_base    1290..1291
                              mod_base = OTHER
                              note = thymine
modified_base    1298
                              mod_base = OTHER
                              note = thymine
modified_base    1302
                              mod_base = OTHER
                              note = thymine
modified_base    1304..1305
                              mod_base = OTHER
                              note = thymine
modified_base    1307..1308
                              mod_base = OTHER
                              note = thymine
modified_base    1310
                              mod_base = OTHER
                              note = thymine
modified_base    1313..1314
                              mod_base = OTHER
                              note = thymine
modified_base    1316
                              mod_base = OTHER
                              note = thymine
modified_base    1320
                              mod_base = OTHER
                              note = thymine
modified_base    1325
                              mod_base = OTHER
                              note = thymine
modified_base    1330
                              mod_base = OTHER
```

-continued

```
                         note = thymine
modified_base            1335..1336
                         mod_base = OTHER
                         note = thymine
modified_base            1343
                         mod_base = OTHER
                         note = thymine
modified_base            1348
                         mod_base = OTHER
                         note = thymine
modified_base            1354..1357
                         mod_base = OTHER
                         note = thymine
modified_base            1359
                         mod_base = OTHER
                         note = thymine
modified_base            1361
                         mod_base = OTHER
                         note = thymine
modified_base            1364..1365
                         mod_base = OTHER
                         note = thymine
modified_base            1371
                         mod_base = OTHER
                         note = thymine
modified_base            1373
                         mod_base = OTHER
                         note = thymine
modified_base            1376
                         mod_base = OTHER
                         note = thymine
modified_base            1385
                         mod_base = OTHER
                         note = thymine
modified_base            1388..1390
                         mod_base = OTHER
                         note = thymine
modified_base            1396..1398
                         mod_base = OTHER
                         note = thymine
modified_base            1402
                         mod_base = OTHER
                         note = thymine
modified_base            1406..1408
                         mod_base = OTHER
                         note = thymine
modified_base            1412..1414
                         mod_base = OTHER
                         note = thymine
modified_base            1416
                         mod_base = OTHER
                         note = thymine
modified_base            1424
                         mod_base = OTHER
                         note = thymine
modified_base            1428
                         mod_base = OTHER
                         note = thymine
modified_base            1431
                         mod_base = OTHER
                         note = thymine
modified_base            1437
                         mod_base = OTHER
                         note = thymine
modified_base            1445..1446
                         mod_base = OTHER
                         note = thymine
modified_base            1457
                         mod_base = OTHER
                         note = thymine
modified_base            1459
                         mod_base = OTHER
                         note = thymine
modified_base            1464..1465
                         mod_base = OTHER
                         note = thymine
modified_base            1469
                         mod_base = OTHER
                         note = thymine
```

-continued

| | | |
|---|---|---|
| modified_base | 1493 | |
| | mod_base = OTHER | |
| | note = thymine | |
| modified_base | 1499 | |
| | mod_base = OTHER | |
| | note = thymine | |
| modified_base | 1502..1503 | |
| | mod_base = OTHER | |
| | note = thymine | |
| modified_base | 1506 | |
| | mod_base = OTHER | |
| | note = thymine | |
| modified_base | 1512 | |
| | mod_base = OTHER | |
| | note = thymine | |
| modified_base | 1518 | |
| | mod_base = OTHER | |
| | note = thymine | |
| modified_base | 1520 | |
| | mod_base = OTHER | |
| | note = thymine | |
| modified_base | 1526..1530 | |
| | mod_base = OTHER | |
| | note = thymine | |
| modified_base | 1532..1533 | |
| | mod_base = OTHER | |
| | note = thymine | |
| modified_base | 1541..1543 | |
| | mod_base = OTHER | |
| | note = thymine | |
| modified_base | 1552 | |
| | mod_base = OTHER | |
| | note = thymine | |
| modified_base | 1555..1556 | |
| | mod_base = OTHER | |
| | note = thymine | |
| modified_base | 1570 | |
| | mod_base = OTHER | |
| | note = thymine | |
| modified_base | 1574 | |
| | mod_base = OTHER | |
| | note = thymine | |
| modified_base | 1583 | |
| | mod_base = OTHER | |
| | note = thymine | |
| modified_base | 1585..1586 | |
| | mod_base = OTHER | |
| | note = thymine | |
| modified_base | 1591 | |
| | mod_base = OTHER | |
| | note = thymine | |
| modified_base | 1596 | |
| | mod_base = OTHER | |
| | note = thymine | |
| modified_base | 1599..1601 | |
| | mod_base = OTHER | |
| | note = thymine | |
| modified_base | 1603..1605 | |
| | mod_base = OTHER | |
| | note = thymine | |
| modified_base | 1607 | |
| | mod_base = OTHER | |
| | note = thymine | |
| modified_base | 1618 | |
| | mod_base = OTHER | |
| | note = thymine | |
| modified_base | 1625..1626 | |
| | mod_base = OTHER | |
| | note = thymine | |
| modified_base | 1630 | |
| | mod_base = OTHER | |
| | note = thymine | |
| modified_base | 1633 | |
| | mod_base = OTHER | |
| | note = thymine | |
| modified_base | 1635 | |
| | mod_base = OTHER | |
| | note = thymine | |
| modified_base | 1638 | |

-continued

```
                       mod_base = OTHER
                       note = thymine
modified_base     1641..1642
                       mod_base = OTHER
                       note = thymine
modified_base     1644..1645
                       mod_base = OTHER
                       note = thymine
modified_base     1654..1655
                       mod_base = OTHER
                       note = thymine
modified_base     1657
                       mod_base = OTHER
                       note = thymine
modified_base     1666
                       mod_base = OTHER
                       note = thymine
modified_base     1669..1670
                       mod_base = OTHER
                       note = thymine
modified_base     1676
                       mod_base = OTHER
                       note = thymine
modified_base     1682
                       mod_base = OTHER
                       note = thymine
modified_base     1684..1687
                       mod_base = OTHER
                       note = thymine
modified_base     1694..1695
                       mod_base = OTHER
                       note = thymine
modified_base     1697..1698
                       mod_base = OTHER
                       note = thymine
modified_base     1706
                       mod_base = OTHER
                       note = thymine
modified_base     1710
                       mod_base = OTHER
                       note = thymine
modified_base     1713
                       mod_base = OTHER
                       note = thymine
modified_base     1716
                       mod_base = OTHER
                       note = thymine
modified_base     1726..1727
                       mod_base = OTHER
                       note = thymine
modified_base     1730
                       mod_base = OTHER
                       note = thymine
modified_base     1740
                       mod_base = OTHER
                       note = thymine
modified_base     1745
                       mod_base = OTHER
                       note = thymine
modified_base     1750
                       mod_base = OTHER
                       note = thymine
modified_base     1754
                       mod_base = OTHER
                       note = thymine
modified_base     1757
                       mod_base = OTHER
                       note = thymine
modified_base     1763..1764
                       mod_base = OTHER
                       note = thymine
modified_base     1772
                       mod_base = OTHER
                       note = thymine
modified_base     1788
                       mod_base = OTHER
                       note = thymine
modified_base     1790
                       mod_base = OTHER
```

-continued

```
               note = thymine
modified_base  1793
               mod_base = OTHER
               note = thymine
modified_base  1795..1796
               mod_base = OTHER
               note = thymine
modified_base  1799
               mod_base = OTHER
               note = thymine
modified_base  1803..1806
               mod_base = OTHER
               note = thymine
modified_base  1811..1812
               mod_base = OTHER
               note = thymine
modified_base  1820
               mod_base = OTHER
               note = thymine
modified_base  1827
               mod_base = OTHER
               note = thymine
modified_base  1831
               mod_base = OTHER
               note = thymine
modified_base  1840..1841
               mod_base = OTHER
               note = thymine
modified_base  1843
               mod_base = OTHER
               note = thymine
modified_base  1847..1848
               mod_base = OTHER
               note = thymine
modified_base  1851
               mod_base = OTHER
               note = thymine
modified_base  1853
               mod_base = OTHER
               note = thymine
modified_base  1857..1858
               mod_base = OTHER
               note = thymine
modified_base  1871
               mod_base = OTHER
               note = thymine
modified_base  1879..1881
               mod_base = OTHER
               note = thymine
modified_base  1884..1885
               mod_base = OTHER
               note = thymine
modified_base  1887
               mod_base = OTHER
               note = thymine
modified_base  1893
               mod_base = OTHER
               note = thymine
modified_base  1899
               mod_base = OTHER
               note = thymine
modified_base  1902
               mod_base = OTHER
               note = thymine
modified_base  1904..1909
               mod_base = OTHER
               note = thymine
modified_base  1914
               mod_base = OTHER
               note = thymine
modified_base  1917
               mod_base = OTHER
               note = thymine
modified_base  1919
               mod_base = OTHER
               note = thymine
modified_base  1926
               mod_base = OTHER
               note = thymine
```

-continued

| | |
|---|---|
| modified_base | 1930<br>mod_base = OTHER<br>note = thymine |
| modified_base | 1940<br>mod_base = OTHER<br>note = thymine |
| modified_base | 1943<br>mod_base = OTHER<br>note = thymine |
| modified_base | 1946<br>mod_base = OTHER<br>note = thymine |
| modified_base | 1953<br>mod_base = OTHER<br>note = thymine |
| modified_base | 1955..1956<br>mod_base = OTHER<br>note = thymine |
| modified_base | 1961<br>mod_base = OTHER<br>note = thymine |
| modified_base | 1963<br>mod_base = OTHER<br>note = thymine |
| modified_base | 1971<br>mod_base = OTHER<br>note = thymine |
| modified_base | 1978..1979<br>mod_base = OTHER<br>note = thymine |
| modified_base | 1983<br>mod_base = OTHER<br>note = thymine |
| modified_base | 1987..1988<br>mod_base = OTHER<br>note = thymine |
| modified_base | 1991..1992<br>mod_base = OTHER<br>note = thymine |
| modified_base | 1997..1998<br>mod_base = OTHER<br>note = thymine |
| modified_base | 2002..2004<br>mod_base = OTHER<br>note = thymine |
| modified_base | 2006<br>mod_base = OTHER<br>note = thymine |
| modified_base | 2009<br>mod_base = OTHER<br>note = thymine |
| modified_base | 2014<br>mod_base = OTHER<br>note = thymine |
| modified_base | 2019..2020<br>mod_base = OTHER<br>note = thymine |
| modified_base | 2025<br>mod_base = OTHER<br>note = thymine |
| modified_base | 2027<br>mod_base = OTHER<br>note = thymine |
| modified_base | 2033..2035<br>mod_base = OTHER<br>note = thymine |
| modified_base | 2037..2038<br>mod_base = OTHER<br>note = thymine |
| modified_base | 2041<br>mod_base = OTHER<br>note = thymine |
| modified_base | 2045<br>mod_base = OTHER<br>note = thymine |
| modified_base | 2048<br>mod_base = OTHER<br>note = thymine |
| modified_base | 2053 |

```
modified_base    mod_base = OTHER
                 note = thymine
                 2057..2059
                 mod_base = OTHER
                 note = thymine
modified_base    2063
                 mod_base = OTHER
                 note = thymine
modified_base    2066..2067
                 mod_base = OTHER
                 note = thymine
modified_base    2073..2074
                 mod_base = OTHER
                 note = thymine
modified_base    2078..2079
                 mod_base = OTHER
                 note = thymine
modified_base    2081
                 mod_base = OTHER
                 note = thymine
modified_base    2085
                 mod_base = OTHER
                 note = thymine
modified_base    2087..2088
                 mod_base = OTHER
                 note = thymine
modified_base    2090..2091
                 mod_base = OTHER
                 note = thymine
modified_base    2093..2094
                 mod_base = OTHER
                 note = thymine
modified_base    2098..2100
                 mod_base = OTHER
                 note = thymine
modified_base    2103
                 mod_base = OTHER
                 note = thymine
modified_base    2107..2108
                 mod_base = OTHER
                 note = thymine
modified_base    2110
                 mod_base = OTHER
                 note = thymine
modified_base    2113
                 mod_base = OTHER
                 note = thymine
modified_base    2132
                 mod_base = OTHER
                 note = thymine
modified_base    2141..2142
                 mod_base = OTHER
                 note = thymine
modified_base    2145
                 mod_base = OTHER
                 note = thymine
modified_base    2149
                 mod_base = OTHER
                 note = thymine
modified_base    2154
                 mod_base = OTHER
                 note = thymine
modified_base    2160
                 mod_base = OTHER
                 note = thymine
modified_base    2162
                 mod_base = OTHER
                 note = thymine
modified_base    2165
                 mod_base = OTHER
                 note = thymine
modified_base    2181..2182
                 mod_base = OTHER
                 note = thymine
modified_base    2191
                 mod_base = OTHER
                 note = thymine
modified_base    2193
                 mod_base = OTHER
```

-continued

| | | |
|---|---|---|
| modified_base | 2195 | mod_base = OTHER<br>note = thymine |
| modified_base | 2198 | mod_base = OTHER<br>note = thymine |
| modified_base | 2204 | mod_base = OTHER<br>note = thymine |
| modified_base | 2209..2210 | mod_base = OTHER<br>note = thymine |
| modified_base | 2212 | mod_base = OTHER<br>note = thymine |
| modified_base | 2216 | mod_base = OTHER<br>note = thymine |
| modified_base | 2222 | mod_base = OTHER<br>note = thymine |
| modified_base | 2224..2226 | mod_base = OTHER<br>note = thymine |
| modified_base | 2228 | mod_base = OTHER<br>note = thymine |
| modified_base | 2235 | mod_base = OTHER<br>note = thymine |
| modified_base | 2237 | mod_base = OTHER<br>note = thymine |
| modified_base | 2244..2245 | mod_base = OTHER<br>note = thymine |
| modified_base | 2247 | mod_base = OTHER<br>note = thymine |
| modified_base | 2252 | mod_base = OTHER<br>note = thymine |
| modified_base | 2258..2259 | mod_base = OTHER<br>note = thymine |
| modified_base | 2266 | mod_base = OTHER<br>note = thymine |
| modified_base | 2268..2269 | mod_base = OTHER<br>note = thymine |
| modified_base | 2271 | mod_base = OTHER<br>note = thymine |
| modified_base | 2276 | mod_base = OTHER<br>note = thymine |
| modified_base | 2279 | mod_base = OTHER<br>note = thymine |
| modified_base | 2282 | mod_base = OTHER<br>note = thymine |
| modified_base | 2284 | mod_base = OTHER<br>note = thymine |
| modified_base | 2286 | mod_base = OTHER<br>note = thymine |
| modified_base | 2289..2290 | mod_base = OTHER<br>note = thymine |
| modified_base | 2294 | mod_base = OTHER<br>note = thymine |
| modified_base | 2297 | mod_base = OTHER<br>note = thymine |

| | |
|---|---|
| modified_base | 2306..2310<br>mod_base = OTHER<br>note = thymine |
| modified_base | 2313<br>mod_base = OTHER<br>note = thymine |
| modified_base | 2315<br>mod_base = OTHER<br>note = thymine |
| modified_base | 2321..2324<br>mod_base = OTHER<br>note = thymine |
| modified_base | 2328<br>mod_base = OTHER<br>note = thymine |
| modified_base | 2330..2334<br>mod_base = OTHER<br>note = thymine |
| modified_base | 2336..2338<br>mod_base = OTHER<br>note = thymine |
| modified_base | 2340<br>mod_base = OTHER<br>note = thymine |
| modified_base | 2349<br>mod_base = OTHER<br>note = thymine |
| modified_base | 2352..2353<br>mod_base = OTHER<br>note = thymine |
| modified_base | 2356<br>mod_base = OTHER<br>note = thymine |
| modified_base | 2361..2364<br>mod_base = OTHER<br>note = thymine |
| modified_base | 2374<br>mod_base = OTHER<br>note = thymine |
| modified_base | 2376<br>mod_base = OTHER<br>note = thymine |
| modified_base | 2386<br>mod_base = OTHER<br>note = thymine |
| modified_base | 2391<br>mod_base = OTHER<br>note = thymine |
| modified_base | 2397<br>mod_base = OTHER<br>note = thymine |
| modified_base | 2399<br>mod_base = OTHER<br>note = thymine |
| modified_base | 2407<br>mod_base = OTHER<br>note = thymine |
| modified_base | 2411..2412<br>mod_base = OTHER<br>note = thymine |
| modified_base | 2414..2415<br>mod_base = OTHER<br>note = thymine |
| modified_base | 2418..2419<br>mod_base = OTHER<br>note = thymine |
| modified_base | 2422..2423<br>mod_base = OTHER<br>note = thymine |
| modified_base | 2425<br>mod_base = OTHER<br>note = thymine |
| modified_base | 2435..2436<br>mod_base = OTHER<br>note = thymine |
| modified_base | 2438<br>mod_base = OTHER<br>note = thymine |
| modified_base | 2440 |

```
                              mod_base = OTHER
                              note = thymine
modified_base   2448..2449
                              mod_base = OTHER
                              note = thymine
modified_base   2451
                              mod_base = OTHER
                              note = thymine
modified_base   2455..2457
                              mod_base = OTHER
                              note = thymine
modified_base   2460
                              mod_base = OTHER
                              note = thymine
modified_base   2467..2469
                              mod_base = OTHER
                              note = thymine
modified_base   2471..2472
                              mod_base = OTHER
                              note = thymine
modified_base   2474
                              mod_base = OTHER
                              note = thymine
modified_base   2479
                              mod_base = OTHER
                              note = thymine
modified_base   2481
                              mod_base = OTHER
                              note = thymine
modified_base   2483..2484
                              mod_base = OTHER
                              note = thymine
modified_base   2487
                              mod_base = OTHER
                              note = thymine
modified_base   2491
                              mod_base = OTHER
                              note = thymine
modified_base   2494
                              mod_base = OTHER
                              note = thymine
modified_base   2499..2500
                              mod_base = OTHER
                              note = thymine
modified_base   2502..2504
                              mod_base = OTHER
                              note = thymine
modified_base   2507
                              mod_base = OTHER
                              note = thymine
modified_base   2509..2510
                              mod_base = OTHER
                              note = thymine
modified_base   2517
                              mod_base = OTHER
                              note = thymine
modified_base   2520
                              mod_base = OTHER
                              note = thymine
modified_base   2524
                              mod_base = OTHER
                              note = thymine
modified_base   2527
                              mod_base = OTHER
                              note = thymine
modified_base   2531
                              mod_base = OTHER
                              note = thymine
modified_base   2540..2543
                              mod_base = OTHER
                              note = thymine
modified_base   2545
                              mod_base = OTHER
                              note = thymine
modified_base   2547..2548
                              mod_base = OTHER
                              note = thymine
modified_base   2556
                              mod_base = OTHER
```

|  |  |
|---|---|
|  | note = thymine |
| modified_base | 2559..2560 |
|  | mod_base = OTHER |
|  | note = thymine |
| modified_base | 2563 |
|  | mod_base = OTHER |
|  | note = thymine |
| modified_base | 2571..2573 |
|  | mod_base = OTHER |
|  | note = thymine |
| modified_base | 2576..2577 |
|  | mod_base = OTHER |
|  | note = thymine |
| modified_base | 2582..2583 |
|  | mod_base = OTHER |
|  | note = thymine |
| modified_base | 2591..2592 |
|  | mod_base = OTHER |
|  | note = thymine |
| modified_base | 2597 |
|  | mod_base = OTHER |
|  | note = thymine |
| modified_base | 2599 |
|  | mod_base = OTHER |
|  | note = thymine |
| modified_base | 2602 |
|  | mod_base = OTHER |
|  | note = thymine |
| modified_base | 2606 |
|  | mod_base = OTHER |
|  | note = thymine |
| modified_base | 2609..2610 |
|  | mod_base = OTHER |
|  | note = thymine |
| modified_base | 2615 |
|  | mod_base = OTHER |
|  | note = thymine |
| modified_base | 2617..2618 |
|  | mod_base = OTHER |
|  | note = thymine |
| modified_base | 2620..2621 |
|  | mod_base = OTHER |
|  | note = thymine |
| modified_base | 2636 |
|  | mod_base = OTHER |
|  | note = thymine |
| modified_base | 2638 |
|  | mod_base = OTHER |
|  | note = thymine |
| modified_base | 2644..2645 |
|  | mod_base = OTHER |
|  | note = thymine |
| modified_base | 2652 |
|  | mod_base = OTHER |
|  | note = thymine |
| modified_base | 2657 |
|  | mod_base = OTHER |
|  | note = thymine |
| modified_base | 2660..2664 |
|  | mod_base = OTHER |
|  | note = thymine |
| modified_base | 2666 |
|  | mod_base = OTHER |
|  | note = thymine |
| modified_base | 2668 |
|  | mod_base = OTHER |
|  | note = thymine |
| modified_base | 2670 |
|  | mod_base = OTHER |
|  | note = thymine |
| modified_base | 2672..2673 |
|  | mod_base = OTHER |
|  | note = thymine |
| modified_base | 2677 |
|  | mod_base = OTHER |
|  | note = thymine |
| modified_base | 2681 |
|  | mod_base = OTHER |
|  | note = thymine |

| | | |
|---|---|---|
| modified_base | 2683 mod_base = OTHER note = thymine | |
| modified_base | 2692..2693 mod_base = OTHER note = thymine | |
| modified_base | 2695..2696 mod_base = OTHER note = thymine | |
| modified_base | 2699..2700 mod_base = OTHER note = thymine | |
| modified_base | 2704..2705 mod_base = OTHER note = thymine | |
| modified_base | 2711..2715 mod_base = OTHER note = thymine | |
| modified_base | 2720..2721 mod_base = OTHER note = thymine | |
| modified_base | 2723 mod_base = OTHER note = thymine | |
| modified_base | 2726 mod_base = OTHER note = thymine | |
| modified_base | 2731..2733 mod_base = OTHER note = thymine | |
| modified_base | 2736..2737 mod_base = OTHER note = thymine | |
| modified_base | 2744..2746 mod_base = OTHER note = thymine | |
| modified_base | 2748..2749 mod_base = OTHER note = thymine | |
| modified_base | 2756..2758 mod_base = OTHER note = thymine | |
| modified_base | 2760..2762 mod_base = OTHER note = thymine | |
| modified_base | 2765..2766 mod_base = OTHER note = thymine | |
| modified_base | 2776..2777 mod_base = OTHER note = thymine | |
| modified_base | 2780 mod_base = OTHER note = thymine | |
| modified_base | 2784 mod_base = OTHER note = thymine | |
| modified_base | 2788 mod_base = OTHER note = thymine | |
| modified_base | 2790..2792 mod_base = OTHER note = thymine | |
| modified_base | 2794 mod_base = OTHER note = thymine | |
| modified_base | 2796..2797 mod_base = OTHER note = thymine | |
| modified_base | 2799 mod_base = OTHER note = thymine | |
| modified_base | 2801 mod_base = OTHER note = thymine | |
| modified_base | 2806 mod_base = OTHER note = thymine | |
| modified_base | 2808 | |

-continued

| | | |
|---|---|---|
| | | mod_base = OTHER |
| | | note = thymine |
| modified_base | 2816 | |
| | | mod_base = OTHER |
| | | note = thymine |
| modified_base | 2825 | |
| | | mod_base = OTHER |
| | | note = thymine |
| modified_base | 2827..2829 | |
| | | mod_base = OTHER |
| | | note = thymine |
| modified_base | 2834 | |
| | | mod_base = OTHER |
| | | note = thymine |
| modified_base | 2838 | |
| | | mod_base = OTHER |
| | | note = thymine |
| modified_base | 2840..2841 | |
| | | mod_base = OTHER |
| | | note = thymine |
| modified_base | 2844 | |
| | | mod_base = OTHER |
| | | note = thymine |
| modified_base | 2846..2847 | |
| | | mod_base = OTHER |
| | | note = thymine |
| modified_base | 2851 | |
| | | mod_base = OTHER |
| | | note = thymine |
| modified_base | 2857 | |
| | | mod_base = OTHER |
| | | note = thymine |
| modified_base | 2861 | |
| | | mod_base = OTHER |
| | | note = thymine |
| modified_base | 2873..2874 | |
| | | mod_base = OTHER |
| | | note = thymine |
| modified_base | 2879 | |
| | | mod_base = OTHER |
| | | note = thymine |
| modified_base | 2882..2884 | |
| | | mod_base = OTHER |
| | | note = thymine |
| modified_base | 2891 | |
| | | mod_base = OTHER |
| | | note = thymine |
| modified_base | 2896 | |
| | | mod_base = OTHER |
| | | note = thymine |
| modified_base | 2898..2899 | |
| | | mod_base = OTHER |
| | | note = thymine |
| modified_base | 2901 | |
| | | mod_base = OTHER |
| | | note = thymine |
| modified_base | 2904..2906 | |
| | | mod_base = OTHER |
| | | note = thymine |
| modified_base | 2910 | |
| | | mod_base = OTHER |
| | | note = thymine |
| modified_base | 2913 | |
| | | mod_base = OTHER |
| | | note = thymine |
| modified_base | 2915..2916 | |
| | | mod_base = OTHER |
| | | note = thymine |
| modified_base | 2920 | |
| | | mod_base = OTHER |
| | | note = thymine |
| modified_base | 2929 | |
| | | mod_base = OTHER |
| | | note = thymine |
| modified_base | 2939..2941 | |
| | | mod_base = OTHER |
| | | note = thymine |
| modified_base | 2946 | |
| | | mod_base = OTHER |

-continued

| | | |
|---|---|---|
| modified_base | 2950..2951<br>mod_base = OTHER<br>note = thymine | |
| modified_base | 2954<br>mod_base = OTHER<br>note = thymine | |
| modified_base | 2956<br>mod_base = OTHER<br>note = thymine | |
| modified_base | 2961..2962<br>mod_base = OTHER<br>note = thymine | |
| modified_base | 2964<br>mod_base = OTHER<br>note = thymine | |
| modified_base | 2966<br>mod_base = OTHER<br>note = thymine | |
| modified_base | 2968<br>mod_base = OTHER<br>note = thymine | |
| modified_base | 2970..2971<br>mod_base = OTHER<br>note = thymine | |
| modified_base | 2973..2975<br>mod_base = OTHER<br>note = thymine | |
| modified_base | 2983..2984<br>mod_base = OTHER<br>note = thymine | |
| modified_base | 2987<br>mod_base = OTHER<br>note = thymine | |
| modified_base | 2989<br>mod_base = OTHER<br>note = thymine | |
| modified_base | 2993<br>mod_base = OTHER<br>note = thymine | |
| modified_base | 2995..2997<br>mod_base = OTHER<br>note = thymine | |
| modified_base | 3002..3003<br>mod_base = OTHER<br>note = thymine | |
| modified_base | 3008..3009<br>mod_base = OTHER<br>note = thymine | |
| modified_base | 3011<br>mod_base = OTHER<br>note = thymine | |
| modified_base | 3013<br>mod_base = OTHER<br>note = thymine | |
| modified_base | 3019<br>mod_base = OTHER<br>note = thymine | |
| modified_base | 3025<br>mod_base = OTHER<br>note = thymine | |
| modified_base | 3032..3034<br>mod_base = OTHER<br>note = thymine | |
| modified_base | 3036<br>mod_base = OTHER<br>note = thymine | |
| modified_base | 3049..3050<br>mod_base = OTHER<br>note = thymine | |
| modified_base | 3053<br>mod_base = OTHER<br>note = thymine | |
| modified_base | 3061<br>mod_base = OTHER<br>note = thymine | |
| modified_base | 3065<br>mod_base = OTHER<br>note = thymine | |

| | |
|---|---|
| modified_base | 3070<br>mod_base = OTHER<br>note = thymine |
| modified_base | 3072<br>mod_base = OTHER<br>note = thymine |
| modified_base | 3076..3078<br>mod_base = OTHER<br>note = thymine |
| modified_base | 3082..3083<br>mod_base = OTHER<br>note = thymine |
| modified_base | 3085<br>mod_base = OTHER<br>note = thymine |
| modified_base | 3096<br>mod_base = OTHER<br>note = thymine |
| modified_base | 3108..3112<br>mod_base = OTHER<br>note = thymine |
| modified_base | 3117<br>mod_base = OTHER<br>note = thymine |
| modified_base | 3120<br>mod_base = OTHER<br>note = thymine |
| modified_base | 3124..3126<br>mod_base = OTHER<br>note = thymine |
| modified_base | 3128..3130<br>mod_base = OTHER<br>note = thymine |
| modified_base | 3141<br>mod_base = OTHER<br>note = thymine |
| modified_base | 3146<br>mod_base = OTHER<br>note = thymine |
| modified_base | 3151..3152<br>mod_base = OTHER<br>note = thymine |
| modified_base | 3157..3158<br>mod_base = OTHER<br>note = thymine |
| modified_base | 3175..3176<br>mod_base = OTHER<br>note = thymine |
| modified_base | 3179<br>mod_base = OTHER<br>note = thymine |
| modified_base | 3185<br>mod_base = OTHER<br>note = thymine |
| modified_base | 3189..3190<br>mod_base = OTHER<br>note = thymine |
| modified_base | 3200<br>mod_base = OTHER<br>note = thymine |
| modified_base | 3204<br>mod_base = OTHER<br>note = thymine |
| modified_base | 3210<br>mod_base = OTHER<br>note = thymine |
| modified_base | 3213<br>mod_base = OTHER<br>note = thymine |
| modified_base | 3215<br>mod_base = OTHER<br>note = thymine |
| modified_base | 3220<br>mod_base = OTHER<br>note = thymine |
| modified_base | 3225<br>mod_base = OTHER<br>note = thymine |
| modified_base | 3228 |

-continued

|                |                                      |
|----------------|--------------------------------------|
|                | mod_base = OTHER                     |
|                | note = thymine                       |
| modified_base  | 3230                                 |
|                | mod_base = OTHER                     |
|                | note = thymine                       |
| modified_base  | 3233                                 |
|                | mod_base = OTHER                     |
|                | note = thymine                       |
| modified_base  | 3236                                 |
|                | mod_base = OTHER                     |
|                | note = thymine                       |
| modified_base  | 3240..3241                           |
|                | mod_base = OTHER                     |
|                | note = thymine                       |
| modified_base  | 3244                                 |
|                | mod_base = OTHER                     |
|                | note = thymine                       |
| modified_base  | 3246                                 |
|                | mod_base = OTHER                     |
|                | note = thymine                       |
| modified_base  | 3248                                 |
|                | mod_base = OTHER                     |
|                | note = thymine                       |
| modified_base  | 3254                                 |
|                | mod_base = OTHER                     |
|                | note = thymine                       |
| modified_base  | 3256                                 |
|                | mod_base = OTHER                     |
|                | note = thymine                       |
| modified_base  | 3259                                 |
|                | mod_base = OTHER                     |
|                | note = thymine                       |
| modified_base  | 3261..3263                           |
|                | mod_base = OTHER                     |
|                | note = thymine                       |
| modified_base  | 3273                                 |
|                | mod_base = OTHER                     |
|                | note = thymine                       |
| modified_base  | 3282                                 |
|                | mod_base = OTHER                     |
|                | note = thymine                       |
| modified_base  | 3287                                 |
|                | mod_base = OTHER                     |
|                | note = thymine                       |
| modified_base  | 3290..3291                           |
|                | mod_base = OTHER                     |
|                | note = thymine                       |
| modified_base  | 3294                                 |
|                | mod_base = OTHER                     |
|                | note = thymine                       |
| modified_base  | 3300                                 |
|                | mod_base = OTHER                     |
|                | note = thymine                       |
| modified_base  | 3302                                 |
|                | mod_base = OTHER                     |
|                | note = thymine                       |
| modified_base  | 3306                                 |
|                | mod_base = OTHER                     |
|                | note = thymine                       |
| modified_base  | 3317                                 |
|                | mod_base = OTHER                     |
|                | note = thymine                       |
| modified_base  | 3323                                 |
|                | mod_base = OTHER                     |
|                | note = thymine                       |
| modified_base  | 3332..3333                           |
|                | mod_base = OTHER                     |
|                | note = thymine                       |
| modified_base  | 3335                                 |
|                | mod_base = OTHER                     |
|                | note = thymine                       |
| modified_base  | 3342..3343                           |
|                | mod_base = OTHER                     |
|                | note = thymine                       |
| modified_base  | 3347                                 |
|                | mod_base = OTHER                     |
|                | note = thymine                       |
| modified_base  | 3354                                 |
|                | mod_base = OTHER                     |

-continued

| | | |
|---|---|---|
| modified_base | 3356 | |
| | mod_base = OTHER | |
| | note = thymine | |
| modified_base | 3360 | |
| | mod_base = OTHER | |
| | note = thymine | |
| modified_base | 3366 | |
| | mod_base = OTHER | |
| | note = thymine | |
| modified_base | 3370 | |
| | mod_base = OTHER | |
| | note = thymine | |
| modified_base | 3372 | |
| | mod_base = OTHER | |
| | note = thymine | |
| modified_base | 3374 | |
| | mod_base = OTHER | |
| | note = thymine | |
| modified_base | 3379 | |
| | mod_base = OTHER | |
| | note = thymine | |
| modified_base | 3385 | |
| | mod_base = OTHER | |
| | note = thymine | |
| modified_base | 3387 | |
| | mod_base = OTHER | |
| | note = thymine | |
| modified_base | 3393..3395 | |
| | mod_base = OTHER | |
| | note = thymine | |
| modified_base | 3401 | |
| | mod_base = OTHER | |
| | note = thymine | |
| modified_base | 3403..3404 | |
| | mod_base = OTHER | |
| | note = thymine | |
| modified_base | 3406 | |
| | mod_base = OTHER | |
| | note = thymine | |
| modified_base | 3408 | |
| | mod_base = OTHER | |
| | note = thymine | |
| modified_base | 3414..3415 | |
| | mod_base = OTHER | |
| | note = thymine | |
| modified_base | 3417 | |
| | mod_base = OTHER | |
| | note = thymine | |
| modified_base | 3419 | |
| | mod_base = OTHER | |
| | note = thymine | |
| modified_base | 3423 | |
| | mod_base = OTHER | |
| | note = thymine | |
| modified_base | 3429..3430 | |
| | mod_base = OTHER | |
| | note = thymine | |
| modified_base | 3432..3434 | |
| | mod_base = OTHER | |
| | note = thymine | |
| modified_base | 3436 | |
| | mod_base = OTHER | |
| | note = thymine | |
| modified_base | 3444 | |
| | mod_base = OTHER | |
| | note = thymine | |
| modified_base | 3451..3454 | |
| | mod_base = OTHER | |
| | note = thymine | |
| modified_base | 3458..3459 | |
| | mod_base = OTHER | |
| | note = thymine | |
| modified_base | 3464..3465 | |
| | mod_base = OTHER | |
| | note = thymine | |
| modified_base | 3470 | |
| | mod_base = OTHER | |
| | note = thymine | |

| | |
|---|---|
| modified_base | 3472<br>mod_base = OTHER<br>note = thymine |
| modified_base | 3475..3477<br>mod_base = OTHER<br>note = thymine |
| modified_base | 3480<br>mod_base = OTHER<br>note = thymine |
| modified_base | 3483..3484<br>mod_base = OTHER<br>note = thymine |
| modified_base | 3488..3489<br>mod_base = OTHER<br>note = thymine |
| modified_base | 3509<br>mod_base = OTHER<br>note = thymine |
| modified_base | 3518..3519<br>mod_base = OTHER<br>note = thymine |
| modified_base | 3521<br>mod_base = OTHER<br>note = thymine |
| modified_base | 3525<br>mod_base = OTHER<br>note = thymine |
| modified_base | 3527<br>mod_base = OTHER<br>note = thymine |
| modified_base | 3534..3535<br>mod_base = OTHER<br>note = thymine |
| modified_base | 3543<br>mod_base = OTHER<br>note = thymine |
| modified_base | 3546<br>mod_base = OTHER<br>note = thymine |
| modified_base | 3551<br>mod_base = OTHER<br>note = thymine |
| modified_base | 3554<br>mod_base = OTHER<br>note = thymine |
| modified_base | 3556..3558<br>mod_base = OTHER<br>note = thymine |
| modified_base | 3572<br>mod_base = OTHER<br>note = thymine |
| modified_base | 3575<br>mod_base = OTHER<br>note = thymine |
| modified_base | 3578<br>mod_base = OTHER<br>note = thymine |
| modified_base | 3581<br>mod_base = OTHER<br>note = thymine |
| modified_base | 3586<br>mod_base = OTHER<br>note = thymine |
| modified_base | 3589..3591<br>mod_base = OTHER<br>note = thymine |
| modified_base | 3596..3599<br>mod_base = OTHER<br>note = thymine |
| modified_base | 3601<br>mod_base = OTHER<br>note = thymine |
| modified_base | 3609..3610<br>mod_base = OTHER<br>note = thymine |
| modified_base | 3622<br>mod_base = OTHER<br>note = thymine |
| modified_base | 3630 |

|     |     |
| --- | --- |
|  | mod_base = OTHER |
|  | note = thymine |
| modified_base | 3633..3634 |
|  | mod_base = OTHER |
|  | note = thymine |
| modified_base | 3637 |
|  | mod_base = OTHER |
|  | note = thymine |
| modified_base | 3643..3645 |
|  | mod_base = OTHER |
|  | note = thymine |
| modified_base | 3648 |
|  | mod_base = OTHER |
|  | note = thymine |
| modified_base | 3650 |
|  | mod_base = OTHER |
|  | note = thymine |
| modified_base | 3653 |
|  | mod_base = OTHER |
|  | note = thymine |
| modified_base | 3657 |
|  | mod_base = OTHER |
|  | note = thymine |
| modified_base | 3660 |
|  | mod_base = OTHER |
|  | note = thymine |
| modified_base | 3662 |
|  | mod_base = OTHER |
|  | note = thymine |
| modified_base | 3665..3667 |
|  | mod_base = OTHER |
|  | note = thymine |
| modified_base | 3676..3677 |
|  | mod_base = OTHER |
|  | note = thymine |
| modified_base | 3686..3687 |
|  | mod_base = OTHER |
|  | note = thymine |
| modified_base | 3690 |
|  | mod_base = OTHER |
|  | note = thymine |
| modified_base | 3693 |
|  | mod_base = OTHER |
|  | note = thymine |
| modified_base | 3696..3697 |
|  | mod_base = OTHER |
|  | note = thymine |
| modified_base | 3705..3706 |
|  | mod_base = OTHER |
|  | note = thymine |
| modified_base | 3710..3713 |
|  | mod_base = OTHER |
|  | note = thymine |
| modified_base | 3718..3719 |
|  | mod_base = OTHER |
|  | note = thymine |
| modified_base | 3722..3723 |
|  | mod_base = OTHER |
|  | note = thymine |
| modified_base | 3725 |
|  | mod_base = OTHER |
|  | note = thymine |
| modified_base | 3728..3729 |
|  | mod_base = OTHER |
|  | note = thymine |
| modified_base | 3731..3733 |
|  | mod_base = OTHER |
|  | note = thymine |
| modified_base | 3745 |
|  | mod_base = OTHER |
|  | note = thymine |
| modified_base | 3756..3757 |
|  | mod_base = OTHER |
|  | note = thymine |
| modified_base | 3767 |
|  | mod_base = OTHER |
|  | note = thymine |
| modified_base | 3773 |
|  | mod_base = OTHER |

-continued

| | | |
|---|---|---|
| modified_base | 3776 | |
| | mod_base = OTHER | |
| | note = thymine | |
| modified_base | 3778..3779 | |
| | mod_base = OTHER | |
| | note = thymine | |
| modified_base | 3781 | |
| | mod_base = OTHER | |
| | note = thymine | |
| modified_base | 3783..3784 | |
| | mod_base = OTHER | |
| | note = thymine | |
| modified_base | 3789..3790 | |
| | mod_base = OTHER | |
| | note = thymine | |
| modified_base | 3792 | |
| | mod_base = OTHER | |
| | note = thymine | |
| modified_base | 3798..3802 | |
| | mod_base = OTHER | |
| | note = thymine | |
| modified_base | 3804 | |
| | mod_base = OTHER | |
| | note = thymine | |
| modified_base | 3807 | |
| | mod_base = OTHER | |
| | note = thymine | |
| modified_base | 3812 | |
| | mod_base = OTHER | |
| | note = thymine | |
| modified_base | 3814 | |
| | mod_base = OTHER | |
| | note = thymine | |
| modified_base | 3819 | |
| | mod_base = OTHER | |
| | note = thymine | |
| modified_base | 3821 | |
| | mod_base = OTHER | |
| | note = thymine | |
| modified_base | 3826..3827 | |
| | mod_base = OTHER | |
| | note = thymine | |
| modified_base | 3829 | |
| | mod_base = OTHER | |
| | note = thymine | |
| modified_base | 3831 | |
| | mod_base = OTHER | |
| | note = thymine | |
| modified_base | 3833..3835 | |
| | mod_base = OTHER | |
| | note = thymine | |
| modified_base | 3845 | |
| | mod_base = OTHER | |
| | note = thymine | |
| modified_base | 3848 | |
| | mod_base = OTHER | |
| | note = thymine | |
| modified_base | 3850..3852 | |
| | mod_base = OTHER | |
| | note = thymine | |
| modified_base | 3854 | |
| | mod_base = OTHER | |
| | note = thymine | |
| modified_base | 3859 | |
| | mod_base = OTHER | |
| | note = thymine | |
| modified_base | 3862 | |
| | mod_base = OTHER | |
| | note = thymine | |
| modified_base | 3868..3870 | |
| | mod_base = OTHER | |
| | note = thymine | |
| modified_base | 3876..3877 | |
| | mod_base = OTHER | |
| | note = thymine | |
| modified_base | 3884 | |
| | mod_base = OTHER | |
| | note = thymine | |

-continued

| | |
|---|---|
| modified_base | 3892<br>mod_base = OTHER<br>note = thymine |
| modified_base | 3895<br>mod_base = OTHER<br>note = thymine |
| modified_base | 3900<br>mod_base = OTHER<br>note = thymine |
| modified_base | 3902<br>mod_base = OTHER<br>note = thymine |
| modified_base | 3904<br>mod_base = OTHER<br>note = thymine |
| modified_base | 3907<br>mod_base = OTHER<br>note = thymine |
| modified_base | 3909..3910<br>mod_base = OTHER<br>note = thymine |
| modified_base | 3913<br>mod_base = OTHER<br>note = thymine |
| modified_base | 3916..3917<br>mod_base = OTHER<br>note = thymine |
| modified_base | 3919..3920<br>mod_base = OTHER<br>note = thymine |
| modified_base | 3922<br>mod_base = OTHER<br>note = thymine |
| modified_base | 3926<br>mod_base = OTHER<br>note = thymine |
| modified_base | 3938..3942<br>mod_base = OTHER<br>note = thymine |
| modified_base | 3954<br>mod_base = OTHER<br>note = thymine |
| modified_base | 3957<br>mod_base = OTHER<br>note = thymine |
| modified_base | 3961..3962<br>mod_base = OTHER<br>note = thymine |
| modified_base | 3964<br>mod_base = OTHER<br>note = thymine |
| modified_base | 3966<br>mod_base = OTHER<br>note = thymine |
| modified_base | 3979..3981<br>mod_base = OTHER<br>note = thymine |
| modified_base | 3984<br>mod_base = OTHER<br>note = thymine |
| modified_base | 3992<br>mod_base = OTHER<br>note = thymine |
| modified_base | 3998..3999<br>mod_base = OTHER<br>note = thymine |
| modified_base | 4002..4004<br>mod_base = OTHER<br>note = thymine |
| modified_base | 4008<br>mod_base = OTHER<br>note = thymine |
| modified_base | 4010<br>mod_base = OTHER<br>note = thymine |
| modified_base | 4014<br>mod_base = OTHER<br>note = thymine |
| modified_base | 4017..4018 |

-continued

| | | |
|---|---|---|
| | mod_base = OTHER | |
| | note = thymine | |
| modified_base | 4020 | |
| | mod_base = OTHER | |
| | note = thymine | |
| modified_base | 4025 | |
| | mod_base = OTHER | |
| | note = thymine | |
| modified_base | 4027..4028 | |
| | mod_base = OTHER | |
| | note = thymine | |
| modified_base | 4030..4031 | |
| | mod_base = OTHER | |
| | note = thymine | |
| modified_base | 4036..4038 | |
| | mod_base = OTHER | |
| | note = thymine | |
| modified_base | 4040 | |
| | mod_base = OTHER | |
| | note = thymine | |
| modified_base | 4046 | |
| | mod_base = OTHER | |
| | note = thymine | |
| modified_base | 4051..4053 | |
| | mod_base = OTHER | |
| | note = thymine | |
| modified_base | 4058..4059 | |
| | mod_base = OTHER | |
| | note = thymine | |
| modified_base | 4066..4067 | |
| | mod_base = OTHER | |
| | note = thymine | |
| modified_base | 4071..4073 | |
| | mod_base = OTHER | |
| | note = thymine | |
| modified_base | 4077 | |
| | mod_base = OTHER | |
| | note = thymine | |
| modified_base | 4079 | |
| | mod_base = OTHER | |
| | note = thymine | |
| modified_base | 4083 | |
| | mod_base = OTHER | |
| | note = thymine | |
| modified_base | 4085 | |
| | mod_base = OTHER | |
| | note = thymine | |
| modified_base | 4087..4089 | |
| | mod_base = OTHER | |
| | note = thymine | |
| modified_base | 4093 | |
| | mod_base = OTHER | |
| | note = thymine | |
| modified_base | 4097 | |
| | mod_base = OTHER | |
| | note = thymine | |
| modified_base | 4103..4105 | |
| | mod_base = OTHER | |
| | note = thymine | |
| modified_base | 4109..4110 | |
| | mod_base = OTHER | |
| | note = thymine | |
| modified_base | 4113..4115 | |
| | mod_base = OTHER | |
| | note = thymine | |
| modified_base | 4125 | |
| | mod_base = OTHER | |
| | note = thymine | |
| modified_base | 4128 | |
| | mod_base = OTHER | |
| | note = thymine | |
| modified_base | 4130..4131 | |
| | mod_base = OTHER | |
| | note = thymine | |
| modified_base | 4134 | |
| | mod_base = OTHER | |
| | note = thymine | |
| modified_base | 4148 | |
| | mod_base = OTHER | |

```
               note = thymine
modified_base  4151..4152
               mod_base = OTHER
               note = thymine
modified_base  4154
               mod_base = OTHER
               note = thymine
modified_base  4166..4168
               mod_base = OTHER
               note = thymine
modified_base  4170
               mod_base = OTHER
               note = thymine
modified_base  4178..4183
               mod_base = OTHER
               note = thymine
modified_base  4188
               mod_base = OTHER
               note = thymine
modified_base  4190
               mod_base = OTHER
               note = thymine
modified_base  4193
               mod_base = OTHER
               note = thymine
modified_base  4205
               mod_base = OTHER
               note = thymine
modified_base  4208
               mod_base = OTHER
               note = thymine
modified_base  4210..4212
               mod_base = OTHER
               note = thymine
modified_base  4215
               mod_base = OTHER
               note = thymine
modified_base  4219
               mod_base = OTHER
               note = thymine
modified_base  4224
               mod_base = OTHER
               note = thymine
modified_base  4229
               mod_base = OTHER
               note = thymine
modified_base  4237
               mod_base = OTHER
               note = thymine
modified_base  4244
               mod_base = OTHER
               note = thymine
modified_base  4246
               mod_base = OTHER
               note = thymine
modified_base  4248
               mod_base = OTHER
               note = thymine
modified_base  4256
               mod_base = OTHER
               note = thymine
modified_base  4265
               mod_base = OTHER
               note = thymine
modified_base  4272
               mod_base = OTHER
               note = thymine
modified_base  4276..4278
               mod_base = OTHER
               note = thymine
modified_base  4281
               mod_base = OTHER
               note = thymine
modified_base  4283
               mod_base = OTHER
               note = thymine
modified_base  4286
               mod_base = OTHER
               note = thymine
```

| | | |
|---|---|---|
| modified_base | 4289..4290<br>mod_base = OTHER<br>note = thymine | |
| modified_base | 4293..4294<br>mod_base = OTHER<br>note = thymine | |
| modified_base | 4300<br>mod_base = OTHER<br>note = thymine | |
| modified_base | 4303<br>mod_base = OTHER<br>note = thymine | |
| modified_base | 4307<br>mod_base = OTHER<br>note = thymine | |
| modified_base | 4313<br>mod_base = OTHER<br>note = thymine | |
| modified_base | 4315..4316<br>mod_base = OTHER<br>note = thymine | |
| modified_base | 4318<br>mod_base = OTHER<br>note = thymine | |
| modified_base | 4321<br>mod_base = OTHER<br>note = thymine | |
| modified_base | 4325<br>mod_base = OTHER<br>note = thymine | |
| modified_base | 4333<br>mod_base = OTHER<br>note = thymine | |
| modified_base | 4335..4337<br>mod_base = OTHER<br>note = thymine | |
| modified_base | 4339<br>mod_base = OTHER<br>note = thymine | |
| modified_base | 4347<br>mod_base = OTHER<br>note = thymine | |
| modified_base | 4351..4354<br>mod_base = OTHER<br>note = thymine | |
| modified_base | 4356..4357<br>mod_base = OTHER<br>note = thymine | |
| modified_base | 4361<br>mod_base = OTHER<br>note = thymine | |
| modified_base | 4368<br>mod_base = OTHER<br>note = thymine | |
| modified_base | 4370..4371<br>mod_base = OTHER<br>note = thymine | |
| modified_base | 4375<br>mod_base = OTHER<br>note = thymine | |
| modified_base | 4377..4378<br>mod_base = OTHER<br>note = thymine | |
| modified_base | 4383<br>mod_base = OTHER<br>note = thymine | |
| modified_base | 4388<br>mod_base = OTHER<br>note = thymine | |
| modified_base | 4390<br>mod_base = OTHER<br>note = thymine | |
| modified_base | 4394<br>mod_base = OTHER<br>note = thymine | |
| modified_base | 4397<br>mod_base = OTHER<br>note = thymine | |
| modified_base | 4399 | |

| | | |
|---|---|---|
| | | mod_base = OTHER |
| | | note = thymine |
| modified_base | 4402 | |
| | | mod_base = OTHER |
| | | note = thymine |
| modified_base | 4405..4408 | |
| | | mod_base = OTHER |
| | | note = thymine |
| modified_base | 4410 | |
| | | mod_base = OTHER |
| | | note = thymine |
| modified_base | 4412..4414 | |
| | | mod_base = OTHER |
| | | note = thymine |
| modified_base | 4416 | |
| | | mod_base = OTHER |
| | | note = thymine |
| modified_base | 4420..4424 | |
| | | mod_base = OTHER |
| | | note = thymine |
| modified_base | 4426 | |
| | | mod_base = OTHER |
| | | note = thymine |
| modified_base | 4430 | |
| | | mod_base = OTHER |
| | | note = thymine |
| modified_base | 4432 | |
| | | mod_base = OTHER |
| | | note = thymine |
| modified_base | 4435..4437 | |
| | | mod_base = OTHER |
| | | note = thymine |
| modified_base | 4439 | |
| | | mod_base = OTHER |
| | | note = thymine |
| modified_base | 4442..4443 | |
| | | mod_base = OTHER |
| | | note = thymine |
| modified_base | 4449 | |
| | | mod_base = OTHER |
| | | note = thymine |
| modified_base | 4452 | |
| | | mod_base = OTHER |
| | | note = thymine |
| modified_base | 4456 | |
| | | mod_base = OTHER |
| | | note = thymine |
| modified_base | 4458..4459 | |
| | | mod_base = OTHER |
| | | note = thymine |
| modified_base | 4461 | |
| | | mod_base = OTHER |
| | | note = thymine |
| modified_base | 4463 | |
| | | mod_base = OTHER |
| | | note = thymine |
| modified_base | 4468 | |
| | | mod_base = OTHER |
| | | note = thymine |
| modified_base | 4471 | |
| | | mod_base = OTHER |
| | | note = thymine |
| modified_base | 4473..4474 | |
| | | mod_base = OTHER |
| | | note = thymine |
| modified_base | 4476 | |
| | | mod_base = OTHER |
| | | note = thymine |
| modified_base | 4479 | |
| | | mod_base = OTHER |
| | | note = thymine |
| modified_base | 4481..4482 | |
| | | mod_base = OTHER |
| | | note = thymine |
| modified_base | 4487..4490 | |
| | | mod_base = OTHER |
| | | note = thymine |
| modified_base | 4492..4493 | |
| | | mod_base = OTHER |

-continued

| | | |
|---|---|---|
| | note = thymine | |
| modified_base | 4500..4503 | |
| | mod_base = OTHER | |
| | note = thymine | |
| modified_base | 4512..4513 | |
| | mod_base = OTHER | |
| | note = thymine | |
| modified_base | 4515 | |
| | mod_base = OTHER | |
| | note = thymine | |
| modified_base | 4517 | |
| | mod_base = OTHER | |
| | note = thymine | |
| modified_base | 4519..4520 | |
| | mod_base = OTHER | |
| | note = thymine | |
| modified_base | 4522..4523 | |
| | mod_base = OTHER | |
| | note = thymine | |
| modified_base | 4525 | |
| | mod_base = OTHER | |
| | note = thymine | |
| modified_base | 4529 | |
| | mod_base = OTHER | |
| | note = thymine | |
| modified_base | 4537 | |
| | mod_base = OTHER | |
| | note = thymine | |
| modified_base | 4539..4541 | |
| | mod_base = OTHER | |
| | note = thymine | |
| modified_base | 4543 | |
| | mod_base = OTHER | |
| | note = thymine | |
| modified_base | 4550..4551 | |
| | mod_base = OTHER | |
| | note = thymine | |
| modified_base | 4553 | |
| | mod_base = OTHER | |
| | note = thymine | |
| modified_base | 4555..4556 | |
| | mod_base = OTHER | |
| | note = thymine | |
| modified_base | 4561 | |
| | mod_base = OTHER | |
| | note = thymine | |
| modified_base | 4563 | |
| | mod_base = OTHER | |
| | note = thymine | |
| modified_base | 4567 | |
| | mod_base = OTHER | |
| | note = thymine | |
| modified_base | 4569 | |
| | mod_base = OTHER | |
| | note = thymine | |
| modified_base | 4571 | |
| | mod_base = OTHER | |
| | note = thymine | |
| modified_base | 4573..4574 | |
| | mod_base = OTHER | |
| | note = thymine | |
| modified_base | 4576 | |
| | mod_base = OTHER | |
| | note = thymine | |
| modified_base | 4580..4581 | |
| | mod_base = OTHER | |
| | note = thymine | |
| modified_base | 4590 | |
| | mod_base = OTHER | |
| | note = thymine | |
| modified_base | 4597 | |
| | mod_base = OTHER | |
| | note = thymine | |
| modified_base | 4599 | |
| | mod_base = OTHER | |
| | note = thymine | |
| modified_base | 4606 | |
| | mod_base = OTHER | |
| | note = thymine | |

| | |
|---|---|
| modified_base | 4610..4611<br>mod_base = OTHER<br>note = thymine |
| modified_base | 4618..4620<br>mod_base = OTHER<br>note = thymine |
| modified_base | 4622<br>mod_base = OTHER<br>note = thymine |
| modified_base | 4624..4625<br>mod_base = OTHER<br>note = thymine |
| modified_base | 4628<br>mod_base = OTHER<br>note = thymine |
| modified_base | 4631<br>mod_base = OTHER<br>note = thymine |
| modified_base | 4633<br>mod_base = OTHER<br>note = thymine |
| modified_base | 4637<br>mod_base = OTHER<br>note = thymine |
| modified_base | 4641<br>mod_base = OTHER<br>note = thymine |
| modified_base | 4646..4647<br>mod_base = OTHER<br>note = thymine |
| modified_base | 4649<br>mod_base = OTHER<br>note = thymine |
| modified_base | 4652..4655<br>mod_base = OTHER<br>note = thymine |
| modified_base | 4657..4660<br>mod_base = OTHER<br>note = thymine |
| modified_base | 4662..4663<br>mod_base = OTHER<br>note = thymine |
| modified_base | 4671<br>mod_base = OTHER<br>note = thymine |
| modified_base | 4673<br>mod_base = OTHER<br>note = thymine |
| modified_base | 4677<br>mod_base = OTHER<br>note = thymine |
| modified_base | 4680..4682<br>mod_base = OTHER<br>note = thymine |
| modified_base | 4686<br>mod_base = OTHER<br>note = thymine |
| modified_base | 4695<br>mod_base = OTHER<br>note = thymine |
| modified_base | 4705..4707<br>mod_base = OTHER<br>note = thymine |
| modified_base | 4709..4710<br>mod_base = OTHER<br>note = thymine |
| modified_base | 4715<br>mod_base = OTHER<br>note = thymine |
| modified_base | 4718<br>mod_base = OTHER<br>note = thymine |
| modified_base | 4720..4721<br>mod_base = OTHER<br>note = thymine |
| modified_base | 4729<br>mod_base = OTHER<br>note = thymine |
| modified_base | 4732..4733 |

-continued

| | | |
|---|---|---|
| | | mod_base = OTHER |
| | | note = thymine |
| modified_base | 4735 | |
| | | mod_base = OTHER |
| | | note = thymine |
| modified_base | 4739..4741 | |
| | | mod_base = OTHER |
| | | note = thymine |
| modified_base | 4745 | |
| | | mod_base = OTHER |
| | | note = thymine |
| modified_base | 4748..4749 | |
| | | mod_base = OTHER |
| | | note = thymine |
| modified_base | 4751..4752 | |
| | | mod_base = OTHER |
| | | note = thymine |
| modified_base | 4764..4767 | |
| | | mod_base = OTHER |
| | | note = thymine |
| modified_base | 4769..4770 | |
| | | mod_base = OTHER |
| | | note = thymine |
| modified_base | 4773 | |
| | | mod_base = OTHER |
| | | note = thymine |
| modified_base | 4781 | |
| | | mod_base = OTHER |
| | | note = thymine |
| modified_base | 4783 | |
| | | mod_base = OTHER |
| | | note = thymine |
| modified_base | 4786 | |
| | | mod_base = OTHER |
| | | note = thymine |
| modified_base | 4789 | |
| | | mod_base = OTHER |
| | | note = thymine |
| modified_base | 4791 | |
| | | mod_base = OTHER |
| | | note = thymine |
| modified_base | 4798 | |
| | | mod_base = OTHER |
| | | note = thymine |
| modified_base | 4805..4806 | |
| | | mod_base = OTHER |
| | | note = thymine |
| modified_base | 4809 | |
| | | mod_base = OTHER |
| | | note = thymine |
| modified_base | 4812 | |
| | | mod_base = OTHER |
| | | note = thymine |
| modified_base | 4817 | |
| | | mod_base = OTHER |
| | | note = thymine |
| modified_base | 4819 | |
| | | mod_base = OTHER |
| | | note = thymine |
| modified_base | 4824 | |
| | | mod_base = OTHER |
| | | note = thymine |
| modified_base | 4826..4828 | |
| | | mod_base = OTHER |
| | | note = thymine |
| modified_base | 4832..4833 | |
| | | mod_base = OTHER |
| | | note = thymine |
| modified_base | 4835..4836 | |
| | | mod_base = OTHER |
| | | note = thymine |
| modified_base | 4838 | |
| | | mod_base = OTHER |
| | | note = thymine |
| modified_base | 4840 | |
| | | mod_base = OTHER |
| | | note = thymine |
| modified_base | 4843..4845 | |
| | | mod_base = OTHER |

-continued

| | | |
|---|---|---|
| | note = thymine | |
| modified_base | 4851..4852 | |
| | mod_base = OTHER | |
| | note = thymine | |
| modified_base | 4857 | |
| | mod_base = OTHER | |
| | note = thymine | |
| modified_base | 4862..4863 | |
| | mod_base = OTHER | |
| | note = thymine | |
| modified_base | 4865..4866 | |
| | mod_base = OTHER | |
| | note = thymine | |
| modified_base | 4870 | |
| | mod_base = OTHER | |
| | note = thymine | |
| modified_base | 4881..4882 | |
| | mod_base = OTHER | |
| | note = thymine | |
| modified_base | 4887 | |
| | mod_base = OTHER | |
| | note = thymine | |
| modified_base | 4894..4895 | |
| | mod_base = OTHER | |
| | note = thymine | |
| modified_base | 4901..4902 | |
| | mod_base = OTHER | |
| | note = thymine | |
| modified_base | 4909 | |
| | mod_base = OTHER | |
| | note = thymine | |
| modified_base | 4914..4915 | |
| | mod_base = OTHER | |
| | note = thymine | |
| modified_base | 4917 | |
| | mod_base = OTHER | |
| | note = thymine | |
| modified_base | 4919 | |
| | mod_base = OTHER | |
| | note = thymine | |
| modified_base | 4922 | |
| | mod_base = OTHER | |
| | note = thymine | |
| modified_base | 4928 | |
| | mod_base = OTHER | |
| | note = thymine | |
| modified_base | 4932..4934 | |
| | mod_base = OTHER | |
| | note = thymine | |
| modified_base | 4936..4938 | |
| | mod_base = OTHER | |
| | note = thymine | |
| modified_base | 4941 | |
| | mod_base = OTHER | |
| | note = thymine | |
| modified_base | 4944 | |
| | mod_base = OTHER | |
| | note = thymine | |
| modified_base | 4948 | |
| | mod_base = OTHER | |
| | note = thymine | |
| modified_base | 4950 | |
| | mod_base = OTHER | |
| | note = thymine | |
| modified_base | 4952..4953 | |
| | mod_base = OTHER | |
| | note = thymine | |
| modified_base | 4956..4958 | |
| | mod_base = OTHER | |
| | note = thymine | |
| modified_base | 4961 | |
| | mod_base = OTHER | |
| | note = thymine | |
| modified_base | 4964 | |
| | mod_base = OTHER | |
| | note = thymine | |
| modified_base | 4975..4976 | |
| | mod_base = OTHER | |
| | note = thymine | |

| | |
|---|---|
| modified_base | 4978..4979<br>mod_base = OTHER<br>note = thymine |
| modified_base | 4982<br>mod_base = OTHER<br>note = thymine |
| modified_base | 4989<br>mod_base = OTHER<br>note = thymine |
| modified_base | 4992..4993<br>mod_base = OTHER<br>note = thymine |
| modified_base | 4996..4997<br>mod_base = OTHER<br>note = thymine |
| modified_base | 5000..5001<br>mod_base = OTHER<br>note = thymine |
| modified_base | 5006..5007<br>mod_base = OTHER<br>note = thymine |
| modified_base | 5023..5024<br>mod_base = OTHER<br>note = thymine |
| modified_base | 5028..5031<br>mod_base = OTHER<br>note = thymine |
| modified_base | 5036<br>mod_base = OTHER<br>note = thymine |
| modified_base | 5045..5048<br>mod_base = OTHER<br>note = thymine |
| modified_base | 5056..5059<br>mod_base = OTHER<br>note = thymine |
| modified_base | 5061<br>mod_base = OTHER<br>note = thymine |
| modified_base | 5063<br>mod_base = OTHER<br>note = thymine |
| modified_base | 5066<br>mod_base = OTHER<br>note = thymine |
| modified_base | 5068<br>mod_base = OTHER<br>note = thymine |
| modified_base | 5070..5071<br>mod_base = OTHER<br>note = thymine |
| modified_base | 5076<br>mod_base = OTHER<br>note = thymine |
| modified_base | 5078<br>mod_base = OTHER<br>note = thymine |
| modified_base | 5085<br>mod_base = OTHER<br>note = thymine |
| modified_base | 5087<br>mod_base = OTHER<br>note = thymine |
| modified_base | 5090..5092<br>mod_base = OTHER<br>note = thymine |
| modified_base | 5094<br>mod_base = OTHER<br>note = thymine |
| modified_base | 5097<br>mod_base = OTHER<br>note = thymine |
| modified_base | 5102<br>mod_base = OTHER<br>note = thymine |
| modified_base | 5111<br>mod_base = OTHER<br>note = thymine |
| modified_base | 5113 |

```
                    mod_base = OTHER
                    note = thymine
modified_base       5120..5121
                    mod_base = OTHER
                    note = thymine
modified_base       5127
                    mod_base = OTHER
                    note = thymine
modified_base       5131..5133
                    mod_base = OTHER
                    note = thymine
modified_base       5137..5140
                    mod_base = OTHER
                    note = thymine
modified_base       5145
                    mod_base = OTHER
                    note = thymine
modified_base       5156..5157
                    mod_base = OTHER
                    note = thymine
modified_base       5159
                    mod_base = OTHER
                    note = thymine
modified_base       5166
                    mod_base = OTHER
                    note = thymine
modified_base       5175
                    mod_base = OTHER
                    note = thymine
modified_base       5178..5182
                    mod_base = OTHER
                    note = thymine
modified_base       5184..5185
                    mod_base = OTHER
                    note = thymine
modified_base       5191
                    mod_base = OTHER
                    note = thymine
modified_base       5193
                    mod_base = OTHER
                    note = thymine
modified_base       5201..5202
                    mod_base = OTHER
                    note = thymine
modified_base       5204
                    mod_base = OTHER
                    note = thymine
SEQUENCE: 6
gcgcaccggg gatcctaggc gtttagttgc gctgtttggt tgcacaactt tcttcgtgag   60
gctgtcagaa gtggacctgg ctgatagcga tgggtcaagg caagtccaga gaggagaaag  120
gcaccaatag tacaaacagg gccgaaatcc taccagatac caccatatct tggccctttaa 180
gctgcaaatc ttgctggcag aaatttgaca gcttggtaag atgccatgac cactaccttt  240
gcaggcactg tttaaacctt ctgctgtcag tatccgacag gtgtcctctt tgtaaatatc  300
cattaccaac cagattgaag atatcaacag ccccaagctc tccacctccc tacgaagagt  360
aacaccgtcc ggccccggcc ccgacaaaca gcccagcaca agggaaccgc acgtcaccca  420
acgcacacag acacagcacc caacacagaa cacgcacaca cacacacaca cacacccaca  480
cgcacgcgcc cccaccaccg gggggcgccc cccccgggg gcggccccc cgggagcccg    540
ggcggagccc cacggagatg cccatcagtc gatgtcctcg gccaccgacc cgcccagcca  600
atcgtcgcag gacctcccct tgagtctaaa cctgccccc actgtttcat acatcaaagt   660
gctcctagat ttgctaaaac aaagtctgca atccttaaag gcgaaccagt ctggcaaaag  720
cgacagtgga atcagcagaa tagatctgtc tatacatagt tcctggagga ttacacttat  780
ctctgaaccc aacaaatgtt caccagttct gaatcgatgc aggaagaggt tcccaaggac  840
atcactaatc ttttcatagc cctcaagtcc tgctagaaaa actttcatgt ccttggtctc  900
cagcttcaca atgatatttt ggacaaggtt tcttccttca aaaagggcac ccatctttac  960
agtcagtggc acaggctccc actcaggtcc aactctctca aagtcaatag atctaatccc 1020
atccagtatt cttttggagc ccaacaactc aagctcaaga gaatcaccaa gtatcaaggg 1080
atcttccatg taatcctcaa actcttcaga tctgatatca aagacaccat cgttcacctt 1140
gaagacagag tctgtcctca gtaagtggag gcattcatca aacattcttc tatctatctc 1200
acccttaaag aggtgagagc atgataaaag ttcagccaca cctggattct gtaattgcaa 1260
cctaaccaag aatatcaatg aaaatttcct taaacagtca gtattattct gattgtgcgt 1320
aaagtccact gaaattgaaa actccaatac ccctttttgtg tagttgagca tgtagtccca 1380
cagatccttt aaggatttaa atgcctttgg gtttgtcagg cctgcctaa tcaacatggc   1440
agcattacac acaacatctc ccattcggta agagaaccac ccaaaaccaa actgcaaatc 1500
attcctaaac ataggcctct ccacatttt gttcaccacc tttgagacaa atgattgaaa  1560
ggggcccagt gcctcagcac catcttcaga tggcatcatt tctttatgag gaaccatga   1620
aaaattgcct aatgtcctgg ttgttgcaac aaattctcga acaaatgatt caaaatacac 1680
ctgttttaag aagttcttgc agacatccct cgtgctaaca acaaattcat caaccagact 1740
ggagtcagat cgctgatgag aattggcaag gtcagaaaac agaacagtgt aatgttcatc 1800
ccttttccac ttaacaacat gagaaatgag tgacaaggat tctgagttaa tatcaattaa 1860
```

-continued

```
aacacagagg tcaaggaatt taattctggg actccacctc atgttttttg agctcatgtc 1920
agacataaat ggaagaagct gatcctcaaa gatcttggga tatagccgcc tcacagattg 1980
aatcacttgg ttcaaattca cttttgtcctc cagtagcctt gagctctcag gctttcttgc 2040
tacataatca catgggttta agtgcttaag agttaggttc tcactgttat tcttcccttt 2100
ggtcggttct gctaggaccc aaacacccaa ctcaaaagag ttgctcaatg aaatacaaat 2160
gtagtcccaa agaagaggcc ttaaaaggca tatatgatca cggtgggctt ctggatgaga 2220
ctgtttgtca caaatgtaca gcgttatacc atcccgattg caaactcttg tcacatgatc 2280
atctgtggtt agatcctcaa gcagcttttt gatatacaga ttttccctat ttttgtttct 2340
cacacacctg cttcctagag ttttgcaaag gcctataaag ccagatgaga tacaactctg 2400
gaaagctgac ttgttgattg cttctgacag cagcttctgt gcaccccttg tgaatttact 2460
acaaagtttg ttctggagtg tcttgatcaa tgatgggatt cttttcctctt ggaaagtcat 2520
cactgatgga taaaccacct tttgtcttaa accatccttt aatgggaaca tttcattcaa 2580
attcaaccag ttaacatctg ctaactgatt cagatcttct tcaagaccga ggaggtctcc 2640
caattgaaga atggcctcct ttttatctct gttaaatagg tctaagaaaa attcttcatt 2700
aaattcacca tttttgagct tatgatgcag tttccttaca agctttctta caacctttgt 2760
ttcattagga cacagttcct caatgagtct ttgtattctg taacctctag aaccatccag 2820
ccaatctttc acatcagtgt tggtattcag tagaaatgga tccaaaggga aattggcata 2880
ctttaggagg tccagtgttc tcctttggat actattaact agggagactg ggacgccatt 2940
tgcgatggct tgatctgcaa ttgtatctat tgtttcacaa agttgatgtg gctctttaca 3000
cttgacattg tgtagcgctg cagatacaaa cttttgtgaga agagggactt cctccccca 3060
tacatagaat ctagatttaa attctgcagc gaacctccca gccacacttt tgggctgat 3120
aaattttgttt aacaagccgc tcagatgaga ttggaattcc aacaggacaa ggacttcctc 3180
cggatcactt acaaccaggt cactcagcct cctatcaaat aaagtgatct gatcatcact 3240
tgatgtgtaa gcctctggtc tttcgccaaa gataacacca atgcagtagt tgatgaacct 3300
ctcgctaagc aaaccataga agtcagaagc attatgcaag attccctgcc ccatatcaat 3360
aaggctggat atatgggatg gcactatccc catttcaaaa tattgtctga aaattctctc 3420
agtaacagtg gtttctgaac ccctgagaag ttttagcttc gacttgacat atgatttcat 3480
cattgcattc acaacaggaa aggggaccct gacaagctta tgcatgtgcc aagttaacaa 3540
agtgctaaca tgatctttcc cggaacgcac atactggtca tcacctagtt tgagattttg 3600
tagaaacatt aagaacaaaa atgggcacat cattggtccc cattgctgt gatccatact 3660
atagtttaag aacccttccc gcacattgat agtcattgac aagattgcat tttcaaattc 3720
cttatcattg tttaaacagg agcctgaaaa gaaacttgaa aaagactcaa aataatcttc 3780
tattaacctt gtgaacattt ttgtcctcaa atctccaata tagagttctc tatttccccc 3840
aacctgctct ttataagata gtgcaaattt cagccttcca gagtcaggac ctactgaggt 3900
gtatgatgtt ggtgattctt ctgagtagaa gcacagattt ttcaaagcag cactcataca 3960
ttgtgtcaac gacagagctt tactaaggga ctcagaatta cttttccctct cactgattct 4020
cacgtcttct tccagtttgt cccagtcaaa tttgaaattc aagccttgcc tttgcatatg 4080
cctgtatttc cctgagtacg catttgcatt catttgcaac agaatcatct tcatgcaaga 4140
aaaccaatca ttctcagaaa agaacttttct acaaaggttt tttgccatct catcgaggcc 4200
acactgatct ttaatgactg aggtgaaata caaaggtgac agctctgtgg aaccctcaac 4260
agcctcacag ataaatttca tgtcatcatt ggttagacat gatgggtcaa agtcttctac 4320
taaatggaaa gatatttctg acaagataac ttttcttaag tgagccatct tccctgttag 4380
aataagctgt aaatgatgta gtccttttgt atttgtaagt ttttcccat ctccttttgc 4440
attggccctc ctacctcttc tgtaccgtgc tattgtggtg ttgaccttt cttcgagact 4500
tttgaagaag cttgtctctt cttctccatc aaaacatatt tctgccaggt tgtcttccga 4560
tctccctgtc tcttctccct tggaaccgat gaccaatcta gagactaact tggaaacttt 4620
atattcatag tctgagtggc tcaacttata cttttgtttt cttacgaaac tctccgtaat 4680
ttgactcaca gcactaacaa gcaatttgtt aaagtcatat tccagaagtc gttctccatt 4740
tagatgctta ttaaccacca cactttgtt actagcaaga tctaatgctg tcgcacatcc 4800
agagttagtc atgggatcta ggctgtttag cttcttctct cctttgaaaa ttaaagtgcc 4860
gttgttaaat gaagacacca ttaggctaaa ggcttccaga ttaacacctg gagttgtatg 4920
ctgacagtca atttctttac tagtgaatct cttcatttgc tcatagaaca cacattcttc 4980
ctcaggagtg attgcttcct tggggttgac aaaaaaacca aattgacttt tgggctcaaa 5040
gaacttttca aaacatttta tctgatcgt tagcctgtca ggggtctcct ttgtgatcaa 5100
atgacacagg tatgacacat tcaacataaa tttaaatttt gcactcaaca acaccttctg 5160
accagtacca aaaatagttt ttattaggaa tctaagcagc ttatacacca ccttctcagc 5220
aggtgtgatc agatcctccc tcaacttatc cattaatgat gtagatgaaa aatctgacac 5280
tattgccatc accaaatatc tgacactctg tacctgcttt tgattctct ttgttgggtt 5340
ggtgagcatt agcaacaata gggtcctcag tgcaacctca atgtcggtga gacagtcttt 5400
caaatcagga catgatctaa tccatgaaat catgatgtct atcatattgt ataagaccctc 5460
atctgaaaaa attggtaaaa agaacctttt aggatctgca tagaaggaaa ttaaatgacc 5520
atccgggcct tgtatggagt agcaccttga agattctcca gtcttctggt ataataggtg 5580
gtattcttca gagtccagtt ttattacttg gcaaaacact tctttgcatt ctaccacttg 5640
atatctcaca gacccatttt gattttgcct tagtctagca actgagctag ttttcatact 5700
gtttgttaag gccagacaaa cagatgataa tcttctcagg ctctgtatgt tcttcagctg 5760
ctctgtgctg ggtggaaat tgtaatcttc aaacttcgta taatacatta tcgggtgagc 5820
tccaattttc ataagttcct caaattcagt gaatggtatg tggcattctt gctcaaggtg 5880
ttcagacagt ccgtaatgct cgaaactcag tcccaccact aacaggccat tttgaattt 5940
tgcaatgaac tcactaatag atgccctaaa caattcctca aaagacacct ttctaaacac 6000
ctttgacttt tttctattcc tcaaaagtct aatgaactcc tctttagtgc tgtgaaagct 6060
taccagccta tcattcacac tactatagca acaacccacc cagtgtttat cattttttaa 6120
cccttttgaat ttcgactgtt ttatcaatga ggaaagacac aaaacatcca gatttaacaa 6180
ctgtctcctt ctagtattca acagtttcaa actcttgact ttgtttaaca tagagaggag 6240
cctctcatat tcagtgctag tctcacttcc cctttgctgc ccatgggtct ctgcagttat 6300
gaatctcatc aaaggacagg attcgactgc ctccctgctt aatgttaaga tatcatcact 6360
atcagcaagg ttttcataga gctcagaaa ttccttgatc aagccttcag ggtttacttt 6420
ctgaaagttt ctctttaatt tcccacttttc taaatctctt ctaaacctgc tgaaaagaga 6480
gtttattcca aaaccacat catcacagct catgttgggg ttgatgcctt cgtggcacat 6540
cctcataatt tcatcattgt gagttgacct cgcatctttc agaattttca tagagtccat 6600
```

-continued

```
accggagcgc ttgtcgatag tagtcttcag ggactcacag agtctaaaat attcagactc   6660
ttcaaagact ttctcatttt ggttagaata ctccaaaagt ttgaataaaa ggtctctaaa   6720
tttgaagttt gcccactctg gcataaaact attatcataa tcacaacgac catctactat   6780
tggaactaat gtgacacccg caacagcaag gtcttccctg atgcatgcca atttgttagt   6840
gtcctctata aatttcttct caaaactggc tggagtgctc ctaacaaaac actcaagaag   6900
aatgagagaa ttgtctatca gcttgtaacc atcaggaatg ataagtggta gtcctgggca   6960
tacaattcca gactccacca aaattgtttc cacagactta tcgtcgtggt tgtgtgtgca   7020
gccactcttg tctgcactgt ctatttcaat gcagcgtgac agcaacttga gtccctcaat   7080
cagaaccatt ctgggttccc tttgtcccag aaagttgagt ttctgccttg acaacctctc   7140
atcctgttct atatagttta aacataactc tctcaattct gagatgattt catccattgc   7200
gcatcaaaaa gcctaggatc ctcggtgcg                                     7229
```

ADMINISTERING A LYMPHOCYTIC CHORIOMENINGTITIS VIRUS (LCMV) WITH IMPROVED TUMOR REGRESSION PROPERTIES

CROSS-REFERENCE TO RELATED APPLICATIONS

The present application is a continuation of U.S. patent application Ser. No. 16/267,095, filed Feb. 4, 2019, now U.S. Pat. No. 11,801,294, which is a divisional application of U.S. patent application Ser. No. 15/567,343, filed Oct. 17, 2017, which is the United States National stage patent application of International Application No. PCT/EP2016/058347, filed Apr. 15, 2016, which claims the right of priority of German patent application No. 102015207036.0 filed Apr. 17, 2015, with the German Patent Office, the entire contents of each of which are incorporated herein for all purposes.

SEQUENCE LISTING

The application contains a Sequence Listing which has been submitted electronically in .XML format and is hereby incorporated by reference in its entirety. Said .XML copy, created on Mar. 27, 2024, is named "SCH-5000-CT1_SL.xml" and is 2,758, 175 bytes in size. The sequence listing contained in this .XML file is part of the specification and is hereby incorporated by reference herein in its entirety.

FIELD OF THE INVENTION

The invention relates to arenaviruses for use in the treatment and/or prevention of tumors and also methods for preparing arenaviruses with (improved) tumor-regressive properties.

Arenaviruses belong to the family of human pathogenic, pleomorphic RNA viruses. Diseases with these viruses belong to the zoonoses due to their natural reservoir in animals, predominantly rodents. Zoonoses refer to diseases that can be transferred from the animal to humans and vice versa from humans to the animal.

At least eight arenaviruses are known to cause illness in humans. Typical are aseptic meningitis and haemorrhagic fever. Known viruses which can trigger a disease in humans are the lymphocytic choriomeningitis virus (LCMV), Guanarito virus (GTOV), Junin virus (JUNV), Lassa virus (LASV), Lujo virus (LUJV) Machupo virus (MACV), Sabia virus (SABV) and the Whitewater Arroyo virus (WWAV).

Arenaviruses are generally divided into two groups, namely the Old World arenaviruses and the New World arenaviruses. These groups differ geographically and genetically. Old World arenaviruses, such as the lymphocytic choriomeningitis virus, have been found in countries of the eastern hemisphere, such as European, Asian and African countries. In contrast, New World arenaviruses have been found in countries of the western hemisphere, such as Argentina, Bolivia, Venezuela, Brazil and the United States of America.

The name of the virus family is derived from the Latin arenosus (sandy) and arena (sand) to describe the sandy ribosomal structure within the virions. The virions of the arenaviruses have a round to irregular shape and have a diameter, depending on species and preparation of the test material, from 50 nm to 300 nm, usually between 110 nm and 130 nm. Club-shaped glycoprotein spikes, 8 nm to 10 nm long, are embedded in the virus envelope. The individual spikes consist of a tetramer of the viral envelope protein.

The virions also comprise two closed-ring capsids with helical symmetry. The length of the capsids varies between 450 nm and 1300 nm. One molecule of the viral RNA (ribonucleic acid) polymerase (L-protein) is attached to each of them.

Each capsid comprises one molecule of a single-stranded RNA with mixed (i.e. ambisense, +/−) polarity. The two single-stranded RNA molecules represent the viral genome. They are referred to as L (large) and S (small) and are about 7.5 kb (kilobases) or 3.5 kb (kilobases) large. Although the capsids are closed ring-shaped, the RNA strands are linear and thus not circular. A 19 to 30 base long sequence at the 3' end of the RNA is present on both strands and is also conserved within the virus family.

Very exceptional morphologically is the presence of an alternating number of cellular ribosomes within the virions, which give the viral particles their "sandy" appearance. Similarly, in purified virus preparations, a number of different cellular RNAs (also including ribosomal RNA) and also replicative forms of viral RNA are found, as are diverse viral mRNAs (messenger ribonucleic acids bound to the ribosomes) and complete complementary strands of the virus genome. These non-genomic RNAs are found in varying amounts all lying outside the abovementioned capsids.

The use of arenaviruses as vaccination vectors is known. A prominent example is the vaccination virus Candid #1 used against Argentinian hemorrhagic fever. This is a vaccination variant of the Junin virus.

Known from WO 2009/083210 A1 is the use of replication defects, i.e. genetically modified arenavirus particles (virions), inter alia, for the treatment of neo-plastic diseases such as, for example, melanoma, prostate carcinoma, breast carcinoma and lung carcinoma. In the publication "Development of replication-defective lymphocytic choriomeningitis virus vectors for the induction of potent $CD8^+$ T cell immunity" (Nature Medicine, Vol. 16, No. 3, March 2010, pp. 339-345; doi: 10.1038/Nm.2104), cancer immunotherapy is mentioned as a potential area of application for such viral particles.

Furthermore, WO 2006/008074 A1 discloses the use of packaging cells, which produce retroviral virions pseudotyped with arenavirus glycoprotein, for gene therapy of solid tumors.

The methods for the treatment of tumors described in the prior art are based on the use of virus particles which are very complicated to produce by genetic engineering. In the case of gene therapy treatment methods, it is frequently not possible to achieve adequate, therapeutically effective transduction of the tumor tissue with genetically engineered virions or packaging cells which produce virions.

SUMMARY OF THE INVENTION

Object and Solution

The present invention is therefore based on the object of providing a simpler and, in particular, more efficient therapeutic solution for tumors, in particular carcinomas and sarcomas, compared to the prior art.

This object is achieved according to the invention by an arenavirus according to independent claim 1, by a medicament according to claim 14 and also by an in vitro method according to independent claim 15. Preferred embodiments are defined in the dependent claims. The wording of all claims is hereby incorporated by reference into the content of the description. An additional subject of the invention, which achieves the object of the invention, is disclosed in the description.

According to a first aspect, the invention relates to an arenavirus for use in the treatment and/or prevention of a tumor, preferably a malignant tumor, in humans or animals.

The arenavirus is preferably characterized in that it is free of genomic foreign RNA, i.e. it does not comprise any genomic foreign RNA. In other words, the genome of the arenavirus is preferably free of foreign RNA or preferably comprises no foreign RNA.

In the context of the present invention, the expression "genomic foreign RNA" is intended to mean an RNA (ribonucleic acid) or RNA sequence which does not occur or is not present in the genome of a wild-type arenavirus or in the genome of a mutant of a wild-type arenavirus (mutated arenavirus), in particular in the genome of a natural mutant of a wild-type arenavirus (naturally mutated arenavirus). Examples of foreign RNA are artificial or synthetic RNA molecules, RNA of organisms and RNA from other viruses.

In the context of the present invention, (in accordance with the understanding of those skilled in the art), the expression "wild-type arenavirus" is understood to mean an arenavirus whose genome is the genetically normal form occurring in nature.

In the context of the present invention, (in accordance with the understanding of those skilled in the art), the expression "mutant of a wild-type arenavirus" or "mutated arenavirus" is understood to mean an arenavirus whose genome comprises a spontaneous, i.e. naturally-induced, modification or modification induced by mutagenesis, compared to the wild-type genome.

Accordingly, in the context of the present invention, (in accordance with the understanding of those skilled in the art), the expression "natural mutant of a wild-type arenavirus" or "naturally mutated arenavirus" is understood to mean an arenavirus whose genome comprises a spontaneous, i.e. naturally-induced, modification, compared to the wild-type genome. A naturally mutated arenavirus can be produced preferably by passage, in particular serial passage, which will be discussed in more detail below.

The invention is based on the surprising finding that arenaviruses without genomic foreign RNA are able to effect tumor regression. Tumor regression is due to an activation or stimulation of congenital and adaptive immune cells caused by the arenaviruses. The activated immune cells secrete increased antitumoral cytokines such as interferon-α and interferon-γ, thereby counteracting or repelling the tumor. A further surprising finding is the realization that the arenaviruses cause a significantly increased secretion of antitumoral cytokines in the case of a tumor manifestation. Arenaviruses without genomic foreign RNA are thus suitable for use in tumor treatment. This has been successfully verified by the applicant by means of animal experiments. For this purpose, mice were used, inter alia, in which growth of human tumors is possible.

In a further embodiment, the arenavirus is also free of non-genomic foreign RNA. In the context of the present invention, the expression "non-genomic foreign RNA" is intended to mean an RNA or RNA sequence, apart from the arenavirus genome, which does not occur or is not present in a wild-type arenavirus or a mutant of a wild-type arenavirus (mutated arenavirus), in particular of a natural mutant of a wild-type arenavirus (naturally mutated arenavirus). In other words, in this embodiment the arenavirus does not comprise overall any foreign RNA, i.e neither genomic foreign RNA nor non-genomic foreign RNA.

In a preferred embodiment, the arenavirus is a wild-type arenavirus.

In a further embodiment, the arenavirus is a natural mutant of a wild-type arenavirus, i.e. a naturally mutated arenavirus.

The natural mutant or the naturally mutated arenavirus is preferably produced by passage, in particular multiple passage, in host animals and/or host cells.

The natural mutant or the naturally mutated arenavirus is particularly preferably produced by serial passage in host animals and/or host cells.

The arenavirus provided according to the invention is thus preferably an arenavirus which is produced starting from its wild-type form by passage, preferably serial passage, in host animals and/or host cells.

The host animals mentioned in the preceding paragraphs are preferably rodents, particularly mice. The host cells mentioned in the previous paragraphs, on the other hand, are preferably dendritic cells or tumor cells.

In the context of the present invention, in accordance with the understanding of those skilled in the art, the term "passage" is understood to mean a multiple, regular introduction of the arenavirus into host animals and/or host cells.

In the context of the present invention, in accordance with the understanding of those skilled in the art, the expression "serial passage" is understood to mean a multiple, regular introduction of the arenavirus into different host animals, preferably of the same type, and/or different cells, preferably of the same type. Due to the multiple changes of environment (host animal and/or host cell), the arenavirus is subject to an increased adaptation pressure or mutational pressure, thereby increasing the likelihood of advantageous mutations occurring in the genome of the arenavirus from the perspective of tumor regression.

In a further embodiment, the tumor is selected from the group comprising or consisting of carcinoma, melanoma, blastoma, lymphoma and sarcoma.

In the context of the present invention, (in accordance with the understanding of those skilled in the art), the term "carcinoma" is intended to mean malignant neoplasia of epithelial origin.

In the context of the present invention, (in accordance with the understanding of those skilled in the art), the term "sarcoma" is intended to mean malignant neoplasia of mesodermal origin.

In the context of the present invention, (in accordance with the understanding of those skilled in the art), the term "melanoma" is intended to mean malignant neoplasia of melanocytic origin.

In the context of the present invention, (in accordance with the understanding of those skilled in the art), the term "lymphoma" is intended to mean malignant neoplasia of lymphocytic origin.

In the context of the present invention, (in accordance with the understanding of those skilled in the art), the term "blastoma" is intended to mean malignant neoplasia of embryonic origin.

In a preferred embodiment, the carcinoma is selected from the group comprising or consisting of anal carcinoma, bronchial carcinoma, lung carcinoma, endometrial carcinoma, gallbladder carcinoma, hepatocellular carcinoma, testicular carcinoma, colorectal carcinoma, laryngeal carcinoma, oesophogeal cancer, gastric carcinoma, breast carcinoma, renal carcinoma, ovarian carcinoma, pancreas tumor, pharyngeal carcinoma, prostate carcinoma, thyroid carcinoma and cervical carcinoma.

In a preferred embodiment, the sarcoma is selected from the group comprising or consisting of angiosarcoma, chondrosarcoma, Ewing's sarcoma, fibrosarcoma, Kaposi's sarcoma, liposarcoma, leiomyosarcoma, malignant fibrous histiocytoma, neurogenic sarcoma, osteosarcoma and rhabdomyosarcoma.

In a preferred embodiment, the arenavirus is an Old World arenavirus which is preferably selected from the group comprising or consisting of Ippy virus (IP-PYV), Lassa virus (LASV), lymphocytic choriomeningitis virus (LCMV), Mobala virus (MOBV) and Mopeia virus (MOPV).

In a particularly preferred embodiment, the arenavirus is the lymphocytic choriomeningitis virus, preferably a strain which is selected from the group comprising or consisting of WE, Armstrong, Clone 13 and Docile.

In a preferred embodiment, the arenavirus is a New World arenavirus, which is preferably selected from the group comprising or consisting of Allpaahuayo virus (ALLV), Amapari virus (AMAV), Bear Canyon virus (BCNV), Chapare virus, Cupixi virus (CPXV), Flexal virus (FLEV), Guanarito virus (GTOV), Junin virus (JUNV), Latino virus (LATV), Machupo virus (MACV), Oliveros virus (OLVV), Parana virus (PARV), Pichinde virus (PICV), Pirital virus (PIRV), Sabia virus (SABV), Tacaribe virus (TCRV), Tamiami virus (TAMV) and Whitewara Arroyo virus (WWAV).

In a particularly preferred embodiment, the arenavirus is a Junin virus, in particular the strain Candid #1 (Candid No.1).

In a further embodiment, the Junin virus, in particular the strain Candid #1 (Candid No.1), has a nucleic acid sequence, in particular an S-ribonucleic acid sequence or ambisense sequence, according to SEQ ID No. 1 (according to sequence listing).

In a further embodiment, the Junin virus, in particular the strain Candid #1 (Candid No.1), has a nucleic acid sequence, in particular an L-ribonucleic acid sequence or ambisense sequence, according to SEQ ID No. 2 (according to sequence listing).

In a further embodiment, the Junin virus, in particular the strain Candid #1 (Candid No.1), has a nucleic acid sequence, in particular an S-ribonucleic acid sequence or ambisense sequence, according to SEQ ID No. 3 (according to sequence listing).

In a further embodiment, the Junin virus, in particular the strain Candid #1 (Candid No.1), has a nucleic acid sequence, in particular an L-ribonucleic acid sequence or ambisense sequence, according to SEQ ID No. 4 (according to sequence listing).

In a further embodiment, the lymphocytic choriomeningitis virus (LCMV virus) mentioned above has a nucleic acid sequence, in particular an S-ribonucleic acid sequence or ambisense sequence, according to SEQ ID No. 5 (according to sequence listing).

In a further embodiment, the lymphocytic choriomeningitis virus (LCMV virus) mentioned above has a nucleic acid sequence, in particular an L-ribonucleic acid sequence or ambisense sequence, according to SEQ ID No. 6 (according to sequence listing).

In a further embodiment, the arenavirus is isolated from tumor lysates, organ lysates, urine or blood.

In an alternative embodiment, the arenavirus is isolated from a cell culture medium, in particular from a human tumor cell line.

In a further embodiment, the arenavirus is for administration in the form of virions, i.e. in the form of arenavirus particles, which are outside a cell.

In a further embodiment, the arenavirus is provided, preferably prepared, for local, in particular intramuscular, intraperitoneal or subcutaneous administration. In other words, the arenavirus is used in a further embodiment for local, in particular intramuscular, intraperitoneal or subcutaneous administration.

Preferably the arenavirus is provided, preferably prepared, for local administration at a dose of 1 PFU (Plaque Forming Unit)/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight. In other words, the arenavirus is used, preferably for local administration, at a dose of 1 PFU (Plaque Forming Unit)/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight.

In an alternative embodiment, the arenavirus is provided, preferably prepared, for systemic, in particular intravenous, administration. In other words, the arenavirus is used in an alternative embodiment for systemic, in particular intravenous, administration.

Preferably, the arenavirus is provided, preferably prepared, for systemic administration at a dose of 1 PFU/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight. In other words, the arenavirus is used, preferably for systemic administration, at a dose of 1 PFU/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight.

According to a second aspect, the invention relates to a medicament for use in the treatment and/or prevention of a tumor, in particular a malignant tumor.

The medicament is characterized in particular by the fact that it has an arenavirus according to the first aspect of the invention.

The medicament preferably further comprises a pharmaceutically acceptable carrier. The carrier may in particular be selected from the group comprising or consisting of water, saline solution, buffer solution and cell culture medium.

In a further embodiment, the medicament also comprises an active ingredient. The active ingredient can in particular be a cytostatic agent, an antibody and/or a cytokine.

With regard to further features and advantages of the medicament, in particular of the arenavirus and also the tumor, reference is made fully to the present description in order to avoid repetitions.

According to a third aspect, the invention relates to a method for producing an arenavirus with tumor-regressive, i.e. tumor-repelling/counteracting properties or improved tumor-regressive properties.

The tumor is preferably a malignant tumor, preferably a carcinoma, melanoma, blastoma, lymphoma or sarcoma. Accordingly, the method is preferably a method for producing an arenavirus with (improved) carcinoma-, melanoma-, blastoma-, lymphoma- or sarcoma-regressive properties.

The method comprises the following steps:

a) infecting dendritic cells or tumor cells with an arenavirus,
b) culturing the arenavirus in the infected dendritic cells or infected tumor cells and c) isolating the cultured arenavirus or a subset of the cultured arenavirus from the infected dendritic cells or infected tumor cells.

The sequence of steps a) to c) may also be referred to as a (single) passage of the arenavirus in the dendritic cells or tumor cells.

In a preferred embodiment, the arenavirus is an arenavirus which has been subjected to a serial passage in host animals prior to carrying out step a). For further details and advantages, reference may be made to the corresponding statements made in the context of the fourth aspect of the invention.

In a further embodiment, the dendritic cells or tumor cells are in the form of a cell culture (dendritic cell culture or tumor cell culture).

The tumor cells are preferably malignant tumor cells, in particular carcinoma, melanoma, blastoma, lymphoma or sarcoma cells.

The carcinoma cells may be selected from the group comprising or consisting of anal carcinoma cells, bronchial carcinoma cells, lung carcinoma cells, endometrial carcinoma cells, gallbladder carcinoma cells, hepatocellular carcinoma cells, testicular carcinoma cells, colorectal carcinoma cells, laryngeal carcinoma cells, oesophogeal carcinoma cells, gastric carcinoma cells, breast carcinoma cells, renal carcinoma cells, ovarian carcinoma cells, pancreas tumor cells, pharyngeal carcinoma cells, prostate carcinoma cells, thyroid carcinoma cells and cervical carcinoma cells.

The sarcoma cells may be selected from the group comprising or consisting of angiosarcoma cells, chondrosarcoma cells, Ewing's sarcoma cells, fibrosarcoma cells, Kaposi's sarcoma cells, liposarcoma cells, leiomyosarcoma cells, malignant fibrous histiocytoma cells, neurogenic sarcoma cells, osteosarcoma cells and rhabdo-myosarcoma cells.

In a further embodiment, the tumor cells are immortalized immune cells, in particular immortalized macrophages.

The dendritic cells or tumor cells are infected according to step a) preferably by adding the arenavirus to the cells.

In a preferred embodiment, the sequence of steps a) to c) is repeated with new, in particular non-infected, dendritic cells, preferably of the same type, or with new, in particular non-infected, tumor cells, preferably of the same type (the same tumor type).

In a particularly preferred embodiment, the sequence of steps a) to c) is repeated many times. By way of preference, new, in particular non-infected, dendritic cells, preferably of the same type, or new, in particular non-infected, tumor cells, preferably of the same type, are used for each repetition.

The sequence of steps a) to c) is preferably repeated once to 1000 times, particularly 10 times to 100 times, preferably 30 times to 60 times, wherein new, in particular non-infected, dendritic cells, preferably of the same type, or new, in particular non-infected, tumor cells, preferably of the same type, are used for each repetition.

By multiple repetition of steps a) to c), the arenavirus is constantly forced to adapt to a new environment, i.e. to new dendritic cells or tumor cells. This permanent adaptation pressure favors the occurrence of mutations, which can produce or improve the tumor-regressive properties of the arenavirus.

During the culturing of the arenavirus according to step b), a replication of the arenavirus genome and a propagation of the arenavirus occur within the dendritic cells or tumor cells.

The arenavirus according to step b) is preferably cultured under standard cell culture conditions.

The arenavirus is preferably cultured in the dendritic cells or tumor cells for a period of 1 minute to 1 year, in particular 10 hours to 1 month, preferably 24 hours to 72 hours.

The cultured arenavirus according to step c) is preferably isolated from a cell culture supernatant.

Preferably, the dendritic cells or tumor cells are sorted according to specific properties, preferably by means of a cell sorting device, and subsequently cultured, prior to isolating according to step c). The sorted cells are preferably cultured over a period of 24 hours.

In a preferred embodiment, the method further comprises the following steps:
 d) cloning the isolated arenavirus and
 e) sequenzing the isolated arenavirus.

With regard to further features and advantages of the method, in particular of the arenavirus and also the tumor, reference is made to the present description.

According to a fourth aspect, the invention relates to a method for producing an arenavirus with tumor-regressive, i.e. tumor-repelling/counteracting, properties or improved tumor-regressive properties.

The tumor is preferably a malignant tumor, preferably a carcinoma, melanoma, blastoma, lymphoma or sarcoma. Accordingly, the method is preferably a method for producing an arenavirus with (improved) carcinoma-, melanoma-, blastoma-, lymphoma- or sarcoma-regressive properties.

The method comprises the following steps:
 a) infecting a host animal, which has a tumor, with an arenavirus,
 b) culturing the arenavirus in the infected host animal and
 c) isolating the cultured arenavirus or a subset of the cultured arenavirus from the infected host animal.

The sequence of steps a) to c) may also be referred to as a (single) passage of the arenavirus in the host animal.

In a preferred embodiment, tumor tissue is transplanted to the host animal prior to carrying out step a).

In an alternative embodiment, a genetically modified host animal is used which spontaneously develops the tumor.

Rodents in particular, preferably mice, can be used as host animals. For example, NOD SCID mice or LoxP-Tag mice can be used as host animals. In the Nod SCID mice, the SCID (Severe Combined Immunodeficiency) mutation is combined with a NOD (non-obese diabetic) type. In mice that are homozygous for the SCID mutation, no functional T-cells or B-cells are formed. By means of this immunodeficiency, these animals are exceptionally suitable for tolerating foreign body cells, for example transplanted tumors.

The host animal can be infected according to step a), for example by systemic, particularly intravenous, or local, for example subcutaneous, administration of the arenavirus.

In particular, the host animal can be infected by administration, preferably injection, of the arenavirus into the tumor of the host animal.

In a preferred embodiment, the sequence of steps a) to c) is repeated with a new, in particular non-infected, host animal, preferably of the same type.

In a particularly preferred embodiment, the sequence of steps a) to c) is repeated many times. A new, in particular non-infected host animal, preferably of the same type, is preferably used for each repetition. In other words, it is preferred according to the invention if the arenavirus is subjected to serial passage in host animals, preferably of the same type.

The sequence of steps a) to c) is preferably repeated once to 1000 times, particularly 10 times to 100 times, preferably 30 times to 60 times, wherein a new, in particular non-infected, host animal, preferably of the same type, is used for each repetition.

By multiple repetition of steps a) to c), the arenavirus is constantly forced to adapt to a new environment, i.e. to a new host animal. This permanent adaptation pressure favors the occurrence of mutations, which can produce or improve the tumor-regressive properties of the arenavirus.

During the culturing of the arenavirus according to step b), a replication of the arenavirus genome and a propagation of the arenavirus occur within the host animal.

The arenavirus is preferably cultured in the host animal for a period of 1 minute to 500 days, in particular 10 minutes to 100 days, preferably 1 hour to 30 days.

In a preferred embodiment, the arenavirus is isolated from urine, blood, the tumor, or organ lysates of the host animal.

In a further embodiment, the method further comprises the following steps:

d) infecting dendritic cells or tumor cells with the arenavirus isolated according to step c),
e) culturing the arenavirus in the infected dendritic cells or infected tumor cells and
f) isolating the cultured arenavirus or a subset of the cultured arenavirus from the infected dendritic cells or infected tumor cells.

The sequence of steps d) to f) may also be referred to as a (single) passage of the arenavirus in the dendritic cells or tumor cells.

The dendritic cells or tumor cells are infected according to step d) preferably by adding the arenavirus to the cells.

In a preferred embodiment, the sequence of steps d) to f) is repeated with new, in particular non-infected, dendritic cells, preferably of the same type, or with new, in particular non-infected, tumor cells, preferably of the same type (the same tumor type).

In a particularly preferred embodiment, the sequence of steps d) to f) is repeated many times. By way of preference, new, in particular non-infected, dendritic cells, preferably of the same type, or new, in particular non-infected, tumor cells, preferably of the same type, are used for each repetition. In other words, it is particularly preferred according to the invention if the arenavirus is additionally subjected to a serial passage in dendritic cells, preferably of the same type, or tumor cells, preferably of the same type.

The sequence of steps d) to f) is preferably repeated once to 1000 times, particularly 10 times to 100 times, preferably 30 times to 60 times, wherein new, in particular non-infected, dendritic cells, preferably of the same type, or new, in particular non-infected, tumor cells, preferably of the same type, are preferably used for each repetition.

The combination of a serial passage of the arenavirus in host animals, preferably of the same type, with a serial passage of the arenavirus in dendritic cells, preferably of the same type, or tumor cells, preferably of the same type, is suitable, because of the additionally increased adaptation pressure or mutation pressure in a particular manner, for producing arenaviruses with (improved) tumor-regressive properties.

The arenavirus is preferably cultured in the dendritic cells or tumor cells for a period of 1 minute to 500 days, in particular 10 minutes to 100 days, preferably 1 hour to 30 days.

Preferably, the dendritic cells or tumor cells are sorted according to specific properties, preferably by means of a cell sorting device, and subsequently cultured, prior to isolating according to step f). The sorted cells are preferably cultured over a period of 24 hours.

In a preferred embodiment, the method further comprises the following steps:

g) cloning the arenavirus isolated according to step f) and
h) sequencing the isolated arenavirus.

Alternatively, it can be provided according to the invention that the arenavirus isolated according to step c) is cloned and subsequently sequenced.

With regard to other features and advantages of the method, in particular the arenavirus, the tumor and also the dendritic cells and tumor cells, the present description is also fully incorporated by way of reference in order to avoid unnecessary repetitions.

Further features and advantages of the invention will emerge from the following description of preferred embodiments in the form of working examples, the associated figures and the claims. The embodiments described below are merely for the purpose of illustration and for the better understanding of the invention and are in no way to be understood as limiting.

BRIEF DESCRIPTION OF THE DRAWINGS

FIG. 1 shows LCMV (WE strain) replication results in immortalized macrophages ("tumour") and macrophages ("primary") generated from primary bone marrow.

FIG. 2 shows the effect of LCMV (WE strain) administration on MOPC (mouse plasmacytoma cell) tumor growth in C57BL/6 mice.

FIG. 3 shows the effect of LCMV (WE strain) administration on MC38 (mouse colon adenocarcinoma cell) tumor growth in C57BL/6 mice.

FIG. 4 shows the effect of LCMV (WE strain) administration on spontaneous liver carcinoma tumor growth in LoxP-TAg mice.

FIG. 5 shows the effect of LCMV (WE strain) on interferon-γ secretion in MOPC tumor-bearing C57BL/6 mice.

FIG. 6 shows the effect of LCMV (WE strain) administration on MOPC tumor growth in Map3k14$^{aly/aly}$ mice compared to corresponding wild type mice.

FIG. 7 shows the effect of LCMV (WE strain) administration on MOPC tumor growth in Irf3×Ir7$^{-/-}$ mice compared to corresponding wild type mice.

FIG. 8A shows effect of LCMV (WE strain) administration on tumor microvessel density (MDV) and vessel-vessel spacing in MOPC tumor-bearing wild type mice.

FIG. 8B shows effect of LCMV (WE strain) administration on tumor hypoxic regions in MOPC tumor-bearing wild type mice.

FIG. 9 shows the effect of LCMV (WE strain) administration (ipsilateral, contralateral, and intravenous) on MOPC tumor growth in C57BL/6 mice.

FIG. 10 shows effect of LCMV (WE strain) administration on survival in A431 (squamous carcinoma) tumor-bearing NOD.SCID mice.

FIG. 11 shows effect of LCMV (WE strain) administration on tumor growth in A431 (colon adenocarcinoma) tumor-bearing NOD.SCID mice.

FIG. 12 shows effect of Candid #1 administration on tumor growth in HeLa cell-bearing NOD.SCID mice.

FIG. 13 shows effect of Candid #1 administration on tumor growth in HepG2 (hepatocellular carcinoma) tumor-bearing NOD.SCID mice.

FIG. 14 shows LCMV (MOI 1) replication results in primary hepatocytes, colon epithelial cells, and melanocytes) and in tumour cells from the same tissue source.

FIG. 15A shows the effect of LCMV administration on metastatic MOPC tumor growth in C57BL/6 mice.

FIG. 15B shows the effect of LCMV administration on survival in MOPC metastatic tumor-bearing C57BL/6 mice.

FIG. 16 shows the effect of LCMV administration on B16F10 (melanoma) tumor growth in C57BL/6 mice.

FIG. 17 shows the effect of LCMV administration on spontaneous melanoma tumor growth in MT/ret mice.

FIG. 18A shows the effect of LCMV administration on Sw872 (fibrosarcoma) tumor growth in NOD.SCID mice.

FIG. 18B shows the effect of LCMV administration on survival in Sw872 (fibrosarcoma) tumor-bearing NOD.SCID mice.

FIG. 19A shows the effect of LCMV administration on FaDu (pharyngeal carcinoma) tumor growth in NOD.SCID mice.

FIG. 19B shows the effect of LCMV administration on survival in FaDu (pharyngeal carcinoma) tumor-bearing NOD.SCID mice.

FIG. 20 shows the effect of LCMV on T-cell expression of PD-1, IL2 receptor, and IL7 receptor in B16F10 tumor-bearing mice.

FIG. 21A shows the effect of LCMV administration on EL4 (lymphoma) tumor growth in C57BL/6 mice.

FIG. 21B shows the effect of LCMV administration on survival in EL4 (lymphoma) tumor-bearing C57BL/6 mice.

EXPERIMENTAL SECTION

1. Methods and Materials 1.1 Mice

Unless mentioned otherwise, the mice used were from a C57BL/6 background. Map3k14$^{aly/aly}$ mice lack NF-kB signals and are therefore highly immunosuppressed. Irf3×Ir7$^{-/-}$ mice cannot produce any interferon. NOD.SCID mice have no adaptive immune system. Therefore, it is possible to grow human tumors in these mice. LoxP-Tag mice spontaneously develop liver tumors.

1.2 Cell Lines and Reagents

MOPC cells are murine oropharynx carcinoma cells. Mc38 are murine colon carcinoma cells. Raw cells are immortalized macrophages. A431 are human lung carcinoma cells; Sw40 are human colon carcinoma cells, Hela are human cervical carcinoma cells. Primary macrophages were cultured from bone marrow precursor cells by means of M-CSF. Cells were maintained in Dulbecco's modified Eagle's medium with 10% fetal bovine serum (Sigma-Aldrich), 2 mmol/l L-glutamine and 100 U/ml penicillin. All cells were cultured in 5% CO2.

1.3 Viruses

The LCMV strain WE was obtained from the laboratory of Prof. Zinkernagel (Experimental Immunology, Zurich, Switzerland) and was propagated in L929 cells. Candid #1 was obtained from Professor Paula Cannon (University of Southern California).

1.4 Tumor Growth and Treatments

Approximately 5×10$^5$ tumor cells (in 100 microL) were injected subcutaneously into the right flank of 6 to 12 week old mice. The longest tumor diameter was measured by. Mice were treated by peritumoral injections of 2×10$^4$ PFU LCMV-WE or Candid #1 (in 100-200 microL).

1.5 Morphometric Analysis of Tumor Vessels

Morphometric analyses were performed with successive frozen sections, in which the endothelial cell marker CD31 was stained. Quantification of the microvessel density (MVD) was calculated using the mean of three tumor sections. MVD was calculated as the number of vessels per tumor area.

1.6 Detection of Hypoxia

Hypoxic tumor regions were detected by the formation of pimonidazole adducts after injection of pimonidazole into tumor-transplanted animals for 30 min. The tumor sections were stained using the Hypoxyprobe-1 Plus kit according to the manufacturer's instructions (Pharmacia Natur International, Inc.).

1.7 IFN-α ELISA

Serum IFN-α levels were determined by ELISA according to the manufacturer's data (Research Diagnostics RDI, Flanders, NJ).

1.8 Statistical Analysis

The mean values were compared using an unpaired two-sided student t-test. The data are shown as mean±SEM. The level of statistical significance was set at $p<0.05$.

2. Investigations 2.1 Immortalized Macrophages (Tumour Cells) and Macrophages (Primary) generated from primary bone marrow were infected with LCMV (WE strain). Replication was measured after 24 hours (n=3).

It could be shown that LCMV (WE strain) replicates both in immortalized and healthy cells. The results obtained are shown graphically in FIG. 1.

Figure 1:
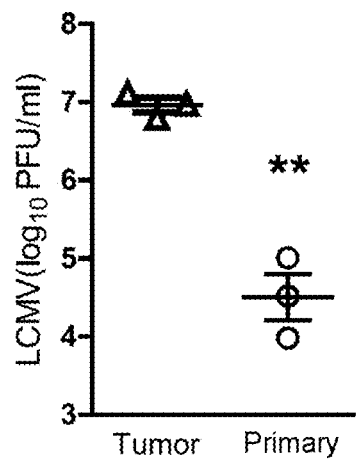

FIG. 1 has the following legend:
Ordinate: LCMV ($\log_{10}$ PFU/ml)
Abscissa: Tumor cells/healthy macrophages (primary)

2.2 WT C57BL/6 mice were treated with 5×10$^5$ MOPC cells (day 3). One group of mice was additionally treated peritumorally with 2×10$^4$ PFU LCMV (WE strain) (day 0). Tumor growth was observed.

It could be shown that the treatment with LCMV caused almost complete tumor regression. The results obtained are shown graphically in FIG. 2.

Figure 2:
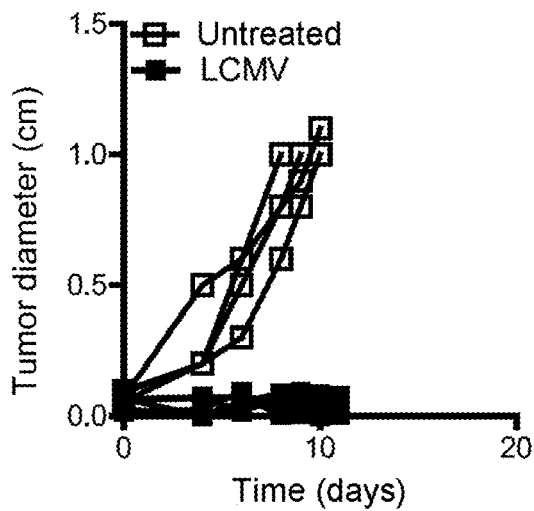

FIG. 2 has the following legend:
Ordinate: Tumor diameter (cm)
Abscissa: Time (days)

2.3 WT C57BL/6 mice were treated with 5×10$^5$ MC38 cells (day 3). One group of mice was additionally treated peritumorally with 2×10$^4$ PFU LCMV (WE strain) (day 0). Tumor growth was observed.

It could be shown that the treatment with LCMV caused a significant tumor regression. The results obtained are shown graphically in FIG. 3.

Figure 3:
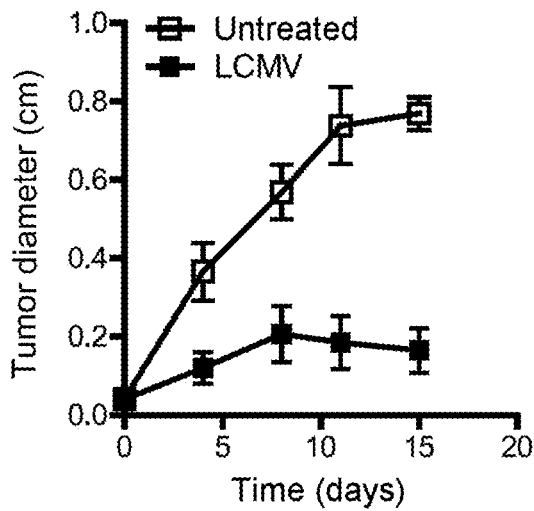

FIG. 3 has the following legend:
Ordinate: Tumor diameter (cm)
Abscissa: Time (days)

2.4 About nine month old LoxP-TAg mice with spontaneously developed liver carcinomas were infected intravenously with 2×10$^6$ PFU LCMV or left untreated. The tumor nodes (diameters>=3 mm) were quantified macroscopically on day 6 (n=3) and day 20 (n=4-5).

It could be shown that the treatment with LCMV significantly reduced the number of carcinomatous liver nodes. The results obtained are shown graphically in FIG. 4.

Figure 4:
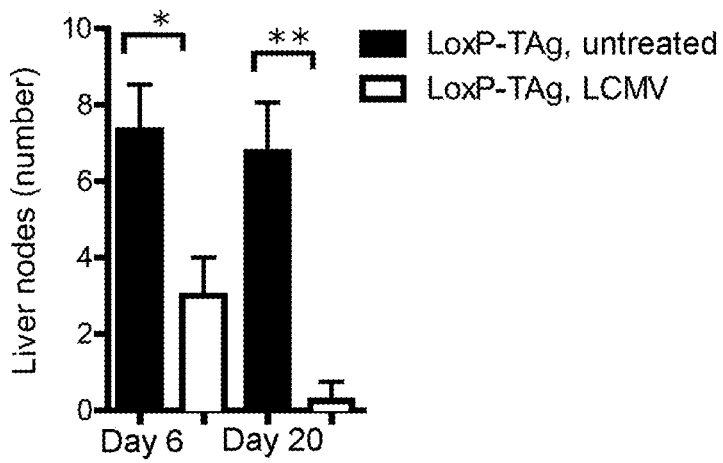

FIG. 4 has the following legend:
Ordinate: Liver nodes (number)
Abscissa: Time 2.5 WT C57BL/6 mice (n=4/group) were injected subcutaneously with 5×10$^5$ MOPC cells (day −3) or LCMV (WE strain) 2×10$^4$ PFU (day 0) or both 5×10$^5$ MOPC cells (day −3) and 2×10$^4$ PFU LCMV (day 0). Serum samples were collected on day 3 and an IFN-α-ELISA was performed.

It could be shown that the LCMV caused a drastically increased secretion of interferon-γ in experimental animals which were simultaneously administered carcinoma cells. The results obtained are shown graphically in FIG. 5.

Figure 5:
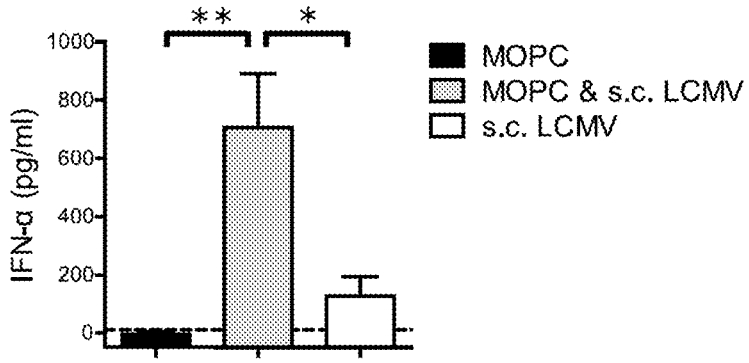

FIG. 5 has the following legend:
Ordinate: IFN-α (pg/ml)

2.6 Map3k14$^{aly/aly}$ mice and WT mice were treated with 5×10$^5$ MOPC cells (day 3). One group of mice was additionally treated peritumorally with 2×10$^4$ PFU LCMV (WE strain) (day 0). Tumor growth was observed.

It could be shown that the treatment with LCMV caused tumor regression. The results obtained are shown graphically in FIG. 6.

Figure 6:
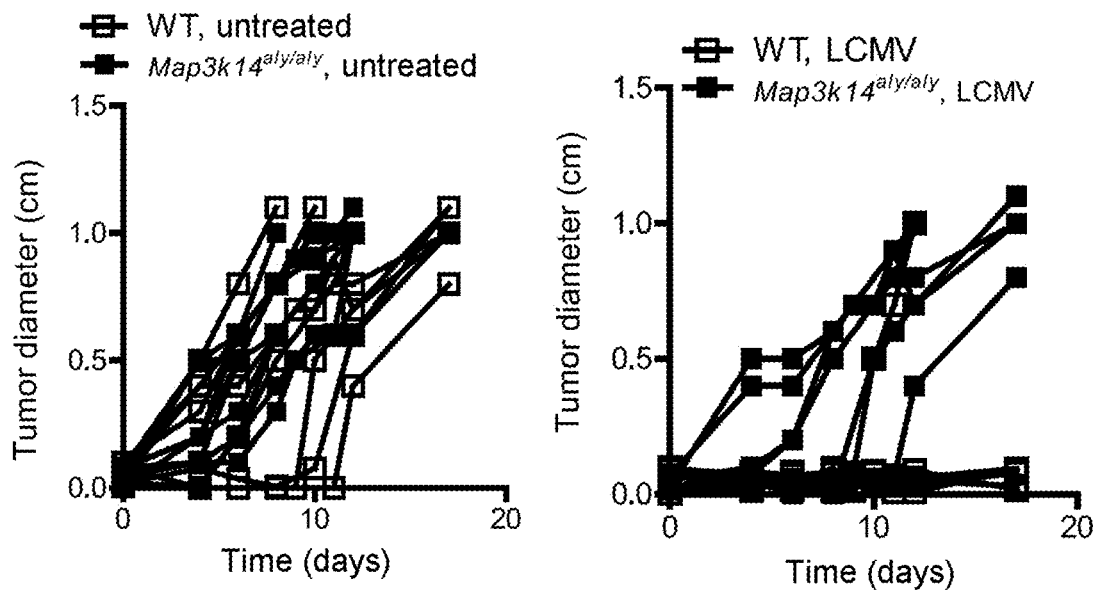

FIG. 6 has the following legend:
Ordinate: Tumor diameter (cm)
Abscissa: Time (days)

2.7 Irf3×Ir7$^{-/-}$ mice and WT mice were treated with 5×10$^5$ MOPC cells (day 3). One group of mice was additionally treated peritumorally with 2×10$^4$ PFU LCMV (WE strain) (day 0). Tumor growth was observed.

It could be shown that the treatment with LCMV caused tumor regression. The results obtained are shown graphically in FIG. 7.

Figure 7:
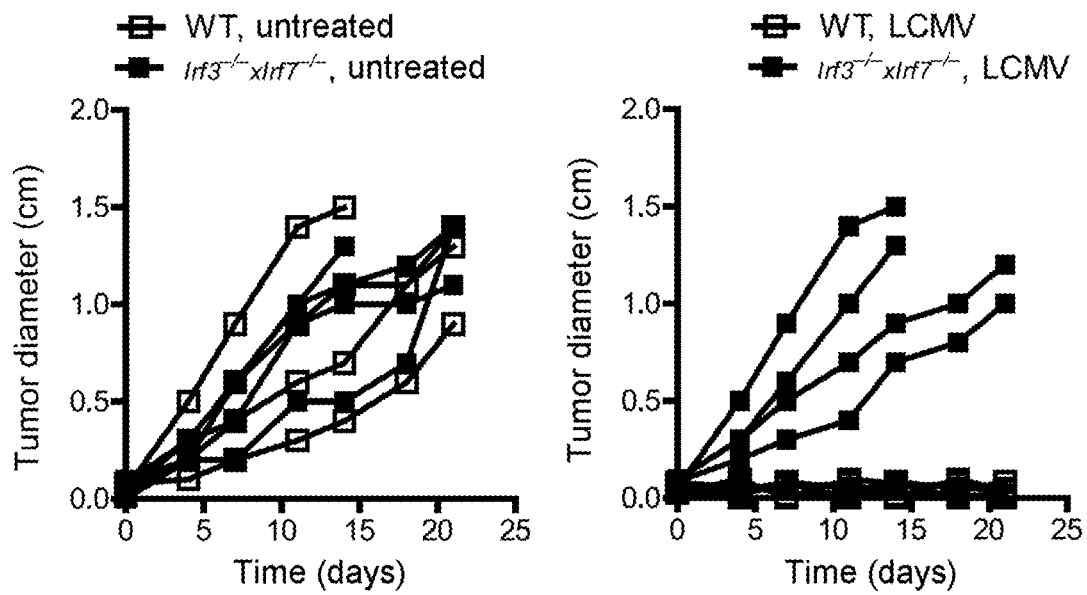

FIG. 7 has the following legend:
Ordinate: Tumor diameter (cm)
Abscissa: Time (days)

2.8 WT mice were treated with 5×10$^5$ MOPC cells (day 3). One group of mice was additionally treated peritumorally with 2×10$^4$ PFU LCMV (WE strain) (day 0). On day 9 after the tumor graft, the tumors were analyzed histologically with CD31 staining. The microvessel density (MDV) and the vessel-vessel spacing were quantified.

It could be shown that the treatment with LCMV caused a decrease in tumor vessel density. The results obtained are shown graphically in FIG. 8A.

Figure 8A:
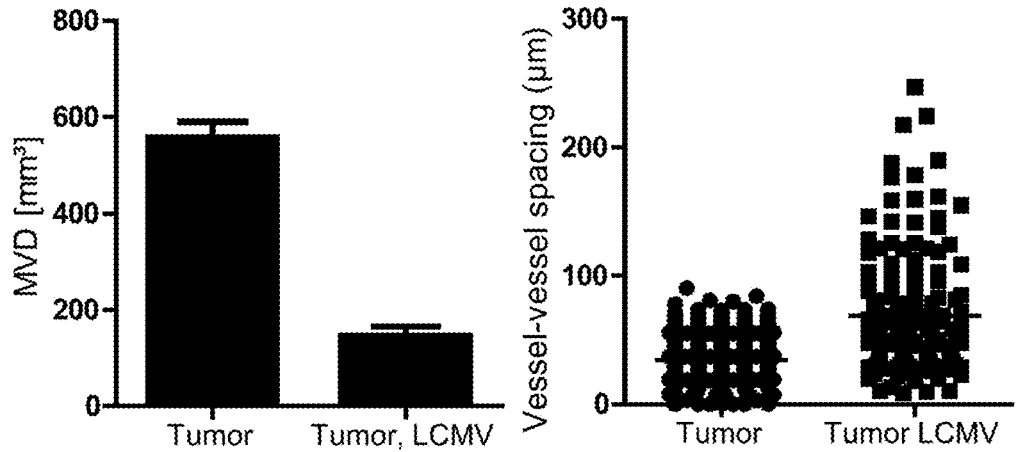

FIG. 8A has the following legends:
Left side: Right side:
Ordinate: MVD [mm$^3$]
Ordinate: Vessel-vessel spacing (µm)
Abscissa: Tumor/Tumor LCMV Abscissa: Tumor/Tumor LCMV 2.9 WT mice were treated with 5×10$^5$ MOPC cells (day 3). One group of mice was additionally treated peritumorally with 2×10$^4$ PFU LCMV (WE strain) (day 0). On day 9, the animals were injected with pimonidazole, and the tumors were then analyzed histologically for hypoxic regions.

It could be shown that the treatment with LCMV caused oxygen deficiency in the carcinoma tissue. The results obtained are shown graphically in FIG. 8B.

Figure 8B:
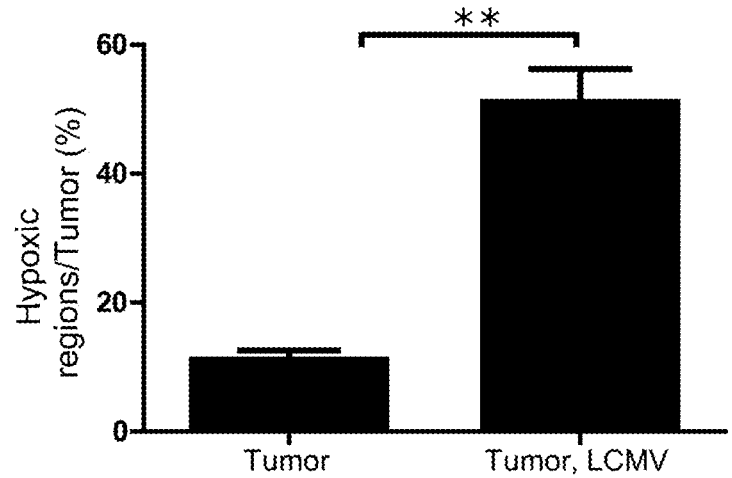

FIG. 8B has the following legend:
Ordinate: Hypoxic regions/tumor (%)
Abscissa: Tumor/Tumor LCMV 2.10 WT C57BL/6 mice were injected subcutaneously with 5×10$^5$ MOPC cells in the right flank (day 3). On day 0, a group of animals were treated with 2×10$^4$ PFU LCMV (WE strain) in the right flank (ipsilateral), left flank (contralateral) or intravenously. Tumor growth was observed.

It could be shown that the treatment with LCMV caused tumor regression even with systemic administration. The results obtained are shown graphically in FIG. 9.

Figure 9:
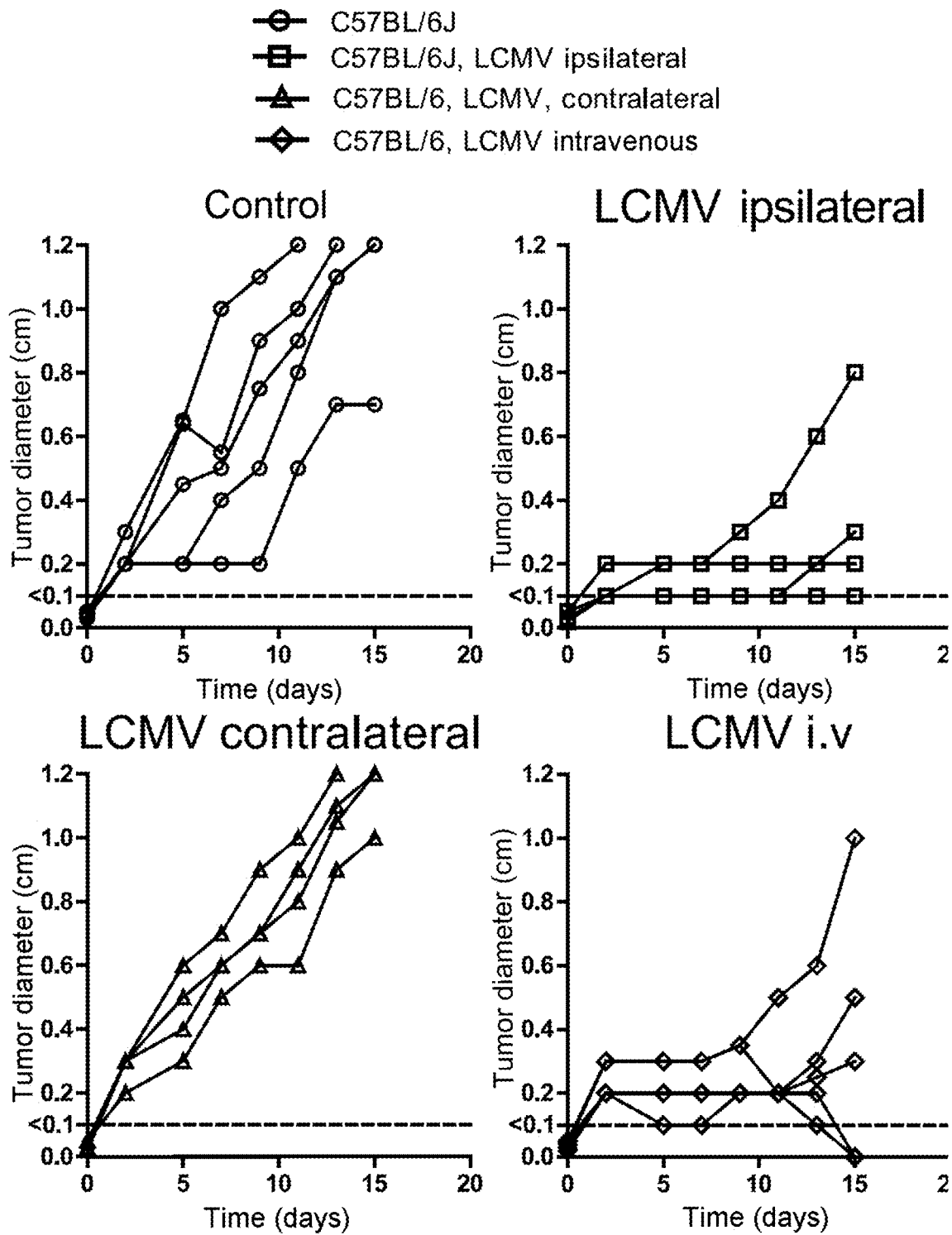

FIG. 9 has the following legend:
Ordinate: Tumor diameter (cm)
Abscissa: Time (days)

2.11 NOD.SCID mice were injected subcutaneously with 5×10$^5$ A431 cells (day −3) and then either left untreated or treated with 2×10$^4$ PFU LCMV (WE strain). The tumor size (longest diameter) was measured on the specified day. The mice were sacrificed when the tumor size reached 12 mm.

It could be shown that the treatment with LCMV increased the survival rate in the experimental animals. The results obtained are shown graphically in FIG. 10.

Figure 10:
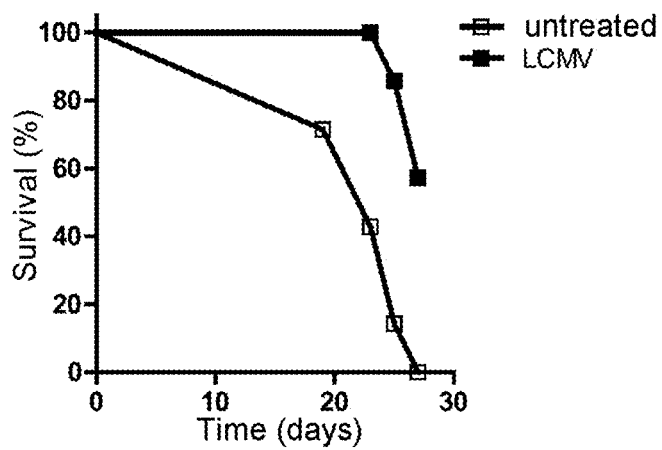

FIG. 10 has the following legend:
Ordinate: Survival (%)
Abscissa: Time (days)

2.12 NOD.SCID mice were treated with 5×10$^5$ Sw40 cells (day 0). A group of mice was additionally treated peritumorally with 2×10$^4$ PFU LCMV (WE strain) or 2×10$^4$ PFU Candid #1 (day 0). Tumor growth was observed.

It could be shown that the treatment with LCMV and Candid #1 caused tumor regression. The results obtained are shown graphically in FIG. 11.

Figure 11:
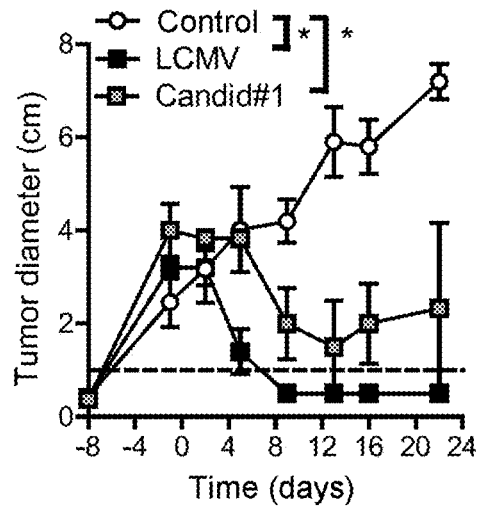

FIG. 11 has the following legend:
Ordinate: Tumor diameter (cm)
Abscissa: Time (days)

2.13 NOD.SCID mice were treated with 5×10$^5$ Hela cells (day 0). A group of mice was additionally treated peritumorally with 2×10$^4$ PFU LCMV (WE strain) (day 3). Tumor growth was observed.

It could be shown that the treatment with LCMV caused tumor regression. The results obtained are shown graphically in FIG. 12.

Figure 12:
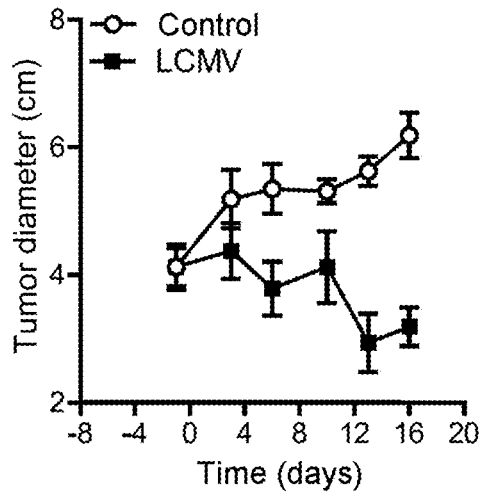

FIG. 12 has the following legend:
Ordinate: Tumor diameter (cm)
Abscissa: Time (days)

2.14 NOD.SCID mice were treated with 5×10$^5$ HepG2 cells (day 10) and then additionally treated peritumorally with or without 2×10$^4$ PFU Candid #1 (day 0). Tumor growth was observed.

It could be shown that the treatment with Candid #1 caused tumor regression with this tumor type. The results obtained are shown graphically in FIG. 13.

Figure 13:
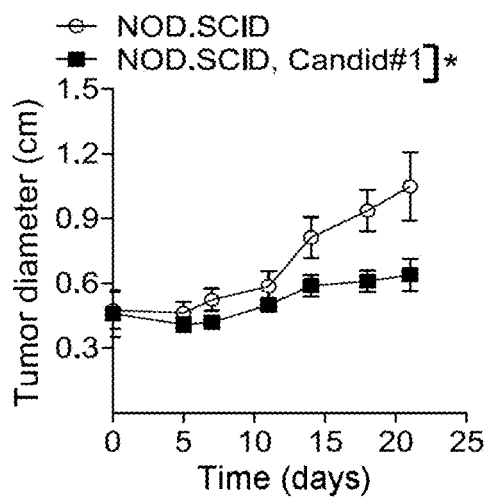

FIG. 13 has the following legend:
Ordinate: Tumor diameter (cm)
Abscissa: Time (days)

2.15 Primary human cells (hepatocytes, colon epithelial cells, melanocytes) and tumour cells from the same tissue source were infected with LCMV (MOI 1). The amount of virus was measured in the supernatant after 1, 2 and 3 days.

In this experiment it was shown that arenaviruses are replicated in tumor cells in comparison to healthy tissue.

Figure 14:
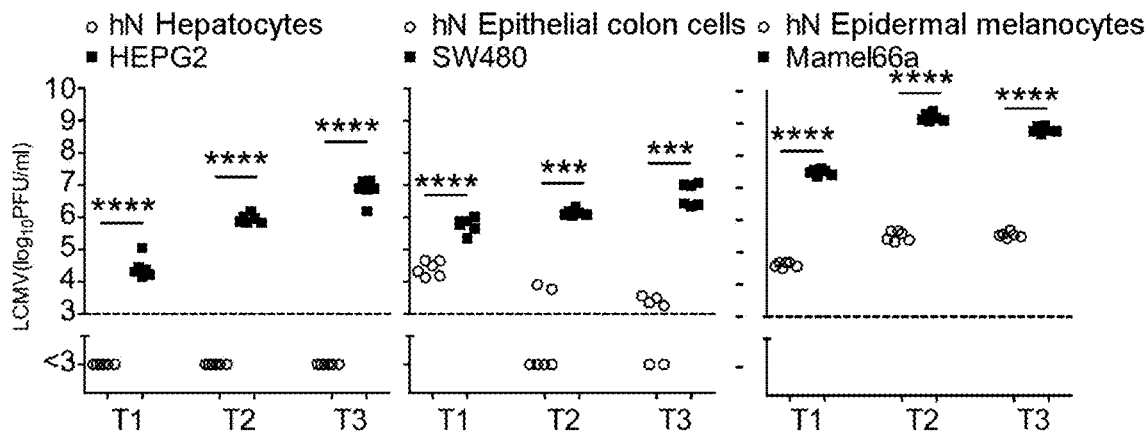

FIG. 14 has the following legend:
Ordinate: Infectious virus in cell culture supernatant (logarithmic plaque forming units)
Abscissa: Time (days)

2.16 Tumor diameter (A) and survival (B) of C57BL/6 mice bearing a metastasis in the shoulder and a metastasis in the flank (MOPC cells), which were left untreated or had been treated intravenously with 2×10$^6$ PFU LCMV.

It could be shown in this experiment that intravenous therapy of LCMV acts very efficiently on two local metastases and thus prolongs survival.

Figure 15A:
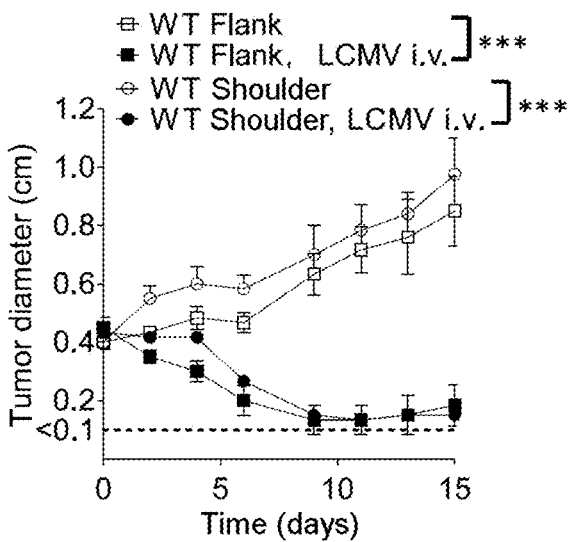

FIG. 15A has the following legend:
Ordinate: Tumor diameter of both metastases (cm)
Abscissa: Time (days)

Figure 15B:
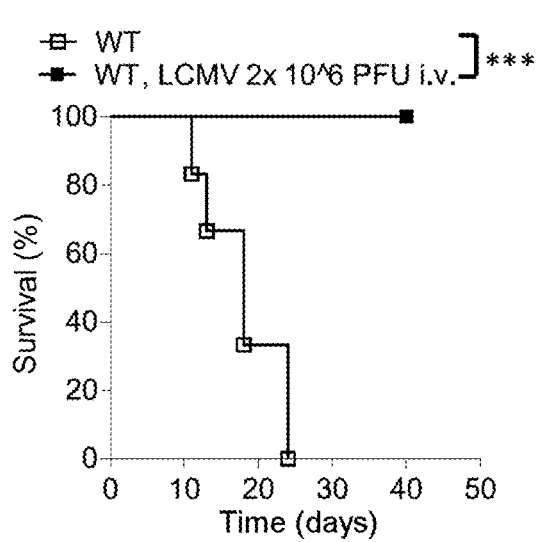

FIG. 15B has the following legend:
Ordinate: Survival in percent
Abscissa: Time (days)

2.17 Tumor diameter of C57BL/6 mice bearing a melanoma (B16F10 cells) which were left untreated or were treated intratumorally with 2×10$^4$ PFU LCMV.

It could be shown in this experiment that local therapy with LCMV is very efficient in melanoma.

FIG. 16 has the following legend:
Ordinate: Tumor diameter of the melanoma (cm)
Abscissa: Time (days)
2.18 Number of melanomas of MT/ret mice (develop endogenous melanomas), which were left untreated or were treated intravenously with $2\times10^6$ PFU LCMV.

It could be shown in this experiment that systemic therapy with LCMV is very efficient in melanoma.

FIG. 17 has the following legend:
Ordinate: Number of melanomas
2.19 Tumor diameter (A) and survival (B) of NOD.SCID mice bearing a human fibrosarcoma (Sw872 cells), which were left untreated or were treated intratumorally with $2\times10^6$ PFU Candid #1.

It could be shown in this experiment that Candid #1 acts very efficiently also in the case of fibrosarcoma and thus prolongs survival.

FIG. 18A has the following legend:
Ordinate: Tumor diameter (cm)
Abscissa: Time (days)
FIG. 18B has the following legend:
Ordinate: Survival in percent
Abscissa: Time (days)
2.20 Tumor diameter (A) and survival (B) of NOD.SCID mice bearing a human pharyngeal carcinoma (FaDu cells), which were left untreated or were treated intratumorally with $2\times10^6$ PFU LCMV.

It could be shown in this experiment that LCMV acts very efficiently also in the case of pharyngeal carcinoma and thus prolongs survival.

FIG. 19A has the following legend:
Ordinate: Tumor diameter (cm)
Abscissa: Time (days)
FIG. 19B has the following legend:
Ordinate: Survival in percent
Abscissa: Time (days)
2.21 Expression of receptors on tumor-specific T cells (PD-1, IL2 receptor, IL7 receptor), which influence the function of T cells. Tumor-specific T cells are derived from the blood of mice with B16F10 tumors, which were additionally treated intratumorally with or without LCMV.

It could be shown in this experiment that LCMV positively influences the tumor-specific T cells.

FIG. 20 has the following legend:
Ordinate: Potency of the expression of the different receptors (mean fluorescence intensity)
2.22 Tumor diameter (A) and survival (B) of C57BL/6 mice bearing a murine subcutaneous lymphoma (EL4 cells) which were treated with or without tumor-specific T cells (OT1 cells) and additionally intratumorally with or without LCMV ($2\times10^6$ PFU).

It could be shown in this experiment that LCMV acts synergistically with T cell therapy.

FIG. 21A has the following legend:
Ordinate: Tumor diameter (cm)
Abscissa: Time (days)
FIG. 21B has the following legend:
Ordinate: Survival in percent
Abscissa: Time (days)
2.23 Survival of C57BL/6 mice and PD-1 deficient mice ($Pdcd1^{-/-}$ mice) bearing a murine pharyngeal carcinoma (MOPC cells) and which were treated intratumorally with LCMV ($2\times10^4$ PFU).

It could be shown in this experiment that LCMV acts synergistically with a PD-1 blockade.

Figure 22:
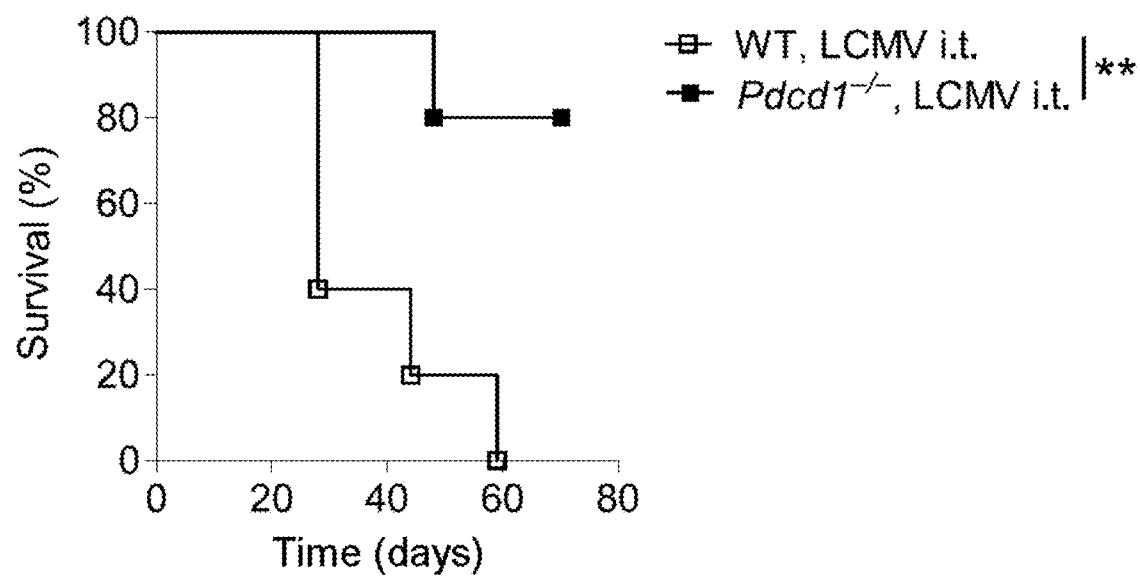
FIG. 22 shows the effect of LCMV administration on survival in MOPC tumor-bearing C57BL/6 and Pdcd1$^{-/-}$ mice.

FIG. 22 has the following legend:
Ordinate: Survival in percent
Abscissa: Time (days)

The nucleic acid sequences SEQ ID No. 1 to SEQ ID No. 6 mentioned in the general description correspond to the nucleic acid sequences disclosed in the following sequence listing.

---

The invention claimed is:

1. A method of treating a tumor comprising administering to a subject in need thereof a lymphocytic choriomeningitis virus (LCMV), wherein the sequences of the L-ribonucleic acids of the LCMV are selected from the group consisting of WE, Clone 13 and Docile L-ribonucleic acid sequences, and the S-ribonucleic acids of the LCMV are selected from the group consisting of WE, Clone 13 and Docile S-ribonucleic acid sequences.

2. The method of claim 1, wherein the method comprises activating innate (congenital) or adaptive immune cells and thereby effecting tumor regression.

3. The method of claim 1, wherein the method comprises effecting increased secretion of anti-tumoral cytokines by immune cells by activating said immune cells.

4. The method of claim 3, wherein the anti-tumoral cytokine is interferon-α, interferon-β or interferon-γ.

5. The method of claim 1, wherein the tumor is selected from the group consisting of carcinoma, melanoma, blastoma, lymphoma, and sarcoma.

6. The method of claim 1, wherein the arenavirus comprises a nucleic acid comprising an S-ribonucleic acid sequence according to SEQ ID No. 5 or ambisense sequence thereof, or a nucleic acid comprising an L-ribonucleic acid sequence according to SEQ ID No. 6 or ambisense sequence thereof.

7. The method of claim 1, wherein the lymphocytic choriomeningitis virus is a lymphocytic choriomeningitis virus strain WE.

8. The method of claim 1, wherein the subject is a human.

9. The method of claim 1, wherein the L-and S-ribonucleic acids of the LCMV are WE L-and S-ribonucleic acids.

10. A method of treating a tumor comprising administering to a subject in need thereof a lymphocytic choriomeningitis virus (LCMV), wherein the sequences of the L-ribonucleic acids of the LCMV are selected from the group consisting of WE, Clone 13 and Docile L-ribonucleic acid sequences, the S-ribonucleic acids of the LCMV are selected from the group consisting of WE, Clone 13 and Docile S-ribonucleic acid sequences, and the tumor is a solid tumor.

11. The method of claim 10, wherein the tumor is carcinoma.

12. The method of claim 10, wherein the tumor is melanoma.

13. The method of claim 10, wherein the subject is a human.

14. A method of treating a tumor comprising administering to a subject in need thereof a lymphocytic choriomeningitis virus (LCMV), wherein the sequences of the L-ribonucleic acids of the LCMV are selected from the group consisting of WE, Clone 13 and Docile L-ribonucleic acid sequences, the S-ribonucleic acids of the LCMV are selected from the group consisting of WE, Clone 13 and Docile S-ribonucleic acid sequences, and the tumor is selected from the group consisting of oropharynx cancer, colon cancer, lung cancer, cervical cancer, liver cancer, melanoma, pharyngeal cancer, lymphoma, thyroid cancer, and bladder cancer.

15. The method of claim 14, wherein the tumor is selected from the group consisting of oropharynx cancer, colon cancer, lung cancer, cervical cancer, liver cancer, melanoma, pharyngeal cancer, and lymphoma.

16. The method of claim 14, wherein the subject is a human.

* * * * *